(12) United States Patent
Winneroski, Jr. et al.

(10) Patent No.: US 7,608,639 B2
(45) Date of Patent: Oct. 27, 2009

(54) PHENOXYETHER DERIVATIVES AS PPAR MODULATORS

(75) Inventors: Leonard Larry Winneroski, Jr., Greenwood, IN (US); Yanping Xu, Fishers, IN (US); Jeremy Schulenburg York, Noblesville, IN (US)

(73) Assignee: Eli Lilly and Company, Indianapolis, IN (US)

( * ) Notice: Subject to any disclaimer, the term of this patent is extended or adjusted under 35 U.S.C. 154(b) by 413 days.

(21) Appl. No.: 10/571,961

(22) PCT Filed: Oct. 8, 2004

(86) PCT No.: PCT/US2004/030911

§ 371 (c)(1),
(2), (4) Date: Mar. 13, 2006

(87) PCT Pub. No.: WO2005/037763

PCT Pub. Date: Apr. 28, 2005

(65) Prior Publication Data

US 2007/0037812 A1    Feb. 15, 2007

Related U.S. Application Data

(60) Provisional application No. 60/510,865, filed on Oct. 14, 2003.

(51) Int. Cl.
*A61K 31/44*    (2006.01)
*C07D 211/92*    (2006.01)

(52) U.S. Cl. .................. 514/546; 514/557; 546/290; 562/465

(58) Field of Classification Search .............. None
See application file for complete search history.

(56) References Cited

FOREIGN PATENT DOCUMENTS

| | | | |
|---|---|---|---|
| EP | 0 307 103 A2 | 8/1988 | |
| EP | 0 307 103 A3 | 8/1988 | |
| EP | 0 597 102 A1 | 7/1992 | |
| EP | 0 696 585 A1 | 4/1994 | |
| EP | 0 647 612 A1 | 9/1994 | |
| GB | 1563871 | * | 4/1980 |
| JP | 08 059 638 A | 3/1996 | |
| WO | WO 2004/093799 A2 | 11/2004 | |

OTHER PUBLICATIONS

Crews, A.D. et al, "Synthesis and Herbalicidal Activity of bis-Aryloxybenzenes: A New Structural Class of Protox Inhibitors Derived from N-Phenyl Benzotriazoles", ACS Symposium Series, 686 (Synthesis and Chemistry of Argochemicals V), 48-54 CODEN: ACSMC8; ISSN: 0097-6156, 1998, XP009044229.

Ebisawa, M. et al, "Thiazolidinediones With Thyroid Hormone Receptor Agonistic Activity", Chemical and Pharmaceutical Bulletin, Pharmaceutical Society of Japan. Tokyo, JP, vol. 47, No. 9, 1999, pp. 1348-1350, XP000906992; ISSN: 0009-2363.

Hutter, Michael C. et al, "QSAR of human steriod 5. alpha-reductase inhibitors: Where are the differences between isoenzyme type 1 and 2?", Chemical Abstracts Services, XP002318310 retrieved from STN, 2004.

* cited by examiner

*Primary Examiner*—Zinna N Davis
(74) *Attorney, Agent, or Firm*—MaCharri Vorndran-Jones

(57) ABSTRACT

The present invention is directed to a compound of formula (I), or a pharmaceutically acceptable salt, solvate, hydrate or stereoisomer thereof, which is useful in treating or preventing disorders mediated by a peroxisome proliferator activated receptor (PPAR), such as syndrome X, type II diabetes, hyperglycemia, hyperlipidemia, obesity, coagaulopathy, hypertension, arteriosclerosis, and other disorders related to syndrome X and cardiovascular diseases.

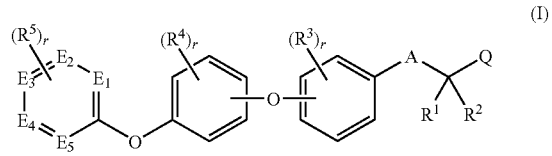

(I)

18 Claims, No Drawings

PHENOXYETHER DERIVATIVES AS PPAR MODULATORS

This application is a United States national phase entry, pursuant to 35 U.S.C. 371, of PCT/US2004/030911, filed on Oct. 8, 2004, which claims the benefit of United States provisional patent application Ser. No. 60/510865, filed Oct. 14, 2003, and hereby incorporated by reference in their entirety.

Information disclosed and/or claimed in this patent application has been generated pursuant to a joint research agreement among Eli Lilly and Company and Ligand Pharmaceuticals, Inc.

FIELD OF THE INVENTION

The present invention relates to compounds of peroxisome proliferator activated receptor (PPAR) agonists, more specifically phenoxyether derivatives as PPAR modulators, which are useful for the treatment and/or prevention of disorders modulated by a PPAR agonist.

BACKGROUND OF THE INVENTION

The peroxisome proliferator activated receptors (PPARs) are members of the nuclear receptor gene family that are activated by fatty acids and fatty acid metabolites. The PPARs belong to the subset of nuclear receptors that function as heterodimers with the 9-cis retinoic acid receptor (RXR). Three subtypes, designated PPARα, PPARγ and PPARδ, are found in species ranging from *Xenopus* to humans.

PPARα is the main subtype in the liver and has facilitated analysis of the mechanism by which peroxisome proliferators exert their pleiotropic effects. PPARα is activated by a number of medium and long-chain fatty acids, and it is involved in stimulating β-oxidation of fatty acids. PPARα is also involved with the activity of fibrates and fatty acids in rodents and humans. Fibric acid derivatives such as clofibrate, fenofibrate, bezafibrate, ciprofibrate, beclofibrate and etofibrate, as well as gemfibrozil, produce a substantial reduction in plasma triglycerides along with moderate reduction in low-density lipoprotein (LDL) cholesterol, and they are used particularly for the treatment of hypertriglyceridemia.

PPARγ is the main subtype in adipose tissue and involved in activating the program of adipocyte differentiation. PPARγ is not involved in stimulating peroxisome proliferation in the liver. There are two isomers of PPARγ: PPARγ1 and PPARγ2, which differ only in that PPARγ2 contains an additional 28 amino acids present at the amino terminus. The DNA sequences for the PPARγ receptors are described in Elbrecht, et al., BBRC 224; 431-437 (1996). Although peroxisome proliferators, including the fibrates and fatty acids, activate the transcriptional activity of PPAR's, only prostaglandin $J_2$ derivatives have been identified as natural ligands for PPARγ, which also binds the anti-diabetic agents thiazolidinediones with high affinity. The physiological functions of PPARα and PPARγ in lipid and carbohydrate metabolism were uncovered once it was recognized that they were the receptors for the fibrate and glitazone drugs, respectively.

PPARα and PPARγ receptors have been implicated in diabetes mellitus, cardiovascular disease, obesity, and gastrointestinal disease, such as inflammatory bowel disease and other inflammation related illnesses. Such inflammation related illnesses include, but are not limited to Alzheimer's disease, Crohn's disease, rheumatoid arthritis, psoriasis, and ischemia reprofusion injury.

By contrast, PPARδ (also referred to as PPARβ and NUC1) is not reported to be receptor for any known class of drug molecules, and its role in mammalian physiology has remained undefined. The human nuclear receptor gene PPARδ (hPPARδ) has been cloned from a human osteosarcoma cell cDNA library and is fully described in A. Schmidt et al., *Molecular Endocrinology*, 6:1634-1641 (1992).

Diabetes is a disease in which a mammal's ability to regulate glucose levels in the blood is impaired because the mammal has a reduced ability to convert glucose to glycogen for storage in muscle and liver cells. In Type I diabetes, this reduced ability to store glucose is caused by reduced insulin production. "Type II Diabetes" or "non-insulin dependent diabetes mellitus" (NIDDM) is the form of diabetes, which is due to a profound resistance to insulin stimulating or regulatory effect on glucose and lipid metabolism in the main insulin-sensitive tissues, muscle, liver and adipose tissue. This resistance to insulin responsiveness results in insufficient insulin activation of glucose uptake, oxidation and storage in muscle and inadequate insulin repression of lipolysis in adipose tissue and of glucose production and secretion in liver. When these cells become desensitized to insulin, the body tries to compensate by producing abnormally high levels of insulin and hyperinsulemia results. Hyperinsulemia is associated with hypertension and elevated body weight. Since insulin is involved in promoting the cellular uptake of glucose, amino acids and triglycerides from the blood by insulin sensitive cells, insulin insensitivity can result in elevated levels of triglycerides and LDL (known as the "bad" cholesterol) which are risk factors in cardiovascular diseases. The constellation of symptoms, which includes hyperinsulemia, combined with hypertension, elevated body weight, elevated triglycerides and elevated LDL is known as Syndrome X.

Hyperlipidemia is a condition, which is characterized by an abnormal increase in serum lipids, such as cholesterol, triglycerides and phospholipids. These lipids do not circulate freely in solution in plasma, but are bound to proteins and transported as macromolecular complexes called lipoproteins. One form of hyperlipidemia is hypercholesterolemia, characterized by the existence of elevated LDL cholesterol levels. The initial treatment for hypercholesterolemia is often a diet low in fat and cholesterol coupled with appropriate physical exercise. Drug intervention is initiated if LDL-lowering goals are not met by diet and exercise alone. It is desirable to lower elevated levels of LDL cholesterol and increase levels of HDL cholesterol. Generally, it has been found that increased levels of HDL are associated with lower risk for coronary heart disease (CHD). See Gordon, et al., *Am. J. Med.*, 62, 707-714 (1977); Stampfer, et al., *N. England J. Med.*, 325, 373-381 (1991); and Kannel, et al., *Ann. Internal Med.*, 90, 85-91 (1979). An example of an HDL raising agent is nicotinic acid, but the quantities needed to achieve HDL elevation are associated with undesirable effects, such as flushing.

There are several treatments currently available for treating diabetes mellitus but these treatments still remain unsatisfactory and have limitations. While physical exercise and reduction in dietary intake of calories will improve the diabetic condition, compliance with this approach can be poor because of sedentary lifestyles and excess food consumption, in particular high fat-containing food. Therefore, treatment with hypoglycemics, such as sulfonylureas (e.g., chlorpropamide, tolbutamide, tolazamide and acetohexamide) and biguanides (e.g. phenformin and metformin) are often necessary as the disease progresses. Sulfonylureas stimulate the β cells of the pancreas to secrete more insulin as the disease progresses. However, the response of the β cells eventually fails and treatment with insulin injections is necessary. In addition, both sulfonylurea treatment and insulin injection have the life threatening side effect of hypoglycemic coma, and thus patients using these treatments must carefully control dosage.

It has been well established that improved glycemic control in patients with diabetes (Type I and Type II) is accompanied by decreased microvasclular complications (DCCT and UKPDS). Due to difficulty in maintaining adequate glycemic control over time in patients with Type II diabetes, the use of insulin sensitizers in the therapy of Type II diabetes is growing. There is also a growing body of evidence that PPARγ agonist, insulin sensitizer, may have benefits in the treatment of Type II diabetes beyond their effects in improving glycemic control.

In the last decade a class of compounds known as thiazolidinediones (TZD) (e.g. U.S. Pat. Nos. 5,089,514; 4,342,771; 4,367,234; 4,340,605; and 5,306,726) have emerged as effective antidiabetic agents that have been shown to increase the sensitivity of insulin sensitive tissues, such as skeletal muscle, liver and adipose, to insulin. Increasing insulin sensitivity rather than the amount of insulin in the blood reduces the likelihood of hypoglycemic coma. Although thiazolidinediones have been shown to increase insulin sensitivity by binding to PPARγ receptors, this treatment also produces unwanted side effects such as weight gain and, for troglitazone, liver toxicity.

Recently, compounds that are not TZDs have also been reported.

Adams et al. (WO 97/28115, WO 97/28135 and U.S. Pat. No. 5,895,051) discloses acetylphenols, which are useful as antiobesity and antidiabetic compounds.

Leibowitz et al. (WO 97/28149) discloses compounds which are PPARδ agonists and useful for treating cardiovascular diseases and related conditions.

Brooks et al. (WO 02/100813) discloses compounds of PPAR modulators that are useful for treating type II diabetes and other PPAR-mediated diseases and conditions.

In view of the above, an objective of the present invention is to provide new pharmaceutical agents, which modulate PPAR receptors, to prevent, treat and/or alleviate these diseases or conditions while reducing and or eliminating one or more of the unwanted side effects associated with the current treatments.

SUMMARY OF THE INVENTION

The present invention relates to a compound of novel peroxisome proliferator activated receptor (PPAR) agonist having a structural formula I, A compound having a formula I,

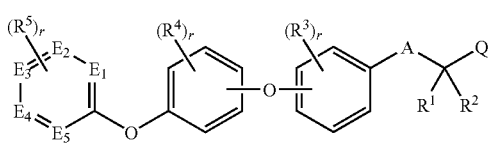

or a pharmaceutically acceptable salt, solvate, hydrate or stereoisomer thereof, wherein: $E_1$, $E_2$, $E_3$, $E_4$ and $E_5$ are each CH or substituted carbon bearing $R^5$; or at least one of $E_1$, $E_2$, $E_3$, $E_4$ and $E_5$ is nitrogen and each of others being CH or substituted carbon bearing $R^5$;

A is: a bond, $CH_2$, $(CH_2)_2$, O, S; or A and $R^1$ or A and $R^2$ together being a 3- to 6-membered carbocyclyl when A is a carbon;

Q is: —$C(O)OR^6$ or $R^{6A}$;
n is: 1, 2, 3, 4, 5 or 6
p is: 1 or 2;
r is: 1, 2, 3, or 4;
$R^1$ and $R^2$ are each independently:
 hydrogen, $C_1$-$C_6$ alkyl, or $R^1$ and $R^2$ together being a 3- to 8-membered carbocyclic ring;
$R^3$ and $R^4$ are each independently:
 hydrogen,
 nitro,
 cyano,
 hydroxyl,
 halo,
 haloalkyl,
 haloalkyloxy,
 $C_1$-$C_6$ alkyl,
 $C_1$-$C_6$ alkoxy, or
 $C_3$-$C_8$ cycloalkyl
$R^5$ is: hydrogen,
 nitro,
 cyano,
 hydroxyl,
 halo,
 haloalkyl,
 haloalkyloxy,
 aryloxy,
 $C_1$-$C_6$ alkyl,
 $C_1$-$C_6$ alkoxy,
 [T]-aryl,
 [T]-heteroaryl,
 [T]-heterocyclyl,
 [T]-$(CH_2)_n C_3$-$C_8$ cycloalkyl,
 $C(O)_p R^7$,
 $O(CH_2)_n R^7$,
 $SR^7$,
 $S(O)_p R^7$ or
 $OS(O)_p R^7$,
 wherein aryl, aryloxy, alkyl, heteroaryl, heterocyclyl and cycloalkyl are being optionally substituted with one or more substituents independently selected from $R^8$;
[T] is: a bond, O, C(O), S, $NR^7$, or $C_1$-$C_6$ alkyl;
$R^6$ is: hydrogen, $C_1$-$C_6$ alkyl or aminoalkyl;
$R^{6A}$ is: carboxamide, sulfonamide, acylsulfonamide, tetrazole,

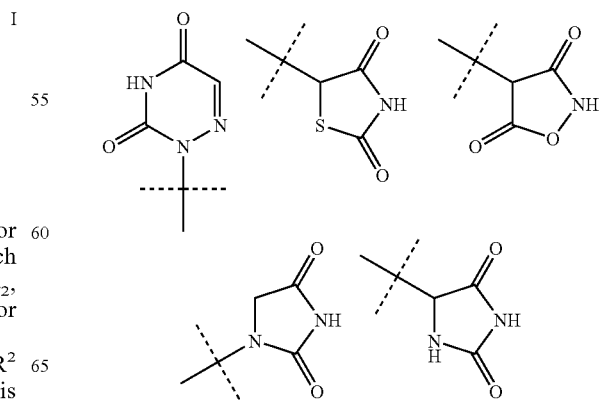

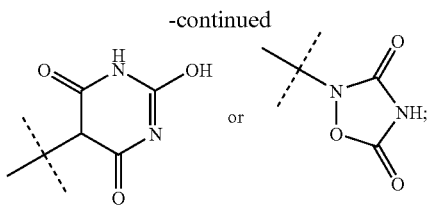

$R^7$ is: hydrogen,
$C_1$-$C_6$ alkyl,
$C_3$-$C_8$ cycloalkyl,
aryl,
heteroaryl or
heterocyclyl,
wherein alkyl, cycloalkyl, aryl, heteroaryl or heterocyclyl being optionally substituted with one or more substituents independently selected from $R^8$; and $R^8$ is: hydrogen, nitro, cyano, hydroxyl, halo, haloalkyl, haloalkyloxy, aryloxy, oxo, acyl, $C_1$-$C_6$ alkyl, $C_1$-$C_6$ alkoxy or $C_3$-$C_8$ cycloalkyl.

The compounds of the present invention are useful in the treatment and/or prevention of diseases or condition relates to hyperglycemia, dyslipidemia, Type II diabetes, Type I diabetes, hypertriglyceridemia, syndrome X, insulin resistance, heart failure, diabetic dyslipidemia, hyperlipidemia, hypercholesteremia, hypertension, obesity, anorexia bulimia, anorexia nervosa, cardiovascular disease and other diseases where insulin resistance is a component.

In one embodiment, the present invention also relates to a pharmaceutical composition comprising a compound of the present invention, or a pharmaceutically acceptable salt, solvate or hydrate thereof and a pharmaceutically acceptable carrier. Within the scope of this invention also include a pharmaceutical composition containing additional therapeutic agent as well as a compound of the present invention, or a pharmaceutically acceptable salt, solvate or hydrate thereof and a pharmaceutically acceptable carrier.

In another embodiment, the present invention relates to a method of modulating a PPAR by contacting the receptor with a compound of the present invention, and a pharmaceutically acceptable salt, solvate or hydrate thereof.

DETAILED DESCRIPTION OF THE INVENTION

The compounds of the present invention are directed to peroxisome proliferator activated receptor (PPAR) agonists, more specifically phenoxyether derivatives as PPAR modulators. The compounds of the present invention are directed to PPAR-γ/δ dual agonists. The compounds of the present invention are useful for the treatment and/or prevention of disorders modulated by a PPAR, such as Type II diabetes, hyperglycemia, dyslipidemia, Type I diabetes, hypertriglyceridemia, syndrome X, insulin resistance, heart failure, diabetic dyslipidemia, hyperlipidemia, hypercholesteremia, hypertension, obesity, anorexia bulimia, anorexia nervosa, cardiovascular disease and other related diseases.

An embodiment of the present invention is a compound of novel peroxisome proliferator activated receptor (PPAR) agonists having a structural formula I, or a pharmaceutically acceptable salt, solvate, hydrate or stereoisomer thereof, wherein: $E_1$, $E_2$, $E_3$, $E_4$ and $E_5$ are each CH or substituted carbon bearing $R^5$; or at least one of $E_1$, $E_2$, $E_3$, $E_4$ and $E_5$ is nitrogen and each of others being CH or substituted carbon bearing $R^5$;

A is: a bond, $CH_2$, $(CH_2)_2$, O, S; or A and $R^1$ or A and $R^2$ together being a 3- to 6-membered carbocyclyl when A is a carbon;

Q is: —C(O)$OR^6$ or $R^{6A}$;

n is: 1, 2, 3, 4, 5 or 6 p is: 1 or 2;

r is: 1, 2, 3, or 4;

$R^1$ and $R^2$ are each independently:
hydrogen, $C_1$-$C_6$ alkyl, or $R^1$ and $R^2$ together being a 3- to 8-membered carbocyclic ring;

$R^3$ and $R^4$ are each independently:
hydrogen,
nitro,
cyano,
hydroxyl,
halo,
haloalkyl,
haloalkyloxy,
$C_1$-$C_6$ alkyl,
$C_1$-$C_6$ alkoxy, or
$C_3$-$C_8$ cycloalkyl $R^5$ is: hydrogen,
nitro,
cyano,
hydroxyl,
halo,
haloalkyl,
haloalkyloxy,
aryloxy,
$C_1$-$C_6$ alkyl,
$C_1$-$C_6$ alkoxy,
[T]-aryl,
[T]-heteroaryl,
[T]-heterocyclyl,
[T]-$(CH_2)_n$$C_3$-$C_8$ cycloalkyl,
$C(O)_pR^7$,
$O(CH_2)_nR^7$,
$SR^7$,
$S(O)_pR^7$ or
$OS(O)_pR^7$,
wherein aryl, aryloxy, alkyl, heteroaryl, heterocyclyl and cycloalkyl are being optionally substituted with one or more substituents independently selected from $R^8$;

[T] is: a bond, O, C(O), S, NR$^7$, or C$_1$-C$_6$ alkyl;

R$^6$ is: hydrogen, C$_1$-C$_6$ alkyl or aminoalkyl;

R$^{6A}$ is: carboxamide, sulfonamide, acylsulfonamide, tetrazole,

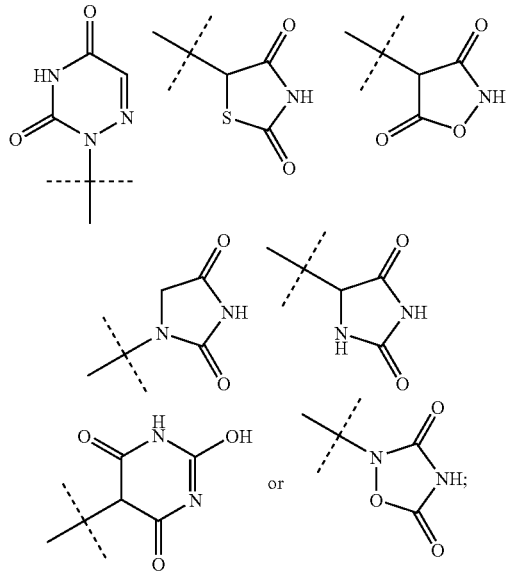

R$^7$ is: hydrogen,
C$_1$-C$_6$ alkyl,
C$_3$-C$_8$ cycloalkyl,
aryl,
heteroaryl or
heterocyclyl,
wherein alkyl, cycloalkyl, aryl, heteroaryl or heterocyclyl being optionally substituted with one or more substituents independently selected from R$^8$; and R$^8$ is: hydrogen, nitro, cyano, hydroxyl, halo, haloalkyl, haloalkyloxy, aryloxy, oxo, acyl, C$_1$-C$_6$ alkyl, C$_1$-C$_6$ alkoxy or C$_3$-C$_8$ cycloalkyl.

A preferred embodiment of the present invention is a compound having a structural formula II,

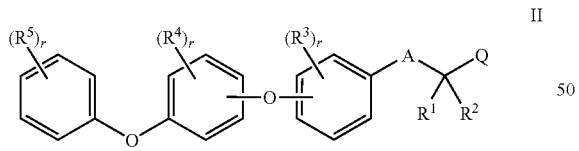

or a pharmaceutically acceptable salt, solvate, hydrate or stereoisomer thereof, wherein:

A is: a bond, CH$_2$, (CH$_2$)$_2$, O, S; or A and R$^1$ or A and R$^2$ together being a 3- to 6-membered carbocyclyl when A is a carbon;

Q is: —C(O)OR$^6$ or R$^{6A}$;

n is: 1, 2, 3, 4, 5 or 6 p is: 1 or 2;

r is: 1, 2, 3, or 4;

R$^1$ and R$^2$ are each independently:
hydrogen, C$_1$-C$_6$ alkyl, or R$^1$ and R$^2$ together being a 3- to 8-membered carbocyclic ring;

R$^3$ and R$^4$ are each independently:
hydrogen,
nitro,
cyano,
hydroxyl,
halo,
haloalkyl,
haloalkyloxy,
C$_1$-C$_6$ alkyl,
C$_1$-C$_6$ alkoxy, or
C$_3$-C$_8$ cycloalkyl;

R$^5$ is: hydrogen,
nitro,
cyano,
hydroxyl,
halo,
haloalkyl,
haloalkyloxy,
aryloxy,
C$_1$-C$_6$ alkyl,
C$_1$-C$_6$ alkoxy,
[T]-aryl,
[T]-heteroaryl,
[T]-heterocyclyl,
[T]-(CH$_2$)$_n$C$_3$-C$_8$ cycloalkyl,
C(O)$_p$R$^7$,
O(CH$_2$)$_n$R$^7$,
SR$^7$,
S(O)$_p$R$^7$ or
OS(O)$_p$R$^7$, wherein aryl, aryloxy, alkyl, heteroaryl, heterocyclyl and cycloalkyl are being optionally substituted with one or more substituents independently selected from R$^8$;

[T] is: a bond, O, C(O), S, NR$^7$, or C$_1$-C$_6$ alkyl;

R$^6$ is: hydrogen, C$_1$-C$_6$ alkyl or aminoalkyl;

R$^{6A}$ is: carboxamide, sulfonamide, acylsulfonamide, tetrazole,

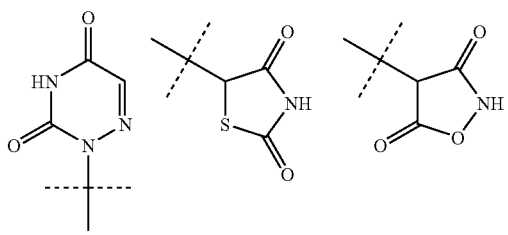

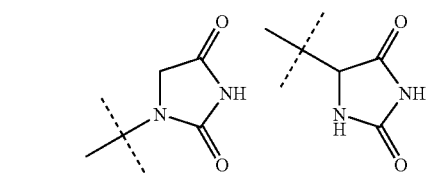

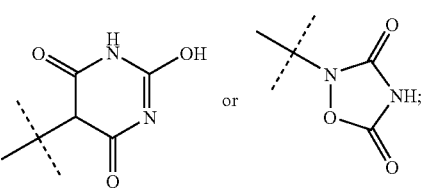

R⁷ is: hydrogen,
  $C_1$-$C_6$ alkyl,
  $C_3$-$C_8$ cycloalkyl,
  aryl,
  heteroaryl or
  heterocyclyl,
    wherein alkyl, cycloalkyl, aryl, heteroaryl or heterocyclyl being optionally substituted with one or more substituents independently selected from R⁸; and
R⁸ is: hydrogen, nitro, cyano, hydroxyl, halo, haloalkyl, haloalkyloxy, aryloxy, oxo, acyl, $C_1$-$C_6$ alkyl, $C_1$-$C_6$ alkoxy or $C_3$-$C_8$ cycloalkyl.

Another preferred embodiment of the present invention is a compound having a structural formula III,

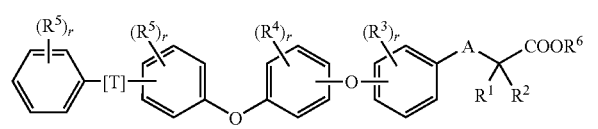

III or a pharmaceutically acceptable salt, solvate, hydrate or stereoisomer thereof.

Yet another preferred embodiment of the present invention is the compound having a structural formula IV,

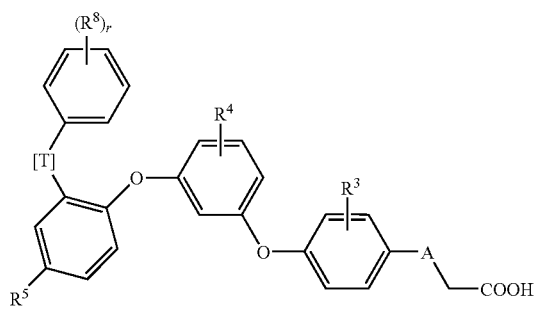

IV or a pharmaceutically acceptable salt, solvate, hydrate or stereoisomer thereof, wherein:
A is: $CH_2$, O, S;
[T] is: a bond, O, C(O) or $C_1$-$C_3$ alkyl;
R³ and R⁴ are each independently:
  hydrogen, $C_1$-$C_3$ alkyl, halo, haloalkyl or haloalkyloxy;
R⁵ and R⁸ are each independently:
  hydrogen, $C_1$-$C_6$ alkyl, halo, haloalkyl or haloalkyloxy; and
r is 1 or 2.

Yet another preferred embodiment of the present invention is the compound having a structural formula V,

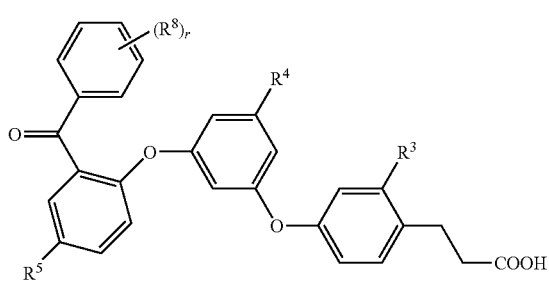

V or a pharmaceutically acceptable salt, solvate, hydrate or stereoisomer thereof, wherein:
R³ and R⁴ are each independently: hydrogen, methyl, ethyl, Br, Cl or F;
R⁵ and R⁸ are each independently: hydrogen, $C_1$-$C_4$ alkyl, Br, Cl, F or $CF_3$; and
r is 1 or 2.

Yet another embodiment of the present invention is a compound having a structural formula VI,

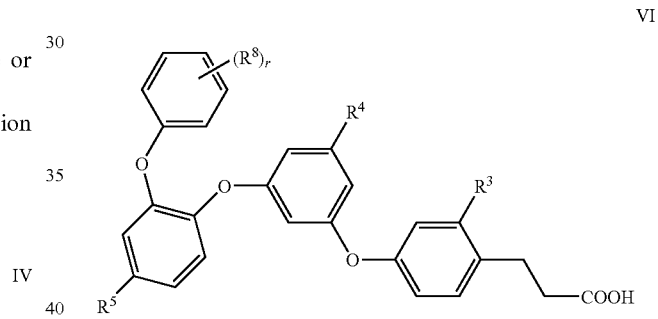

VI or a pharmaceutically acceptable salt, solvate, hydrate or stereoisomer thereof, wherein:
R³ and R⁴ are each independently: hydrogen, methyl, ethyl, Br, Cl or F;
R⁵ and R⁸ are each independently: hydrogen, $C_1$-$C_4$ alkyl, Br, Cl, F or $CF_3$; and
r is 1 or 2.

Yet another preferred embodiment of the present invention is the compound having a structural formula VII,

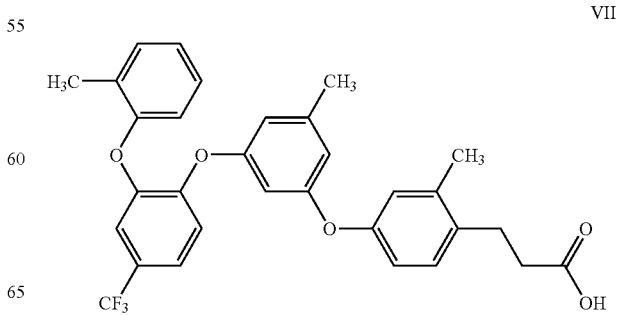

VII or a pharmaceutically acceptable salt, solvate or hydrate thereof.

Yet another preferred embodiment of the present invention is the compound having a structural formula VIII,

VIII or a pharmaceutically acceptable salt, solvate or hydrate thereof.

Yet another preferred embodiment of the present invention is a compound having a structural formula IX,

IX or a pharmaceutically acceptable salt, solvate, hydrate or stereoisomer thereof, wherein:

$R^3$ and $R^4$ are each independently: hydrogen, methyl, ethyl, Br, Cl or F;

$R^5$ and $R^8$ are each independently: hydrogen, $C_1$-$C_4$ alkyl, Br, Cl, F or $CF_3$; and r is 1 or 2.

Yet another preferred embodiment of the present invention is a compound having a structural formula X,

X or a pharmaceutically acceptable salt, solvate, hydrate or stereoisomer thereof, wherein:

(Het)

is a 5- or 6-membered heteroaryl or heterocyclyl, wherein heteroaryl and heterocyclyl being optionally substituted with one or more substituents independently selected from $R^8$.

The compound as recited above in formula X, wherein the heteroaryl is pyrazolyl, pyrrolyl, pyrazinyl, pyridyl, pyrimidyl or pyrimidinyl Yet another preferred embodiment of the present invention is a compound having a structural formula XI,

XI or a pharmaceutically acceptable salt, solvate, hydrate or stereoisomer thereof, wherein:

[T] is: a bond, O, C(O) or $C_1$-$C_3$ alkyl;

$R^3$ and $R^4$ are each independently: hydrogen, methyl, ethyl, Br, Cl or F;

$R^5$ and $R^8$ are each independently: hydrogen, $C_1$-$C_4$ alkyl, Br, Cl, F or $CF_3$; and r is 1 or 2.

Yet another preferred embodiment of the present invention is a compound having a structural formula XII,

XII or a pharmaceutically acceptable salt, solvate, hydrate or stereoisomer thereof.

Yet another preferred embodiment of the present invention is a compound having a structural formula XIII,

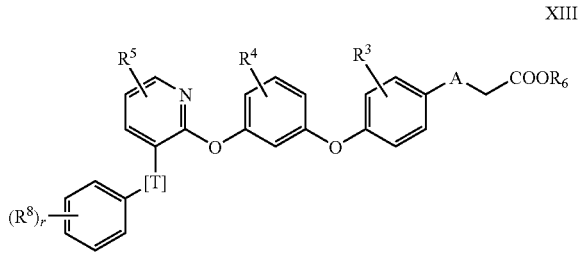

XIII or a pharmaceutically acceptable salt, solvate, hydrate or stereoisomer thereof, wherein:
A is: $CH_2$, O, S;
[T] is: a bond, O, C(O) or $C_1$-$C_3$ alkyl;
$R^3$ and $R^4$ are each independently:
  hydrogen, $C_1$-$C_3$ alkyl, halo, haloalkyl or haloalkyloxy;
$R^5$ and $R^8$ are each independently:
  hydrogen, $C_1$-$C_6$ alkyl, halo, haloalkyl or haloalkyloxy; and
$R^6$ is: hydrogen or $C_1$-$C_6$ alkyl; and
r is 1 or 2.

Yet another preferred embodiment of the present invention is a compound having a structural formula XIV,

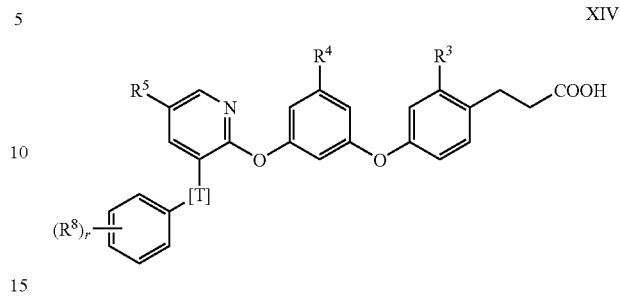

XIV or a pharmaceutically acceptable salt, solvate, hydrate or stereoisomer thereof, wherein:
[T] is: a bond, O or $C_1$-$C_3$ alkyl;
$R^3$ and $R^4$ are each independently: hydrogen, methyl, ethyl, Br, Cl or F;
$R^5$ and $R^8$ are each independently: hydrogen, $C_1$-$C_4$ alkyl, Br, Cl, F or $CF_3$; and
r is 1 or 2.

Yet more preferred embodiment of the present invention is the compounds listed below:

| No. | Structure | Name |
|---|---|---|
| 1 | 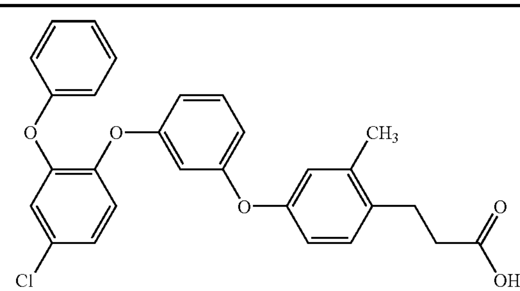 | 3-{4-[3-(4-Chloro-2-phenoxy-phenoxy)phenoxy]-2-methyl-phenyl}-propionic acid |
| 2 | 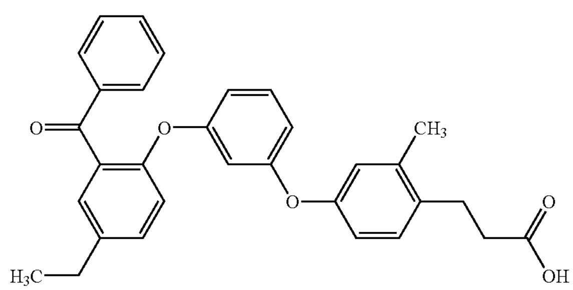 | 3-{4-[3-(2-Benzoyl-4-ethyl-phenoxy)-phenoxy]-2-methyl-phenyl}-propionic acid |
| 3 | 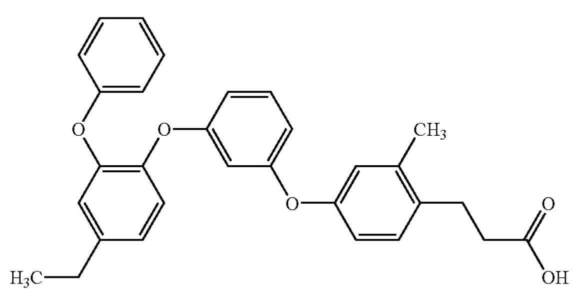 | 3-{4-[3-(4-Ethyl-2-phenoxy-phenoxy)-phenoxy]-2-methyl-phenyl}-propionic acid |

-continued

| No. | Structure | Name |
|---|---|---|
| 4 | 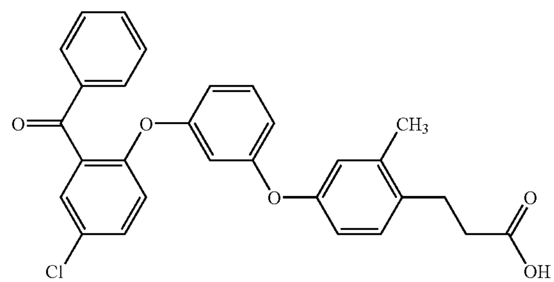 | 3-{4-[3-(2-Benzoyl-4-chloro-phenoxy)-phenoxy]-2-methyl-phenyl}-propionic acid |
| 5 | 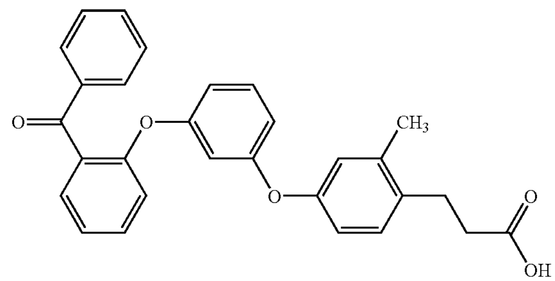 | 3-{4-[3-(2-Benzoyl-phenoxy)-phenoxy]-2-methyl-phenyl}-propionic acid |
| 6 | 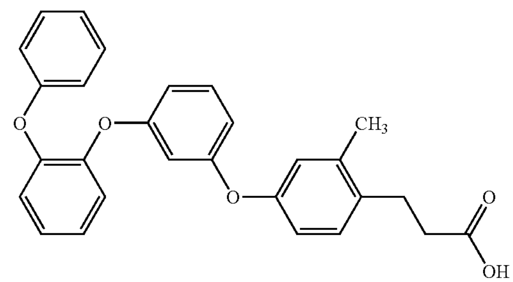 | 3-{2-Methyl-4-[3-(2-phenoxy-phenoxy)-phenoxy]-phenyl}-propionic acid |
| 7 | 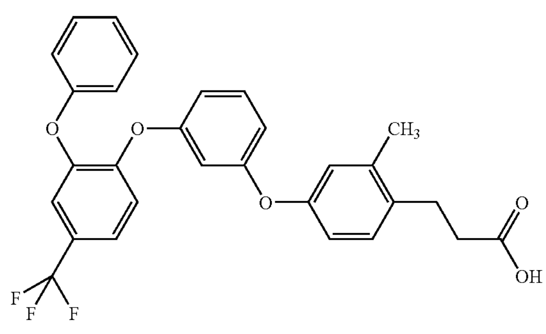 | 3-{2-Methyl-4-[3-(2-phenoxy-4-trifluoromethyl-phenoxy)-phenoxy]-phenyl}-propionic acid |
| 8 | 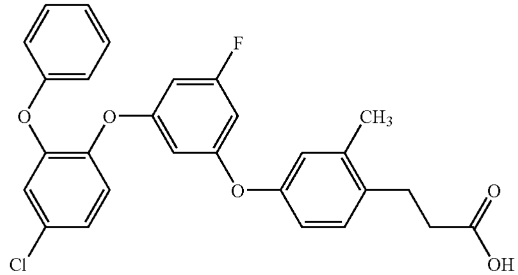 | 3-{4-[3-(4-Chloro-2-phenoxy-phenoxy)-5-fluoro-phenoxy]-2-methyl-phenyl}-propionic acid |

-continued

| No. | Structure | Name |
|---|---|---|
| 9 | 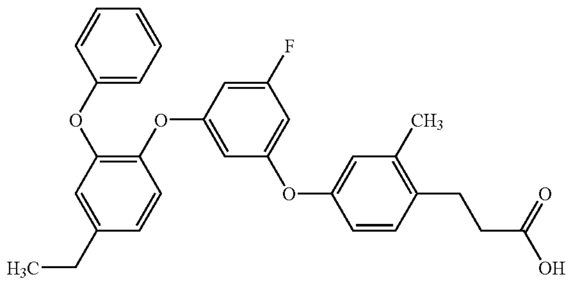 | 3-{4-[3-(4-Ethyl-2-phenoxy-phenoxy)-5-fluoro-phenoxy]-2-methyl-phenyl}-propionic acid |
| 10 | 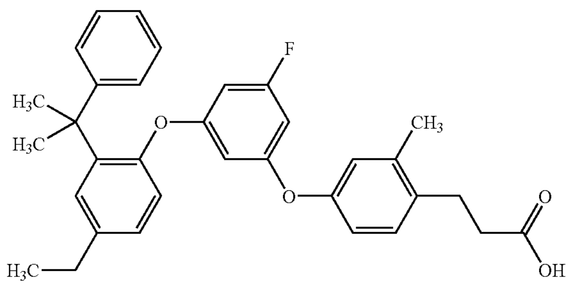 | 3-(4-{3-[4-Ethyl-2-(1-methyl-1-phenyl-ethyl)-phenoxy]-5-fluoro-phenoxy}-2-methyl-phenyl)-propionic acid |
| 11 | 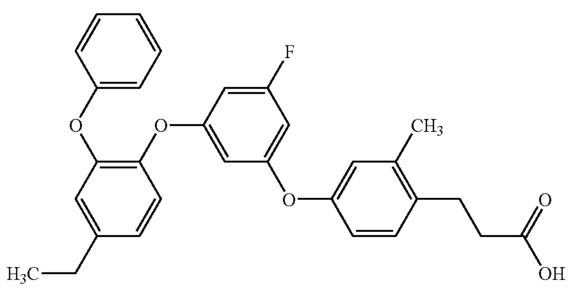 | 3-{4-[3-(4-Ethyl-2-phenoxy-phenoxy)-5-fluoro-phenoxy]-2-methyl-phenyl}-propionic acid |
| 12 | 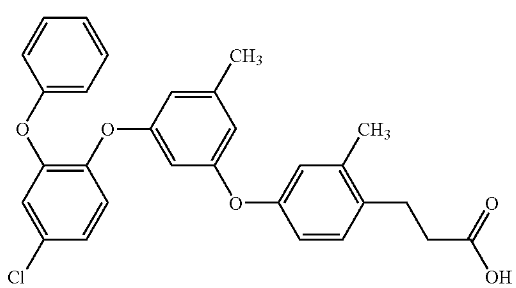 | 3-{4-[3-(4-Chloro-2-phenoxy-phenoxy)-5-methyl-phenoxy]-2-methyl-phenyl}-propionic acid |
| 13 | 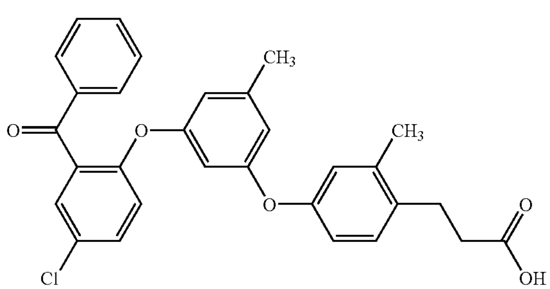 | 3-{4-[3-(2-Benzoyl-4-chloro-phenoxy)-5-methyl-phenoxy]-2-methyl-phenyl}-propionic acid |

-continued

| No. | Structure | Name |
|---|---|---|
| 14 | 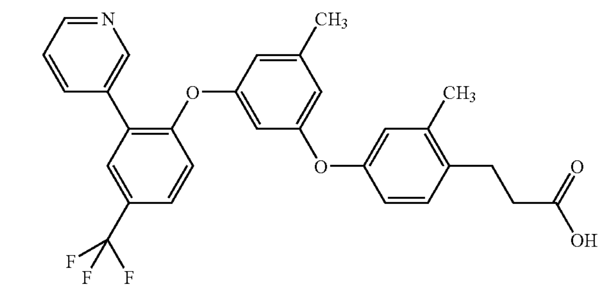 | 3-{2-Methyl-4-[3-methyl-5-(2-pyridin-3-yl-4-trifluoromethyl-phenoxy)-phenoxy]-phenyl}-propionic acid |
| 15 | 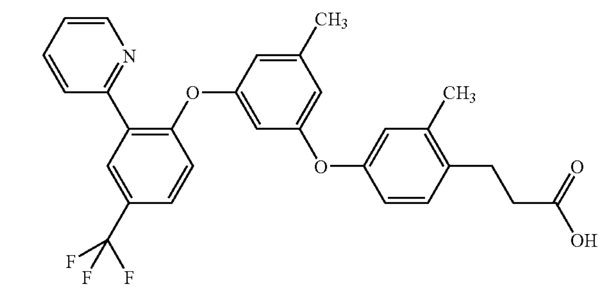 | 3-{2-Methyl-4-[3-methyl-5-(2-pyridin-2-yl-4-trifluoromethyl-phenoxy)-phenoxy]-phenyl}-propionic acid |
| 16 | 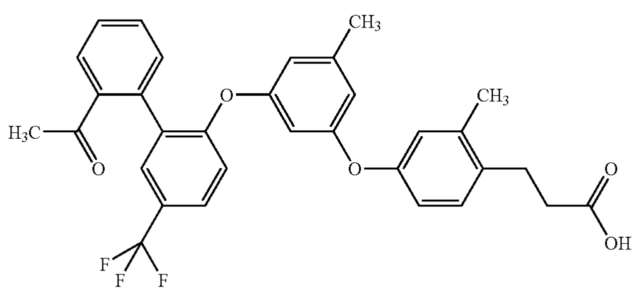 | 3-{4-[3-(2'-Acetyl-5-trifluoromethyl-biphenyl-2-yloxy)-5-methyl-phenoxy]-2-methyl-phenyl}-propionic acid |
| 17 | 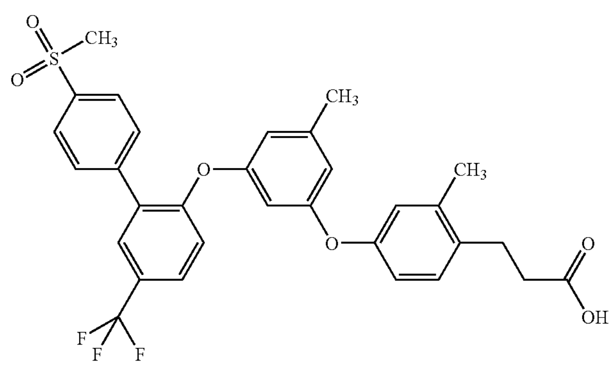 | 3-{4-[3-(4'-Methanesulfonyl-5-trifluoromethyl-biphenyl-2-yloxy)-5-methyl-phenoxyl]-2-methyl-phenyl}-propionic acid |
| 18 | 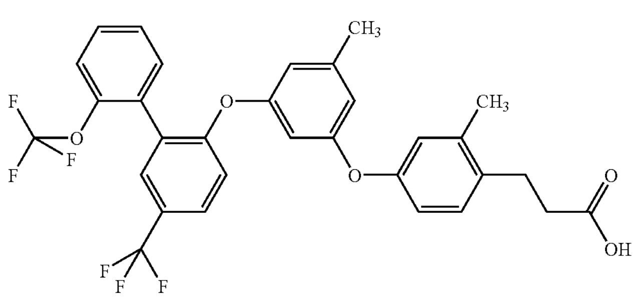 | 3-{2-Methyl-4-[3-methyl-5-(2'-trifluoromethoxy-5-trifluoromethyl-biphenyl-2-yloxy)-phenoxy]-phenyl}-propionic acid |

-continued

| No. | Structure | Name |
|---|---|---|
| 19 | 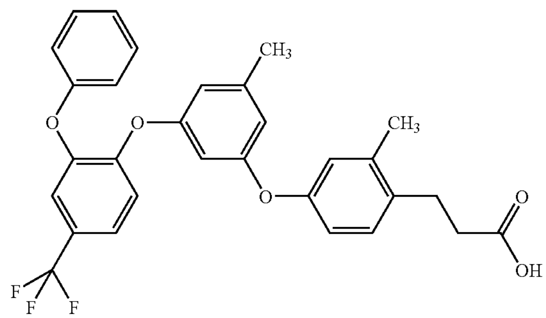 | 3-{2-Methyl-4-[3-methyl-5-(2-phenoxy-4-trifluoromethyl-phenoxy)-phenoxy]-phenyl}-propionic acid |
| 20 | 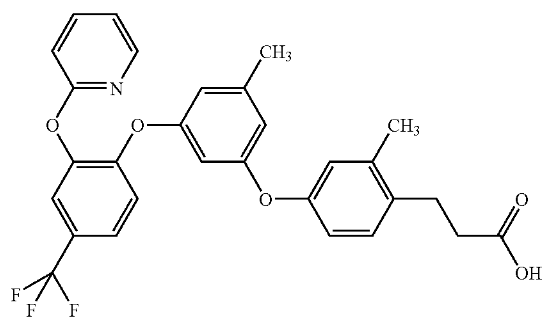 | 3-(2-Methyl-4-{3-methyl-5-[2-(pyridin-2-yloxy)-4-trifluoromethyl-phenoxyl]-phenoxy}-phenyl)-propionic acid |
| 21 | 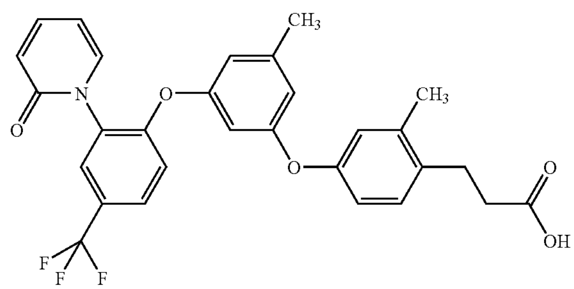 | 3-(2-Methyl-4-{3-methyl-5-[2-(2-oxo-2H-pyridin-1-yl)-4-trifluoromethyl-phenoxy]-phenoxy}-phenyl)-propionic acid |
| 22 | 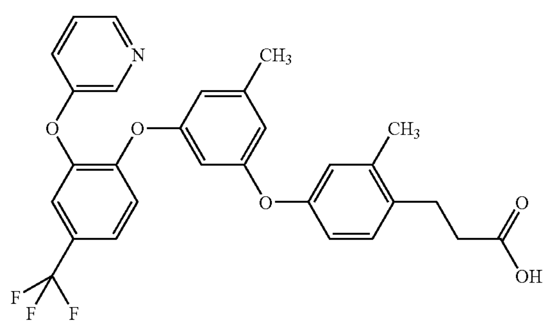 | 3-(2-Methyl-4-{3-methyl-5-[2-(pyridin-3-yloxy)-4-trifluoromethyl-phenoxy]-phenoxy}-phenyl)-propionic acid |
| 23 | 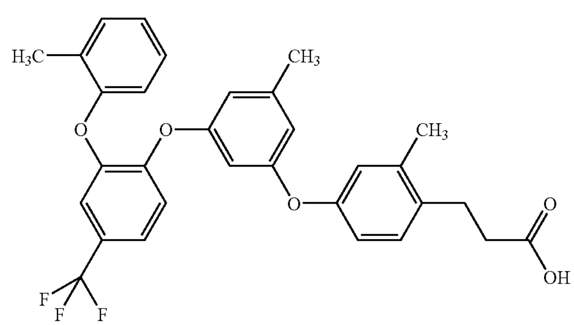 | 3-{2-Methyl-4-[3-methyl-5-(2-o-tolyloxy-4-trifluoromethyl-phenoxy)-phenoxy]-phenyl}-propionic acid |

| No. | Structure | Name |
|---|---|---|
| 24 | 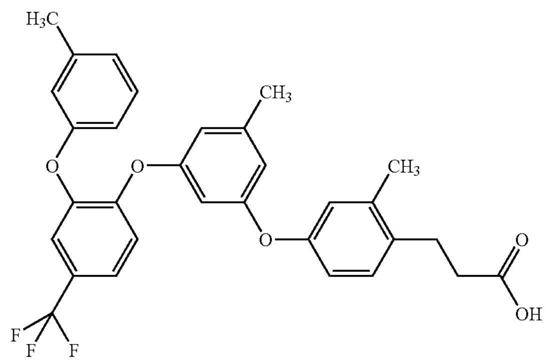 | 3-{2-Methyl-4-[3-methyl-5-(2-m-tolyloxy-4-trifluoromethyl-phenoxy)-phenoxy]-phenyl}-propionic acid |
| 25 | 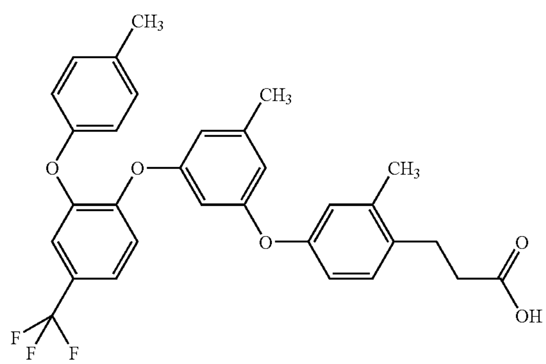 | 3-{2-Methyl-4-[3-methyl-5-(2-p-tolyloxy-4-trifluoromethyl-phenoxy)-phenoxy]-phenyl}-propionic acid |
| 26 | 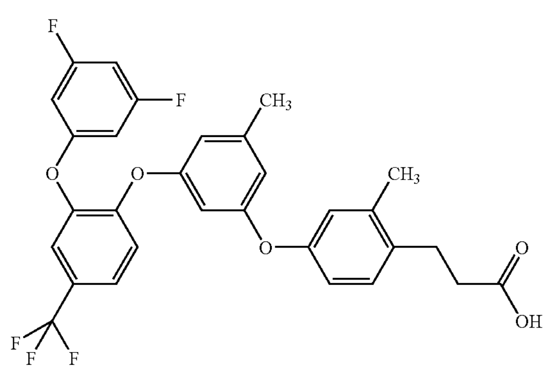 | 3-(4-{3-[2-(3,5-Difluoro-phenoxy)-4-trifluoromethyl-phenoxy]-5-methyl-phenoxy}-2-methyl-phenyl)-propionic acid |
| 27 | 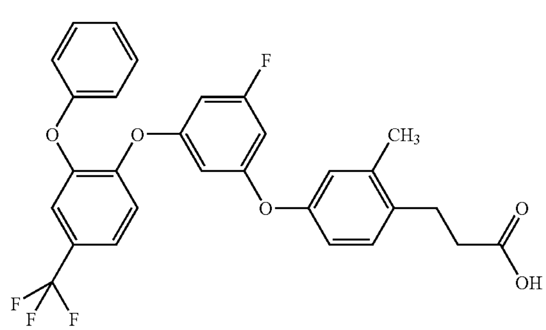 | 3-{4-[3-Fluoro-5-(2-phenoxy-4-trifluoromethyl-phenoxy)-phenoxy]-2-methyl-phenyl}-propionic acid |

-continued

| No. | Structure | Name |
|---|---|---|
| 28 | 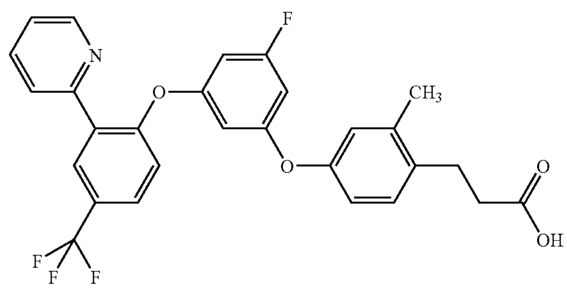 | 3-{4-[3-Fluoro-5-(2-pyridin-2-yl-4-trifluoromethyl-phenoxy)-phenoxy]-2-methyl-phenyl}-propionic acid |
| 29 | 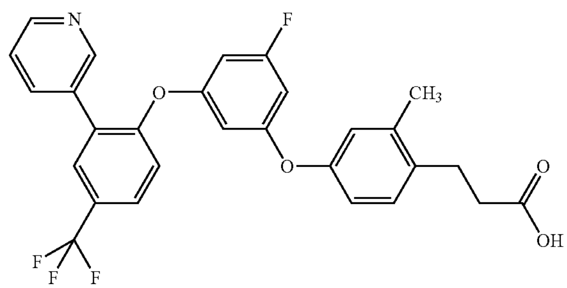 | 3-{4-[3-Fluoro-5-(2-pyridin-3-yl-4-trifluoromethyl-phenoxy)-phenoxy]-2-methyl-phenyl}-propionic acid |
| 30 | 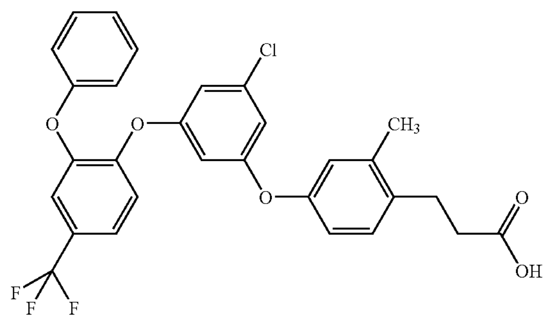 | 3-{4-[3-Chloro-5-(2-phenoxy-4-trifluoromethyl-phenoxy)-phenoxy]-2-methyl-phenyl}-propionic acid |
| 31 | 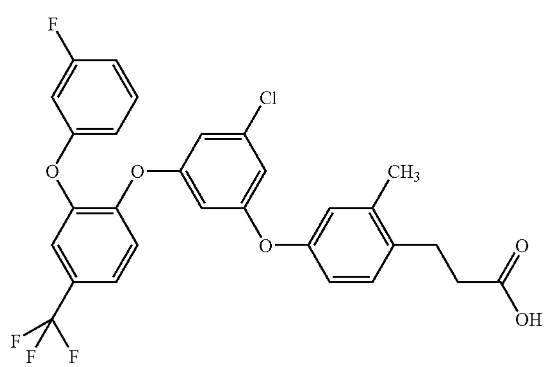 | 3-(4-{3-Chloro-5-[2-(3-fluoro-phenoxy)-4-trifluoromethyl-phenoxy]-phenoxy}-2-methyl-phenyl)-propionic acid |
| 32 | 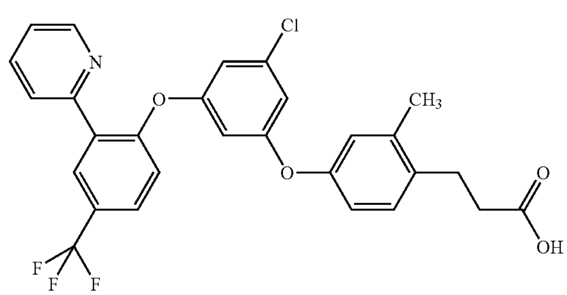 | 3-{4-[3-Chloro-5-(2-pyridin-2-yl-4-trifluoromethyl-phenoxy)-phenoxy]-2-methyl-phenyl}-propionic acid |

| No. | Structure | Name |
|---|---|---|
| 33 | 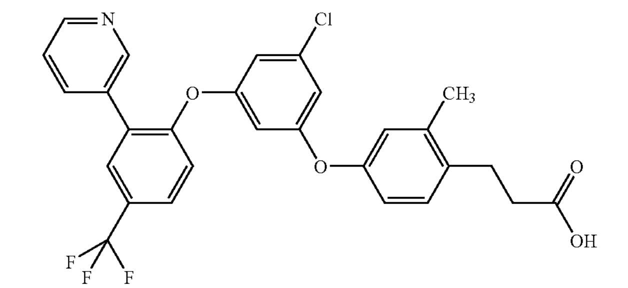 | 3-{4-[3-Chloro-5-(2-pyridin-3-yl-4-trifluoromethyl-phenoxy)-phenoxy]-2-methyl-phenyl}-propionic acid |
| 34 | 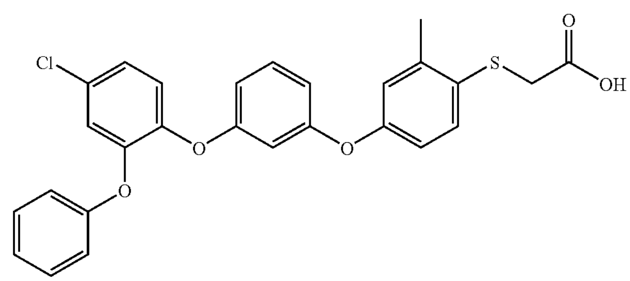 | {4-[3-(4-Chloro-2-phenoxy-phenoxy)-phenoxy]-2-methyl-phenylsulfanyl}-acetic acid |
| 35 | 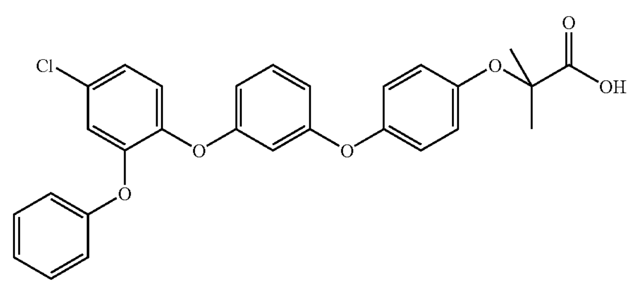 | 2-{4-[3-(4-Chloro-2-phenoxy-phenoxy)-phenoxy]-phenoxy}-2-methyl-propionic acid |
| 36 | 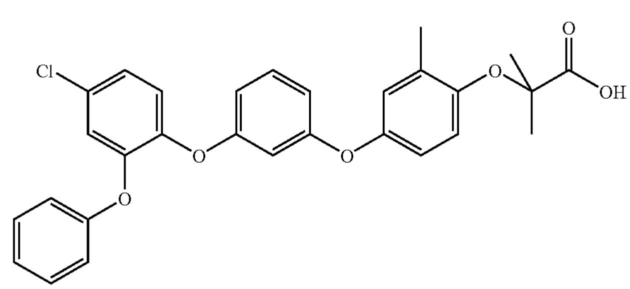 | 2-{4-[3-(4-Chloro-2-phenoxy-phenoxy)-phenoxy]-2-methyl-phenoxy}-2-methyl-propionic acid |
| 37 | 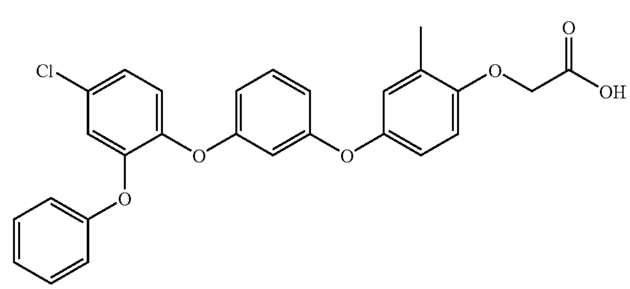 | {4-[3-(4-Chloro-2-phenoxy-phenoxy)-phenoxy]-2-methyl-phenoxy}-acetic acid |

-continued
| No. | Structure | Name |
|---|---|---|
| 38 | 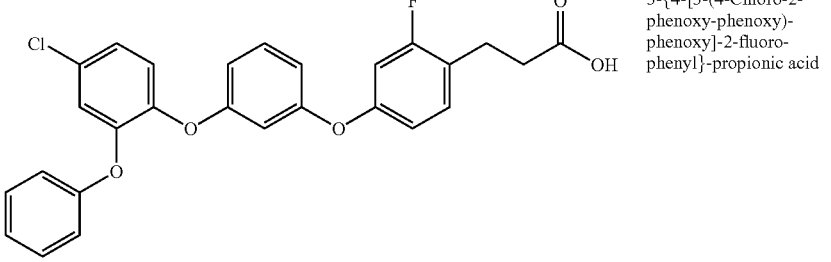 | 3-{4-[3-(4-Chloro-2-phenoxy-phenoxy)-phenoxy]-2-fluoro-phenyl}-propionic acid |
| 39 | 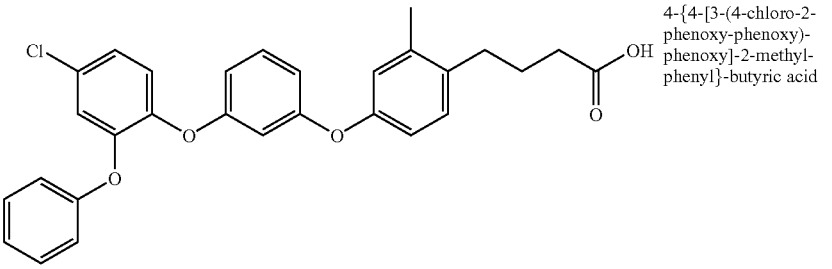 | 4-{4-[3-(4-chloro-2-phenoxy-phenoxy)-phenoxy]-2-methyl-phenyl}-butyric acid |
| 40 | 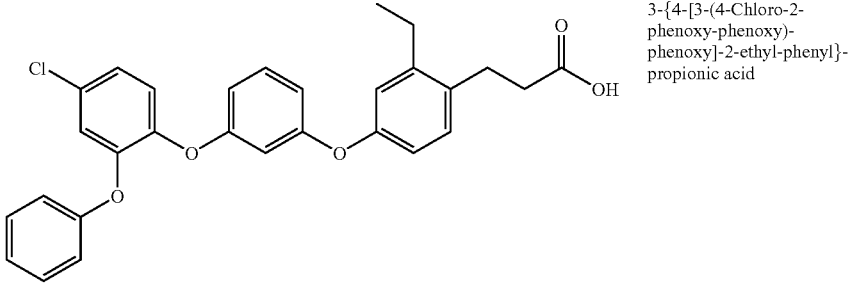 | 3-{4-[3-(4-Chloro-2-phenoxy-phenoxy)-phenoxy]-2-ethyl-phenyl}-propionic acid |
| 41 | 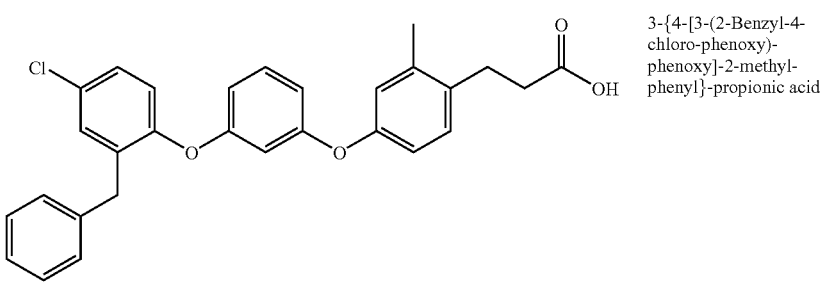 | 3-{4-[3-(2-Benzyl-4-chloro-phenoxy)-phenoxy]-2-methyl-phenyl}-propionic acid |
| 42 | 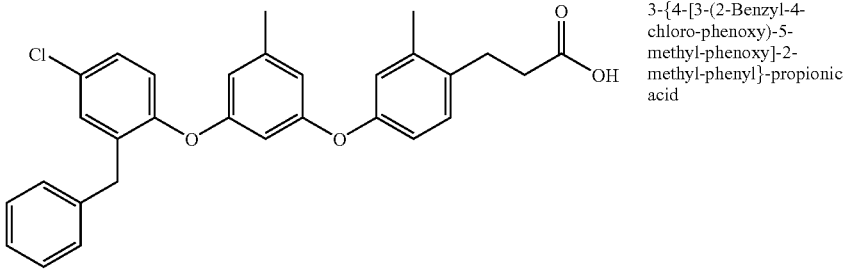 | 3-{4-[3-(2-Benzyl-4-chloro-phenoxy)-5-methyl-phenoxy]-2-methyl-phenyl}-propionic acid |

-continued

| No. | Structure | Name |
|---|---|---|
| 43 | 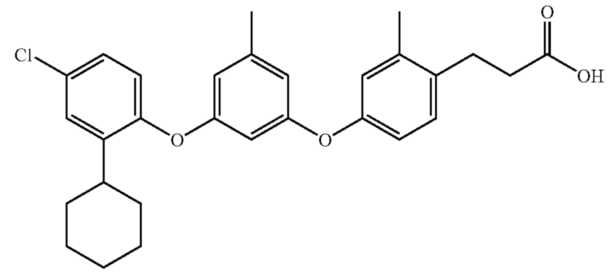 | 3-{4-[3-(4-Chloro-2-cyclohexyl-phenoxy)-5-methyl-phenoxy]-2-methyl-phenyl}-propionic acid |
| 44 | 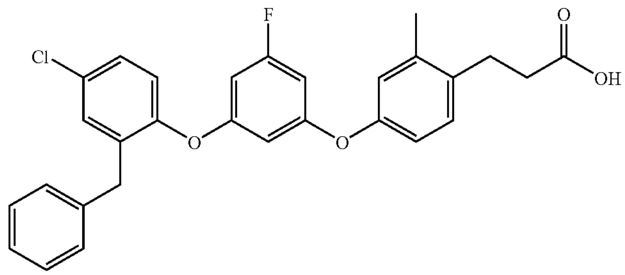 | 3-{4-[3-(2-Benzyl-4-chloro-phenoxy)-5-fluoro-phenoxy]-2-methyl-phenyl}-propionic acid |
| 45 | 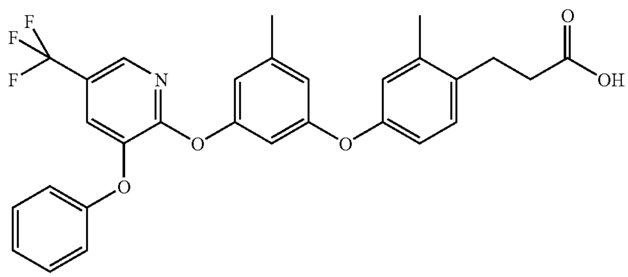 | 3-{2-Methyl-4-[3-methyl-5-(3-phenoxy-5-trifluoromethyl-pyridin-2-yloxy)-phenoxy]-phenyl}-propionic acid |

Yet more preferred embodiment of the present invention is the compounds of 3-{4-[3-(4-chloro-2-phenoxy-phenoxy)-5-methyl-phenoxy]-2-methyl-phenyl}-propionic acid having the following structure,

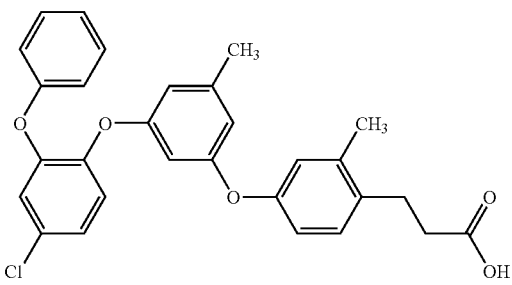

or a pharmaceutically acceptable salt, solvate or hydrate thereof.

Yet more preferred embodiment of the present invention is the compounds of {4-[3-(4-chloro-2-phenoxy-phenoxy)-phenoxy]-2-methyl-phenoxy}-acetic acid having the following structure,

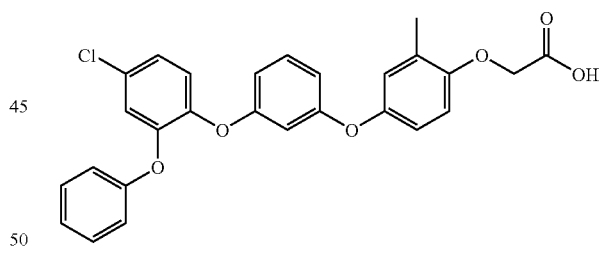

or a pharmaceutically acceptable salt, solvate or hydrate thereof.

Also encompassed by the present invention is a pharmaceutical composition comprising a pharmaceutically acceptable carrier and a compound of the present invention or a pharmaceutically acceptable salt, solvate or hydrate thereof.

Also encompassed by the present invention is a pharmaceutical composition comprising: (1) a compound of the present invention, or a pharmaceutically acceptable salt, solvate, hydrate or stereoisomer thereof; (2) a second therapeutic agent selected from the group consisting of: insulin sensitizers, sulfonylureas, biguanides, meglitinides, thiazolidinediones, α-glucosidase inhibitors, insulin secretogogues, insulin, antihyperlipidemic agents, plasma HDL-raising agents, HMG-CoA reductase inhibitors, statins, acryl CoA:

cholestrol acyltransferase inhibitors, antiobesity compounds, antihypercholesterolemic agents, fibrates, vitamins and aspirin; and (3) optionally a pharmaceutically acceptable carrier.

Also encompassed by the present invention is a method of modulating a peroxisome proliferator activated receptor (PPAR) comprising the step of contacting the receptor with a compound of the present invention or a pharmaceutically acceptable salt, solvate or hydrate thereof.

The method recited above, wherein the PPAR is an alpha (α)-receptor.

The method recited above, wherein the PPAR is a gamma (γ)-receptor.

The method recited above, wherein the PPAR is a delta (δ)-receptor.

The method recited above, wherein the PPAR is a gamma/delta (γ/δ)-receptor.

The method recited above, wherein the PPAR is a alpha/gamma/delta (α/γ/δ)-receptor.

Also encompassed by the present invention is a method for treating and/or preventing a PPAR-γ mediated disease or condition in a mammal comprising the step of administering an effective amount of a compound of the present invention.

Also encompassed by the present invention is a method for treating and/or preventing a PPAR-δ mediated disease or condition in a mammal comprising the step of administering an effective amount of a compound of the present invention.

Also encompassed by the present invention is a method for treating and/or preventing a PPAR-γδ mediated disease or condition in a mammal comprising the step of administering an effective amount of a compound of the present invention.

Also encompassed by the present invention is a method for treating and/or preventing a PPARα/γ/δ-mediated disease or condition in a mammal comprising the step of administering an effective amount of a compound of the present invention.

Also encompassed by the present invention is a method for lowering blood-glucose in a mammal comprising the step of administering an effective amount of a compound of the present invention.

Also encompassed by the present invention is a method of treating and/or preventing disease or condition in a mammal selected from the group consisting of hyperglycemia, dyslipidemia, Type II diabetes, Type I diabetes, hypertriglyceridemia, syndrome X, insulin resistance, heart failure, diabetic dyslipidemia, hyperlipidemia, hypercholesteremia, hypertension, obesity, anorexia bulimia, anorexia nervosa, cardiovascular disease and other diseases where insulin resistance is a component, comprising the step of administering an effective amount of a compound of a compound of the present invention.

Also encompassed by the present invention is a method of treating and/or preventing diabetes mellitus in a mammal comprising the step of administering to a mammal a therapeutically effective amount of a compound of the present invention.

Also encompassed by the present invention is a method of treating and/or preventing cardiovascular disease in a mammal comprising the step of administering to a mammal a therapeutically effective amount of a compound of the present invention, or a pharmaceutically acceptable salt, solvate, hydrate or stereoisomer thereof.

Also encompassed by the present invention is a method of treating and/or preventing syndrome X in a mammal comprising the step of administering to the mammal a therapeutically effective amount of a compound of the present invention, or a pharmaceutically acceptable salt, solvate, hydrate or stereoisomer thereof.

Also encompassed by the present invention is a method of treating and/or preventing disease or condition in a mammal selected from the group consisting of hyperglycemia, dyslipidemia, Type II diabetes, Type I diabetes, hypertriglyceridemia, syndrome X, insulin resistance, heart failure, diabetic dyslipidemia, hyperlipidemia, hypercholesteremia, hypertension, obesity, anorexia bulimia, anorexia nervosa, cardiovascular disease and other diseases where insulin resistance is a component, comprising the step of administering an effective amount of a compound of the present invention, and an effective amount of second therapeutic agent selected from the group consisting of insulin sensitizers, sulfonylureas, biguanides, meglitinides, thiazolidinediones, α-glucosidase inhibitors, insulin secretogogues, insulin, antihyperlipidemic agents, plasma HDL-raising agents, HMG-CoA reductase inhibitors, statins, acryl CoA:cholestrol acyltransferase inhibitors, antiobesity compounds, antihypercholesterolemic agents, fibrates, vitamins and aspirin.

Also encompassed by the present invention is use of a compound of the present invention and a pharmaceutically acceptable salt, solvate, hydrate or stereoisomer thereof, for the manufacture of a medicament for the treatment of a condition modulated by a PPAR.

The terms used to describe the present invention have the following meanings unless otherwise indicated.

The term "alkyl," unless otherwise indicated, refers to those alkyl groups of a designated number of carbon atoms of either a straight or branched saturated configuration. Examples of "alkyl" include, but are not limited to: methyl, ethyl, n-propyl, isopropyl, n-butyl, isobutyl, sec-butyl and tert-butyl, pentyl, hexyl, isopentyl and the like. Alkyl as defined above may be optionally substituted with a designated number of substituents as set forth in the embodiment recited above.

The term "alkoxy" represents an alkyl group of indicated number of carbon atoms attached through an oxygen bridge, such as methoxy, ethoxy, propoxy, isopropoxy, butoxy, tert-butoxy, pentoxy, and the like. Alkoxy as defined above may be optionally substituted with a designated number of substituents as set forth in the embodiment recited above.

The term "cycloalkyl" refers to a saturated or partially saturated carbocycle containing one or more rings of from 3 to 12 carbon atoms, more typically 3 to 8 carbon atoms. Examples of cycloalkyl includes, but are not limited to cyclopropyl, cyclobutyl, cyclopentyl, cyclohexyl and cycloheptyl, and the like. Cycloalkyl as defined above may also includes a tricycle, such as adamantyl. Cycloalkyl as defined above may be optionally substituted with a designated number of substituents as set forth in the embodiment recited above.

The term "halo" refers to fluoro, chloro, bromo and iodo.

The term "haloalkyl" is a $C_1$-$C_6$ alkyl group, which is substituted with one or more halo atoms selected from F, Br, Cl and I. Examples of haloalkyl group are trifluoromethyl, $CH_2CF_3$ and the like.

The term "haloalkyloxy" represents a $C_1$-$C_6$ haloalkyl group attached through an oxygen bridge, such as $OCF_3$. The "haloalkyloxy" as defined above may be optionally substituted with a designated number of substituents as set forth in the embodiment recited above.

The term "aryl" includes carbocyclic aromatic ring systems (e.g. phenyl), fused polycyclic aromatic ring systems (e.g. naphthyl and anthracenyl) and aromatic ring systems fused to carbocyclic non-aromatic ring systems (e.g., 1,2,3,4-tetrahydronaphthyl). The "aryl" as defined above may be optionally substituted with a designated number of substituents as set forth in the embodiment recited above.

The term "aryloxy" represents an aryl group attached through an oxygen bridge, such as phenoxy (—O-phenyl). The "aryloxy" as defined above may be optionally substituted with a designated number of substituents as set forth in the embodiment recited above.

The "acyl" represent an "alkyl-C(=O)-" group. Preferred acyl group are those in which the alkyl group is lower alkyl, such $C_1$-$C_4$ alkyl.

The term "heteroaryl" group, as used herein, is an aromatic ring system having at least one heteroatom such as nitrogen, sulfur or oxygen and includes monocyclic, bicyclic or tricyclic aromatic ring of 5- to 14-carbon atoms containing one or more heteroatoms selected from O, N, or S. The heteroaryl as defined above also includes heteroaryl fused with another heteroaryl, aryl fused with heteroaryl or aryl fused with heterocyclyl as defined herein. The "heteroaryl" may also be optionally substituted with a designated number of substituents as set forth in the embodiment recited above. Examples of heteroaryl are, but are not limited to: furanyl, thienyl (also referred to as "thiophenyl"), thiazolyl, imidazolyl, indolyl, isoindolyl, isooxazolyl, oxazoyl, pyrazolyl, pyrrolyl, pyrazinyl, pyridyl, pyrimidyl, pyrimidinyl and purinyl, cinnolinyl, benzofuranyl, benzothienyl (or benzothiophenyl), benzotriazolyl, benzoxazolyl, quinoline, isoxazolyl, isoquinoline 1,4 benzodioxan, or 2,3-dihydrobenzofuranyl and the like.

The term "heterocyclyl" refers to a non-aromatic ring which contains one or more heteroatoms selected from O, N or S, which includes a monocyclic, bicyclic or tricyclic ring of 5- to 14-carbon atoms containing one or more heteroatoms selected from O, N or S. The "heterocyclyl" as defined above may be optionally substituted with a designated number of substituents as set forth in the embodiment recited above. Examples of heterocyclyl include, but are not limited to, morpholine, piperidine, piperazine, pyrrolidine, and thiomorpholine.

The term "carbocyclyl" (or carbocyclic ring) refers to a saturated or partially saturated carbocyclic ring. Examples of carbocyclyl are, but are not limited to, cyclopentyl, cyclohexyl, cyclopentenyl, cyclohexenyl and the like.

An "arylalkyl" as used herein is an aryl substituent that is linked to a compound by an alkyl group having from one to six carbon atoms. The "arylalkyl" as defined above may be optionally substituted with a designated number of substituents as set forth in the embodiment recited above.

The "aminoalkyl" as used herein contains both a basic amino group ($NH_2$) and an alkyl group as defined above.

The term $R^{64}$ (or acid bioisosteres) as used herein includes, but are not limited to, carboxamide, sulfonamide, acylsulfonamide, tetrazole or the following moiety.

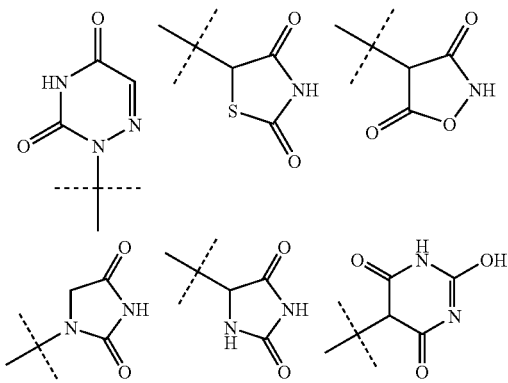

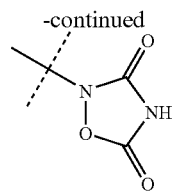

Carboxamide, sulfonamide, acylsulfonamide and tetrazole may be optionally substituted with one or more suitable substituents selected from haloalkyl, aryl, heteroaryl, and $C_1$-$C^6$ alkyl. The heteroalkyl, aryl, heteroaryl and alkyl may further optionally substituted with one or more substituents selected from the list provided for $R^8$. The examples of $R^{64}$ (or acid bioisosteres) are, but not limited to, hydroxamic acid, acyl cyanamide, tetrazoles, sulfinylazole, sulfonylazole, 3-hydroxyisoxazole, hydroxythiadiazole, sulphonate and acylsulfonamide.

The term "active ingredient" means the compounds generically described by Formula I as well as the salts, solvates and prodrugs of such compounds.

The term "pharmaceutically acceptable" means that the carrier, diluents, excipients and salt must be compatible with the other ingredients of the composition, and not deleterious to the recipient thereof. Pharmaceutical compositions of the present invention are prepared by procedures known in the art using well-known and readily available ingredients.

"Preventing" refers to reducing the likelihood that the recipient will incur or develop any of the pathological conditions described herein.

"Treating" refers to mediating a disease or condition, and preventing or mitigating its further progression or ameliorating the symptoms associated with the disease or condition.

"Pharmaceutically-effective amount" means that amount of a compound of the present invention, or of its salt, solvate, hydrate or prodrug thereof that will elicit the biological or medical response of a tissue, system or mammal. Such an amount can be administered prophylactically to a patient thought to be susceptible to development of a disease or condition. Such amount when administered prophylactically to a patient can also be effective to prevent or lessen the severity of the mediated condition. Such an amount is intended to include an amount, which is sufficient to modulate a PPAR receptor such as a PPARα, PPARγ, PPARδ or PPARγ/δ receptor to mediate a disease or condition. Conditions mediated by PPAR receptors include, for example, diabetes mellitus, cardiovascular disease, Syndrome X, obesity and gastrointestinal disease. Additional conditions associated with the modulation of a PPAR receptor include inflammation related conditions, which include, for example, IBD (inflammatory bowel disease), rheumatoid arthritis, psoriasis, Alzheimer's disease, Chrohn's disease and ischemia reprofusion injury (stroke and miocardial infarction).

A "mammal" is an individual animal that is a member of the taxonomic class mammalia. The class Mammalia includes humans, monkeys, chimpanzees, gorillas, cattle, swine, horses, sheep, dogs, cats, mice, rats and the like.

Administration to a human is most preferred. A human to whom the compounds and compositions of the present invention are administered has a disease or condition in which control blood glucose levels are not adequately controlled without medical intervention, but wherein there is endogenous insulin present in the human's blood. Non-insulin dependent diabetes mellitus (NIDDM) is a chronic disease or condition characterized by the presence of insulin in the blood, even at levels above normal, but resistance or lack of sensitivity to insulin action at the tissues.

Those skilled in the art will recognize that stereocenters exist in compound of the present invention. Accordingly, the present invention includes all possible stereoisomers and geometric isomers of the presently claimed compounds including racemic compounds and the optically active isomers.

The compounds of the present invention contain one or more chiral centers and exist in different optically active forms. When compounds of the present invention contain one chiral center, the compounds exist in two enantiomeric forms and the present invention includes both enantiomers and mixtures of enantiomers, such as racemic mixtures. Resolution of the final product, an intermediate or a starting material may be effected by any suitable method known in the art, for example by formation of diastereoisomeric salts which may be separated by crystallization; formation of diastereoisomeric derivatives or complexes which may be separated by crystallization and gas-liquid or liquid chromatography; selective reaction of one enantiomer with an enantiomer-specific reagent such as enzymatic esterification; and gas-liquid or liquid chromatography in a chiral environment such as on a chiral support, for example silica with a bound chiral ligand or in the presence of a chiral solvent. See also *Sterochemistry of Carbon Compounds* by E. L. Eliel (Mcgraw Hill, 1962) and *Tables of Resolving Agents* by S. H. Wilen. It will be appreciated that where the desired enantiomer is converted into another chemical entity by one of the separation procedures described above, a further step is required to liberate the desired enantiomeric form. Alternatively, specific enantiomers may be synthesized by asymmetric synthesis using optically active reagents, substrates, catalysts or solvents, or by converting one enantiomer into the other by asymmetric transformation.

When a compound of the present invention has more than one chiral substituents, it may exist in diastereoisomeric forms. The diastereoisomeric pairs may be separated by methods known to those skilled in the art, for example chromatography or crystallization and the individual enantiomers within each pair may be separated as described above. The present invention includes each diastereoisomer of compounds of formula I and mixtures thereof.

Certain compounds of the present invention may exist in different stable conformational forms, which may be separable. Torsional asymmetry due to restricted rotation about an asymmetric single bond, for example because of steric hindrance or ring strain, may permit separation of different conformers. The present invention includes each conformational isomer of compounds of formula I and mixtures thereof.

Certain compound of the present invention may exist in zwitterionic form, and the present invention includes each zwitterionic form of compounds of formula I and mixtures thereof.

Certain compounds of the present invention and their salts may exist in more than one crystal form. Polymorphs of compounds of formula I form part of the present invention and may be prepared by crystallization of a compound of formula I under different conditions, such as using different solvents or different solvent mixtures for recrystallization; crystallization at different temperatures; and various modes of cooling ranging from very fast to very slow cooling during crystallization. Polymorphs may also be obtained by heating or melting a compound of formula I followed by gradual or fast cooling. The presence of polymorphs may be determined by solid probe NMR spectroscopy, IR spectroscopy, differential scanning calorimetry, powder X-ray diffraction or other available techniques.

Certain compounds of the present invention and their salts may exist in more than one crystal form, which includes each crystal form and mixtures thereof.

Certain compounds of the present invention and their salts may also exist in the form of solvates, for example hydrates, and thus the present invention includes each solvate and mixtures thereof.

"Pharmaceutically-acceptable salt" refers to salts of the compounds of formula I, which are substantially non-toxic to mammals. Typical pharmaceutically acceptable salts include those salts prepared by reaction of the compounds of the present invention with a mineral, organic acid: an organic base or inorganic base. Such salts are known as base addition salts, respectively. It should be recognized that the particular counterion forming a part of any salt of the present invention is not of a critical nature so long as the salt as a whole is pharmaceutically acceptable and the counterion does not contribute undesired qualities to the salt as a whole.

By virtue of its acidic moiety, a compound of the present invention forms salts with pharmaceutically acceptable bases. Some examples of base addition salts include metal salts such as aluminum; alkali metal salts such as lithium, sodium or potassium; and alkaline earth metal salts such as calcium, magnesium, ammonium, or substituted ammonium salts. Examples of substituted ammonium salts include, for instance, those with lower alkylamines such as trimethylamine and triethylamine; hydroxyalkylamines such as 2-hydroxyethylamine, bis-(2-hydroxyethyl)-amine or tri-(2-hydroxyethyl)-amine; cycloalkylamines such as bicyclohexylamine or dibenzylpiperidine, N-benzyl-β-phenethylamine, dehydroabietylamine, N,N'-bisdehydro-abietylamine, glucamine, N-piperazine methylglucamine; bases of the pyridine type such as pyridine, collidine, quinine or quinoline; and salts of basic amino acids such as lysine and arginine.

Examples of inorganic bases include, without limitation, sodium hydroxide, potassium hydroxide, potassium carbonate, sodium carbonate, sodium bicarbonate, potassium bicarbonate, calcium hydroxide, calcium carbonate, and the like.

Compounds of the present invention, which are substituted with a basic group, may exist as salts with pharmaceutically acceptable acids. The present invention includes such salts. Examples of such salts include hydrochlorides, hydrobromides, sulfates, methanesulfonates, nitrates, maleates, acetates, citrates, fumarates, tartrates [e.g. (+)-tartrates, (−)-tartrates or mixtures thereof including racemic mixtures], succinates, benzoates and salts with amino acids such as glutamic acid. These salts may be prepared by methods known to those skilled in the art.

Certain compounds of the present invention and their salts may also exist in the form of solvates, for example hydrates, and thus the present invention includes each solvate and mixtures thereof.

The compounds of present invention, which bind to and activate the PPARs, lower one or more of glucose, insulin, triglycerides, fatty acids and/or cholesterol, and are therefore useful for the treatment and/or prevention of hyperglycemia, dyslipidemia and in particular Type II diabetes as well as other diseases including syndrome X, Type I diabetes, hypertriglyceridemia, insulin resistance, diabetic dyslipidemia, hyperlipidemia, hypercholesteremia, heart failure, coagaulopathy, hypertension, and cardiovascular diseases, especially arteriosclerosis. In addition, these compounds are indicated to be useful for the regulation of appetite and food intake in subjects suffering from disorders such as obesity, anorexia bulimia and anorexia nervosa.

The compounds and compositions of the present invention are also useful to treat acute or transient disorders in insulin sensitivity, which sometimes occurs following a surgery, trauma, myocardial infarction and the like. The compounds and compositions of the present invention are also useful for lowering serum triglyceride levels. Elevated triglyceride level, whether caused by genetic predisposition or by a high fat diet, is a risk factor for the development of heart disease, stroke, and circulatory system disorders and diseases. The physician of ordinary skill will know how to identify humans who can benefit from administration of the compounds and compositions of the present invention.

The present invention further provides a method for the treatment and/or prophylaxis of hyperglycemia in a human or non-human mammal which comprises administering an effective, non-toxic amount of a compound of formula I, or a tautomeric form thereof and/or a pharmaceutically acceptable salt thereof and/or a pharmaceutically acceptable solvate thereof to a hyperglycemic human or non-human mammal in need thereof.

The compounds of the present invention are useful as therapeutic substances in preventing or treating Syndrome X, diabetes mellitus and related endocrine and cardiovascular disorders and diseases in human or non-human animals.

The present invention also relates to the use of a compound of formula I as described above for the manufacture of a medicament for treating a PPARγ or PPARδ mediated condition, separately or in combination.

A therapeutically effective amount of a compound of the present invention can be used for the preparation of a medicament useful for treating Syndrome X, diabetes, treating obesity, lowering tryglyceride levels, raising the plasma level of high density lipoprotein, and for treating, preventing or reducing the risk of developing arteriosclerosis, and for preventing or reducing the risk of having a first or subsequent atherosclerotic disease event in mammals, particularly in humans. In general, a therapeutically effective amount of a compound of formula I of the present invention typically reduces serum glucose levels, more specifically HbA1c, of a patient by about 0.7% or more; typically reduces serum triglyceride levels of a patient by about 20% or more; and increases serum HDL levels in a patient. Preferably, HDL levels can be increased by about 30% or more.

Additionally, an effective amount of a compound of the present invention and a therapeutically effective amount of one or more active agents selected from antihyperlipidemic agent, plasma HDL-raising agents, antihypercholesterolemic agents, fibrates, vitamins, aspirin, insulin secretogogues, insulin and the like can be used together for the preparation of a medicament useful for the above described treatments.

Advantageously, compositions containing the compound of the present invention or their salts may be provided in dosage unit form, preferably each dosage unit containing from about 1 to about 500 mg. It is understood that the amount of the compounds or compounds of the present invention that will be administered is determined by a physician considering of all the relevant circumstances.

Syndrome X includes pre-diabetic insulin resistance syndrome and the resulting complications thereof, insulin resistance, non-insulin dependent diabetes, dyslipidemia, hyperglycemia obesity, coagulopathy, hypertension and other complications associated with diabetes. The methods and treatments mentioned herein include the above and encompass the treatment and/or prophylaxis of any one of or any combination of the following: pre-diabetic insulin resistance syndrome, the resulting complications thereof, insulin resistance, Type II or non-insulin dependent diabetes, dyslipidemia, hyperglycemia, obesity and the complications associated with diabetes including cardiovascular disease, especially arteriosclerosis.

The compositions are formulated and administered in the same general manner as detailed herein. The compounds of the present invention may be used effectively alone or in combination with one or more additional active agents depending on the desired target therapy. Combination therapy includes administration of a single pharmaceutical dosage composition, which contains a compound of the present invention and one or more additional active agents, as well as administration of a compound of the present invention and each active agent in its own separate pharmaceutical dosage. For example, a compound of the present invention or thereof and an insulin secretogogue such as biguanides, meglitinides, thiazolidinediones, sulfonylureas, insulin or α-glucosidose inhibitors can be administered to the patient together in a single oral dosage composition such as a tablet or capsule, or each agent administered in separate oral dosages. Where separate dosages are used, a compound of the present invention and one or more additional active agents can be administered at essentially the same time, i.e., concurrently or at separately staggered times, i.e., sequentially; combination therapy is understood to include all these regimens.

An example of combination treatment or prevention of arteriosclerosis may involve administration of a compound of the present invention or salts thereof in combination with one or more of second active therapeutic agents: antihyperlipidemic agents; plasma HDL-raising agents; antihypercholesterolemic agents, fibrates, vitamins, aspirin and the like. As noted above, the compounds of the present invention can be administered in combination with more than one additional active agent.

Another example of combination therapy can be seen in treating diabetes and related disorders wherein the compounds of the present invention or salts thereof can be effectively used in combination with second active therapeutic, such as sulfonylureas, biguanides, meglitinides, thiazolidinediones, α-glucosidase inhibitors, other insulin secretogogues, insulin as well as the active agents discussed above for treating arteriosclerosis.

The examples of second therapeutic agents are insulin sensitizers, PPARγ agonists, glitazones, troglitazone, pioglitazone, englitazone, MCC-555, BRL 49653, biguanides, metformin, phenformin, insulin, insulin minetics, sufonylureas, tolbutamide, glipizide, alpha-glucosidase inhibitors, acarbose, cholesterol lowering agent, HMG-CoA reductase inhibitors, lovastatin, simvastatin, pravastatin, fluvastatin, atrovastatin, rivastatin, other statins, sequestrates, cholestyramine, colestipol, dialkylaminoalkyl derivatives of a cross-linked dextran, nicotinyl alcohol, nicotinic acid: a nicotinic acid salt, PPARα agonists, fenofibric acid derivatives, gemfibrozil, clofibrate, fenofibrate, benzafibrate, inhibitors of cholesterol absorption, beta-sitosterol, acryl CoA:cholesterol acyltransferase inhibitors, melinamide, probucol, PPARδ agonists, antiobesity compounds, fenfluramine, dexfenfluramine, phentiramine, sulbitramine, orlistat, neuropeptide Y5 inhibitors, $\beta_3$ adrenergic receptor agonists, and ileal bile acid transporter inhibitors.

The compounds of the present invention and the pharmaceutically acceptable salts, solvates and hydrates thereof have valuable pharmacological properties and can be used in pharmaceutical compositions containing a therapeutically effective amount of a compound of the present invention, or pharmaceutically acceptable salts, esters or prodrugs thereof, in combination with one or more pharmaceutically acceptable excipients. Excipients are inert substances such as, without limitation carriers, diluents, fillers, flavoring agents, sweeteners, lubricants, solubilizers, suspending agents, wetting agents, binders, disintegrating agents, encapsulating material and other conventional adjuvants. Proper excipient is dependent upon the route of administration chosen. Pharmaceutical compositions typically contain from about 1 to about 99 weight percent of the active ingredient, which is a compound of the present invention.

Preferably, the pharmaceutical formulation is in unit dosage form. A "unit dosage form" is a physically discrete unit containing a unit dose suitable for administration in human subjects or other mammals. For example, a unit dosage form can be a capsule or tablet, or a number of capsules or tablets. A "unit dose" is a predetermined quantity of the active compound of the present invention, calculated to produce the desired therapeutic effect, in association with one or more pharmaceutically acceptable excipients. The quantity of active ingredient in a unit dose may be varied or adjusted from about 0.1 to about 1000 milligrams or more according to the particular treatment involved.

The dosage regimen utilizing the compounds of the present invention is selected by one of ordinary skill in the medical or veterinary arts considering various factors, such as without limitation, the species, age, weight, sex, medical condition of the recipient, the severity of the condition to be treated, the route of administration, the level of metabolic and excretory function of the recipient, the dosage form employed, the particular compound and salt thereof employed, and the like.

Preferably, the compounds of the present invention are administered in a single daily dose, or the total daily dose may be administered in divided doses of two, three or more times per day. Where delivery is via transdermal forms, administration is continuous.

Suitable routes of administration of pharmaceutical compositions of the present invention include, for example, oral, eye drop, rectal, transmucosal, topical or intestinal administration; parenteral delivery (bolus or infusion), including intramuscular, subcutaneous, intramedullary injections, as well as intrathecal, direct intraven-tricular, intravenous, intraperitoneal, intranasal, or intraocular injections. The compounds of the present invention can also be administered in a targeted drug delivery system, such as in a liposome coated with endothelial cell-specific antibody.

For oral administration, the compounds of the present invention can be formulated readily by combining the active compounds with pharmaceutically acceptable carriers well known in the art. Such carriers enable the compounds of the present invention to be Formulated as tablets, pills, powders, sachets, granules, dragees, capsules, liquids, elixirs, tinctures, gels, emulsions, syrups, slurries, suspensions and the like, for oral ingestion by a patient to be treated. Pharmaceutical preparations for oral use can be obtained by combining the active compound with a solid excipient, optionally grinding a resulting mixture, and processing the mixture of granules, after adding suitable auxiliaries, if desired, to obtain tablets or dragee cores.

For oral administration in the form of a tablet or capsule, the active ingredient may be combined with an oral, non-toxic, pharmaceutically-acceptable carrier, such as, without limitation, lactose, starch, sucrose, glucose, methyl cellulose, calcium carbonate, calcium phosphate, calcium sulfate, sodium carbonate, mannitol, sorbitol, and the like; together with, optionally, disintegrating agents, such as, without limitation, cross-linked polyvinyl pyrrolidone, maize, starch, methyl cellulose, agar, bentonite, xanthan gum, alginic acid; or a salt thereof such as sodium alginate, and the like; and, optionally, binding agents, for example, without limitation, gelatin, acacia, natural sugars, beta-lactose, corn sweeteners, natural and synthetic gums, acacia, tragacanth, sodium alginate, carboxymethyl-cellulose, polyethylene glycol, waxes, and the like; and, optionally, lubricating agents, for example, without limitation, magnesium stearate, sodium stearate, stearic acid: sodium oleate, sodium benzoate, sodium acetate, sodium chloride, talc, and the like. When a dosage unit form is a capsule, it may contain, in addition to materials of the above type, a liquid carrier such as a fatty oil.

Solid forms include powders, tablets and capsules. A solid carrier can be one or more substances, which may also act as flavoring agents, lubricants, solubilisers, suspending agents, binders, tablet disintegrating agents and encapsulating material.

In powders, the carrier is a finely divided solid, which is in admixture with the finely divided active ingredient. In tablets, the active ingredient is mixed with a carrier having the necessary binding properties in suitable proportions and compacted in the shape and size desired.

Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor.

Sterile liquids include suspensions, emulsions, syrups, and elixirs. The active ingredient can be dissolved or suspended in a pharmaceutically acceptable carrier, such as sterile water, sterile organic solvent, or a mixture of both sterile water and sterile organic solvent.

The active ingredient can also be dissolved in a suitable organic solvent, for example, aqueous propylene glycol. Other compositions can be made by dispersing the finely divided active ingredient in aqueous starch or sodium carboxymethyl cellulose solution or in a suitable oil.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations, which can be used orally, include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added.

All formulations for oral administration should be in dosages suitable for such administration. Particularly suitable compositions for oral administration are unit dosage forms such as tablets and capsules.

For parental administration, the compounds of the present invention or salts thereof can be combined with sterile aqueous or organic media to form injectable solutions or suspensions. Formulations for injection may be presented in unit dosage form, such as in ampoules or in multi-dose containers, with an added preservative. The compositions may take such forms as suspensions, solutions or emulsions in oily or aqueous vehicles, and may contain formulatory agents such as suspending, stabilizing and/or dispersing agents. The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that each syringability exists. It must be stable under the conditions of manufacture and storage and must be preserved against any contamination. The carrier can be solvent or dispersion medium containing, for example, water, preferably in physiologically compatible buffers such as Hanks' solution, Ringer's solution, or physiological saline buffer, ethanol, polyol (e.g. glycerol, propylene glycol and liquid polyethylene glycol), propylene glycol and liquid polyethylene glycol), suitable mixtures thereof, and vegetable oils. Under ordinary conditions of storage and use, these preparations contain a preservative to prevent the growth of microorganisms.

The injectable solutions prepared in this manner can then be administered intravenously, intraperitoneally, subcutaneously, or intramuscularly, with intramuscular administration being preferred in humans.

For transmucosal administration, penetrants appropriate to the barrier to be permeated are used in the formulation. Such penetrants are generally known in the art. The active compounds can also be administered intranasally as, for example, liquid drops or spray.

For buccal administration, the compositions may take the form of tablets or lozenges Formulated in a conventional manner.

For administration by inhalation, the compounds for use according to the present invention are conveniently delivered in the form of a dry powder inhaler, or an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of pressurized aerosol the dosage unit may be determined by providing a valve to deliver a metered amount. Capsules and cartridges of gelatin for use in an inhaler or insufflator may be formulated containing a powder mix of the compound and a suitable powder base such as lactose or starch.

Pharmaceutical compositions of the present invention can be manufactured in a manner that is itself known, e.g., by means of conventional mixing, dissolving, granulating, dragee-making, levigating, emulsifying, encapsulating, entrapping or lyophilizing processes.

In making the compositions of the present invention, the active ingredient will usually be admixed with a carrier, or diluted by a carrier, or enclosed within a carrier, which may be in the form of a capsule, sachet, paper or other container. When the carrier serves as a diluent, it may be a solid, lyophilized solid or paste, semi-solid, or liquid material which acts as a vehicle, or can be in the form of tablets, pills, powders, lozenges, elixirs, suspensions, emulsions, solutions, syrups, aerosols (as a solid or in a liquid medium), or ointment, containing for example up to 10% by weight of the active compound. The compounds of the present invention are preferably formulated prior to administration.

Binding and Cotransfection Studies

The in vitro potency of compounds in modulating PPARγ, PPARα and PPARδ receptors are determined by the procedures detailed below. DNA-dependent binding (ABCD binding) is carried out using Scintillation Proximity Assay (SPA) technology with PPAR receptors. Tritium-labeled PPARα and PPARγ agonists are used as radioligands for generating displacement curves and $IC_{50}$ values with compounds of the present invention. Cotransfection assays are carried out in CV-1 cells. The reporter plasmid contains an acylCoA oxidase (AOX) PPRE and TK promoter upstream of the luciferase reporter cDNA. Appropriate PPARs and RXRα are constitutively expressed using plasmids containing the CMV promoter. Since for PPARα and PPARβ, interference by endogenous PPARγ in CV-1 cells is an issue, in order to eliminate such interference, a GAL4 chimeric system is used in which the DNA binding domain of the transfected PPAR is replaced by that of GAL4, and the GAL4 response element is utilized in place of the AOX PPRE. Receptor activation by compounds of the present invention is determined relative to PPARα agonist and PPARγ agonist reference molecules to obtain percent efficacies. EC50 values are determined by computer fit to a concentration-response curve. A typical range for concentration determination is from 1 nM to 10 μM. For binding or cotransfection studies with receptors other than PPARs, similar assays are carried out using appropriate ligands, receptors, reporter constructs and etc. for that particular receptor. In some cases, a single high concentration of agonist (10 μM) was used.

These studies are carried out to evaluate the ability of compounds of the present invention to bind to and/or activate various nuclear transcription factors, particularly huPPARα ("hu" indicates "human"), huPPARγ and huPPARδ. These studies provide in-vitro data concerning efficacy and selectivity of compounds of the present invention. Furthermore, binding and cotransfection data for compounds of the present invention are compared with corresponding data for reference compounds that act oil either huPPARα or huPPARγ.

The typical range of concentration for binding is from 1 nM to 10 μM. The concentration of test compound required to effect 50% maximal activation of PPARα ($IC_{50}α$) and PPARγ ($IC_{50}γ$) is determined. The compounds of the present invention, in general, have $IC_{50}$ or $EC_{50}$ in the range of about 1 nM to about 1000 nM for PPAR alpha, gamma or delta.

Evaluation of Triglyceride and Cholesterol Level in HuapoAI Transgenic Mice

Five to six week old male mice, transgenic for human apoAI [C57B1/6-tgn(apoa1)1rub, Jackson Laboratory, Bar Harbor, Me.] are housed five per cage (10"×20"×8" with aspen chip bedding) with food (Purina 5001) and water available at all times. After an acclimation period of 2 weeks, animals are individually identified by ear notches, weighed and assigned to groups based on body weight. Beginning the following morning, mice are dosed daily by oral gavage for 7 days using a 20 gauge, 1½" curved disposable feeding needle. Treatments are test compounds (30 mg/kg), a positive control (fenofibrate, 100 mg/kg) or vehicle [1% carboxymethylcellulose (w/v)/0.25% Tween80 (w/v); 0.2 ml/mouse]. Prior to termination on day 7, mice are weighed and dosed. Three hours after dosing, animals are anesthetized by inhalation of isoflurane (2-4%) and blood obtained via cardiac puncture (0.7-1.0 ml). Whole blood is transferred to serum separator tubes (Vacutainer SST), chilled on ice and permitted to clot. Serum is obtained after centrifugation at 4° C. and frozen until analysis for triglycerides, total cholesterol, compound levels and serum lipoprotein profile by fast protein liquid chromatography (FPLC) coupled to an inline detection system. After sacrifice by cervical dislocation, the liver, heart and epididymal fat pads are excised and weighed.

The animals dosed with vehicle have average triglycerides values of about 60 to 80 mg/dl, which are reduced by the positive control fenofibrate (33-58 mg/dl with a mean reduction of 37%). The animals dosed with vehicle have average total serum cholesterol values of about 140 to 180 mg/dl, which are increased by fenofibrate (about 190 to 280 mg/dl with a mean elevation of 41%). When subject to FPLC analysis, pooled sera from vehicle-treated hu apoAI transgenic mice have a high-density lipoprotein cholesterol (HDLc) peak area, which ranges from 47v-sec to 62v-sec. Fenofibrate increases the amount of HDLc (68-96v-sec with a mean percent increase of 48%). Test compounds evaluated in terms of percent increase in the area under the curve. Representative compounds of the present invention are tested using the above methods or substantially similar methods.

Evaluation of Glucose Levels in db/db Mice

Five week old male diabetic (db/db) mice [C57B1Ks/j-m +/+ Lepr(db), Jackson Laboratory, Bar Harbor, Me.] or lean littermates (db+) are housed 6 per cage (10"×20"×8" with aspen chip bedding) with food (Purina 5015) and water available at all times. After an acclimation period of 2 weeks, animals are individually identified by ear notches, weighed and bled via the tail vein for determination of initial glucose levels. Blood is collected (100 µl) from unfasted animals by wrapping each mouse in a towel, cutting the tip of the tail with a scalpel, and milking blood from the tail into a heparinized capillary tube balanced on the edge of the bench. Sample is discharged into a heparinized microtainer with gel separator (VWR) and retained on ice. Plasma is obtained after centrifugation at 4° C. and glucose is measured immediately. Remaining plasma is frozen until the completion of the experiment, and glucose and triglycerides are assayed in all samples. Animals are grouped based on initial glucose levels and body weights. Beginning the following morning, mice are dosed daily by oral gavage for 7 days using a 20 gauge, 1½" curved disposable feeding needle. Treatments are test compounds (30 mg/kg), a positive control agent (30 mg/kg) or vehicle [1% carboxymethylcellulose (w/v)/0.25% Tween80 (w/v); 0.3 ml/mouse]. On day 7, mice are weighed and bled (tail vein) for about 3 hours after dosing. Twenty-four hours after the 7$^{th}$ dose (i.e., day 8), animals are bled again (tail vein). Samples obtained from conscious animals on days 0, 7 and 8 are assayed for glucose. After 24 hour bleed, animals are weighed and dosed for the final time. Three hours after dosing on day 8, animals are anesthetized by inhalation of isoflurane, and blood obtained is via cardiac puncture (0.5-0.7 ml). Whole blood is transferred to serum separator tubes, chilled on ice and permitted to clot. Serum is obtained after centrifugation at 4° C. and frozen until analysis for compound levels. After sacrifice by cervical dislocation, the liver, heart and epididymal fat pads are excised and weighed.

The animals dosed with vehicle have average triglycerides values of about 170 to 230 mg/dl, which are reduced by the positive PPARγ control (about 70 to 120 mg/dl with a mean reduction of 50%). Male db/db mice are hyperglycemic (average glucose of about 680 to 730 mg/dl on the 7$^{th}$ day of treatment), while lean animals have average glucose levels between about 190 and 230 mg/dl. Treatment with the positive control agent reduces glucose significantly (about 350 to 550 mg/dl with a mean decrease towards normalization of 56%).

Glucose is measured calorimetrically by using commercially purchased reagents (Sigma #315-500). According to the manufacturers, the procedures are modified from published work (McGowan et al. *Clin Chem*, 20:470-5 (1974) and Keston, A. Specific colorimetric enzymatic analytical reagents for glucose. Abstract of papers 129th Meeting ACS, 31C (1956).); and depend on the release of a mole of hydrogen peroxide for each mole of analyte coupled with a color reaction first described by Trinder (Trinder, P. *Ann Clin Biochem*, 6:24 (1969)). The absorbance of the dye produced is linearly related to the analyte in the sample. The assays are further modified for use in a 96 well format. Standards (Sigma #339-11, Sigma #16-11, and Sigma #CC0534 for glucose, triglycerides and total cholesterol, respectively), quality control plasma (Sigma # A2034), and samples (2 or 5 µl/well) are measured in duplicate using 200 µl of reagent. An additional aliquot of sample, pipetted to a third well and diluted in 200 µl water, provided a blank for each specimen. Plates are incubated at room temperature (18, 15, and 10 minutes for glucose, triglycerides and total cholesterol, respectively) on a plate shaker and absorbance read at 500 nm (glucose and total cholesterol) or 540 nm (triglycerides) on a plate reader. Sample absorbance is compared to a standard curve (100-800, 10-500, and 100-400 mg/dl for glucose, triglycerides and total cholesterol, respectively). Values for the quality control sample are consistently within the expected range and the coefficient of variation for samples is below 10%. All samples from an experiment are assayed at the same time to minimize inter-assay variability.

Serum lipoproteins are separated and cholesterol is quantitated with an in-line detection system. Sample is applied to a Superose® 6 HR 10/30-size exclusion column (Amersham Pharmacia Biotech) and eluted with phosphate buffered saline-EDTA at 0.5 ml/min. Cholesterol reagent (Roche Diagnostics Chol/HP 704036) at 0.16 ml/min is mixed with the column effluent through a T-connection, and the mixture is passed through a 15 m×0.5 mm id knitted tubing reactor immersed in a 37° C. water bath. The colored product produced in the presence of cholesterol is monitored in the flow stream at 505 nm, and the analog voltage from the monitor is converted to a digital signal for collection and analysis. The change in voltage corresponding to change in cholesterol concentration is plotted against time, and the area under the curve corresponding to the elution of VLDL, LDL and HDL is calculated (Perkin Elmer Turbochrome software).

The compounds of the present invention can be prepared according to the procedures of the following schemes and examples, which may further illustrate details for the preparation of the compounds of the present invention. The compounds illustrated in the schemes and examples are, however, not to be construed as forming the only genus that is considered as the present invention.

The compounds of the present invention, in general, may be prepared according to the Reaction Schemes 1-5 described below. It is understood that the reaction can be carried out under various coupling conditions as appropriate, such as Ullmann, Suzuki and Stille coupling conditions.

Reaction Scheme 1

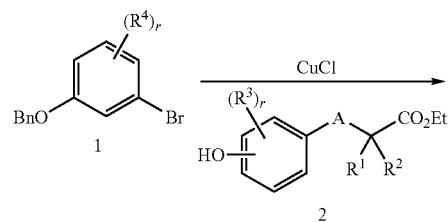

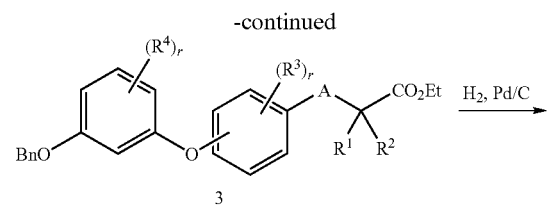

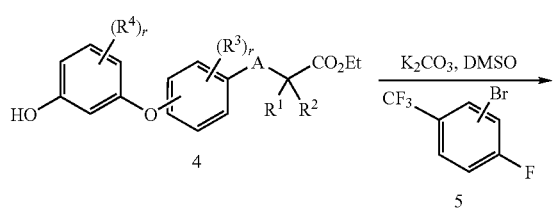

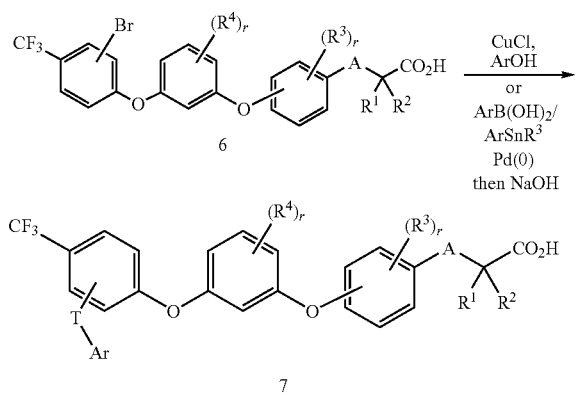

As shown in Reaction Scheme 1, aryl bromide 1 is treated with various phenols 2 under the Ullmann coupling condition to afford a coupled intermediate compound 3. Benzyl group is removed from 3 under a catalytic hydrogenation condition to provide phenol 4. The second phenoxy ether moiety is introduced by treating compound 4 with aryl fluoride 5 under a basic condition. Final substituent on the tail phenoxy ring (T-Ar) is installed under the Ullmann or Suzuki coupling condition, and a final acid compound 7 is obtained via a saponification.

Reaction Scheme 2

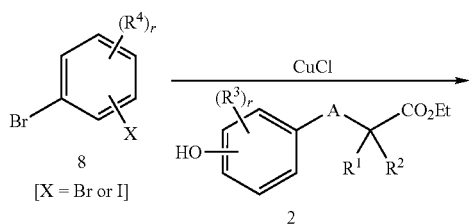

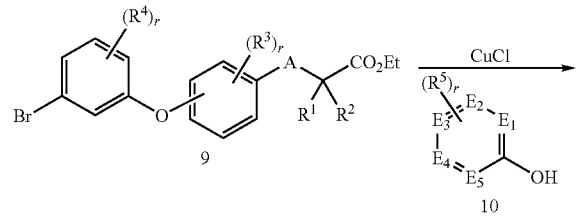

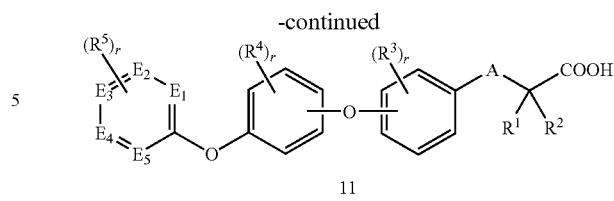

then hydrolysis

As shown in Reaction Scheme 2, aryl halide 8 is treated with various phenols 2 under the Ullmann coupling condition to afford a coupled intermediate compound 9. The second phenoxy ether moiety is introduced by treating 9 with phenol 10 under the Ullmann condition and then a subsequent saponification affords the acid compound 11.

Reaction Scheme 3

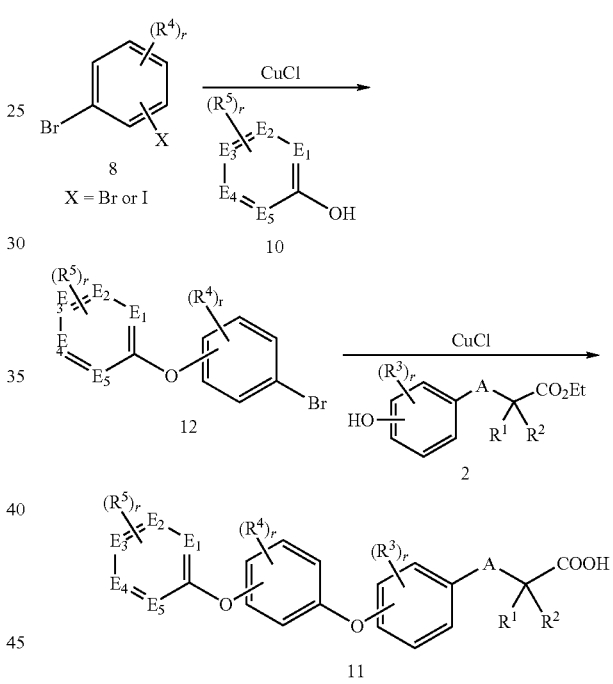

then hydrolysis

Alternatively, acid compound 11 can be prepared via a route shown in Reaction Scheme 3. Aryl halide 8 is treated with various phenols 10 under the Ullmann coupling condition to afford a coupled intermediate compound 12. The second phenoxy ether moiety is introduced by treating 12 with phenol 2 under the Ullmann condition. Subsequent saponification affords the acid compound 11.

Reaction Scheme 4

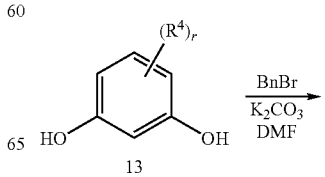

-continued

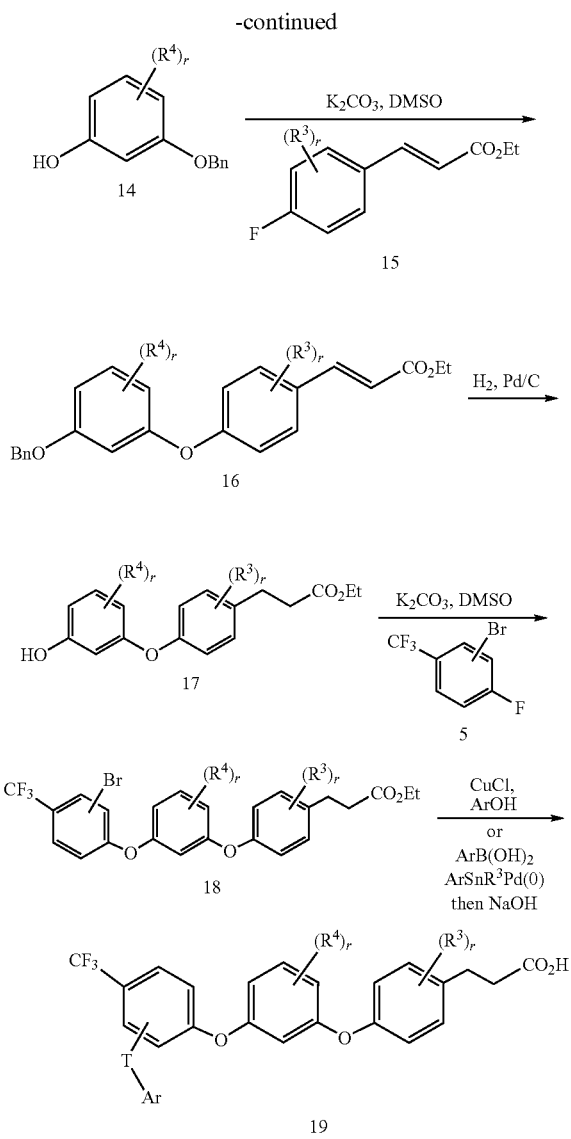

As shown in Reaction Scheme 4, phenol 13 is monobenzylated to give compound 14. The phenoxy ether moiety is introduced by treating 14 with aryl fluoride 15 under a basic condition. Removal of benzyl group under a catalytic hydrogenation condition and reduction of cinnamate double bond affords intermediate 17, which is then treated with aryl fluoride 5 to provide compound 18. Final substituent on the tail phenoxy ring (T-Ar) is installed under the Ullmann or Suzuki coupling condition, and a subsequent saponification afford the acid compound 19.

Reaction Scheme 5

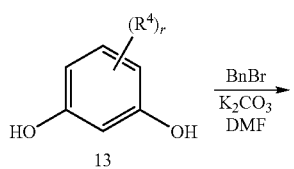

-continued

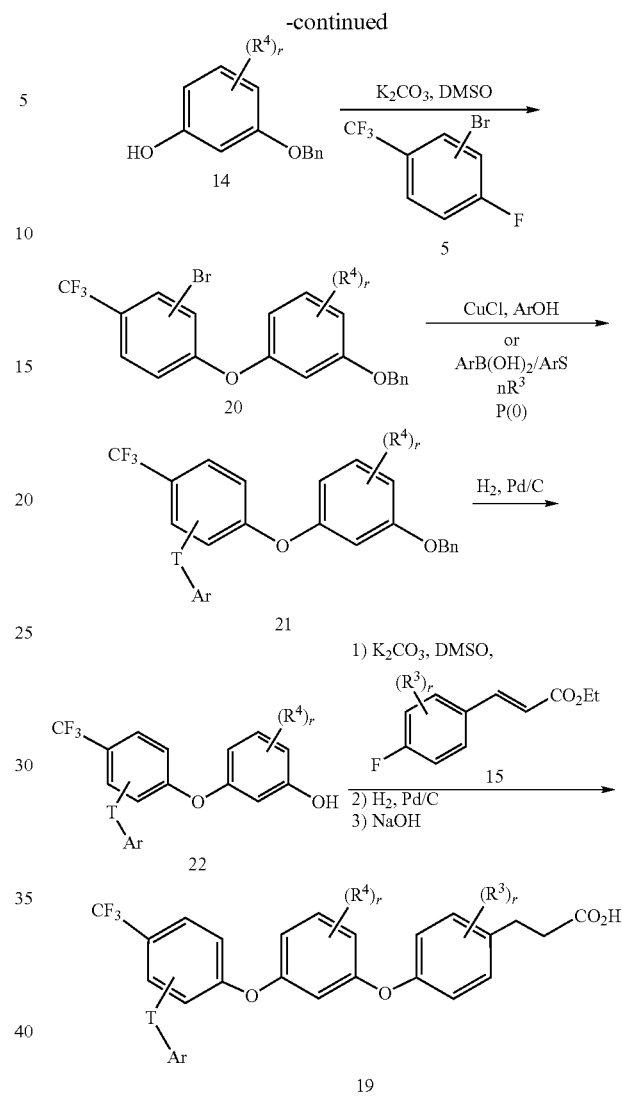

Alternatively, compound 19 can be prepared via a route shown in Reaction Scheme 5. Phenol 13 is monobenzylated to give compound 14, which is then treated with aryl fluoride 5 to give compound 20. Under the Ullmann or Suzuki condition, the substituent on the tail phenyl ring (T-Ar) is installed to give compound 21. Benzyl group is then removed under a catalytic hydrogenation condition to provide compound 22. The second phenoxy moiety is introduced by treating compound 22 with aryl fluoride 15 under a basic condition. The double bond in the cinnamate 15 is reduced via a catalytic hydrogenation, and a subsequent saponification affords the final acid compound 19.

In the Schemes, Procedures and Examples below, various reagent symbols and abbreviations have the following meanings.

ACN Acetonitrile
BINAP 2,2'-Bis(diphenylphosphino)-1,1'-binaphthyl
DCM dichloromethane
DEAD diethyl azodicarboxylate
DIAD diisopropyl azodicarboxylate
DIPEA diisopropylethylamine
DMAP 4-dimethylamino pyridine
DMF N,N-dimethylformamide DMSO dimethylsulfoxide
eq (equiv) equivalent(s)
ESI-MS electron spray ion-mass spectroscopy
Et ethyl
EtOAc ethyl acetate
h hours
HOAc acetic acid
HPLC high performance liquid chromatography
HRMS high resolution mass
LRMS low resolution mass
Me methyl
Ms methanesulfonyl
NBS N-bromosuccinimide
Ph phenyl
Pr propyl
rt (r.t.) room temperature
TBAI tetrabutylammonium iodide
TBS tertbutyldimethylsilyl
TFA trifluoroacetic acid
TEA triethylamine
THF tetrahydrofuran
TLC thin-layer chromatography

EXAMPLE 1

{4-[3-(4-Chloro-2-phenoxy-phenoxy)-phenoxy]-2-methyl-phenylsulfanyl}-acetic acid

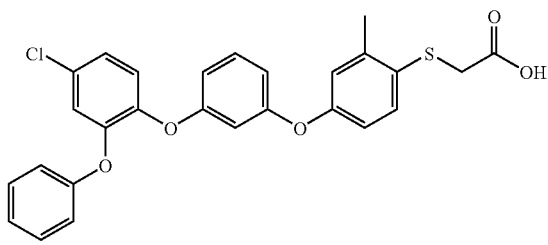

Step A 1-(3-Bromo-phenoxy)-4-chloro-2-phenoxy-benzene

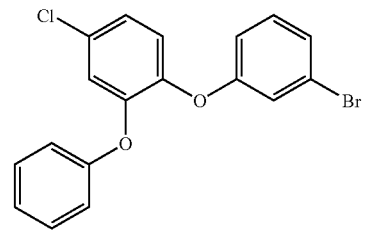

A solution of 4-chloro-2-phenoxy-phenol (1.65 g, 7.5 mmol), 1-bromo-3-iodobenzene (6.35 g, 22.4 mmol), copper (I) chloride (0.37 g, 3.74 mmol), 2,2,6,6-tetramethyl-3,5-heptanedione (0.345 g, 1.87 mmol), and cesium carbonate (2.93 g, 9 mmol) in NMP (20 mL) is heated to 120° C. The reaction is stirred overnight and cooled to rt. The reaction is quenched with 1N aqueous HCL and extracted with ethyl ether. The organic is washed with brine, dried over sodium sulfate, filtered, and the solvent is removed. The crude is purified by silica gel column chromatography using 5/1 hexanes/ethyl acetate to elute the pure product. The solvent is removed to afford 1.13 g (40%) of the desired product. $^1$H NMR (400 MHz, CDCl$_3$); MS (ES$^+$) m/z mass calculated for C$_{18}$H$_{12}$BrClO$_2$ 374, found 375 and 377 (M+1 and M+3, 100%).

Step B

{4-[3-(4-Chloro-2-phenoxy-phenoxy)-phenoxy]-2-methyl-phenylsulfanyl}-acetic acid A solution of 1-(3-bromo-phenoxy)-4-chloro-2-phenoxy-benzene (0.15 g, 0.4 mmol), (4-hydroxy-2-methyl-phenylsulfanyl)-acetic acid ethyl ester (99 mg, 0.44 mmol), copper(I) chloride (20 mg, 0.2 mmol), 2,2,6,6-tetramethyl-3,5-heptanedione (0.02 mL, 0.1 mmol), and cesium carbonate (156 mg, 0.48 mmol) in NMP (3 mL) is heated to 120° C. The reaction is stirred overnight and cooled to rt. The reaction is quenched with 1N aqueous HCl and extracted with ethyl ether. The organic is washed with brine, dried over sodium sulfate, and filtered. The solvent is removed to afford the crude ester intermediate. The intermediate is treated with 5N NaOH (0.4 mL, 2.2 mmol) in MeOH (5 mL) and heated to reflux. The reaction is stirred at reflux for 2 hours and then cooled. The reaction is quenched with 1N aqueous HCl to give pH=4. The aqueous layer is extracted with ethyl ether. The organic layer is washed with brine, dried over sodium sulfate, and filtered. The solvent is removed to afford the crude product. The crude is purified by prep HPLC to afford 78 mg (40%) of desired product. $^1$H NMR (400 MHz, CDCl$_3$); MS (ES$^+$) m/z mass calculated for C$_{27}$H$_{21}$ClO$_5$S 492, found 493 and 495 (M+1 and M+3, 100%).

EXAMPLE 2

2-{4-[3-(4-Chloro-2-phenoxy-phenoxy)-phenoxy]-phenoxy}-2-methyl-propionic acid

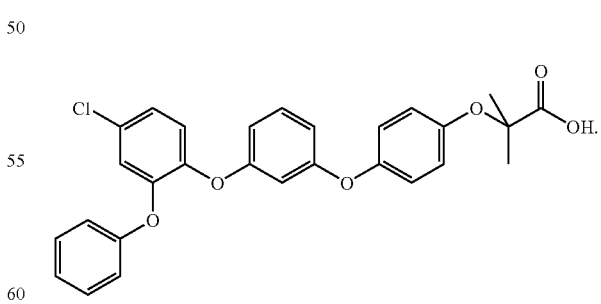

The title compound is prepared according to Example 1, Step B by using 2-(4-hydroxy-phenoxy)-2-methyl-propionic acid ethyl ester to afford 63 mg (32%). $^1$H NMR (400 MHz, CDCl$_3$); MS (ES$^+$) m/z mass calculated for C$_{28}$H$_{23}$ClO$_6$ 490, found 491 and 493 (M+1 and M+3, 100%).

EXAMPLE 3

2-{4-[3-(4-Chloro-2-phenoxy-phenoxy)-phenoxy]-2-methyl-phenoxy}-2-methyl-propionic acid

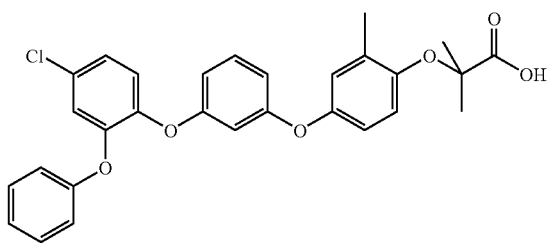

The title compound is prepared according to Example 1, Step B by using 2-(4-hydroxy-2-methyl-phenoxy)-2-methyl-propionic acid ethyl ester to afford 33 mg (16%). $^1$H NMR (400 MHz, CDCl$_3$); MS (ES$^+$) m/z mass calculated for C$_{29}$H$_{25}$ClO$_6$ 504, found 505 and 507 (M+1 and M+3, 100%).

EXAMPLE 4

{4-[3-(4-Chloro-2-phenoxy-phenoxy)-phenoxy]-2-methyl-phenoxy}-acetic acid

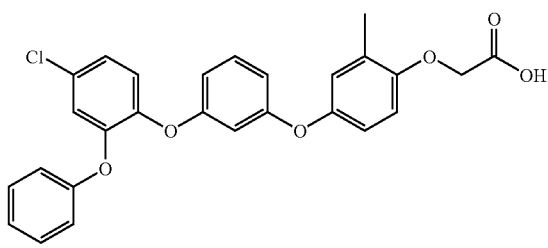

The title compound is prepared according to Example 1, Step B by using (4-hydroxy-2-methyl-phenoxy)-acetic acid ethyl ester to afford 30 mg (16%). $^1$H NMR (400 MHz, CDCl$_3$); MS (ES$^-$) m/z mass calculated for C$_{27}$H$_{21}$ClO$_6$ 476, found 475 and 477 (M−1 and M+1, 100%).

EXAMPLE 5

3-{4-[3-(4-Chloro-2-phenoxy-phenoxy)-phenoxy]-2-fluoro-phenyl}-propionic acid

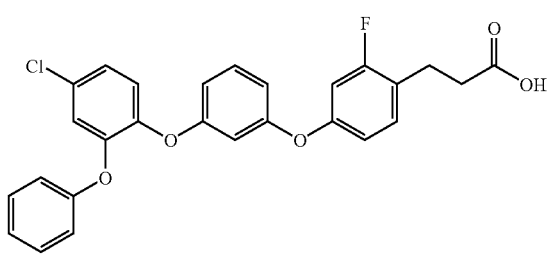

The title compound is prepared according to Example 1, Step B by using 3-(2-fluoro-4-hydroxy-phenyl)-propionic acid ethyl ester to afford 94 mg (49%). $^1$H NMR (400 MHz, CDCl$_3$); MS (ES$^+$) m/z mass calculated for C$_{27}$H$_{20}$ClFO$_5$ 478, found 479 and 481 (M+1 and M+3, 100%).

EXAMPLE 6

4-{4-[3-(4-Chloro-2-phenoxy-phenoxy)-phenoxy]-2-methyl-phenyl}-butyric acid

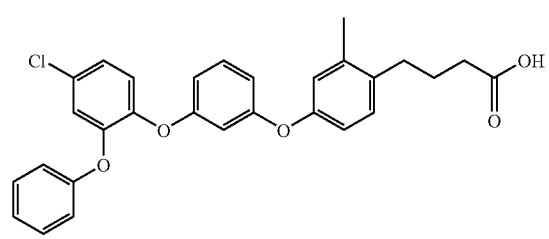

The title compound is prepared according to Example 1, Step B by using 4-(4-Hydroxy-2-methyl-phenyl)-butyric acid ethyl ester to afford 35 mg (18%). $^1$H NMR (400 MHz, CDCl$_3$); MS (ES$^+$) m/z mass calculated for C$_{29}$H$_{25}$ClO$_5$ 488, found 487 and 489 (M−1 and M+1, 100%).

EXAMPLE 7

3-{4-[3-(4-Chloro-2-phenoxy-phenoxy)-phenoxy]-2-ethyl-phenyl}-propionic acid

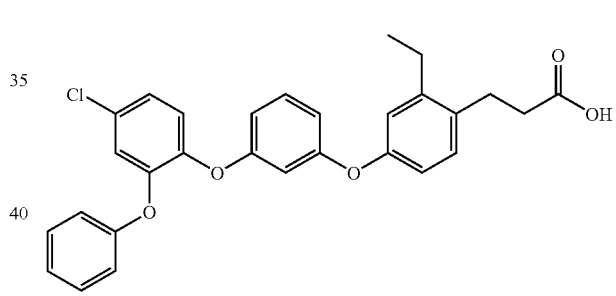

The title compound is prepared according to Example 1, Step B by using 3-(2-ethyl-4-hydroxy-phenyl)-propionic acid ethyl ester to afford 28 mg (16%). $^1$H NMR (400 MHz, CDCl$_3$); MS (ES$^+$) m/z mass calculated for C$_{29}$H$_{25}$ClO$_5$ 488, found 489 and 491 (M+1 and M+3, 100%).

EXAMPLE 8

3-{4-[3-(2-Benzyl-4-chloro-phenoxy)-phenoxy]-2-methyl-phenyl}-propionic acid

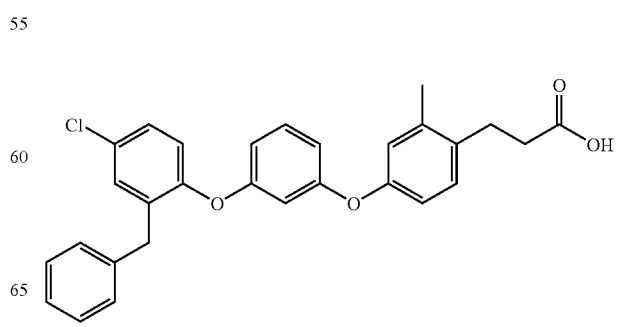

A solution of 3-[4-(3-bromo-phenoxy)-2-methyl-phenyl]-propionic acid methyl ester (0.1 g, 0.3 mmol), 2-benzyl-4-chloro-phenol (69 mg, 0.32 mmol), copper(I) chloride (14 mg, 0.14 mmol), 2,2,6,6-tetramethyl-3,5-heptanedione (0.01 mL, 0.07 mmol), and cesium carbonate (113 mg, 0.35 mmol) in NMP (3 mL) is heated to 120° C. The reaction is stirred overnight and cooled to rt. The reaction is then quenched with 1N aqueous HCl and extracted with ethyl ether. The organic is washed with brine, dried over sodium sulfate, and filtered. The solvent is removed to afford the crude ester intermediate. The intermediate is treated with 5N NaOH (0.4 mL, 2.2 mmol) in MeOH (5 mL) and heated to reflux. The reaction is stirred at reflux for 2 hours and then cooled. The reaction is quenched with 1N aqueous HCl to obtain pH=4. The aqueous layer is extracted with ethyl ether. The organic layer is washed with brine, dried over sodium sulfate, and filtered. The solvent is removed to afford the crude product. The crude is purified by prep HPLC to afford 63 mg (47%) of desired product. $^1$H NMR (400 MHz, CDCl$_3$); MS (ES$^+$) m/z mass calculated for C$_{29}$H$_{25}$ClO$_4$ 472, found 473 and 475 (M+1 and M+3, 100%).

EXAMPLE 9

3-{4-[3-(2-Benzyl-4-chloro-phenoxy)-5-methyl-phenoxy]-2-methyl-phenyl}-propionic acid

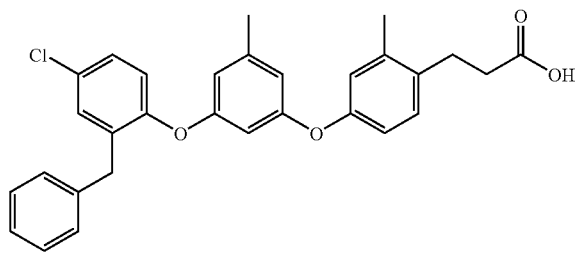

The title compound is prepared according to Example 8 by using 3-[4-(3-bromo-5-methyl-phenoxy)-2-methyl-phenyl]-propionic acid methyl ester to afford 63 mg (48%). $^1$H NMR (400 MHz, CDCl$_3$); MS (ES$^+$) m/z mass calculated for C$_{30}$H$_{27}$ClO$_4$ 486, found 487 and 489 (M+1 and M+3, 100%).

EXAMPLE 10

3-{4-[3-(2-Benzyl-4-chloro-phenoxy)-5-fluoro-phenoxy]-2-methyl-phenyl}-propionic acid

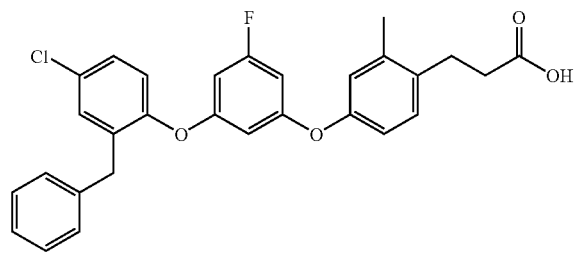

The title compound is prepared according to Example 8 by using 3-[4-(3-Bromo-5-fluoro-phenoxy)-2-methyl-phenyl]-propionic acid methyl ester to afford 54 mg (41%). $^1$H NMR (400 MHz, CDCl$_3$); MS (ES$^+$) m/z mass calculated for C$_{29}$H$_{24}$ClFO$_4$ 490, found 491 and 493 (M+1 and M+3, 100%).

EXAMPLE 11

3-{4-[3-(4-Chloro-2-cyclohexyl-phenoxy)-5-methyl-phenoxy]-2-methyl-phenyl}-propionic acid

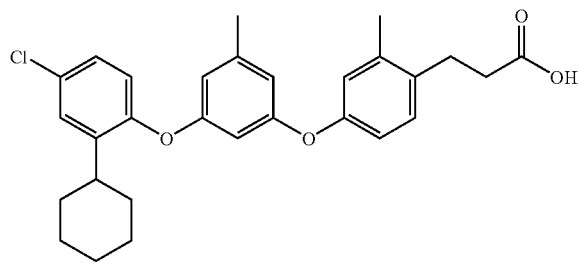

A solution of 3-[4-(3-bromo-5-methyl-phenoxy)-2-methyl-phenyl]-propionic acid methyl ester (0.1 g, 0.27 mmol), 4-chloro-2-cyclohexyl-phenol (63 mg, 0.3 mmol), copper(I) chloride (13 mg, 0.13 mmol), 2,2,6,6-tetramethyl-3,5-heptanedione (0.01 mL, 0.07 mmol), and cesium carbonate (105 mg, 0.32 mmol) in NMP (3 mL) is heated to 120° C. The reaction is stirred overnight and cooled to rt. The reaction is quenched with 1N aqueous HCl and extracted with ethyl ether. The organic layer is washed with brine, dried over sodium sulfate, and filtered. The solvent is removed to afford the crude ester intermediate. The intermediate is treated with 5N NaOH (0.4 mL, 2.2 mmol) in MeOH (5 mL) and heated to reflux. The reaction stirred at reflux for 2 hours and then cooled. The reaction is quenched with 1N aqueous HCl to obtain pH=4. The aqueous layer is extracted with ethyl ether. The organic layer is washed with brine, dried over sodium sulfate, and filtered. The solvent is removed to afford the crude product. The crude is purified by HPLC to afford 49 mg (38%) of desired product. $^1$H NMR (400 MHz, CDCl$_3$); MS (ES$^+$) m/z mass calculated for C$_{29}$H$_{31}$ClO$_4$ 478, found 479 and 481 (M+1 and M+3, 100%).

EXAMPLE 12

3-{4-[3-(4-Chloro-2-cyclohexyl-phenoxy)-5-fluoro-phenoxy]-2-methyl-phenyl}-propionic acid The title compound is prepared according to Example 8 by using 3-[4-(3-Bromo-5-fluoro-phenoxy)-2-methyl-phenyl]-propionic acid methyl ester to afford 25 mg (19%). $^1$H NMR (400 MHz, CDCl$_3$); MS (ES$^+$) m/z mass calculated for C$_{28}$H$_{28}$ClFO$_4$ 482, found 483 and 485 (M+1 and M+3, 100%).

EXAMPLE 13

3-{4-[3-(4-Chloro-2-phenoxy-phenoxy)-4-fluoro-phenoxy]-2-methyl-phenyl}-propionic acid

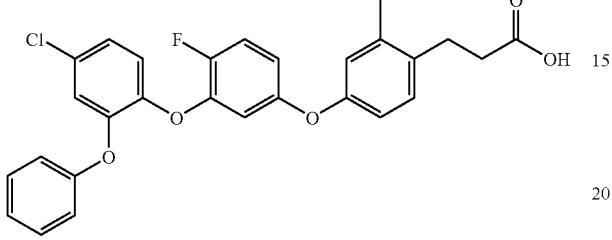

Step A

3-[4-(3-Bromo-4-fluoro-phenoxy)-2-methyl-phenyl]-propionic acid methyl ester and 3-[4-(5-Bromo-2-fluoro-phenoxy)-2-methyl-phenyl]-propionic acid methyl ester

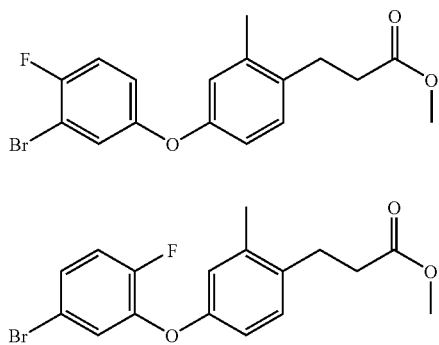

A solution of 3-(4-hydroxy-2-methyl-phenyl)-propionic acid methyl ester (10 g, 52 mmol), 2,4-dibromofluorobenzene (19.6 g, 77.2 mmol), copper(I) chloride (2.54 g, 25.7 mmol), 2,2,6,6-tetramethyl-3,5-heptanedione (2.65 mL, 12.9 mmol), and cesium carbonate (20 g, 61.8 mmol) in NMP (150 mL) is heated to 120° C. The reaction is stirred overnight and cooled to rt. The reaction is then quenched with 1N aqueous HCl and extracted with ethyl ether. The organic layer is washed with brine, dried over sodium sulfate, filtered, and the solvent is removed. The crude is purified by silica gel column chromatography using 9/1 hexanes/acetone to elute the pure product. The solvent is removed to afford 4.36 g (23%) of the two desired products. $^1$H NMR (400 MHz, CDCl$_3$); MS (ES$^+$) m/z mass calculated for C$_{17}$H$_{16}$BrFO$_3$ 366, found 367 (M+1, 100%).

Step B

3-[4-(3-Bromo-4-fluoro-phenoxy)-2-methyl-phenyl]-propionic acid methyl ester

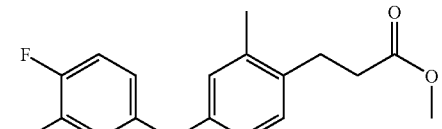

The mixture from Step A (1.0 g) is separated by prep HPLC to afford 0.29 g (29%) of the desired product. $^1$H NMR (400 MHz, CDCl$_3$); MS (ES$^+$) m/z mass calculated for C$_{17}$H$_{16}$BrFO$_3$ 366, found 367 (M+1, 100%).

Step C

3-{4-[3-(4-Chloro-2-phenoxy-phenoxy)-4-fluoro-phenoxy]-2-methyl-phenyl}-propionic acid A solution of 3-[4-(3-bromo-4-fluoro-phenoxy)-2-methyl-phenyl]-propionic acid methyl ester (0.1 g, 0.27 mmol), 4-chloro-2-phenoxy-phenol (60 mg, 0.27 mmol), copper(I) chloride (13 mg, 0.13 mmol), 2,2,6,6-tetramethyl-3,5-heptanedione (0.01 mL, 0.07 mmol), and cesium carbonate (105 mg, 0.32 mmol) in NMP (3 mL) is heated to 120° C. The reaction is stirred overnight and cooled to rt. The reaction is then quenched with 1N aqueous HCl and extracted with ethyl ether. The organic layer is washed with brine, dried over sodium sulfate, and filtered. The solvent is removed to afford the crude ester intermediate. The intermediate is treated with 5N NaOH (0.4 mL, 2.2 mmol) in MeOH (5 mL) and heated to reflux. The reaction is stirred at reflux for 2 hours and then cooled. The reaction is quenched with 1N aqueous HCl to obtain pH=4. The aqueous layer is extracted with ethyl ether. The organic layer is washed with brine, dried over sodium sulfate, and filtered. The solvent is removed to afford the crude product. The crude is purified by prep HPLC to afford 15 mg (11%) of desired product.

$^1$H NMR (400 MHz, CDCl$_3$); MS (ES$^+$) m/z mass calculated for C$_{28}$H$_{22}$ClFO$_5$ 492, found 493 and 495 (M+1 and M+3, 100%).

EXAMPLE 14

3-{4-[3-(4-Ethyl-2-phenoxy-phenoxy)-4-fluoro-phenoxy]-2-methyl-phenyl}-propionic acid

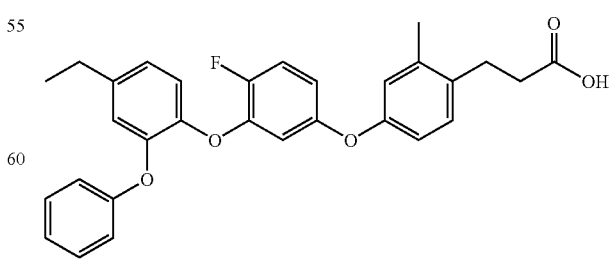

The title compound is prepared according to Example 13, Step C by using 4-ethyl-2-phenoxy-phenol to afford 20 mg (15%). ¹H NMR (400 MHz, CDCl₃); MS (ES⁺) m/z mass calculated for $C_{30}H_{27}FO_5$ 486, found 487 (M+1, 100%).

EXAMPLE 15

3-{4-[3-(4-Isopropyl-2-phenoxy-phenoxy)-4-fluoro-phenoxy]-2-methyl-phenyl}-propionic acid

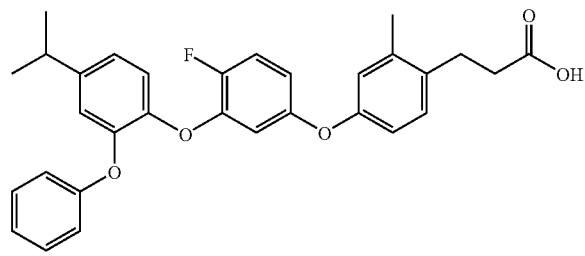

The title compound is prepared according to Example 13, Step C by using 4-isopropyl-2-phenoxy-phenol to afford 9 mg (7%). ¹H NMR (400 MHz, CDCl₃); MS (ES⁺) m/z mass calculated for $C_{31}H_{29}FO_5$ 500, found 501 (M+1, 100%).

EXAMPLE 16

3-{4-[3-(4-Chloro-2-phenoxy-phenoxy)-4-fluoro-phenoxy]-2-methyl-phenyl}-propionic acid

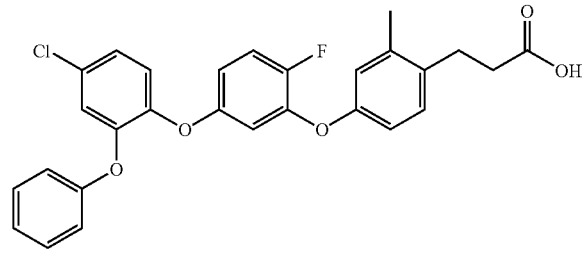

Step A

3-[4-(5-Bromo-2-fluoro-phenoxy)-2-methyl-phenyl]-propionic acid methyl ester

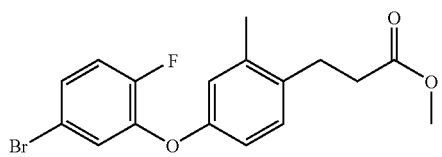

The mixture from Example 13, Step A (1.0 g) is separated by prep HPLC to afford 0.195 g (20%) of the desired product. ¹H NMR (400 MHz, CDCl₃); MS (ES⁺) m/z mass calculated for $C_{17}H_{16}BrFO_3$ 366, found 367 (M+1, 100%).

Step B

3-{4-[3-(4-Chloro-2-phenoxy-phenoxy)-4-fluoro-phenoxy]-2-methyl-phenyl}-propionic acid The title compound is prepared according to Example 13, Step C by using 3-[4-(5-bromo-2-fluoro-phenoxy)-2-methyl-phenyl]-propionic acid methyl ester to afford 2.9 mg (2%). ¹H NMR (400 MHz, CDCl₃); MS (ES⁺) m/z mass calculated for $C_{29}H_{22}ClFO_5$ 492, found 493 and 495 (M+1 and M+3, 100%).

EXAMPLE 17

3-{4-[5-(4-Ethyl-2-phenoxy-phenoxy)-2-fluoro-phenoxy]-2-methyl-phenyl}-propionic acid

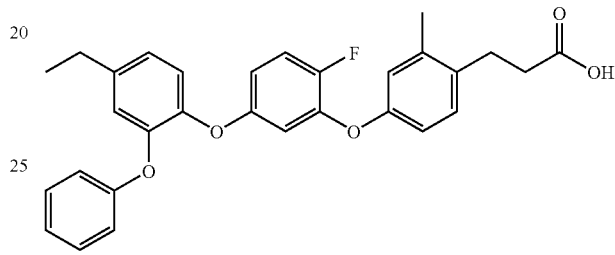

The title compound is prepared according to Example 13, Step C by using 3-[4-(5-bromo-2-fluoro-phenoxy)-2-methyl-phenyl]-propionic acid methyl ester and 4-ethyl-2-phenoxy-phenol to afford 15 mg (11%). ¹H NMR (400 MHz, CDCl₃); MS (ES⁺) m/z mass calcd for $C_{30}H_{27}FO_5$ 486, found 487 (M+1, 100%).

EXAMPLE 18

3-{4-[3-(4-Chloro-2-phenoxy-phenoxy)-phenoxy]-2-methyl-phenyl}-propionic acid

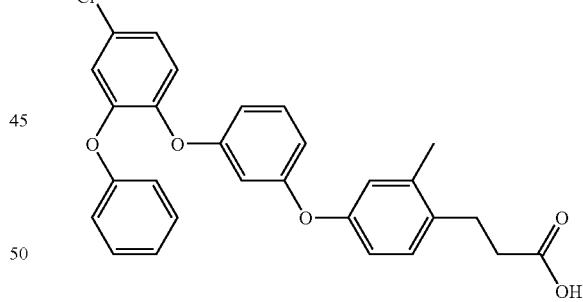

Step A

3-[4-(3-Bromo-phenoxy)-2-methyl-phenyl]-propionic acid methyl ester

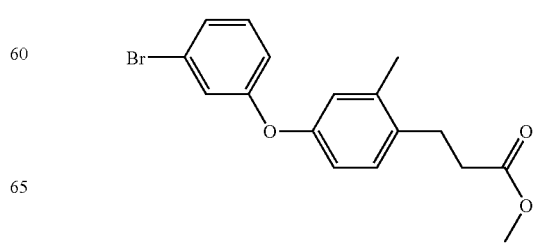

A mixture of 3-(4-hydroxy-2-methyl-phenyl)-propionic acid methyl ester (4.0 g, 20.6 mmol), 1-bromo-3-iodobenzene (17.49 g, 61.8 mmol), cesium carbonate (8.05 g, 24.7 mmol), copper (I) chloride (1.02 g, 10.3 mmol) and 2,2,6,6-tetramethyl-3,5-heptanedione (0.95 g, 5.15 mmol) in 1-methyl-2-pyrrolidinone (40 mL) is heated to 120° C. for 17 hours under $N_2$. The reaction is cooled and quenched with 1 N HCl (50 mL). The mixture is then diluted with $Et_2O$ and extracted with water. The organic layer is dried ($Na_2SO_4$), and the solvent is removed in vacuo to afford crude product that is absorbed on silica gel and purified by flash chromatography using 9/1 hexanes/ethyl acetate to afford 4.30 g (60%) of the title compound. $R_f$=0.33 (4/1 hexanes/EtOAc). $^1$H NMR (400 MHz, $CDCl_3$); MS ($ES^+$) m/z mass calculated for $C_{17}H_{17}O_3Br$ 348, found 349 and 351 (M+1 and M+3, 100%).

Step B

3-{4-[3-(4-Chloro-2-phenoxy-phenoxy)-phenoxy]-2-methyl-phenyl}-propionic acid methyl ester

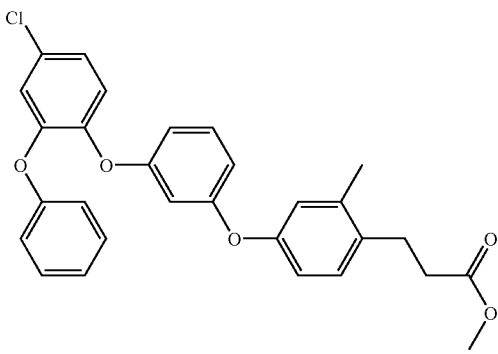

A mixture of 3-[4-(3-bromo-phenoxy)-2-methyl-phenyl]-propionic acid methyl ester (0.474 g, 1.36 mmol), 4-chloro-2-phenoxy-phenol (0.30 g, 1.36 mmol), cesium carbonate (0.531 g, 1.63 mmol), copper (I) chloride (0.067 g, 0.677 mmol) and 2,2,6,6-tetramethyl-3,5-heptanedione (0.063 g, 0.342 mmol) in 1-methyl-2-pyrrolidinone (5 mL) is heated to 120° C. for 20 hours under $N_2$. The reaction is cooled and quenched with 1 N HCl (20 mL). The mixture is then diluted with $Et_2O$ and extracted with water. The organic layer is dried ($Na_2SO_4$), and the solvent is removed in vacuo to afford crude product that is absorbed on silica gel and purified by flash chromatography using 9/1 hexanes/ethyl acetate to afford 0.221 g (33%) of the title compound. $R_f$=0.29 (4/1 hexanes/EtOAc). $^1$H NMR (400 MHz, $CDCl_3$); MS ($ES^+$) m/z mass calculated for $C_{29}H_{25}O_5Cl$ 488, found 489 and 351 (M+1 and M+3, 100%).

Step C

3-{4-[3-(4-Chloro-2-phenoxy-phenoxy)-phenoxy]-2-methyl-phenyl}-propionic acid

A solution of 3-{4-[3-(4-chloro-2-phenoxy-phenoxy)-phenoxy]-2-methyl-phenyl}-propionic acid methyl ester (0.221, 0.452 mmol) in methanol (7 mL) is treated with 5 N NaOH (2 mL) and heated to reflux until saponification is completed. The mixture is cooled, and the solvent is removed in vacuo to afford a residue that is acidified with 1 N HCl. The mixture is diluted with water and extracted with ethyl acetate. The organic layer is dried ($Na_2SO_4$), and the solvent removed in vacuo to afford 0.230 g (100%) of the title compound. $^1$H NMR (400 MHz, $CDCl_3$); MS ($ES^+$) m/z mass calculated for $C_{28}H_{23}O_5Cl$ 474, found 475 and 477 (M+1 and M+3, 100%).

EXAMPLE 19

3-{4-[3-(2-Benzoyl-4-ethyl-phenoxy)-phenoxy]-2-methyl-phenyl}-propionic acid

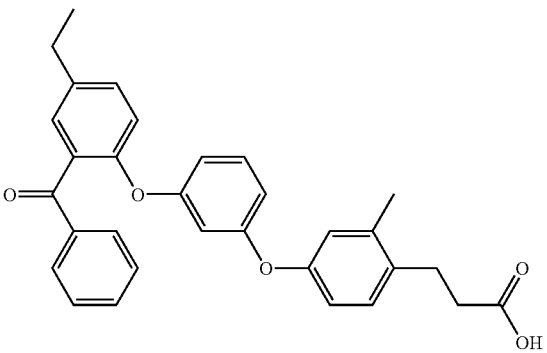

The title compound is prepared by reacting the compound of 3-[4-(3-bromo-phenoxy)-2-methyl-phenyl]-propionic acid methyl ester with (5-ethyl-2-hydroxy-phenyl)-phenyl-methanone as in Example 18 to afford 0.220 g (50%). $^1$H NMR (400 MHz, $CDCl_3$); HRMS ($ES^+$) m/z exact mass calculated for $C_{31}H_{28}O_5$ 481.2015, found 481.2032 (M+1).

EXAMPLE 20

3-{4-[3-(4-Ethyl-2-phenoxy-phenoxy)-phenoxy]-2-methyl-phenyl}-propionic acid

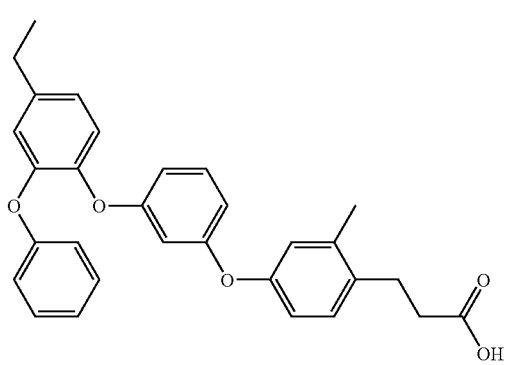

The title compound is prepared by reacting the compound of 3-[4-(3-bromo-phenoxy)-2-methyl-phenyl]-propionic acid methyl ester with 4-ethyl-2-phenoxy-phenol as in Example 18 to afford 0.200 g (35%). $^1$H NMR (400 MHz, $CDCl_3$); MS ($ES^+$) m/z mass calculated for $C_{30}H_{28}O_5$ 468, found 469 (M+1, 100%).

EXAMPLE 21

3-{4-[3-(2-Benzoyl-4-chloro-phenoxy)-phenoxy]-2-methyl-phenyl}-propionic acid

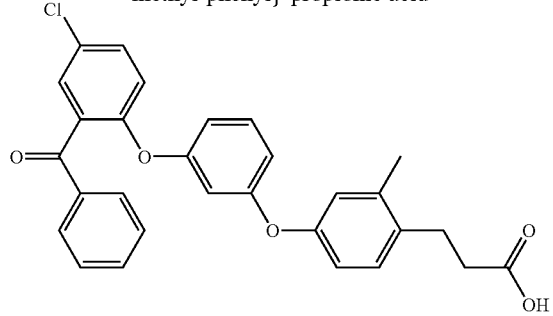

The title compound is prepared by reacting the compound of 3-[4-(3-bromo-phenoxy)-2-methyl-phenyl]-propionic acid methyl ester with (5-chloro-2-hydroxy-phenyl)-phenyl-methanone as in Example 18 to afford 0.080 g. $^1$H NMR (400 MHz, CDCl$_3$); MS (ES$^+$) m/z mass calculated for C$_{29}$H$_{23}$O$_5$Cl 486, found 487 and 489 (M+1 and M+3, 100%).

EXAMPLE 22

3-{4-[3-(4-Chloro-phenoxy)-phenoxy]-2-methyl-phenyl}-propionic acid

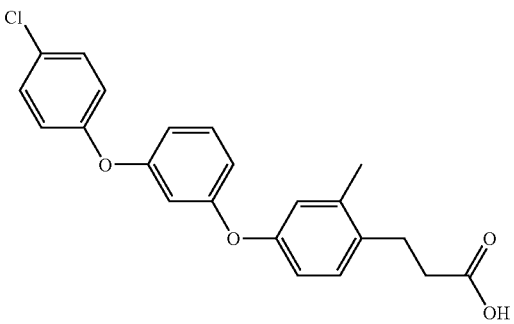

The title compound is prepared by reacting the compound of 3-[4-(3-bromo-phenoxy)-2-methyl-phenyl]-propionic acid methyl ester with 4-chlorophenol as in Example 18 to afford 0.019 g (9%). $^1$H NMR (400 MHz, CDCl$_3$); HRMS (ES$^+$) m/z exact mass calculated for C$_{22}$H$_{19}$O$_4$Cl 383.1050, found 383.1033 (M+1).

EXAMPLE 23

3-{4-[3-(4-Ethyl-phenoxy)-phenoxy]-2-methyl-phenyl}-propionic acid

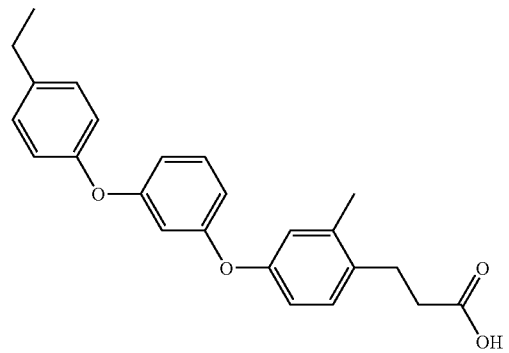

The title compound is prepared by reacting the compound of 3-[4-(3-bromo-phenoxy)-2-methyl-phenyl]-propionic acid methyl ester with 4-ethylphenol as in Example 18 to afford 0.020 g (14%). $^1$H NMR (400 MHz, CDCl$_3$); HRMS (ES$^+$) m/z exact mass calculated for C$_{24}$H$_{24}$O$_4$ 377.1753, found 377.1747.

EXAMPLE 24

3-{4-[3-(2-Benzoyl-phenoxy)-phenoxy]-2-methyl-phenyl}-propionic acid

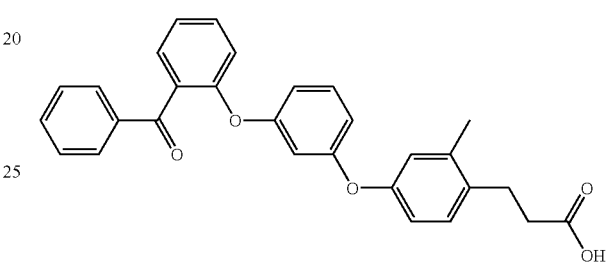

The title compound is prepared by reacting the compound of 3-[4-(3-bromo-phenoxy)-2-methyl-phenyl]-propionic acid methyl ester with (2-hydroxy-phenyl)-phenyl-methanone as in Example 18 to afford 0.020 g (14%). $^1$H NMR (400 MHz, CDCl$_3$); HRMS (ES$^+$) m/z mass calculated for C$_{29}$H$_{24}$O$_5$ 453.1702, found 453.1699.

EXAMPLE 25

3-{2-Methyl-4-[3-(2-phenoxy-phenoxy)-phenoxy]-phenyl}-propionic acid

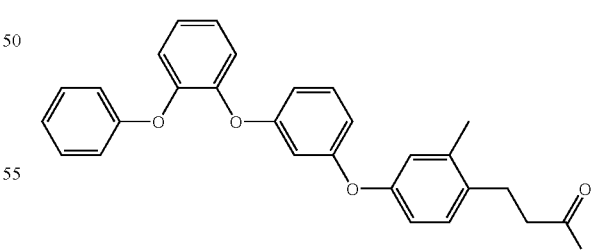

The title compound is prepared by reacting the compound of 3-[4-(3-bromo-phenoxy)-2-methyl-phenyl]-propionic acid methyl ester with 2-phenoxy-phenol as in Example 18 to afford 0.106 g (42%). $^1$H NMR (400 MHz, CDCl$_3$); MS (ES$^+$) m/z mass calculated for C$_{28}$H$_{24}$O$_5$ 440, found 441 (M+1).

EXAMPLE 26

3-{2-Methyl-4-[3-(2-phenoxy-4-trifluoromethyl-phenoxy)-phenoxy]-phenyl}-propionic acid

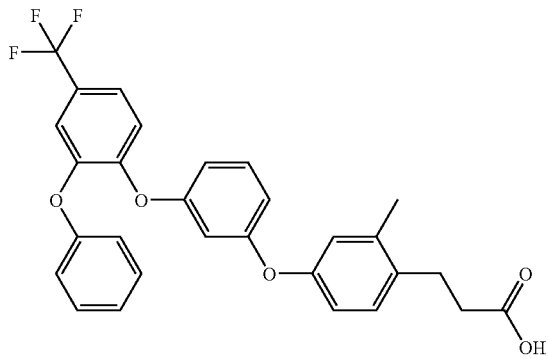

The title compound is prepared by reacting the compound of 3-[4-(5-bromo-pyridin-3-yloxy)-2-methyl-phenyl]-propionic acid methyl ester with 2-phenoxy-4-trifluoromethyl-phenol as in Example 18 to afford 0.084 g (15%). $^1$H NMR (400 MHz, CDCl$_3$); MS (ES$^-$) m/z mass calculated for C$_{29}$H$_{23}$O$_5$F$_3$ 508, found 507 (M−1).

EXAMPLE 27

3-{4-[3-(4-Chloro-2-phenoxy-phenoxy)-5-fluoro-phenoxy]-2-methyl-phenyl}-propionic acid

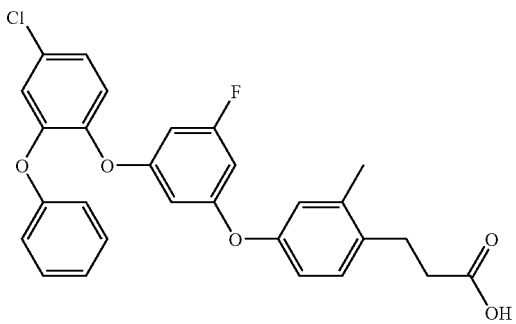

Step A

3-[4-(3-Bromo-5-fluoro-phenoxy)-2-methyl-phenyl]-propionic acid methyl ester

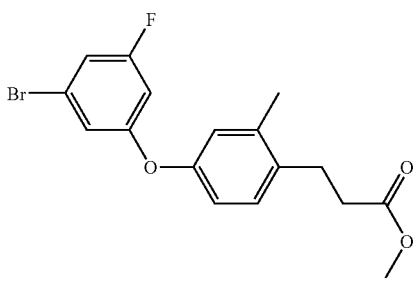

A mixture of 3-(4-hydroxy-2-methyl-phenyl)-propionic acid methyl ester (4.0 g, 20.6 mmol), 1,3-dibromo-5-fluorobenzene (15.71 g, 61.9 mmol), cesium carbonate (8.05 g, 24.7 mmol), copper (I) chloride (1.02 g, 10.3 mmol) and 2,2,6,6-tetramethyl-3,5-heptanedione (0.95 g, 5.15 mmol) in 1-methyl-2-pyrrolidinone (40 mL) is heated to 120° C. for 7 hours under N$_2$. The reaction is cooled and quenched with 1 N HCl (40 mL). The mixture is then diluted with Et$_2$O and extracted with water. The organic layer is dried (Na$_2$SO$_4$), and the solvent is removed in vacuo to afford crude product that is absorbed on silica gel and purified by flash chromatography using 9/1 hexanes/ethyl acetate to afford 3.43 g (45%) of the title compound. R$_f$=0.38 (4/1 hexanes/EtOAc). $^1$H NMR (400 MHz, CDCl$_3$); MS (ES$^+$) m/z mass calculated for C$_{17}$H$_{16}$O$_3$BrF 366, found 384 and 386 (M+NH$_4$, 100%).

Step B

3-{4-[3-(4-Chloro-2-phenoxy-phenoxy)-5-fluoro-phenoxy]-2-methyl-phenyl}-propionic acid The title compound is prepared by reacting the compound of 3-[4-(3-bromo-5-fluoro-phenoxy)-2-methyl-phenyl]-propionic acid methyl ester with 4-chloro-2-phenoxy-phenol as in Example 18 to afford 0.118 g (22%). $^1$H NMR (400 MHz, CDCl$_3$); MS (ES$^+$) m/z mass calculated for C$_{28}$H$_{22}$O$_5$ClF 492, found 493 and 495 (M+1 and M+3).

EXAMPLE 28

3-{4-[3-(4-Ethyl-2-phenoxy-phenoxy)-5-fluoro-phenoxy]-2-methyl-phenyl}-propionic acid

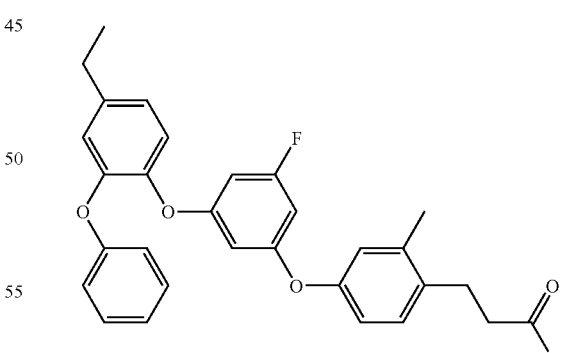

The title compound is prepared by reacting the compound of 3-[4-(3-bromo-5-fluoro-phenoxy)-2-methyl-phenyl]-propionic acid methyl ester with 4-ethyl-2-phenoxy-phenol as in Example 18 to afford 0.139 g (52%). $^1$H NMR (400 MHz, CDCl$_3$); MS (ES$^-$) m/z mass calculated for C$_{30}$H$_{27}$O$_5$F 486, found 485 (M−1).

EXAMPLE 29

3-{4-[3-(2-Benzyl-4-ethyl-phenoxy)-5-fluoro-phenoxy]-2-methyl-phenyl}-propionic acid

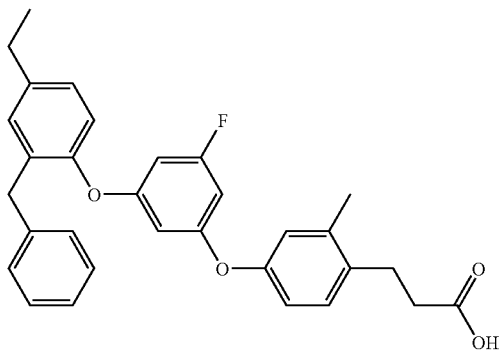

The title compound is prepared by reacting the compound of 3-[4-(3-bromo-5-fluoro-phenoxy)-2-methyl-phenyl]-propionic acid methyl ester with 2-benzyl-4-ethyl-phenol as in Example 18 to afford 0.040 g (13%). $^1$H NMR (400 MHz, CDCl$_3$); MS (ES$^+$) m/z mass calculated for C$_{31}$H$_{29}$O$_4$F 484, found 485 (M+1, 100%).

EXAMPLE 30

3-(4-{3-[4-Ethyl-2-(1-phenyl-ethyl)-phenoxy]-5-fluoro-phenoxy}-2-methyl-phenyl)-propionic acid

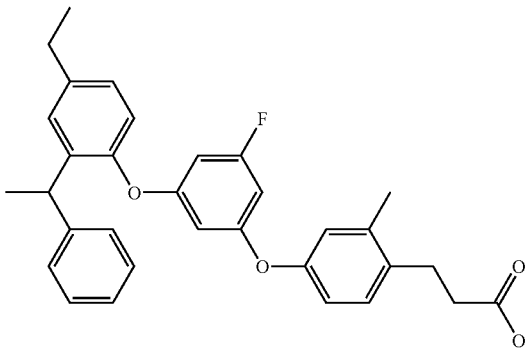

The title compound is prepared by reacting the compound of 3-[4-(3-bromo-5-fluoro-phenoxy)-2-methyl-phenyl]-propionic acid methyl ester with 4-ethyl-2-(1-phenyl-ethyl)-phenol as in Example 18 to afford 0.078 g (29%). $^1$H NMR (400 MHz, CDCl$_3$); MS (ES$^+$) m/z mass calculated for C$_{32}$H$_{31}$O$_4$F 498, found 499 (M+1, 100%).

EXAMPLE 31

3-(4-{3-[4-Ethyl-2-(1-methyl-1-phenyl-ethyl)-phenoxy]-5-fluoro-phenoxy}-2-methyl-phenyl)-propionic acid

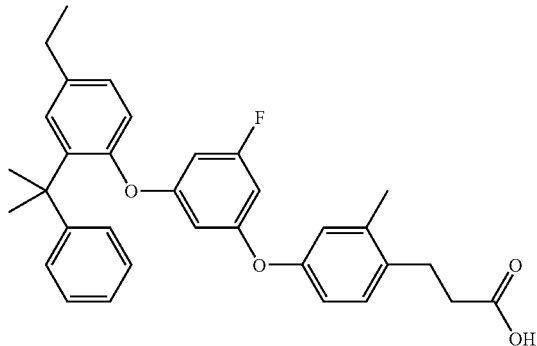

The title compound is prepared by reacting the compound of 3-[4-(3-bromo-5-fluoro-phenoxy)-2-methyl-phenyl]-propionic acid methyl ester with 4-ethyl-2-(1-methyl-1-phenyl-ethyl)-phenol as in Example 18 to afford 0.027 g (10%). $^1$H NMR (400 MHz, CDCl$_3$); MS (ES$^+$) m/z mass calculated for C$_{33}$H$_{33}$O$_4$F 512, found 513 (M+1, 100%).

EXAMPLE 32

3-{4-[3-(4-Bromo-2-trifluoromethoxy-phenoxy)-5-fluoro-phenoxy]-2-methyl-phenyl}-propionic acid

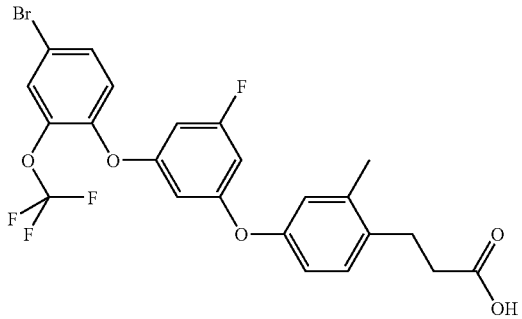

The title compound is prepared by reacting the compound of 3-[4-(3-bromo-5-fluoro-phenoxy)-2-methyl-phenyl]-propionic acid methyl ester with 4-bromo-2-trifluoromethoxy-phenol as in Example 18 to afford 0.013 g (5%). $^1$H NMR (400 MHz, CDCl$_3$); MS (ES$^+$) m/z mass calculated for C$_{23}$H$_{17}$O$_5$F$_4$Br 528, found 529 (M+1, 100%).

EXAMPLE 33

3-{4-[3-(4-Ethyl-2-phenoxy-phenoxy)-5-fluoro-phenoxy]-2-methyl-phenyl}-propionic acid

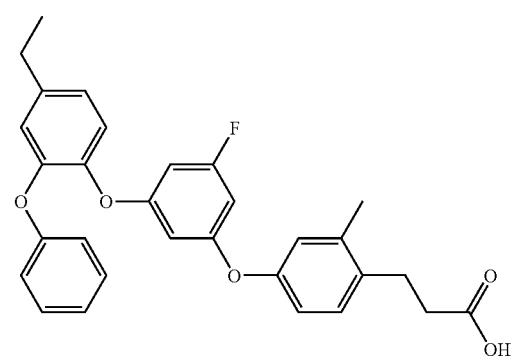

The title compound is prepared by reacting the compound of 3-[4-(3-bromo-5-fluoro-phenoxy)-2-methyl-phenyl]-propionic acid methyl ester with 4-ethyl-2-phenoxy-phenol as in Example 18 to afford 0.139 g (52%). $^1$H NMR (400 MHz, CDCl$_3$); MS (ES$^+$) m/z mass calculated for C$_{30}$H$_{27}$O$_5$F 487.1921, found 487.1906.

EXAMPLE 34

3-{4-[4-(4-Chloro-2-phenoxy-phenoxy)-phenoxy]-2-methyl-phenyl}-propionic acid

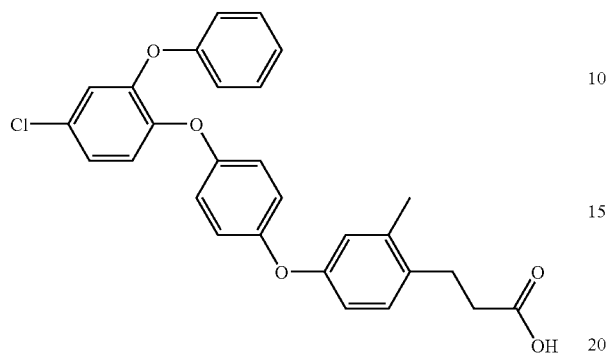

Step A

3-[4-(4-Bromo-phenoxy)-2-methyl-phenyl]-propionic acid methyl ester

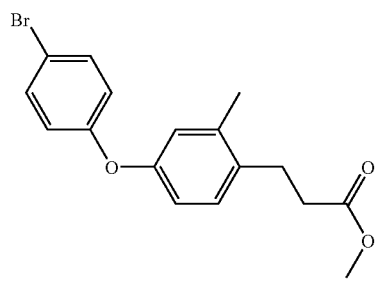

A mixture of 3-(4-hydroxy-2-methyl-phenyl)-propionic acid methyl ester (2.0 g, 10.3 mmol), 1-bromo-4-iodobenzene (8.74 g, 30.9 mmol), cesium carbonate (4.03 g, 12.4 mmol), copper (I) chloride (0.51 g, 5.15 mmol) and 2,2,6,6-tetramethyl-3,5-heptanedione (0.47 g, 2.55 mmol) in 1-methyl-2-pyrrolidinone (20 mL) is heated to 120° C. for 1 hour under $N_2$. The reaction is cooled and quenched with 1 N HCl. The mixture is then diluted with $Et_2O$ and extracted with water. The organic layer is dried ($Na_2SO_4$), and the solvent is removed in vacuo to afford crude product that is absorbed on silica gel and purified by flash chromatography using 9/1 hexanes/ethyl acetate to afford 1.51 g (42%) of the title compound. $R_f$=0.35 (4/1 hexanes/EtOAc). $^1$H NMR (400 MHz, $CDCl_3$).

Step B

3-{4-[4-(4-Chloro-2-phenoxy-phenoxy)-phenoxy]-2-methyl-phenyl}-propionic acid

The title compound is prepared by reacting the compound of 3-[4-(4-bromo-phenoxy)-2-methyl-phenyl]-propionic acid methyl ester with 4-chloro-2-phenoxy-phenol as in Example 18 to afford 0.133 g (19%). $^1$H NMR (400 MHz, $CDCl_3$); MS (ES$^-$) m/z mass calculated for $C_{28}H_{23}O_5Cl$ 474, found 473 and 475 (M−1, and M+1, 100%).

EXAMPLE 35

3-{4-[2-(4-Chloro-2-phenoxy-phenoxy)-phenoxy]-2-methyl-phenyl}-propionic acid

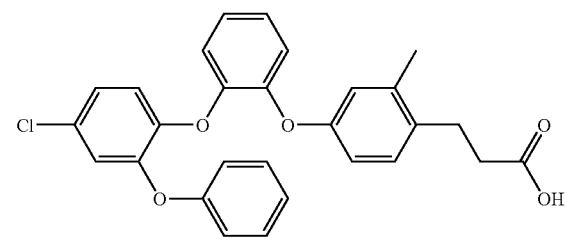

Step A

3-[4-(2-Bromo-phenoxy)-2-methyl-phenyl]-propionic acid methyl ester

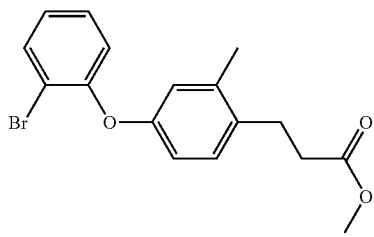

A mixture of 3-(4-hydroxy-2-methyl-phenyl)-propionic acid methyl ester (2.0 g, 10.3 mmol), 1-bromo-2-iodobenzene (8.74 g, 30.9 mmol), cesium carbonate (4.03 g, 12.4 mmol), copper (I) chloride (0.51 g, 5.15 mmol) and 2,2,6,6-tetramethyl-3,5-heptanedione (0.47 g, 2.55 mmol) in 1-methyl-2-pyrrolidinone (20 mL) is heated to 120° C. for 10 hours under $N_2$. The reaction is cooled and quenched with 1 N HCl. The mixture is then diluted with $Et_2O$ and extracted with water. The organic layer is dried ($Na_2SO_4$), and the solvent is removed in vacuo to afford crude product that is absorbed on silica gel and purified by flash chromatography using 9/1 hexanes/ethyl acetate to afford 1.09 g (30%) of the title compound. $R_f$=0.34 (4/1 hexanes/EtOAc). $^1$H NMR (400 MHz, $CDCl_3$).

Step B

3-{4-[2-(4-Chloro-2-phenoxy-phenoxy)-phenoxy]-2-methyl-phenyl}-propionic acid

The title compound is prepared by reacting the compound of 3-[4-(2-bromo-phenoxy)-2-methyl-phenyl]-propionic acid methyl ester with 4-chloro-2-phenoxy-phenol as in Example 18 to afford 0.039 g (8%). $^1$H NMR (400 MHz, $CDCl_3$); MS (ES$^-$) m/z mass calculated for $C_{28}H_{23}O_5Cl$ 474, found 473 and 475 (M−1, and M+1).

EXAMPLE 36

3-{4-[3-(4-Chloro-2-phenoxy-phenoxy)-5-methyl-phenoxy]-2-methyl-phenyl}-propionic acid

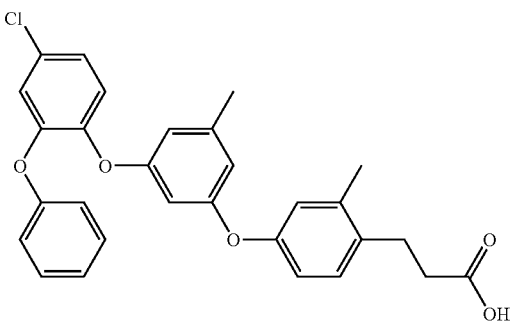

Step A

3-[4-(3-Bromo-5-methyl-phenoxy)-2-methyl-phenyl]-propionic acid methyl ester

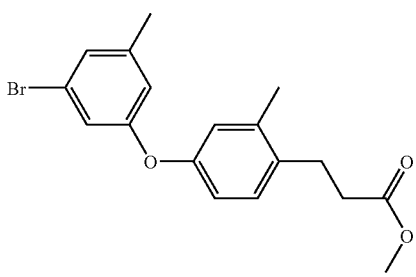

The mixture of 1,3-dibromo-5-methyl-benzene (15 g, 0.06 mol), 3-(4-hydroxy-2-methyl-phenyl)-propionic acid methyl ester (3.9 g, 0.02 mol), CuCl (1 g, 0.01 mol), 2,2,6,6-tetramethyl-heptane-3,5-dione (0.92 g, 0.005 mol) and Cs2CO3 (7.8 g, 0.024 mol) in 40 mL of dry NMP is heated to 120° C. for overnight. The mixture is cooled to rt and diluted with Et$_2$O and filtered through a pad of celite. Organic layer is washed with 1N HCl, H$_2$O and brine, and then dried over Na$_2$SO$_4$, filtered and concentrated. Crude material is purified by chromatography (hexanes/acetone=20:1) to afford the title compound (59%) as a yellow oil. R$_f$=0.29 (20/1 hexanes/acetone). $^1$H NMR (400 MHz, CDCl$_3$).

Step B

3-{4-[3-(4-Chloro-2-phenoxy-phenoxy)-5-methyl-phenoxy]-2-methyl-phenyl}-propionic acid The title compound is prepared by reacting the compound of 3-[4-(3-bromo-5-methyl-phenoxy)-2-methyl-phenyl]-propionic acid methyl ester with 4-chloro-2-phenoxy-phenol as in Example 18 to afford 0.118 g (22%). $^1$H NMR (400 MHz, CDCl$_3$); HRMS (ES$^+$) m/z exact mass calculated for C$_{29}$H$_{25}$O$_5$Cl 489.1469, found 489.1457.

EXAMPLE 37

3-{4-[3-(2-Benzoyl-4-chloro-phenoxy)-5-methyl-phenoxy]-2-methyl-phenyl}-propionic acid

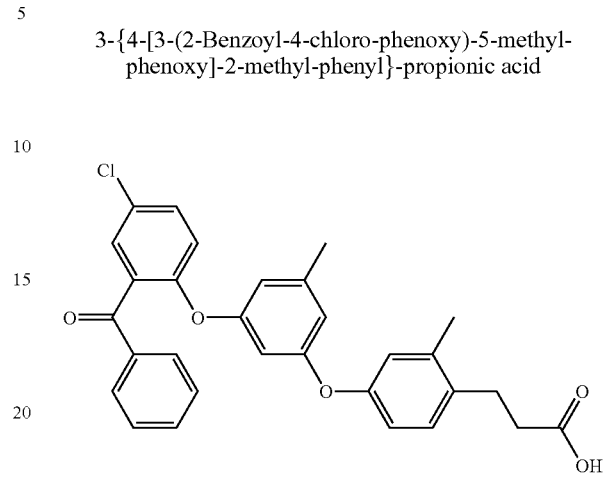

The title compound is prepared by reacting the compound of 3-[4-(3-bromo-5-methyl-phenoxy)-2-methyl-phenyl]-propionic acid methyl ester with (5-chloro-2-hydroxy-phenyl)-phenyl-methanone as in Example 18 to afford 0.244 g (38%). $^1$H NMR (400 MHz, CDCl$_3$); HRMS (ES$^+$) m/z exact mass calculated for C$_{30}$H$_{25}$O$_5$Cl 501.1469, found 501.1474.

EXAMPLE 38

3-{2-Methyl-4-[3-methyl-5-(2-pyridin-3-yl-4-trifluoromethyl-phenoxy)-phenoxy]-phenyl}-propionic acid

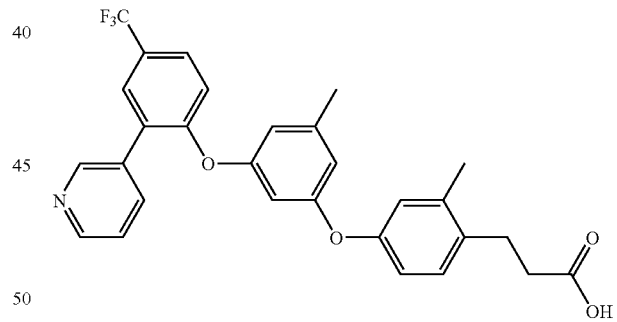

Step A

4-Fluoro-2-methyl-benzaldehyde

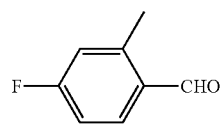

A −78° C. solution of 2-bromo-5-fluorotoluene (12.0 g, 63.5 mmol) in dry THF (60 mL) is treated with a 1.6 M hexanes solution of n-butyl lithium (59.5 mL, 95.3 mmol) and then stirred for 15 minutes at −78° C. under N₂. The mixture is then treated with DMF (27.8 g, 0.381 mol) and warmed to rt. The reaction is acidified with 1 N HCl, diluted with Et₂O and extracted with water. The organic layer is dried (Na₂SO₄), and the solvent removed in vacuo to afford crude product that is absorbed on silica gel and purified by flash chromatography using a gradient of 5/1 to 3/1 to hexanes/ethyl acetate to afford 6.24 g (71%) of the title compound. $R_f$=0.49 (2/1 hexanes/EtOAc). ¹H NMR (400 MHz, CDCl₃).

Step B 3-(4-Fluoro-2-methyl-phenyl)-acrylic acid ethyl ester

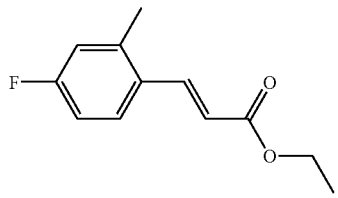

A mixture of 4-fluoro-2-methyl-benzaldehyde (1.16 g, 8.40 mmol), triethyl phosphonoacetate (2.26 g, 10.1 mmol), and 325 mesh potassium carbonate (3.48 g, 25.2 mmol) in ethanol (15 mL) is heated to reflux for 5 hours under N₂. The reaction is cooled, filtered and the filtrate is acidified with 1 N HCl. The mixture is then diluted with Et₂O and extracted with water. The organic layer is dried (Na₂SO₄, and the solvent is removed in vacuo to afford crude product that is absorbed on silica gel and purified by flash chromatography using 6/1 hexanes/ethyl acetate to afford 1.21 g (69%) of the title compound. $R_f$=0.58 (2/1 hexanes/EtOAc). ¹H NMR (400 MHz, CDCl₃); MS (ES⁺) m/z mass calculated for $C_{12}H_{13}O_2F$ 208, found 209 (M+1, 100%).

Step C

3-Benzyloxy-5-methyl-phenol

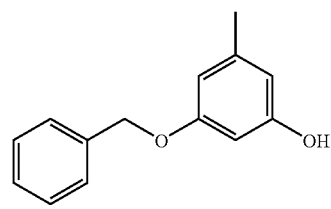

A 0° C. mixture of orcinol (10.0 g, 80.6 mmol) and 325 mesh potassium carbonate (12.25 g, 88.6 mmol) in DMF (100 mL) is treated dropwise with benzyl bromide (6.91 g, 40.4 mmol). The mixture was then warmed to rt and stirred for 20 hours under N₂. The reaction is filtered, and the filtrate is acidified with 1 N HCl. The mixture is then diluted with Et₂O and extracted with water. The organic layer is dried (Na₂SO₄), and the solvent is removed in vacuo to afford crude product that is absorbed on silica gel and purified by flash chromatography using 5/1 hexanes/ethyl acetate to afford 4.88 g(57%) of the title compound. $R_f$=0.40 (2/1 hexanes/EtOAc).

¹H NMR (400 MHz, CDCl₃); MS (ES⁺) m/z mass calculated for $C_{14}H_{14}O_2$ 214, found 215 (M+1, 100%).

Step D

3-[4-(3-Benzyloxy-5-methyl-phenoxy)-2-methyl-phenyl]-acrylic acid ethyl ester

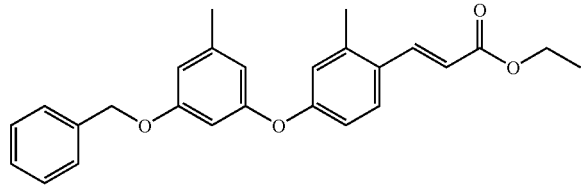

A mixture of 3-benzyloxy-5-methyl-phenol (3.24 g, 15.1 mmol), 3-(4-fluoro-2-methyl-phenyl)-acrylic acid ethyl ester (3.15 g, 15.1 mmol) and 325 mesh potassium carbonate (2.51 g, 18.2 mmol) in dry DMSO (40 mL) is heated to 130° C. and stirred for 20 hours under N₂. The reaction is cooled and acidified with 1 N HCl (30 mL). The mixture is then diluted with Et₂O and extracted with water. The organic layer is dried (Na₂SO₄), and the solvent is removed in vacuo to afford crude product that is absorbed on silica gel and purified by flash chromatography using 9/1 hexanes/ethyl acetate to afford 3.56 g (58%) of the title compound. $R_f$=0.39 (4/1 hexanes/EtOAc). ¹H NMR (400 MHz, CDCl₃); MS (ES⁺) m/z mass calculated for $C_{26}H_{26}O_4$ 402, found 403 (M+1, 100%).

Step E

3-[4-(3-Hydroxy-5-methyl-phenoxy)-2-methyl-phenyl]-propionic acid ethyl ester

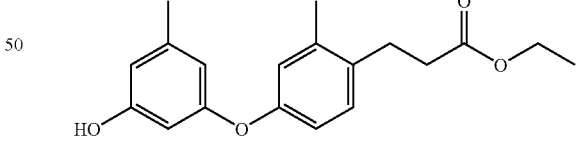

A mixture of 3-[4-(3-benzyloxy-5-methyl-phenoxy)-2-methyl-phenyl]-acrylic acid ethyl ester (3.56 g, 88.5 mmol) and 10% Pd/C (1.75 g) in ethyl acetate (90 mL) is purged with N₂, then purged with H₂ and stirred under a hydrogen balloon. Upon completion, the mixture is filtered through hyflo, and the solvent is removed in vacuo to afford 2.83 g (100%) the title compound. $R_f$=0.35 (2/1 hexanes/EtOAc). ¹H NMR (400 MHz, CDCl₃); MS (ES⁺) m/z mass calculated for $C_{19}H_{22}O_4$ 314, found 315 (M+1, 100%).

Step F

3-{4-[3-(2-Bromo-4-trifluoromethyl-phenoxy)-5-methyl-phenoxy]-2-methyl-phenyl}-propionic acid ethyl ester

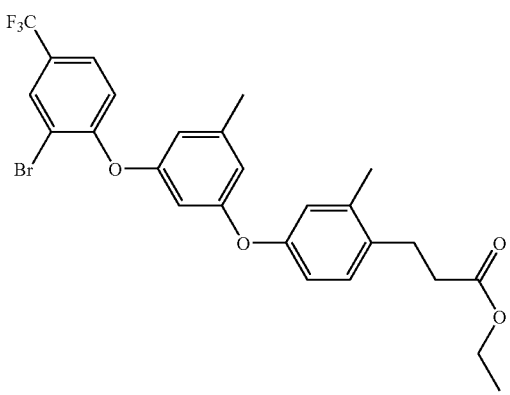

A mixture of 3-[4-(3-hydroxy-5-methyl-phenoxy)-2-methyl-phenyl]-propionic acid ethyl ester (2.83 g, 9.01 mmol), 3-bromo-4-fluorobenzotrifluoride (2.19 g, 9.01 mmol) and 325 mesh potassium carbonate (1.49 g, 10.8 mmol) in dry DMSO (36 mL) is heated to 100° C. and stirred for 5 hours under $N_2$. The reaction is cooled and acidified with 1 N HCl. The mixture is then diluted with $Et_2O$ and extracted with water. The organic layer is dried ($Na_2SO_4$), and the solvent removed in vacuo to afford crude product that is absorbed on silica gel and purified by flash chromatography using 9/1 hexanes/ethyl acetate to afford 3.45 g (71%) of the title compound. $R_f$=0.54 (2/1 hexanes/EtOAc). $^1$H NMR (400 MHz, $CDCl_3$); MS ($ES^+$) m/z mass calculated for $C_{26}H_{24}O_4F_3Br$ 536, found 554 and 556 ($M+NH_4$, 100%).

Step G

3-{2-Methyl-4-[3-methyl-5-(2-pyridin-3-yl-4-trifluoromethyl-phenoxy)-phenoxy]-phenyl}-propionic acid ethyl ester

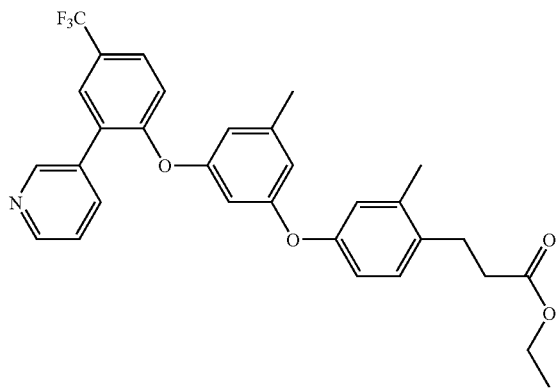

A mixture of 3-{4-[3-(2-bromo-4-trifluoromethyl-phenoxy)-5-methyl-phenoxy]-2-methyl-phenyl}-propionic acid ethyl ester (0.112 g, 0.209 mmol), pyridine-3-boronic acid (0.077 g, 0.626 mmol), and cesium fluoride (0.111 g, 0.731 mmol) in dry ACN (7 mL) is purged with $N_2$ and then treated with 1,1'-bis(diphenylphophino)-ferrocene palladium (II) chloride complex with DCM (0.031 g, 0.042 mmol). The mixture is heated to 100° C. and stirred for 5 hours under $N_2$. The reaction is cooled, and the crude mixture is absorbed on silica gel and purified by flash chromatography using 2/1 hexanes/ethyl acetate to afford 0.089 g (79%) of the title compound. $R_f$=0.33 (1/1 hexanes/EtOAc). $^1$H NMR (400 MHz, $CDCl_3$); MS ($ES^+$) m/z mass calculated for $C_{31}H_{28}O_4NF_3$ 535, found 536 (M+1, 100%).

Step H

3-{2-Methyl-4-[3-methyl-5-(2-pyridin-3-yl-4-trifluoromethyl-phenoxy)-phenoxy]-phenyl}-propionic acid A solution of 3-{2-methyl-4-[3-methyl-5-(2-pyridin-3-yl-4-trifluoromethyl-phenoxy)-phenoxy]-phenyl}-propionic acid ethyl ester (0.089, 0.166 mmol) in ethanol (7 mL) is treated with 5 N NaOH (2 mL) and heated to until saponification is completed. The mixture is cooled, and the solvent is removed in vacuo to afford a residue that is neutralized with 1 N HCl. The mixture is diluted with water and extracted with ethyl acetate. The organic layer is dried ($Na_2SO_4$), and the solvent is removed in vacuo to afford 0.093 g (100%) of the title compound. $^1$H NMR (400 MHz, $CDCl_3$); HRMS ($ES^+$) m/z exact mass calculated for $C_{29}H_{24}O_4F_3N$ 508.1736, found 508.1724.

EXAMPLE 39

3-{2-Methyl-4-[3-methyl-5-(2-pyridin-2-yl-4-trifluoromethyl-phenoxy)-phenoxy]-phenyl}-propionic acid

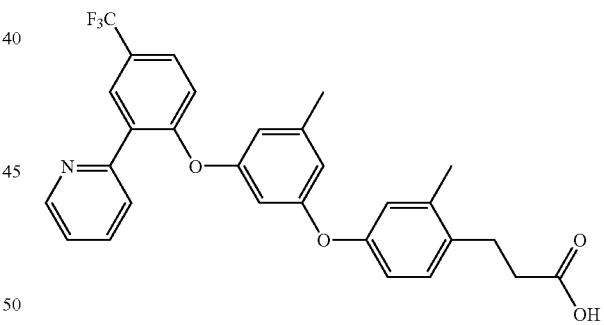

A mixture of 3-{4-[3-(2-bromo-4-trifluoromethyl-phenoxy)-5-methyl-phenoxy]-2-methyl-phenyl}-propionic acid ethyl ester (0.155 g, 0.289 mmol) and 2-tributylstannyl pyridine (0.210 g, 0.571 mmol) in dry toluene (8 mL) is purged with $N_2$ and then tetrakis(triphenylphospine)pallium (0) (0.033 g, 0.029 mmol) is added. The reaction is heated to 100° C. and stirred for 20 hours under $N_2$. The reaction is cooled, and the solvent is removed in vacuo to give crude 3-{2-methyl-4-[3-methyl-5-(2-pyridin-2-yl-4-trifluoromethyl-phenoxy)-phenoxy]-phenyl}-propionic acid ethyl ester. This ester is dissolved in ethanol (8 mL), treated with 5 N NaOH (2 mL) and heated to reflux until saponification is complete. The mixture is cooled, and the solvent is removed in vacuo to afford a residue that is acidified with 1 N HCl. The mixture is diluted with water and extracted with ethyl acetate. The organic layer is dried (Na$_2$SO$_4$), and the solvent is removed in vacuo to give crude product that is purified by preparative HPLC to afford 0.056 g (38%) of the title compound. $^1$H NMR (400 MHz, CDCl$_3$); MS (ES$^+$) m/z mass calculated for C$_{29}$H$_{24}$NO$_4$F$_3$ 507, found 508 (M+1, 100%).

EXAMPLE 40

3-{2-Methyl-4-[3-methyl-5-(2-pyridin-4-yl-4-trifluoromethyl-phenoxy)-phenoxy]-phenyl}-propionic acid

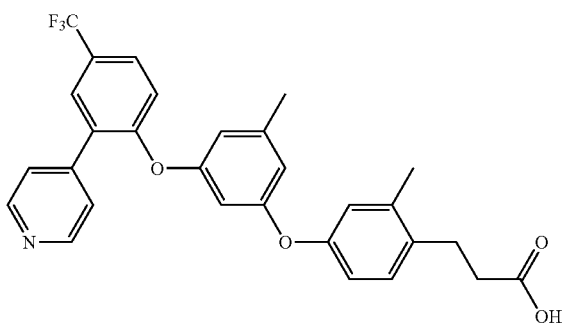

The title compound is prepared by reacting the compound of 3-{4-[3-(2-bromo-4-trifluoromethyl-phenoxy)-5-methyl-phenoxy]-2-methyl-phenyl}-propionic acid ethyl ester with 4-pyridyl boronic acid as in Example 38 to afford 0.011 g (9%). $^1$HNMR (400 MHz, CDCl$_3$); MS (ES$^+$) m/z mass calculated for C$_{29}$H$_{24}$NO$_4$F$_3$ 507, found 508 (M+1, 100%).

EXAMPLE 41

3-[2-Methyl-4-[3-methyl-5-(5-trifluoromethyl-biphenyl-2-yloxy)-phenoxy]-phenyl]-propionic acid

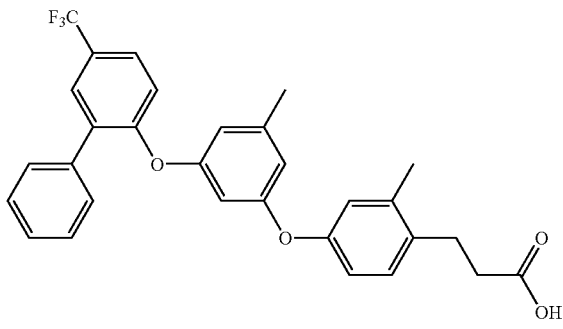

The title compound is prepared by reacting the compound of 3-{4-[3-(2-bromo-4-trifluoromethyl-phenoxy)-5-methyl-phenoxy]-2-methyl-phenyl}-propionic acid ethyl ester with phenyl boronic acid as in Example 38 to afford 0.024 g (21%). $^1$H NMR (400 MHz, CDCl$_3$); HRMS (ES$^+$) m/z exact mass calculated for C$_{30}$H$_{26}$O$_4$F$_3$ 507.1783, found 507.1797.

EXAMPLE 42

3-{4-[3-(2'-Acetyl-5-trifluoromethyl-biphenyl-2-yloxy)-5-methyl-phenoxy]-2-methyl-phenyl}-propionic acid

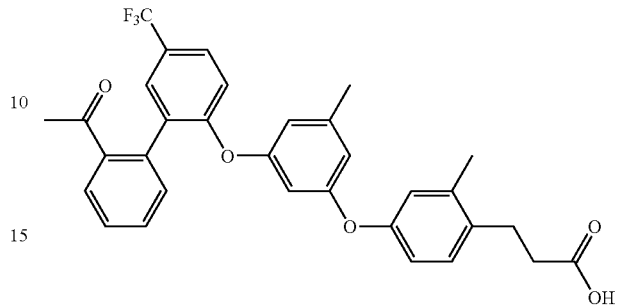

The title compound is prepared by reacting the compound of 3-{4-[3-(2-bromo-4-trifluoromethyl-phenoxy)-5-methyl-phenoxy]-2-methyl-phenyl}-propionic acid ethyl ester with 2-acetyl phenyl boronic acid as in Example 38 to afford 0.032 g (28%).
$^1$H NMR (400 MHz, CDCl$_3$); HRMS (ES$^+$) m/z exact mass calculated for C$_{32}$H$_{28}$O$_5$F$_3$ 549.1888, found 549.1870.

EXAMPLE 43

3-{4-[3-(4'-Methanesulfonyl-5-trifluoromethyl-biphenyl-2-yloxy)-5-methyl-phenoxy]-2-methyl-phenyl}-propionic acid

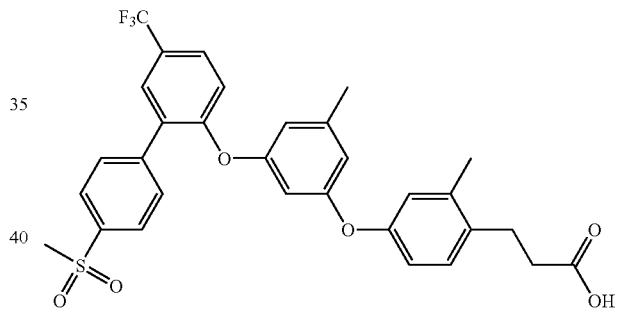

The title compound is prepared by reacting the compound of 3-{4-[3-(2-bromo-4-trifluoromethyl-phenoxy)-5-methyl-phenoxy]-2-methyl-phenyl}-propionic acid ethyl ester with 4-(methylsulfonyl)phenyl boronic acid as in Example 38 to afford 0.062 g (48%). $^1$H NMR (400 MHz, CDCl$_3$); MS (ES$^+$) m/z mass calculated for C$_{31}$H$_{27}$O$_6$SF$_3$ 584, found 585 (M+1, 100%).

EXAMPLE 44

3-{2-Methyl-4-[3-methyl-5-(2'-trifluoromethoxy-5-trifluoromethyl-biphenyl-2-yloxy)-phenoxy]-phenyl}-propionic acid

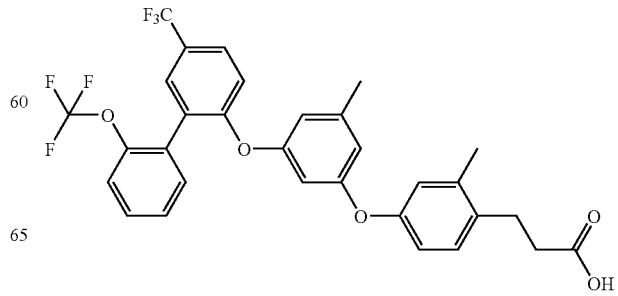

The title compound is prepared by reacting the compound of 3-{4-[3-(2-bromo-4-trifluoromethyl-phenoxy)-5-methyl-phenoxy]-2-methyl-phenyl}-propionic acid ethyl ester with 2-trifluoromethoxyphenyl boronic acid as in Example 38 to afford 0.058 g (39%). $^1$H NMR (400 MHz, CDCl$_3$); HRMS (ES$^+$) m/z exact mass calculated for C$_{31}$H$_{25}$O$_5$F$_6$ 591.1606, found 591.1619.

EXAMPLE 45

3-{2-Methyl-4-[3-methyl-5-(2-phenoxy-4-trifluoromethyl-phenoxy)-phenoxy]-phenyl}-propionic acid

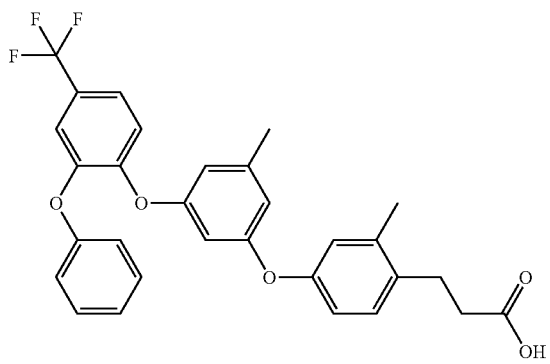

Step A

3-{2-Methyl-4-[3-methyl-5-(2-phenoxy-4-trifluoromethyl-phenoxy)-phenoxy]-phenyl}-propionic acid ethyl ester

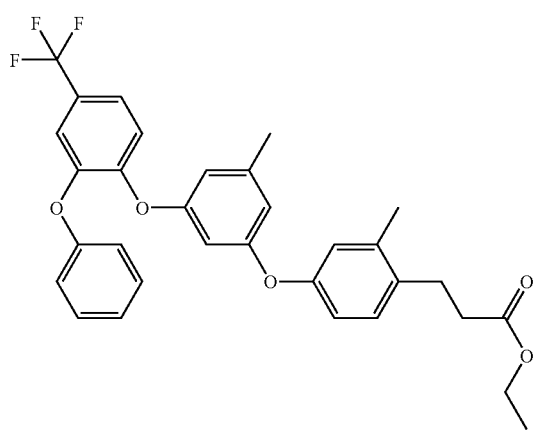

A mixture of 3-{4-[3-(2-bromo-4-trifluoromethyl-phenoxy)-5-methyl-phenoxy]-2-methyl-phenyl}-propionic acid ethyl ester (0.309 g, 0.576 mmol), phenol (0.163 g, 1.73 mmol), cesium carbonate (0.56 g, 1.72 mmol), copper (I) chloride (0.029 g, 0.293 mmol) and 2,2,6,6-tetramethyl-3,5-heptanedione (0.027 g, 0.147 mmol) in 1-methyl-2-pyrrolidinone (10 mL) is heated to 120° C. for 20 hours under N$_2$. The reaction is cooled and quenched with 1 N HCl (20 mL). The mixture is then diluted with Et$_2$O and extracted with water. The organic layer is dried (Na$_2$SO$_4$), and the solvent is removed in vacuo to afford crude product that is absorbed on silica gel and purified by flash chromatography using 9/1 hexanes/ethyl acetate to afford 0.173 g (43%) of the title compound. R$_f$=0.55 (4/1 hexanes/EtOAc). $^1$H NMR (400 MHz, CDCl$_3$); MS (ES$^+$) M/z mass calculated for C$_{32}$H$_{29}$O$_3$$_5$F$_3$ 550, found 551 (M+1, 100%).

Step B

3-{2-Methyl-4-[3-methyl-5-(2-phenoxy-4-trifluoromethyl-phenoxy)-phenoxy]-phenyl}-propionic acid A solution of 3-{2-methyl-4-[3-methyl-5-(2-phenoxy-4-trifluoromethyl-phenoxy)-phenoxy]-phenyl}-propionic acid ethyl ester (0.137, 0.249 mmol) in ethanol (8 mL) is treated with 5 N NaOH (2 mL) and heated to reflux until saponification is completed. The mixture is cooled, and the solvent is removed in vacuo to afford a residue that is acidified with 1 N HCl. The mixture is diluted with water and extracted with ethyl acetate. The organic layer is dried (Na$_2$SO$_4$), and the solvent is removed in vacuo to afford 0.143 g (100%) of the title compound. $^1$H NMR (400 MHz, CDCl$_3$); HRMS (ES$^+$) m/z exact mass calculated for C$_{30}$H$_{25}$O$_5$F$_3$ 523.1732, found 523.1721.

EXAMPLE 46

3-(2-Methyl-4-{3-methyl-5-[2-(pyridin-2-yloxy)-4-trifluoromethyl-phenoxy]-phenoxy}-phenyl)-propionic acid

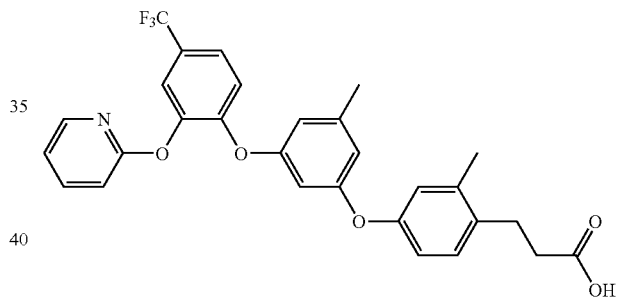

The title compound is prepared by reacting the compound of 3-{4-[3-(2-bromo-4-trifluoromethyl-phenoxy)-5-methyl-phenoxy]-2-methyl-phenyl}-propionic acid ethyl ester with 2-hydroxypyridine as in Example 45 to afford 0.015 g (10%). $^1$H NMR (400 MHz, CDCl$_3$); MS (ES$^+$) m/z mass calculated for C$_{29}$H$_{24}$NO$_5$F$_3$ 523, found 524 (M+1, 100%).

EXAMPLE 47

3-(2-Methyl-4-{3-methyl-5-[2-(2-oxo-2H-pyridin-1-yl)-4-trifluoromethyl-phenoxy]-phenoxy}-phenyl)-propionic acid

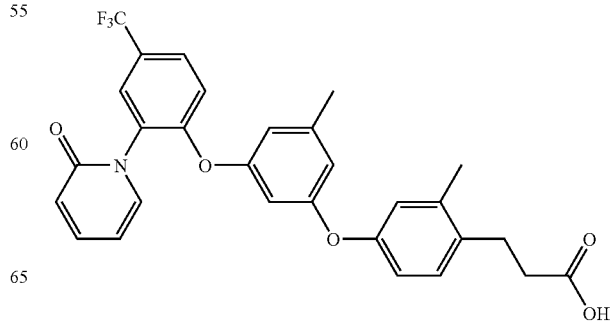

The title compound is prepared by reacting the compound of 3-{4-[3-(2-bromo-4-trifluoromethyl-phenoxy)-5-methyl-phenoxy]-2-methyl-phenyl}-propionic acid ethyl ester with 2-hydroxypyridine as in Example 45 to afford 0.010 g (8%). ¹H NMR (400 MHz, CDCl₃); MS (ES⁺) m/z mass calculated for C₂₉H₂₄NO₅F₃ 523, found 524 (M+1, 100%).

EXAMPLE 48

3-(2-Methyl-4-{3-methyl-5-[2-(pyridin-3-yloxy)-4-trifluoromethyl-phenoxy]-phenoxy}-phenyl)-propionic acid

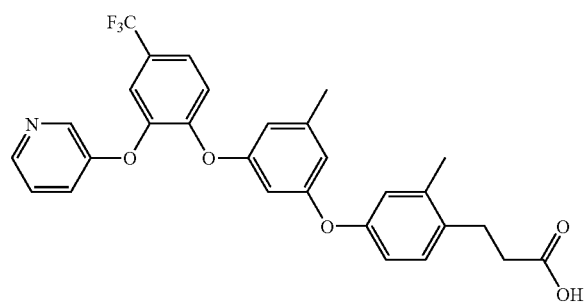

The title compound is prepared by reacting the compound of 3-{4-[3-(2-bromo-4-trifluoromethyl-phenoxy)-5-methyl-phenoxy]-2-methyl-phenyl}-propionic acid ethyl ester with 3-hydroxypyridine as in Example 45 to afford 0.044 g (31%). ¹H NMR (400 MHz, CDCl₃); HRMS (ES⁺) m/z exact mass calculated for C₂₉H₂₄NO₅F₃ 524.1685, found 524.1680.

EXAMPLE 49

3-{2-Methyl-4-[3-methyl-5-(2-o-tolyloxy-4-trifluoromethyl-phenoxy)-phenoxy]-phenyl}-propionic acid

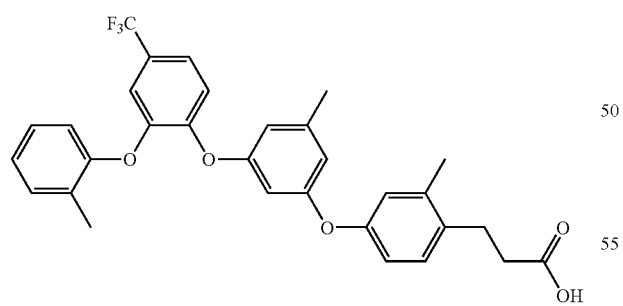

The title compound is prepared by reacting the compound of 3-{4-[3-(2-bromo-4-trifluoromethyl-phenoxy)-5-methyl-phenoxy]-2-methyl-phenyl}-propionic acid ethyl ester with o-cresol as in Example 45 to afford 0.038 g (25%). ¹H NMR (400 MHz, CDCl₃); HRMS (ES⁺) 71 m/Z exact mass calculated for C₃₁H₂₇O₅F₃ 537.1888, found 537.1893.

EXAMPLE 50

3-{2-Methyl-4-[3-methyl-5-(2-m-tolyloxy-4-trifluoromethyl-phenoxy)-phenoxy]-phenyl}-propionic acid

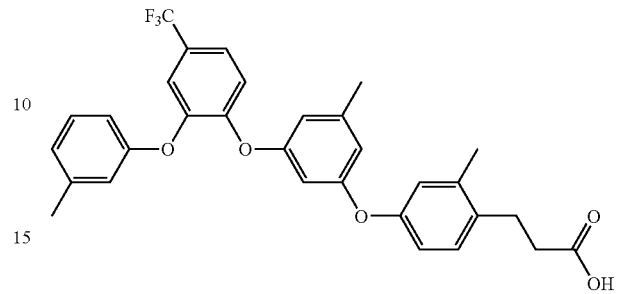

The title compound is prepared by reacting the compound of 3-{4-[3-(2-bromo-4-trifluoromethyl-phenoxy)-5-methyl-phenoxy]-2-methyl-phenyl}-propionic acid ethyl ester with m-cresol as in Example 45 to afford 0.030 g (21%). ¹H NMR (400 MHz, CDCl₃); HRMS (ES⁺) m/z exact mass calculated for C₃₁H₂₇O₅F₃ 537.1888, found 537.1879.

EXAMPLE 51

3-{2-Methyl-4-[3-methyl-5-(2-p-tolyloxy-4-trifluoromethyl-phenoxy)-phenoxy]-phenyl}-propionic acid

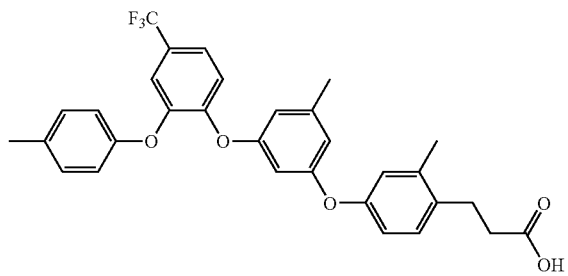

The title compound is prepared by reacting the compound of 3-{4-[3-(2-bromo-4-trifluoromethyl-phenoxy)-5-methyl-phenoxy]-2-methyl-phenyl}-propionic acid ethyl ester with p-cresol as in Example 45 to afford 0.035 g (25%). ¹H NMR (400 MHz, CDCl₃); HRMS (ES⁺) m/z exact mass calculated for C₃₁H₂₇O₅F₃ 537.1888, found 537.1874.

EXAMPLE 52

3-(4-{3-[2-(3,5-Difluoro-phenoxy)-4-trifluoromethyl-phenoxy]-5-methyl-phenoxy}-2-methyl-phenyl)-propionic acid

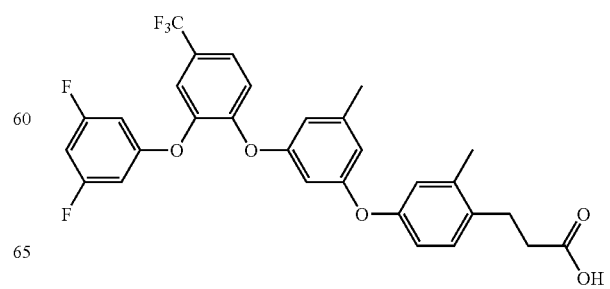

The title compound is prepared by reacting the compound of 3-{4-[3-(2-bromo-4-trifluoromethyl-phenoxy)-5-methyl-phenoxy]-2-methyl-phenyl}-propionic acid ethyl ester with p-cresol as in Example 45 to afford 0.006 g (4%). $^1$H NMR (400 MHz, CDCl$_3$); MS (ES$^+$) m/z mass calculated for C$_{30}$H$_{23}$O$_5$F$_5$ 558, found 559 (M+1, 100%).

EXAMPLE 53

3-{4-[3-Fluoro-5-(2-phenoxy-4-trifluoromethyl-phenoxy)-phenoxy]-2-methyl-phenyl}-propionic acid

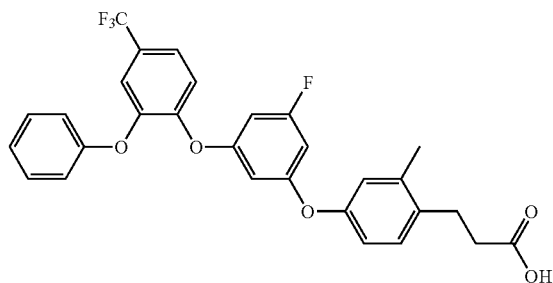

Step A

3-Fluoro-5-methoxy-phenol

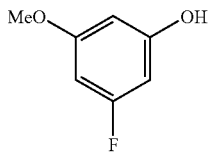

A −78° C. solution of 1-fluoro-3,5-dimethoxybenzene (4.98 g, 31.9 mmol) in dry CH$_2$Cl$_2$ (50 mL) is treated with a 1 M CH$_2$Cl$_2$ solution of boron tribromide (128 mL, 128 mmol), and the mixture is warmed to 0° C. and stirred under N$_2$. Upon completion, the mixture is poured into ice water and extracted with Et$_2$O. The organic layer is dried (Na$_2$SO$_4$), and the solvent is removed in vacuo to afford crude product that is absorbed on silica gel and purified by flash chromatography using a gradient of 5/1 to 1/1 to hexanes/ethyl acetate to afford 2.40 g (53%) of the title compound. R$_f$=0.49 (1/1 hexanes/EtOAc). $^1$H NMR (400 MHz, CDCl$_3$). MS (ES$^−$) m/z mass calculated for C$_7$H$_7$O$_2$F 142, found 141 (M−1, 100%).

Step B 4-(3-Fluoro-5-methoxy-phenoxy)-2-methyl-benzaldehyde

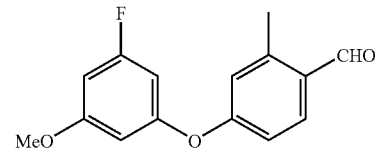

A 0° C. solution of 3-fluoro-5-methoxy-phenol (2.40 g, 16.9 mmol) in dry DMF (20 mL) is treated with a 60% suspension of NaH (0.74 g, 18.5 mmol) and then stirred for 15 minutes under N$_2$. A solution of 4-fluoro-2-methyl-benzaldehyde (2.33 g, 16.9 mmol) in DMF (10 mL) is added dropwise, and the mixture is warmed to 60° C. for 4 hours. The mixture is cooled and acidified with 1 N HCl. The mixture is then diluted with Et$_2$O and extracted with water. The organic layer is dried (Na$_2$SO$_4$), and the solvent is removed in vacuo to afford crude product that is absorbed on silica gel and purified by flash chromatography using 6/1 hexanes/ethyl acetate to afford 1.40 g (32%) of the title compound. R$_f$=0.41 (2/1 hexanes/EtOAc). $^1$H NMR (400 MHz, CDCl$_3$); MS (ES$^+$) m/z mass calculated for C$_{15}$H$_{13}$O$_3$F 260, found 261 (M+1, 100%).

Step C

3-[4-(3-Fluoro-5-methoxy-phenoxy)-2-methyl-phenyl]-acrylic acid ethyl ester

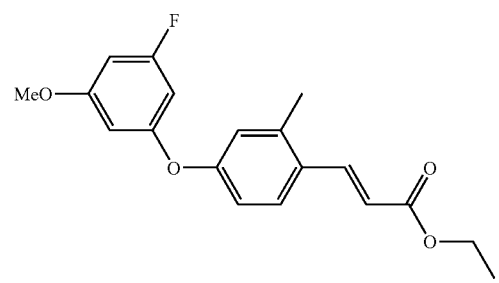

A mixture of 4-(3-fluoro-5-methoxy-phenoxy)-2-methyl-benzaldehyde (1.40 g, 5.38 mmol), triethyl phosphonoacetate (1.45 g, 6.47 mmol), and 325 mesh potassium carbonate (2.23 g, 16.1 mmol) in ethanol (20 mL) is heated to reflux for 5 hours under N$_2$. The reaction is cooled, filtered and the filtrate is acidified with 1 N HCl. The mixture is diluted with EtOAc and extracted with water. The organic layer is dried (Na$_2$SO$_4$), and the solvent is removed in vacuo to afford crude product that is absorbed on silica gel and purified by flash chromatography using 9/1 hexanes/ethyl acetate to afford 0.98 g (55%) of the title compound. R$_f$=0.41 (2/1 hexanes/EtOAc). $^1$H NMR (400 MHz, CDCl$_3$); MS (ES$^+$) m/z mass calculated for C$_{19}$H$_{19}$O$_4$F 330, found 331 (M+1, 100%).

Step D

3-[4-(3-Fluoro-5-methoxy-phenoxy)-2-methyl-phenyl]-propionic acid ethyl ester

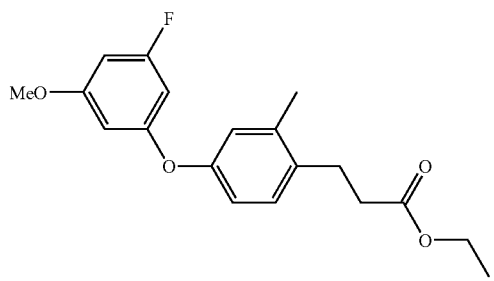

A mixture of 3-[4-(3-fluoro-5-methoxy-phenoxy)-2-methyl-phenyl]-acrylic acid ethyl ester (0.98 g, 2.96 mmol) and 10% Pd/C (0.50 g) in ethyl acetate (50 mL) is purged with $N_2$, and then with $H_2$. The mixture is stirred under a hydrogen balloon for three hours. The reaction is filtered through hyflo, and the solvent is removed in vacuo to afford 0.715 g (73%) of the title compound. $R_f$=0.53 (2/1 hexanes/EtOAc). $^1$H NMR (400 MHz, CDCl$_3$); MS (ES$^+$) m/z mass calculated for $C_{19}H_{21}O_4F$ 332, found 333 (M+1, 100%).

Step E

3-[4-(3-Fluoro-5-hydroxy-phenoxy)-2-methyl-phenyl]-propionic acid ethyl ester

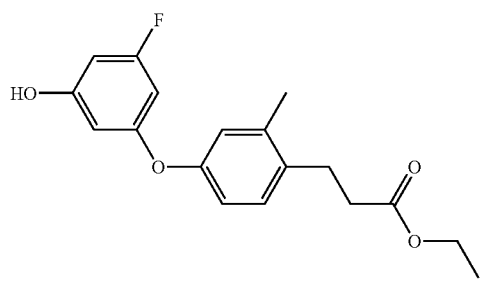

A −78° C. solution of 3-[4-(3-fluoro-5-methoxy-phenoxy)-2-methyl-phenyl]-propionic acid ethyl ester (0.715 g, 2.15 mmol) in dry CH$_2$Cl$_2$ (10 mL) is treated with a 1 M CH$_2$Cl$_2$ solution of boron tribromide (6.5 mL, 6.5 mmol). The mixture is warmed to 0° C. and stirred for 1 hour under $N_2$. Upon completion, the mixture is poured into ice water and extracted with Et$_2$O. The organic layer is dried (Na$_2$SO$_4$), and the solvent is removed in vacuo to afford crude product that is absorbed on silica gel and purified by flash chromatography using a gradient of 5/1 to 1/1 to hexanes/ethyl acetate to afford 0.558 g (81%) of the title compound. $R_f$=0.36 (2/1 hexanes/EtOAc). $^1$H NMR (400 MHz, CDCl$_3$). MS (ES$^-$) m/z mass calculated for $C_{18}H_{19}O_4F$ 318, found 317 (M−1, 100%).

Step F

3-{4-[3-(2-Bromo-4-trifluoromethyl-phenoxy)-5-fluoro-phenoxy]-2-methyl-phenyl}-propionic acid ethyl ester

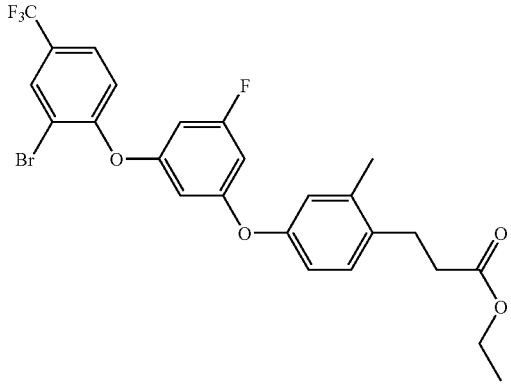

A mixture of 3-[4-(3-fluoro-5-hydroxy-phenoxy)-2-methyl-phenyl]-propionic acid ethyl ester (0.557 g, 1.75 mmol), 3-bromo-4-fluorobenzotrifluoride (0.425 g, 1.75 mmol) and 325 mesh potassium carbonate (0.29 g, 2.10 mmol) in dry DMSO (10 mL) is heated to 100° C. and stirred 2.5 hours under $N_2$. The reaction is cooled and acidified with 1 N HCl. The mixture is then diluted with Et$_2$O and extracted with water. The organic layer is dried (Na$_2$SO$_4$), and the solvent is removed in vacuo to afford crude product that is absorbed on silica gel and purified by flash chromatography using 5/1 hexanes/ethyl acetate to afford 0.735 g (78%) of the title compound. $^1$H NMR (400 MHz, CDCl$_3$); MS (ES$^+$) m/z mass calculated for $C_2H_{21}O_4F_4Br$ 540, found 558 and 560 (M+NH$_4$, 100%).

Step G

3-{4-[3-Fluoro-5-(2-phenoxy-4-trifluoromethyl-phenoxy)-phenoxy]-2-methyl-phenyl}-propionic acid The title compound is prepare by reacting the compound of 3-{4-[3-(2-bromo-4-trifluoromethyl-phenoxy)-5-fluoro-phenoxy]-2-methyl-phenyl}-propionic acid ethyl ester with phenol as in Example 45 to afford 0.080 g (28%). $^1$H NMR (400 MHz, CDCl$_3$); MS (ES$^+$) m/z mass calculated for $C_{29}H_{22}O_5F_4$ 526, found 527 (M+1, 100%).

EXAMPLE 54

3-{4-[3-Fluoro-5-(2-pyridin-2-yl-4-trifluoromethyl-phenoxy)-phenoxy]-2-methyl-phenyl}-propionic acid

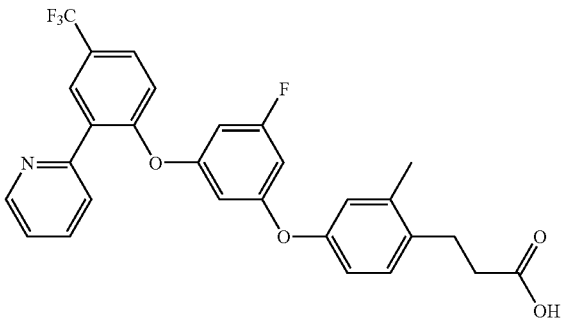

The title compound is prepare by reacting the compound of 3-{4-[3-(2-bromo-4-trifluoromethyl-phenoxy)-5-fluoro-phenoxy]-2-methyl-phenyl}-propionic acid ethyl ester with 2-tributylstannyl pyridine as in Example 39 to afford 0.085 g (36%). $^1$H NMR (400 MHz, CDCl$_3$); HRMS (ES$^+$) m/z exact mass calculated for C$_{28}$H$_{21}$NO$_4$F$_4$ 512.1485, found 512.1487.

EXAMPLE 55

3-{4-[3-Fluoro-5-(2-pyridin-3-yl-4-trifluoromethyl-phenoxy)-phenoxy]-2-methyl-phenyl}-propionic acid

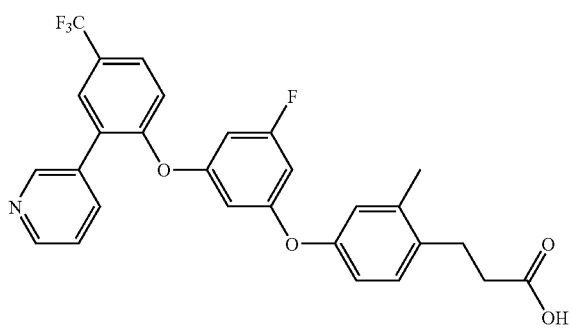

The title compound is prepare by reacting the compound of 3-{4-[3-(2-Bromo-4-trifluoromethyl-phenoxy)-5-fluoro-phenoxy]-2-methyl-phenyl}-propionic acid ethyl ester with pyridine-3-boronic acid as in Example 38 to afford 0.115 g (66%). $^1$H NMR (400 MHz, CDCl$_3$); MS (ES$^+$) m/z mass calculated for C$_{29}$H$_{21}$NO$_4$F$_4$ 511, found 512 (M+1, 100%).

EXAMPLE 56

3-{4-[3-Chloro-5-(2-phenoxy-4-trifluoromethyl-phenoxy)-phenoxy]-2-methyl-phenyl}-propionic acid

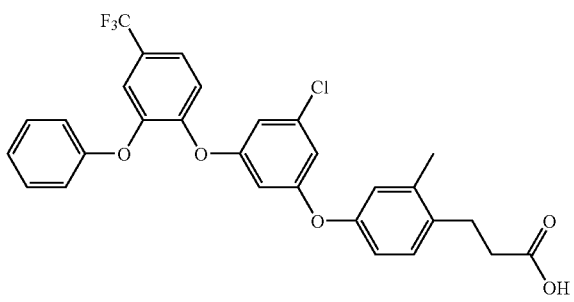

The compound of 3-{4-[3-(2-Bromo-4-trifluoromethyl-phenoxy)-5-chloro-phenoxy]-2-methyl-phenyl}-propionic acid ethyl ester is prepared as described in Example 56 which is then reacted with phenol as in Example 45 to afford 0.033 g (11%) of the title compound. $^1$H NMR (400 MHz, CDCl$_3$); MS (ES$^+$) m/z mass calculated for C$_{29}$H$_{22}$O$_5$F$_3$Cl 542, found 560 and 562 (M+NH$_4$, 100%).

EXAMPLE 57

3-(4-{3-Chloro-5-[2-(3-fluoro-phenoxy)-4-trifluoromethyl-phenoxy]-phenoxy}-2-methyl-phenyl)-propionic acid

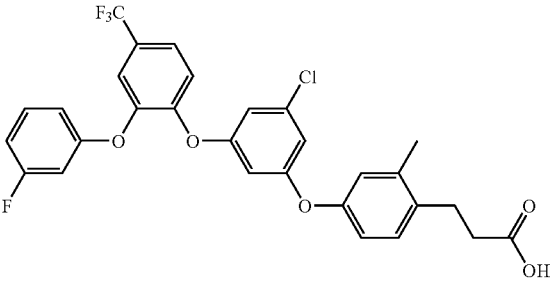

The title compound is prepare by reacting the compound of 3-{4-[3-(2-Bromo-4-trifluoromethyl-phenoxy)-5-chloro-phenoxy]-2-methyl-phenyl}-propionic acid ethyl ester with 3-fluorophenol as in Example 45 to afford 0.025 g (23%). $^1$H NMR (400 MHz, CDCl$_3$); MS (ES$^+$) m/z mass calculated for C$_{29}$H$_{21}$O$_5$F$_4$Cl 560, found 578 and 580 (M+NH$_4$, 100%).

EXAMPLE 58

3-{4-[3-Chloro-5-(2-pyridin-2-yl-4-trifluoromethyl-phenoxy)-phenoxy]-2-methyl-phenyl}-propionic acid

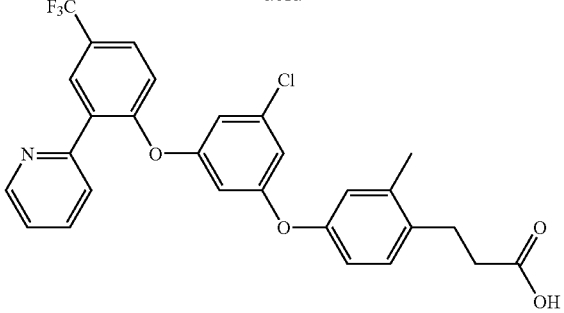

The title compound is prepare by reacting the compound of 3-{4-[3-(2-bromo-4-trifluoromethyl-phenoxy)-5-chloro-phenoxy]-2-methyl-phenyl}-propionic acid ethyl ester with 2-tributylstannyl pyridine as in Example 39 to afford 0.055 g (32%). $^1$H NMR (400 MHz, CDCl$_3$); HRMS (ES$^+$) m/z exact mass calculated for C$_{28}$H$_{21}$NO$_4$F$_3$Cl 528.1190, found 528.1194.

EXAMPLE 59

3-{4-[3-Chloro-5-(2-pyridin-3-yl-4-trifluoromethyl-phenoxy)-phenoxy]-2-methyl-phenyl}-propionic acid

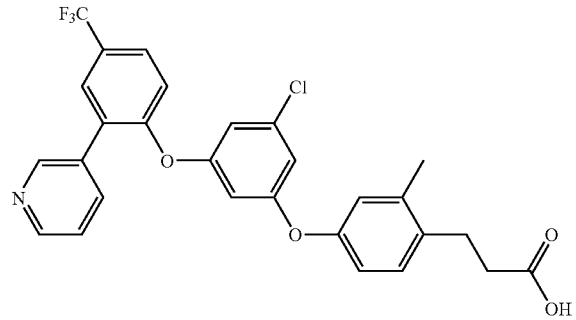

The title compound is prepare by reacting the compound of 3-{4-[3-(2-bromo-4-trifluoromethyl-phenoxy)-5-chloro-phenoxy]-2-methyl-phenyl}-propionic acid ethyl ester with pyridine-3-boronic acid as in Example 38 to afford 0.067 g (63%). $^1$H NMR (400 MHz, CDCl$_3$); HRMS (ES$^+$) m/z exact mass calculated for $C_{28}H_{21}NO_4F_3Cl$ 528.1190, found 528.1186.

EXAMPLE 60

3-{4-[3-(3'-Acetyl-5-trifluoromethyl-biphenyl-2-yloxy)-5-methyl-phenoxy]-2-methyl-phenyl}-propionic acid

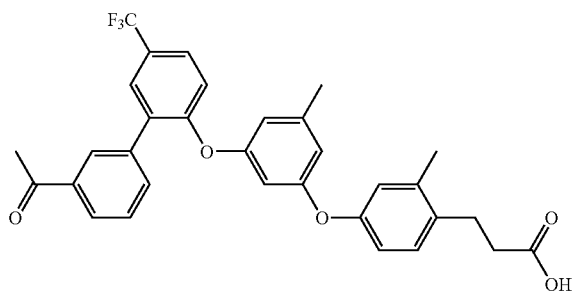

The compound of 3-{4-[3-(2-bromo-4-trifluoromethyl-phenoxy)-5-methyl-phenoxy]-2-methyl-phenyl}-propionic acid ethyl ester is reacted with 3-acetyl phenyl boronic acid as in Example 38 to afford 0.186 g (72%) of the title compound. $^1$H NMR (400 MHz, CDCl$_3$); HRMS (ES$^+$) m/z exact mass calculated for $C_{32}H_{28}O_5F_3$ 549.1888, found 549.1880.

EXAMPLE 61

3-{4-[3-(4'-Acetyl-5-trifluoromethyl-biphenyl-2-yloxy)-5-methyl-phenoxy]-2-methyl-phenyl}-propionic acid

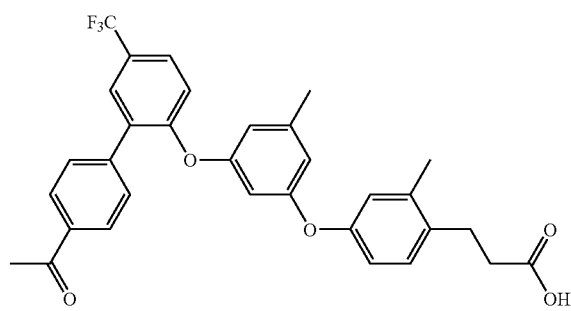

The compound of 3-{4-[3-(2-bromo-4-trifluoromethyl-phenoxy)-5-methyl-phenoxy]-2-methyl-phenyl}-propionic acid ethyl ester is reacted with 4-acetyl phenyl boronic acid as in Example 38 to afford 0.056 g (26%) of the title compound. $^1$H NMR (400 MHz, CDCl$_3$); HRMS (ES$^+$) m/z exact mass calculated for $C_{32}H_{28}O_5F_3$ 549.1888, found 549.1888.

EXAMPLE 62

3 3-(4-{3-[2-(3-Fluoro-phenoxy)-4-trifluoromethyl-phenoxy]-5-methyl-phenoxy}-2-methyl-phenyl)-propionic acid

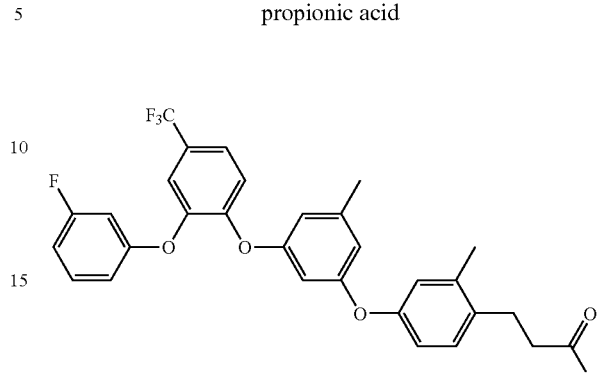

The compound of 3-{4-[3-(2-bromo-4-trifluoromethyl-phenoxy)-5-methyl-phenoxy]-2-methyl-phenyl}-propionic acid ethyl ester is reacted with 3-fluorophenol as in Example 45 to afford 0.106 g (40%) of the title compound. $^1$H NMR (400 MHz, CDCl$_3$); HRMS (ES$^+$) m/z mass calculated for $C_{30}H_{25}O_5F_4$ 541.1638, found 541.1625.

EXAMPLE 63

3-{2-Ethyl-4-[3-methyl-5-(2-o-tolyloxy-4-trifluoromethyl-phenoxy)-phenoxy]-phenyl}-propionic acid

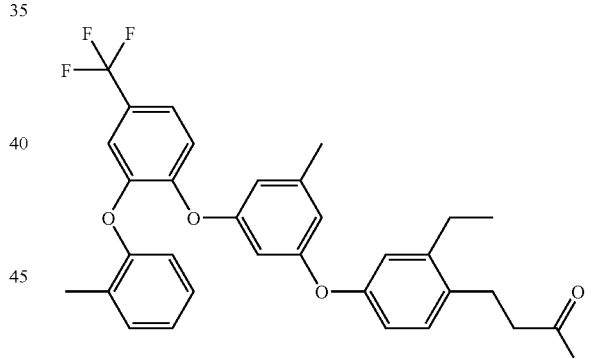

Step A

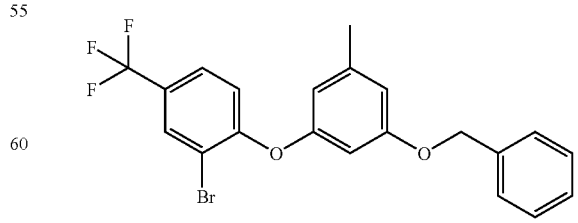

A mixture 3-benzyloxy-5-methyl-phenol (8.50 g, 39.7 mmol), 3-bromo-4-fluorobenzotrifluoride (9.64 g, 39.7 mmol) and 325 mesh potassium carbonate (6.58 g, 47.6 mmol) in dry DMSO (100 mL) is heated to 100° C. and stirred for 8 hours under N₂. The reaction is cooled and acidified with 1 N HCl. The mixture is then diluted with water and extracted with Et₂O. The organic layer is dried (Na₂SO₄), and the solvent is removed in vacuo to afford crude product that is absorbed on silica gel and purified by flash chromatography using 9/1 hexanes/ethyl acetate to afford 14.14 g (81%) product. $R_f$=0.52 (4/1 hexanes/EtOAc). ¹H NMR (400 MHz, CDCl₃).

Step B

3-Methyl-5-(2-o-tolyloxy-4-trifluoromethyl-phenoxy)-phenol

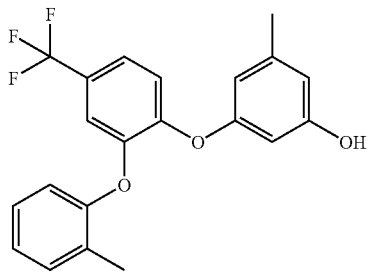

Compound of Step A (23.26 g, 53.2 mmol), o-cresol (17.26 g, 0.159 mol), cesium carbonate (51.99 g, 0.159 mol), and 2,2,6,6-tetramethyl-3,5-heptanedione (2.45 g, 13.3 mmol) in 1-methyl-2-pyrrolidinone (230 mL) is purged with N₂, and then copper (I) chloride (2.63 g, 26.6 mmol) is added. The reaction mixture is heated to 120° C. for 18 hours under N₂. The mixture is diluted with water and extracted with Et₂O. The organic layer is dried (Na₂SO₄), and the solvent is removed in vacuo to afford crude product that is absorbed on silica gel and purified by flash chromatography using 25/1 hexanes/ethyl acetate to afford 23.69 g (96%) as a mixture of products that were carried on as is.

A mixture of 23.69 g of obtained above and 10% Pd/C (6.0 g) in ethyl acetate (200 mL) is purged with N₂ and then H₂, and the mixture is stirred under a H₂ balloon at rt. Upon completion of the reaction, the mixture is filtered through hyflo, and the solvent is removed in vacuo to afford crude product that is purified by flash chromatography using 96/4 CHCl₃/methyl t-butyl ether to afford 6.74 g (35%) of the title compound. $R_f$=0.50 (9/1 CHCl₃/methyl t-butyl ether). ¹H NMR (400 MHz, CDCl₃); MS (ES⁺) m/z mass calculated for C₂₁H₁₇F₃O₃ 374, found 375 (M+1, 100%).

Step C

[3{-methyl-5-(2-o-tolyloxy-4-trifluoromethyl-phenoxy)-phenoxy]-phenyl}-acrylic acid ethyl ester

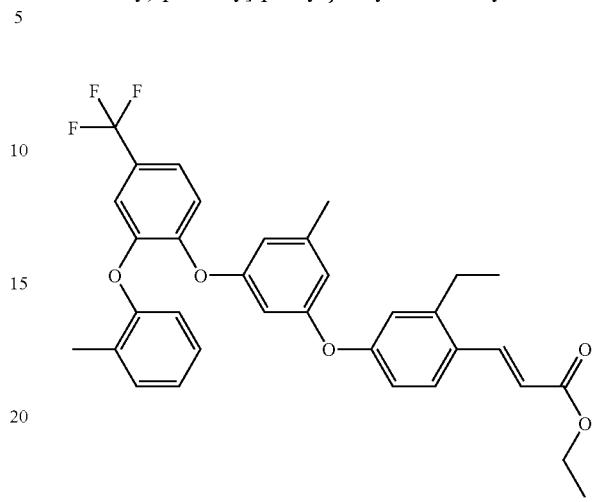

A 3-methyl-5-(2-o-tolyloxy-4-trifluoromethyl-phenoxy)-phenol (3.20 g, 8.54 mmol), 3-(2-ethyl-4-fluoro-phenyl)-acrylic acid ethyl ester (1.90 g, 8.54 mmol) and 325 mesh potassium carbonate (1.42 g, 10.3 mmol), and MgSO₄ (1.03 g, 8.54 mmol) in dry DMSO (35 mL) is heated to 130° C. and stirred for 17 hours under N₂. The reaction is cooled and acidified with 1 N HCl. The mixture is then diluted with water and extracted with Et₂O. The organic layer is dried (Na₂SO₄), and the solvent is removed in vacuo to afford crude product that is absorbed on silica gel and purified by flash chromatography using 16/1 hexanes/ethyl acetate to afford 1.83 g (37%) of the title compound. $R_f$=0.37 (4/1 hexanes/EtOAc). ¹H NMR (400 MHz, CDCl₃); MS (ES⁺) m/z mass calculated for C₃₄H₃₁F₃O₅ 576, found 577 (M+1, 100%).

Step D

3-{2-Ethyl-4-[3-methyl-5-(2-o-tolyloxy-4-trifluoromethyl-phenoxy)-phenoxy]-phenyl}-propionic acid ethyl ester

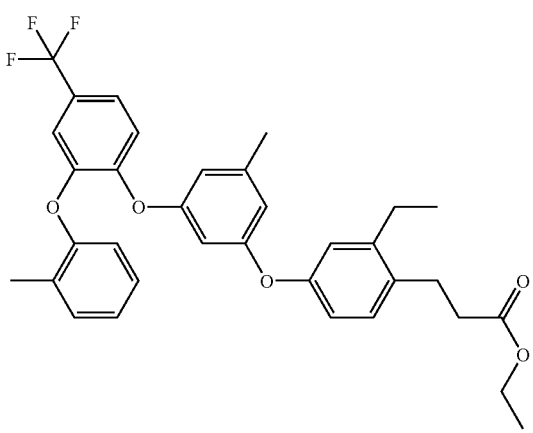

A mixture of 3-{2-ethyl-4-[3-methyl-5-(2-o-tolyloxy-4-trifluoromethyl-phenoxy)phenoxy]-phenyl}-acrylic acid ethyl ester (1.83 g, 3.17 mmol) and 10% Pd/C (1.80 g) in ethyl acetate (100 mL) is purged with $N_2$ then $H_2$ and then stirred under a $H_2$ balloon at rt for 5 hours. The mixture is filtered through hyflo, and the solvent is removed in vacuo to afford 1.77 g (97%) of the title compound. $R_f$=0.22 (9/1 hexanes/EtOAc). $^1$H NMR (400 MHz, $CDCl_3$); MS ($ES^+$) m/z mass calculated for $C_{34}H_{33}F_3O_5$ 578, found 579 (M+1, 100%).

Step E

3-{2-Ethyl-4-[3-methyl-5-(2-o-tolyloxy-4-trifuoromethyl-phenoxy)-phenoxy]-phenyl}-propionic acid A solution of 3-{2-ethyl-4-[3-methyl-5-(2-o-tolyloxy-4-trifluoromethyl-phenoxy)-phenoxy]-phenyl}-propionic acid ethyl ester (1.77, 3.06 mmol) in ethanol (15 mL) is treated with 5 N NaOH (3 mL) and heated to reflux until saponification is completed. The mixture is cooled, and the solvent is removed in vacuo to afford a residue that is acidified with 1 N HCl. The mixture is diluted with water and extracted with ethyl acetate. The organic layer is dried ($Na_2SO_4$), and the solvent is removed in vacuo to afford 1.57 g (93%) of the title compound. $^1$H NMR (400 MHz, $CDCl_3$); HRMS ($ES^+$) m/z exact mass calculated for $C_{32}H_{30}O_5Cl$ 551.2045, found 551.2051.

EXAMPLE 64

3-{2-Ethyl-4-[3-methyl-5-(2-phenoxy-4-trifluoromethyl-phenoxy)-phenoxy]-phenyl}-propionic acid

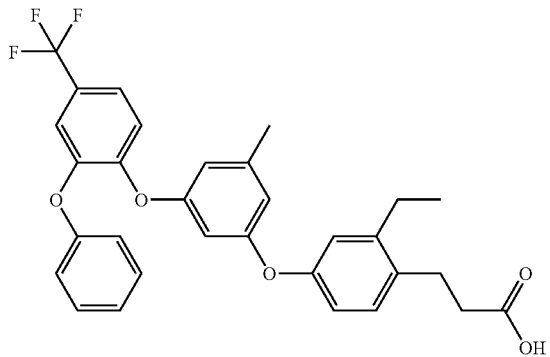

The title compound is prepared by using the procedure and intermediates of Example 63. $^1$H NMR (400 MHz, $CDCl_3$); HRMS ($ES^+$) m/z exact mass calculated for $C_{31}H_{28}O_5F_3$ 537.1888, found 537.1877.

EXAMPLE 65

3-{4-[3-(4-Chloro-2-phenoxy-phenoxy)-5-ethyl-phenoxy]-2-methyl-phenyl}-propionic acid

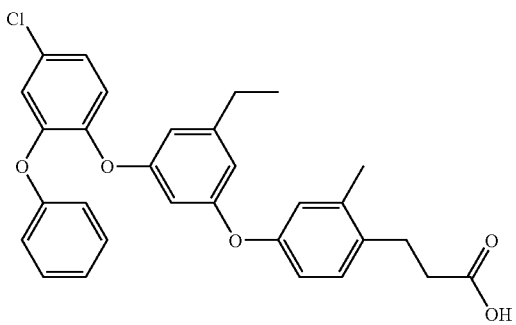

Step A 1,3-Dibromo-5-vinyl-benzene

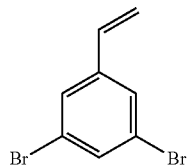

A solution of methyltriphenylphosphonium bromide (20.30 g, 56.8 mmol) in dry THF (50 mL) is cooled to 0° C. under $N_2$ and then treated with solid potassium tert-butoxide (6.38 g, 56.8 mmol) in portions. The resultant yellow slurry is warmed to rt and stirred for 30 minutes. The mixture is cooled to −78° C., and a solution of 3,5-dibromobenzaldehyde (10.0 g, 37.9 mmol) in THF (50 mL) is added dropwise. The reaction is warmed to rt and stirred for 1 hour. The mixture is poured into ice water containing 1 N HCl (56 mL) and then extracted with $Et_2O$. The organic layer is dried ($Na_2SO_4$), and the solvent is removed in vacuo to afford crude product that is absorbed on silica gel and purified by flash chromatography using 10/1 hexanes/ethyl acetate to afford 4.56 g (46%) of the title compound. $R_f$=0.64 (4/1 hexanes/EtOAc). $^1$H NMR (400 MHz, $CDCl_3$).

Step B 1,3-Dibromo-5-ethyl-benzene

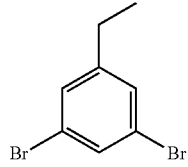

A mixture of 1,3-dibromo-5-vinyl-benzene (4.55 g, 17.4 mmol) and 20% $Pd(OH)_2/C$ (2.0 g) in THF (60 mL) is purged with $N_2$ and then $H_2$, and the mixture is stirred under a $H_2$ balloon at rt for 5 hours. The mixture is filtered through hyflo, and the solvent is removed in vacuo to afford crude product that is absorbed on silica gel and purified by flash chromatography using 15/1 hexanes/ethyl acetate to afford 3.38 g (74%) of the title compound. $R_f$=0.63 (9/1 hexanes/EtOAc). $^1$H NMR (400 MHz, $CDCl_3$).

Step C

3-[4-(3-Bromo-5-ethyl-phenoxy)-2-methyl-phenyl]-propionic acid methyl ester

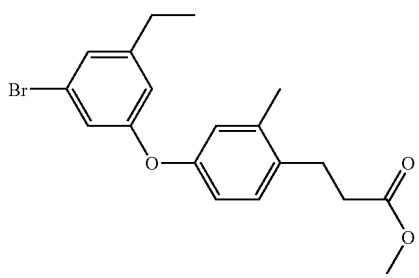

Compound of 1,3-dibromo-5-ethyl-benzene is reacted with 3-(4-hydroxy-2-methyl-phenyl)-propionic acid methyl ester as in Example 18 to afford 0.898 g (56%) of the title compound. $R_f$=0.32 (4/1 hexanes/EtOAc). $^1$H NMR (400 MHz, CDCl$_3$); MS (ES$^+$) m/z mass calculated for C$_{19}$H$_{21}$O$_3$Br 376, found 377 and 379 (M+1 and M+3, 100%).

Step D

3-{4-[3-(4-Chloro-2-phenoxy-phenoxy)-5-ethyl-phenoxy]-2-methyl-phenyl}-propionic acid The compound of 3-[4-(3-bromo-5-ethyl-phenoxy)-2-methyl-phenyl]-propionic acid methyl ester is reacted with 4-chloro-2-phenoxy-phenol as in Example 18 to afford 0.237 g (36%) of the title compound after saponification. $^1$H NMR (400 MHz, CDCl$_3$); HRMS (ES$^+$) m/z exact mass calculated for C$_{30}$H$_{28}$O$_5$Cl 503.1625, found 503.1625.

EXAMPLE 66

3-(4-{3-[2-(2-Fluoro-phenoxy)-4-trifluoromethyl-phenoxy]-5-methyl-phenoxy}-2-methyl-phenyl)-propionic acid

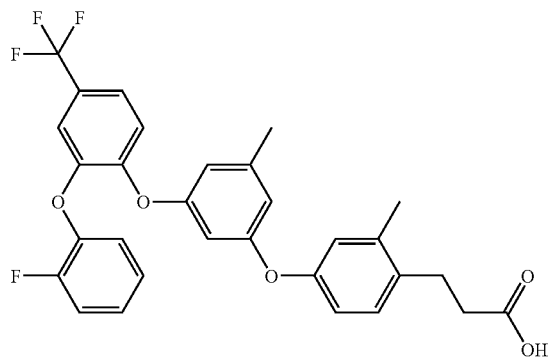

Step A 2-(3-Benzyloxy-5-methyl-phenoxy)-5-trifluoromethyl-phenol

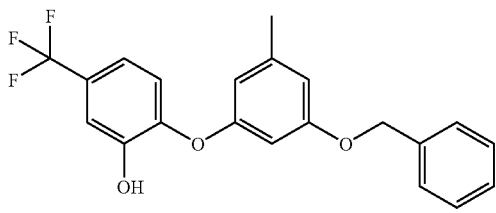

A solution of Example 63, Step A intermediate (5.89 g, 13.5 mmol) in dry THF (60 mL) is cooled to −78° C. and treated with a 1.6 M solution of n-butyl lithium in hexanes (11.8 mL, 18.9 mmol) and stirred for 5 minutes at −78° C. under N$_2$. Trimethyl borate (1.96 g, 18.9 mmol) is added dropwise, and the mixture is warmed to 0° C. and stirred for 20 minutes. The mixture is treated dropwise with a 30% aqueous solution of H$_2$O$_2$ (3.05 g, 26.9 mmol) and stirred for 15 minutes at 0° C. and warmed to rt and stirred for 1 hour. The reaction is acidified with 1 N HCl, diluted with ethyl acetate and then extracted with water and saturated aqueous Na$_2$S$_2$O$_3$. The organic layer is dried (Na$_2$SO$_4$), and the solvent is removed in vacuo to afford crude product that is absorbed on silica gel and purified by flash chromatography using 8/1 hexanes/ethyl acetate to afford 3.68 g (73%) of the title compound. $R_f$=0.49 (2/1 hexanes/EtOAc). $^1$H NMR (400 MHz, CDCl$_3$); HRMS (ES$^-$) m/z mass calculated for C$_{21}$H$_{16}$O$_3$F$_3$ 373.1052, found 373.1039.

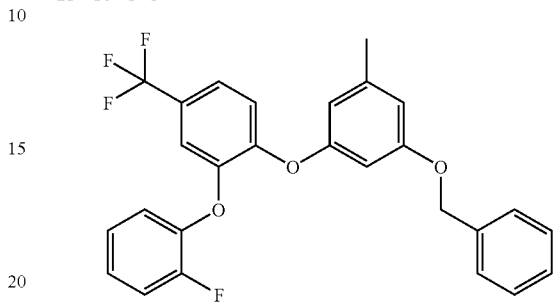

A mixture of 2-(3-benzyloxy-5-methyl-phenoxy)-5-trifluoromethyl-phenol (0.42 g, 1.12 mmol), 1-bromo-2-fluorobenzene (0.39 g, 2.22 mmol), cesium carbonate (0.439 g, 1.35 mmol), and 2,2,6,6-tetramethyl-3,5-heptanedione (0.052 g, 0.282 mmol) and copper (I) chloride (0.056 g, 0.566 mmol) in toluene (8 mL) is heated to reflux for 18 hours under N$_2$. The reaction is cooled, and the mixture is acidified with 1 N HCl. The mixture is diluted with water and extracted with Et$_2$O. The organic layer is dried (Na$_2$SO$_4$) and the solvent is removed in vacuo to afford crude product that is absorbed on silica gel and purified by flash chromatography using 15/1 hexanes/ethyl acetate to afford 0.094 g (18%) of the title compound. $^1$H NMR (400 MHz, CDCl$_3$); MS (ES$^+$) m/z mass calculated for C$_{27}$H$_{20}$O$_3$F$_4$ 468, found 469 (M+1, 100%).

Step C 3-(4-{3-[2-(2-Fluoro-phenoxy)-4-trifluoromethyl-phenoxy]-5-methyl-phenoxy}-2-methyl-phenyl)-propionic acid Compound obtained in Step B is reacted with 3-(4-fluoro-2-methyl-phenyl)-acrylic acid ethyl ester (Example 22) as in Example 63 to afford 0.070 g (19%) of the title compound. $^1$H NMR (400 MHz, CDCl$_3$); MS (ES$^+$) m/z mass calculated for C$_{30}$H$_{24}$O$_5$F 540, found 541 (M+1, 100%).

EXAMPLE 67

3-{4-[3-(4-Chloro-2-phenoxy-phenoxy)-2-methyl-phenoxy]-2-methyl-phenyl}-propionic acid

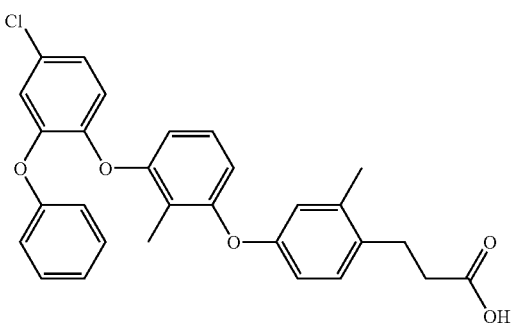

Step A

3-[4-(3-Bromo-2-methyl-phenoxy)-2-methyl-phenyl]-propionic acid methyl ester

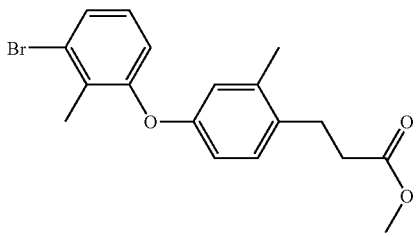

A mixture of 3-(4-hydroxy-2-methyl-phenyl)-propionic acid methyl ester (2.0 g, 10.3 mmol), 2,6-dibromotoluene (7.72 g, 30.9 mmol), cesium carbonate (4.03 g, 12.4 mmol), and 2,2,6,6-tetramethyl-3,5-heptanedione (0.47 g, 2.55 mmol) in 1-methyl-2-pyrrolidinone (20 mL) is purged with $N_2$, and then copper (I) chloride (0.51 g, 5.15 mmol) is added. The reaction is heated to 120° C. for 17 hours under $N_2$, and then cooled and quenched with 1 N HCl (50 mL). The mixture is diluted with water and extracted with $Et_2O$. The organic layer is dried ($Na_2SO_4$), and the solvent is removed in vacuo to afford crude product that is absorbed on silica gel and purified by flash chromatography using 9/1 hexanes/ethyl acetate to afford 2.92 g (78%) of the title compound. $R_f$=0.35 (4/1 hexanes/EtOAc). $^1$H NMR (400 MHz, $CDCl_3$); MS ($ES^+$) m/z mass calculated for $C_{18}H_{19}O_3Br$ 362, found 363 and 365 (M+1 and M+3, 100%).

Step B

3-{4-[3-(4-Chloro-2-phenoxy-phenoxy)-2-methyl-phenoxy]-2-methyl-phenyl}-propionic acid 3-[4-(3-bromo-2-methyl-phenoxy)-2-methyl-phenyl]-propionic acid methyl ester is reacted with 4-chloro-2-phenoxy-phenol as in Example 18 to afford 0.031 g (9%) of the title compound. $^1$H NMR (400 MHz, $CDCl_3$); MS ($ES^+$) m/z mass calculated for $C_{29}H_{25}O_5Cl$ 488, found 489 and 491 (M+1 and M+3, 100%).

EXAMPLE 68

3-{4-[3-(2'-Fluoro-5-trifluoromethyl-biphenyl-2-yloxy)-5-methyl-phenoxy]-2-methyl-phenyl}-propionic acid

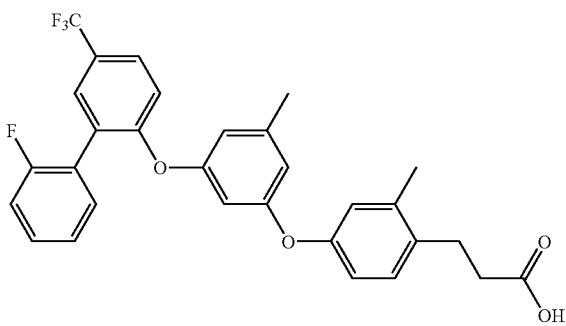

The tile compound is prepared by reacting 3-{4-[3-(2-bromo-4-trifluoromethyl-phenoxy)-5-methyl-phenoxy]-2-methyl-phenyl}-propionic acid ethyl ester with 2-fluorobenzene boronic acid as in Example 38 to afford 0.216 g (88%). $^1$H NMR (400 MHz, $CDCl_3$); HRMS ($ES^+$) m/z exact mass calculated for $C_{30}H_{25}O_4F_4$ 525.1689, found 525.1675.

EXAMPLE 69

3-{4-[3-(4-Chloro-2-phenoxy-phenoxy)-5-methyl-phenoxy]-2-ethyl-phenyl}-propionic acid

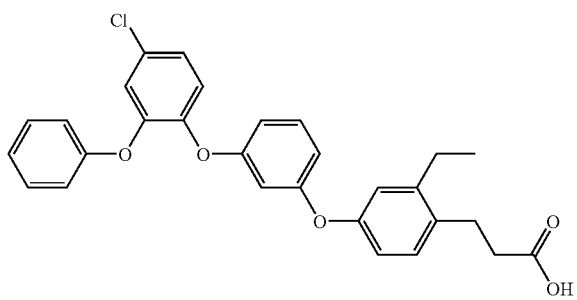

Step A

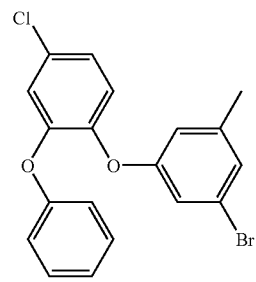

A mixture of 4-chloro-2-phenoxy-phenol (6.46 g, 29.3 mmol), 3,5-dibromotoluene (21.95 g, 87.8 mmol), cesium carbonate (11.45 g, 35.1 mmol), and 2,2,6,6-tetramethyl-3,5-heptanedione (1.35 g, 7.33 mmol) in 1-methyl-2-pyrrolidinone (65 mL) is purged with $N_2$, and copper (I) chloride (1.45 g, 14.6 mmol) is added. The reaction heated to 120° C. for 20 hours under $N_2$. The reaction is cooled and quenched with 1 N HCl (20 mL). The mixture is then diluted with water and extracted with $Et_2O$. The organic layer is dried ($Na_2SO_4$), and the solvent is removed in vacuo to afford crude product that is absorbed on silica gel and purified by flash chromatography using 100% hexanes to afford 7.84 g (69%) of the title compound. $R_f$=0.49 (9/1 hexanes/ethyl acetate). $^1$H NMR (400 MHz, $CDCl_3$).

Step B

3-{4-[3-(4-Chloro-2-phenoxy-phenoxy)-5-methyl-phenoxy]-2-ethyl-phenyl}-propionic acid A mixture of compound obtained in Step A (0.30 g, 0.770 mmol), 3-(2-ethyl-4-hydroxy-phenyl)-propionic acid ethyl ester (0.170 g, 0.77 mmol), cesium carbonate (0.301 g, 0.924 mmol), copper (I) chloride (0.038 g, 0.384 mmol) and 2,2,6,6-tetramethyl-3,5-heptanedione (0.035 g, 0.190 mmol) in 1-methyl-2-pyrrolidinone (6 mL) is heated to 120° C. for 17 hours under $N_2$. The reaction is treated with aqueous 5 N NaOH (3 mL) and then cooled to rt and stirred until saponification is completed. The reaction is acidified with aqueous 1 N HCl, and the resultant mixture is diluted with water and extracted with $Et_2O$. The organic layer is dried ($Na_2SO_4$), and the solvent is removed in vacuo to afford crude product that is purified by preparative HPLC to afford 0.014 g (4%) of the title compound. $^1$H NMR (400 MHz, $CDCl_3$); MS ($ES^+$) m/z mass calculated for $C_{30}H_{27}O_5Cl$ 502, found 503, and 505 (M+1 and M+3, 100%).

EXAMPLE 70

{4-[3-(4-Chloro-2-phenoxy-phenoxy)-5-methyl-phenoxy]-2-methyl-phenylsulfanyl}-acetic acid

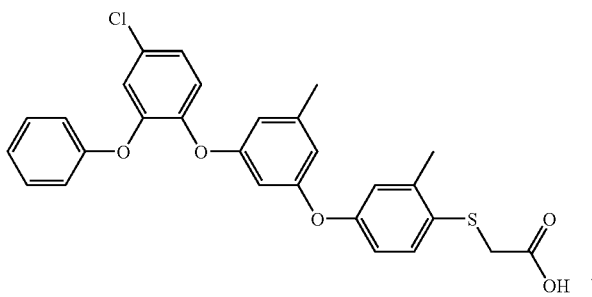

The title compound is prepared by reacting the compound of Example 69, Step A with (4-hydroxy-2-methyl-phenylsulfanyl)-acetic acid ethyl ester to afford 0.037 g (11%). $^1$H NMR (400 MHz, $CDCl_3$); MS ($ES^+$) m/z mass calculated for $C_{28}H_{23}O_5Cl$ 506, found 507 and 509 (M+1 and M+3, 100%).

EXAMPLE 71

{4-[3-(4-Chloro-2-phenoxy-phenoxy)-5-methyl-phenoxy]-3-methyl-phenyl}-acetic acid

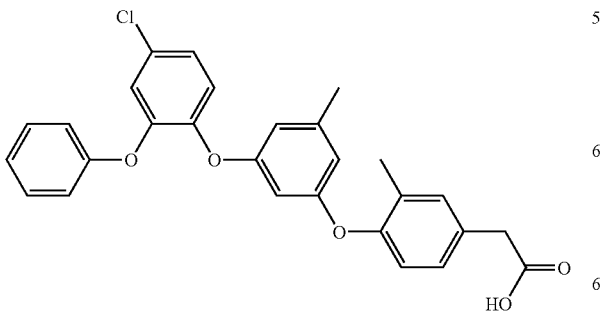

The title compound is prepared by reacting the compound of Example 69, Step A with (4-hydroxy-3-methyl-phenyl)-acetic acid methyl ester to afford 0.019 g (6%).

$^1$H NMR (400 MHz, $CDCl_3$); MS ($ES^+$) m/z mass calculated for $C_{28}H_{23}O_5Cl$ 474, found 475 and 477 (M+1 and M+3, 100%).

EXAMPLE 72

{4-[3-(4-Chloro-2-phenoxy-phenoxy)-5-methyl-phenoxy]-phenyl}-acetic acid

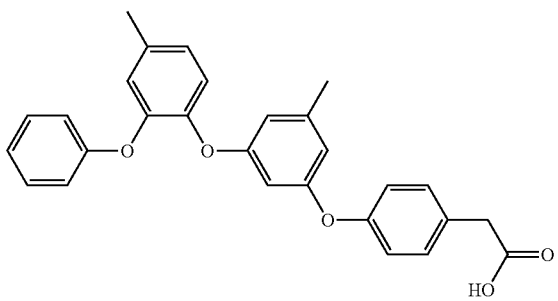

The title compound is prepared by reacting the compound of Example 69, Step A with (4-hydroxy-phenyl)-acetic acid methyl ester to afford 0.034 g (10%). $^1$H NMR (400 MHz, $CDCl_3$); MS ($ES^+$) m/z mass calculated for $C_{27}H_{21}O_5Cl$ 460, found 461 and 463 (M+1 and M+3, 100%).

EXAMPLE 73

3-{3-[3-(4-Chloro-2-phenoxy-phenoxy)-5-methyl-phenoxy]-phenyl}-propionic acid

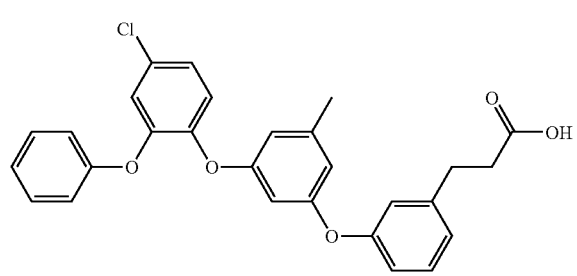

The title compound is prepared by reacting the compound of Example 69, Step A with 3-(3-hydroxy-phenyl)-propionic acid methyl ester to afford 0.011 g (4%). $^1$H NMR (400 MHz, $CDCl_3$); MS ($ES^+$) m/z mass calculated for $C_{28}H_{23}O_5Cl$ 474, found 475 and 475 (M+1 and M+3, 100%).

EXAMPLE 74

{3-[3-(4-Chloro-2-phenoxy-phenoxy)-5-methyl-phenoxy]-phenyl}-acetic acid

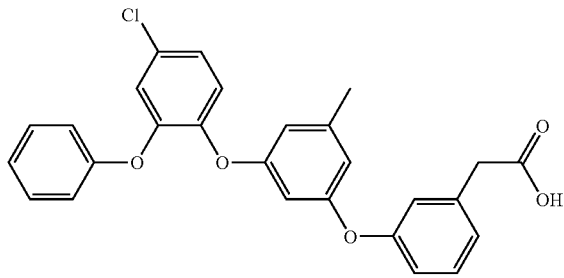

The title compound is prepared by reacting the compound of Example 69, Step A with (3-hydroxy-phenyl)-acetic acid methyl ester to afford 0.070 g (21%). $^1$H NMR (400 MHz, CDCl$_3$); MS (ES$^+$) m/z mass calculated for C$_{27}$H$_{21}$O$_5$Cl 460, found 461 and 463 (M+1 and M+3, 100%).

EXAMPLE 75

3-{2-Methyl-4-[2-methyl-5-(2-phenoxy-4-trifluoromethyl-phenoxy)-phenoxy]-phenyl}-propionic acid

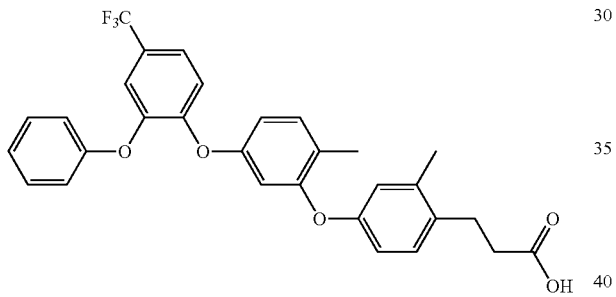

Step A

3-{4-[5-(2-Bromo-4-trifluoromethyl-phenoxy)-2-methyl-phenoxy]-2-methyl-phenyl}-propionic acid ethyl ester

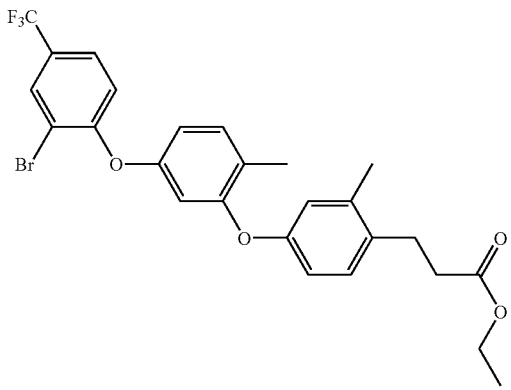

A mixture of 3-[4-(5-hydroxy-2-methyl-phenoxy)-2-methyl-phenyl]-propionic acid ethyl ester (Example 84, Step D) (0.46 g, 1.46 mmol), 3-bromo-4-fluorobenzotrifluoride (0.35 g, 1.45 mmol) and 325 mesh potassium carbonate (0.21 g, 1.52 mmol) in dry DMSO (10 mL) is heated to 100° C. and stirred for 6 hours under N$_2$. The reaction is cooled and acidified with 1 N HCl. The mixture is diluted with water and extracted with Et$_2$O. The organic layer is dried (Na$_2$SO$_4$), and the solvent is removed in vacuo to afford crude product that is absorbed on silica gel and purified by flash chromatography using 9/1 hexanes/ethyl acetate to afford 0.633 g (81%) of the title compound. R$_f$=0.38 (4/1 hexanes/EtOAc). $^1$H NMR (400 MHz, CDCl$_3$); MS (ES$^+$) m/z mass calculated for C$_{26}$H$_{24}$O$_4$F$_3$Br 536, found 554 and 556 (M+NH$_4$, 100%).

Step B

3-{2-Methyl-4-[2-methyl-5-(2-phenoxy-4-trifluoromethyl-phenoxy)-phenoxy]-phenyl}-propionic acid 3-{4-[5-(2-Bromo-4-trifluoromethyl-phenoxy)-2-methyl-phenoxy]-2-methyl-phenyl}-propionic acid ethyl ester is reacted with phenol as in Example 45 to afford 0.168 g (33%) of the title compound. $^1$H NMR (400 MHz, CDCl$_3$); HRMS (ES$^+$) m/z exact mass calculated for C$_{30}$H$_{26}$O$_5$F$_3$ 523.1732, found 523.1736.

EXAMPLE 76

3-{2-Methyl-4-[4-methyl-3-(2-phenoxy-4-trifluoromethyl-phenoxy)-phenoxy]-phenyl}-propionic acid

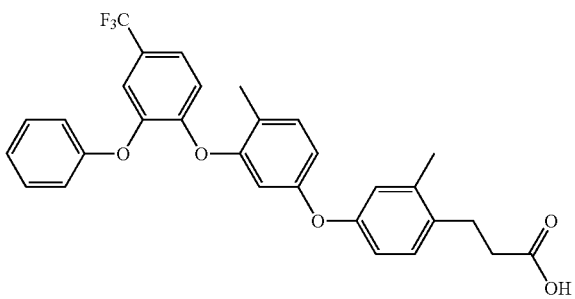

Step A

3-{4-[3-(2-Bromo-4-trifluoromethyl-phenoxy)-4-methyl-phenoxy]-2-methyl-phenyl}-propionic acid ethyl ester

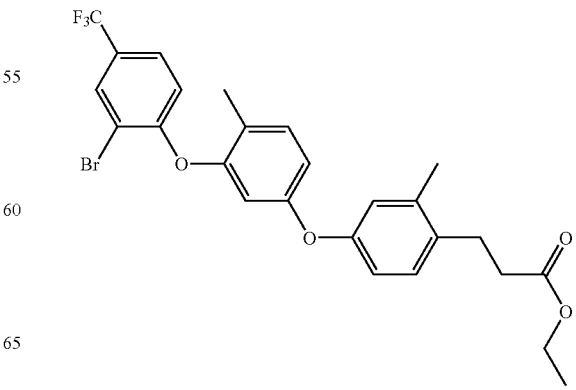

A mixture of 3-[4-(3-hydroxy-4-methyl-phenoxy)-2-methyl-phenyl]-propionic acid ethyl ester (Example 82, Step J) (1.05 g, 3.34 mmol), 3-bromo-4-fluorobenzotrifluoride (0.81 g, 3.34 mmol) and 325 mesh potassium carbonate (0.55 g, 3.97 mmol) in dry DMSO (15 mL) is heated to 100° C. and stirred for 6 hours under $N_2$. The reaction is cooled and acidified with 1 N HCl. The mixture is diluted with water and extracted with $Et_2O$. The organic layer is dried ($Na_2SO_4$), and the solvent is removed in vacuo to afford crude product that is absorbed on silica gel and purified by flash chromatography using 9/1 hexanes/ethyl acetate to afford 1.57 g (88%) of the title compound. $R_f$=0.38 (4/1 hexanes/EtOAc). $^1$H NMR (400 MHz, $CDCl_3$); MS ($ES^+$) m/z mass calculated for $C_{26}H_{24}O_4F_3Br$ 536, found 554 and 556 (M+$NH_4$, 100%).

Step B

3-{2-Methyl-4-[4-methyl-3-(2-phenoxy-4-trifluoromethyl-phenoxy)-phenoxy]-phenyl}-propionic acid The compound of 3-{4-[3-(2-Bromo-4-trifluoromethyl-phenoxy)-4-methyl-phenoxy]-2-methyl-phenyl}-propionic acid ethyl ester is reacted with phenol as in Example 45 to afford 0.256 g (57%) of the title compound. $^1$H NMR (400 MHz, $CDCl_3$); HRMS ($ES^+$) m/z exact mass calculated for $C_{30}H_{26}O_5F_3$ 523.1732, found 523.1749.

EXAMPLE 77

3-{2-Methyl-4-[3-methyl-5-(2-phenoxy-3-trifluoromethyl-phenoxy)-phenoxy]-phenyl}-propionic acid

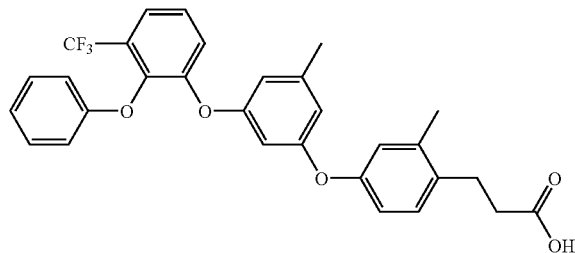

Step A

2-Fluoro-3-methoxybenzotrifluoride

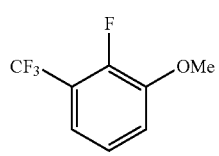

A mixture of 2-fluoro-3-(trifluoromethyl)-phenol (4.87 g, 27.04 mmol) and iodomethane (4.60 g, 32.4 mmol) in acetone (50 mL) is cooled to 0° C. and then 325 mesh potassium carbonate (4.48 g, 32.4 mmol) is added. The reaction is warmed to rt and stirred for 17 hours under $N_2$. The reaction filtered to remove the solids, and the filtrate is acidified with 1 N HCl. The mixture is diluted with water and extracted with $Et_2O$. The organic layer is dried ($Na_2SO_4$), and the solvent is removed in vacuo to afford 4.76 g (91%) of 2-fluoro-3-methoxybenzotrifluoride that is utilized without purification. $R_f$=0.35 (4/1 hexanes/EtOAc). $^1$H NMR (400 MHz, $CDCl_3$).

Step B

2-Phenoxy-3-trifluoromethyl-phenol

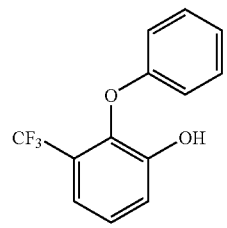

A mixture of 2-fluoro-3-methoxybenzotrifluoride (4.76 g, 24.5 mmol), phenol (2.30 g, 24.4 mmol) and 325 mesh potassium carbonate (4.07 g, 29.4 mmol) in dry DMSO (50 mL) is heated to 130° C. and stirred 17 hours under $N_2$. The reaction filtered to remove the solids, and the filtrate is acidified with 1 N HCl. The mixture is then diluted with water and extracted with $Et_2O$. The organic layer is dried ($Na_2SO_4$) and the solvent is removed in vacuo to afford crude product that is absorbed on silica gel and purified by flash chromatography using 12/1 hexanes/ethyl acetate to afford 3.47 g (53%) of 2-phenoxy-3-trifluoromethyl-anisole ($R_f$=0.30 (4/1 hexanes/EtOAc) that is contaminated with starting 2-fluoro-1-methoxy-3-trifluoromethyl-benzene.

A −78° C. solution of the crude 2-phenoxy-3-trifluoromethyl-anisole (3.47 g, 12.9 mmol) in $CH_2Cl_2$ (35 mL) is treated with $BBr_3$ (12.99 g, 51.8 mmol), and the mixture is warmed to 0° C. and stirred for 1.5 h under $N_2$. The reaction is poured into ice water and then extracted with $Et_2O$. The organic layer is dried ($Na_2SO_4$), and the solvent is removed in vacuo to afford crude material that is absorbed on silica gel and columned with 96/4 chloroform/methyl tert-butyl ether to afford 1.51 g (24%) of 2-phenoxy-3-trifluoromethyl-phenol. $R_f$=0.34 (96/4 chloroform/methyl tert-butyl ether). $^1$H NMR (400 MHz, $CDCl_3$); MS (ES−$^+$) m/z mass calculated for $C_{13}H_9O_2F_3$ 254, found 253 (M+1, 100%).

Step C

3-{2-Methyl-4-[3-methyl-5-(2-phenoxy-3-trifluoromethyl-phenoxy)-phenoxy]-phenyl}-propionic acid 2-Phenoxy-3-trifluoromethyl-phenol is reacted with 3-[4-(3-bromo-5-methyl-phenoxy)-2-methyl-phenyl]-propionic acid methyl ester as in Example 18 to afford 0.125 g (17%) of the title compound. $^1$H NMR (400 MHz, $CDCl_3$); MS ($ES^+$) m/z mass calculated for $C_{30}H_{25}O_5F_3$ 522, found 523 (M+1, 100%).

EXAMPLE 78

3-{2-Methyl-4-[3-methyl-5-(2-phenoxy-5-trifluoromethyl-phenoxy)-phenoxy]-phenyl}-propionic acid

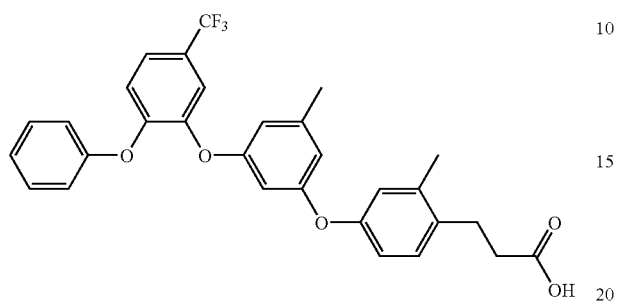

Step A

2-Phenoxy-5-trifluoromethyl-phenol

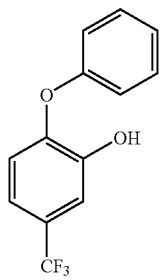

A mixture of 4-fluoro-3-methoxybenzotrifluoride (5.26 g, 28.9 mmol), phenol (2.71 g, 28.8 mmol) and 325 mesh potassium carbonate (4.79 g, 34.7 mmol) in dry DMSO (50 mL) is heated to 130° C. and stirred for 17 hours under $N_2$. The reaction is filtered, and the filtrate is acidified with 1 N HCl. The mixture is diluted with water and extracted with $Et_2O$. The organic layer is dried ($Na_2SO_4$), and the solvent is removed in vacuo to afford crude product that is absorbed on silica gel and purified by flash chromatography using 15/1 hexanes/ethyl acetate to afford 3.79 g (49%) of the title compound ($R_f$=0.47 (4/1 hexanes/EtOAc) that is contaminated with starting 4-fluoro-3-methoxybenzotrifluoride.

A −78° C. solution of the crude 2-phenoxy-5-trifluoromethyl-anisole (3.79 g, 14.1 mmol) in $CH_2Cl_2$ (38 mL) is treated with $BBr_3$ (14.04 g, 56.1 mmol) and then warmed to 0° C. The mixture is stirred for 1.5 h under $N_2$, poured into ice water and extracted with $Et_2O$. The organic layer is dried ($Na_2SO_4$), and the solvent is removed in vacuo to afford crude material that is absorbed on silica gel and columned with 6/1 hexanes/ethyl acetate to afford 1.29 g (18%) of the title compound. $^1$H NMR (400 MHz, $CDCl_3$); MS (ES−$^+$) m/z mass calculated for $C_{13}H_9O_2F_3$ 254, found 253 (M+1, 100%).

Step 13

3-{2-Methyl-4-[3-methyl-5-(2-phenoxy-5-trifluoromethyl-phenoxy)-phenoxy]-phenyl}-propionic acid The compound of 2-phenoxy-5-trifluoromethyl-phenol is reacted with 3-[4-(3-bromo-5-methyl-phenoxy)-2-methyl-phenyl]-propionic acid methyl ester as in Example 18 to afford 0.262 g (34%) of the title compound. $^1$H NMR (400 MHz, $CDCl_3$); MS (ES$^+$) m/z mass calculated for $C_{30}H_{25}O_5F_3$ 522, found 523 (M+1, 100%).

EXAMPLE 79

3-{2-Methyl-4-[3-methyl-5-(3-phenoxy-5-trifluoromethyl-pyridin-2-yloxy)-phenoxy]-phenyl}-propionic acid The title compound is prepared according to Example 8 by using 3-phenoxy-5-trifluoromethyl-pyridin-2-ol and 3-[4-(3-bromo-5-methyl-phenoxy)-2-methyl-phenyl]-propionic acid methyl ester to afford 32 mg (6%). $^1$H NMR (400 MHz, $CDCl_3$); MS (ES$^+$) m/z mass calcd for $C_{29}H_{24}O_5NF_3$ 523, found 524 (M+1, 100%).

EXAMPLE 80

3-{2-Methyl-4-[3-methyl-5-(2-oxo-3-phenoxy-5-trifluoromethyl-2H-pyridin-1-yl)-phenoxy]-phenyl}-propionic acid The title compound is prepared according to Example 8 by using 3-phenoxy-5-trifluoromethyl-pyridin-2-ol and 3-[4-(3-bromo-5-methyl-phenoxy)-2-methyl-phenyl]-propionic acid methyl ester to afford 37 mg (7%). $^1$H NMR (400 MHz, $CDCl_3$); MS (ES$^+$) m/z mass calcd for $C_{29}H_{24}O_5NF_3$ 523, found 524 (M+1, 100%).

EXAMPLE 81

3-{2-Methyl-4-[3-(2-phenoxy-4-trifluoromethyl-phenoxy)-phenoxy]-phenyl}-propionic acid

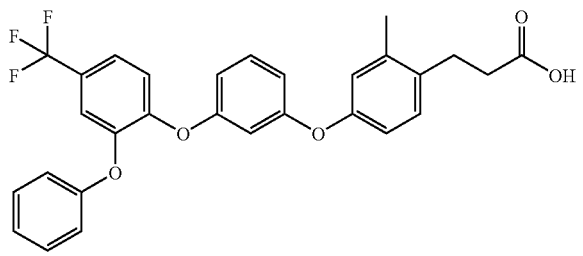

Step A

3-Benzyloxy-1-bromobenzene

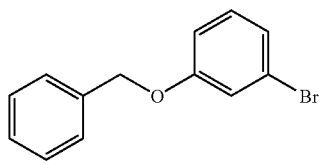

A mixture of 3-bromophenol (10.0 g, 57.8 mmol) and 325 mesh potassium carbonate (8.79 g, 63.6 mmol) in DMF (100 mL) is treated dropwise with benzyl bromide (9.89 g, 57.8 mmol) and then stirred 20 hours at rt under $N_2$. The reaction is filtered, and the filtrate is acidified with 1 N HCl. The mixture is then diluted with water and extracted with $Et_2O$. The organic layer is dried ($Na_2SO_4$), and the solvent is removed in vacuo to afford crude product that is absorbed on silica gel and purified by flash chromatography using 10/1 hexanes/ethyl acetate to afford 14.55 g (96%) of the titled compound. $R_f$=0.86 (4/1 hexanes/EtOAc). $^1$H NMR (400 MHz, $CDCl_3$).

Step B

3-[4-(3-Benzyloxy-phenoxy)-2-methyl-phenyl]-propionic acid methyl ester

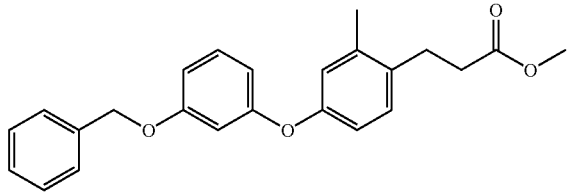

A mixture of 3-benzyloxy-1-bromobenzene (14.53 g, 55.2 mmol), 3-(4-hydroxy-2-methyl-phenyl)-propionic acid methyl ester (10.72 g, 55.2 mmol), cesium carbonate (21.59 g, 66.3 mmol), and 2,2,6,6-tetramethyl-3,5-heptanedione (2.54 g, 13.8 mmol) in 1-methyl-2-pyrrolidinone (100 mL) is purged with $N_2$ and then copper (I) chloride (2.73 g, 27.6 mmol) is added. The reaction mixture is heated to 120° C. for 18 hours under $N_2$. The mixture is then diluted with water and extracted with $Et_2O$. The organic layer is dried ($Na_2SO_4$), and the solvent is removed in vacuo to afford crude product that is absorbed on silica gel and purified by flash chromatography using a gradient of 19/1 to 9/1 hexanes/ethyl acetate to afford 10.54 g (51%) of the titled compound. $R_f$=0.53 (100% hexanes). $^1$H NMR (400 MHz, $CDCl_3$); MS (ES$^+$) m/z mass calcd for $C_{24}H_{24}O_4$ 376, found 377 (M+1, 100%).

Step C

3-[4-(3-Hydroxy-phenoxy)-2-methyl-phenyl]-propionic acid methyl ester

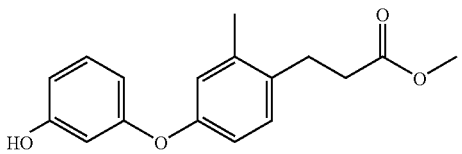

A mixture of 3-[4-(3-benzyloxy-phenoxy)-2-methyl-phenyl]-propionic acid methyl ester (10.54 g, 28.0 mmol) and 10% Pd/C (5 g) in ethyl acetate (150 mL) is purged with $N_2$ and then $H_2$. The mixture is stirred under a hydrogen balloon. Upon completion, the mixture is filtered through hyflo, and the solvent is removed in vacuo to afford 8.18 g (100%) of the titled compound. $R_f$=0.59 (4/1 hexanes/EtOAc). $^1$H NMR (400 MHz, $CDCl_3$); MS (ES$^+$) m/z mass calcd for $C_{17}H_{18}O_4$ 286, found 287 (M+1, 100%).

Step D

3-{4-[3-(2-Bromo-4-trifluoromethyl-phenoxy)-phenoxy]-2-methyl-phenyl}-propionic acid methyl ester

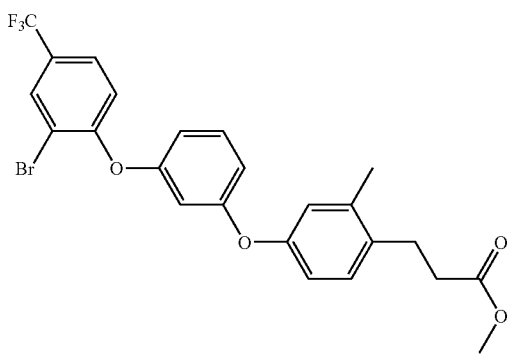

A mixture of 3-[4-(3-hydroxy-phenoxy)-2-methyl-phenyl]-propionic acid methyl ester (8.18 g, 28.6 mmol), 3-bromo-4-fluorobenzotrifluoride (6.80 g, 28.0 mmol) and 325 mesh potassium carbonate (4.64 g, 33.68 mmol) in dry DMSO (80 mL) is heated to 100° C. and stirred 6 hours under $N_2$. The reaction is cooled and acidified with 1 N HCl. The mixture is diluted with water and extracted with $Et_2O$. The organic layer is dried ($Na_2SO_4$, and the solvent is removed in vacuo to afford crude product that is absorbed on silica gel and purified by flash chromatography using 15/1 hexanes/ethyl acetate to afford 11.74 g (81%) of the titled compound. $R_f=0.76$ (9/1 hexanes/EtOAc). $^1$H NMR (400 MHz, CDCl$_3$); MS (ES$^+$) m/z mass calcd for C$_{24}$H$_{20}$O$_4$F$_3$Br 509, found 526 and 528 (M+NH$_4$, 100%).

Step E

3-{2-Methyl-4-[3-(2-phenoxy-4-trifluoromethyl-phenoxy)-phenoxy]-phenyl}-propionic acid The title compound is prepare by reacting the compound of 3-{4-[3-(2-bromo-4-trifluoromethyl-phenoxy)-phenoxy]-2-methyl-phenyl}-propionic acid methyl ester with o-cresol as in Example 45 to afford 0.229 g (21%). $^1$H NMR (400 MHz, CDCl$_3$); MS (ES$^+$) m/z mass calcd for C$_{30}$H$_{25}$O$_5$F$_3$ 522, found 523 (M+1, 100%).

EXAMPLE 82

3-[4-(3-hydroxy-4-methyl-phenoxy)-2-methyl-phenyl]-propionic acid ethyl ester

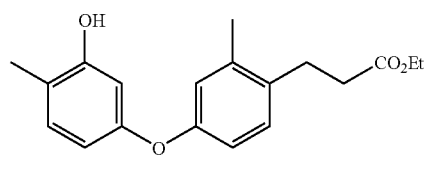

Step A

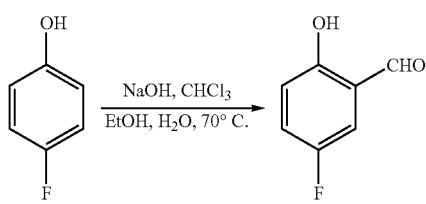

A solution of NaOH (78 g, 1950 mmol) in H$_2$O (400 mL) is added to a solution of 4-fluorophenol (50 g, 446.43 mmol) in a mixture of H$_2$O (200 mL) and EtOH (150 mL). After the mixture is warmed to 70° C., CHCl$_3$ (110 mL) is added dropwise (addition funnel, about 2 h), and the mixture is stirred at this temperature overnight (c.a. 16 h). It is allowed to reach r.t. and acidified with HCl (3M). The reaction is partitioned between brine and CH$_2$Cl$_2$, and the organic layer is dried, filtered and concentrated. The crude residue is flash chromatographed on SiO$_2$ (3% EtOAc/hexanes) to afford 13.6 of the title compound (22%, white solid).

Step B

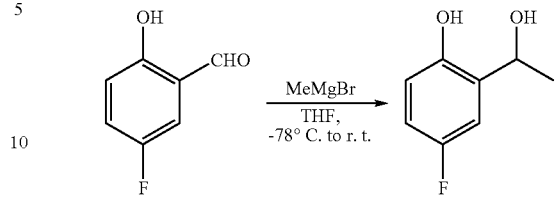

MeMgBr (10 mL, 3 M solution in Et$_2$O) is added to a −78° C. cooled solution of aldehyde (2 g, 14.285 mmol) in THF (30 mL). The mixture is allowed to reach r.t., stirred for 30 min. and poured into brine. It is acidified with diluted HCl and extracted with EtOAc. The organic layer is dried, filtered and concentrated, to give a crude residue that is purified by flash chromatography on SiO$_2$ (10-15% EtOAc/hexanes) to afford 2.1 g of the addition product (94%, colorless oil).

Step C

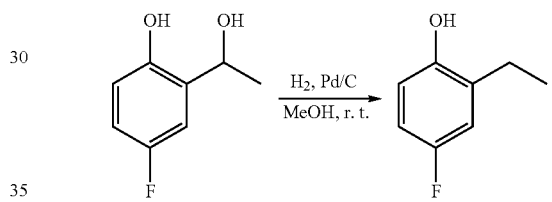

A mixture of Pd/C (1.2 g, 10% Pd on activated carbon, 1.128 mmol) and the hydroxyphenol (11.6 g, 74.35 mmol) in MeOH (100 mL) is stirred under H$_2$ atmosphere (balloon) for 7 h. The mixture is filtered through Celite (EtOAc washings), and the solvent is removed in a rotatory evaporator. The crude residue is flash chromatographed on SiO$_2$ (10-15% EtOAc/hexanes) to afford 10.25 g of 2-ethyl-4-fluorophenol (99%, colorless oil).

Step D

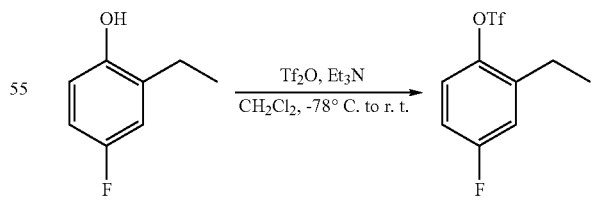

Triflic anhydride (13.4 mL, 79.65 mmol) is added to a −78° C. cooled solution of ethylfluorophenol (10.2 g, 72.85 mmol) and Et$_3$N (20 mL, 143.38 mmol) in CH$_2$Cl$_2$ (100 mL). The mixture is allowed to reach r.t., poured into brine, and extracted with CH$_2$Cl$_2$. The organic layer is washed with HCl (3%) and brine, dried, filtered and concentrated to give a crude residue that is flash chromatographed on SiO$_2$ (3% EtOAc/hexanes) affording 13.9 g of the desired triflate (70%, colorless oil).

Step E

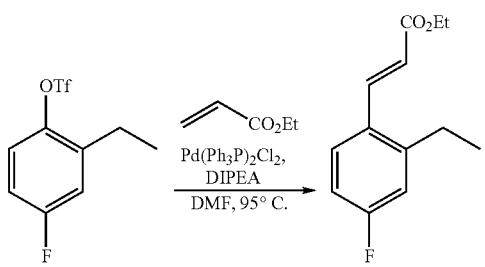

A mixture of ethyl acrylate (25 mL, 277.6 mmol), DIPEA (25 mL, 143.52 mmol), Pd(Ph$_3$P)$_2$Cl$_2$ (2 g, 2.85 mmol) and ehtylfluorotriflate (10 g, 36.764 mmol) in DMF (60 mL) is warmed to 95° C. and stirred at this temperature for 70 h. The mixture is allowed to reach r.t., filtered through Celite (EtOAc washings) and partitioned between EtOAc and brine. The organic layer is washed with HCl (3%), dried, filtered and concentrated to give a crude residue that is flash chromatographed on SiO$_2$ (1% EtOAc/hexanes) affording 4.6 g of the title compound and 3.5 g of unreacted starting triflate (56%, colorless oil).

Step F

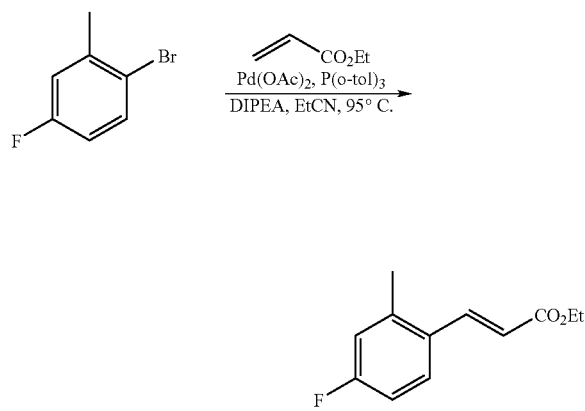

A mixture of 4-bromo-3-methylfluorobenzene (8 g, 42.32 mmol), ethyl acrylate (12 mL, 133.25 mmol), Pd(OAc)$_2$ (960 mg, 4.276 mmol), P(o-tol)$_3$ (2.56 g, 8.41 mmol) and DIPEA (12 mL, 68.89 mmol) in EtCN (100 mL) is warmed to 95° C., and stirred at this temperature for 7 h. The reaction is allowed to reach r.t., filtered through Celite, and partitioned between EtOAc and HCl (3%). The organic layer is dried, filtered and concentrated to give a crude residue that is flash chromatographed on SiO$_2$ (2% EtOAc/hexanes) affording 8.1 g of the Heck product (92%, colorless oil).

Step G

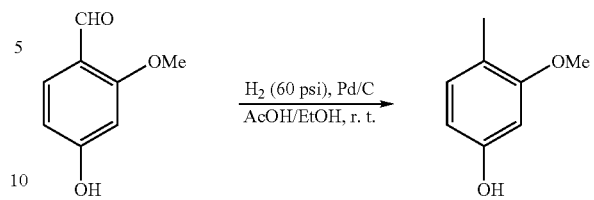

A mixture of Pd/C (1 g, 10% Pd on activated C, 0.94 mmol) and the aldehyde (3.9 g, 25.658 mmol) in EtOH (75 mL) and glacial AcOH (15 mL) is stirred at r.t. under H$_2$ atmosphere (60 psi) overnight (c.a. 14 h). The mixture is filtered through Celite, and the solvent is removed in a rotatory evaporator. The crude residue is purified by flash chromatography on SiO$_2$ (15% EtOAc/hexanes) to afford 3.14 g of 4-methyl-3-methoxyphenol (89%, colorless oil).

Step H

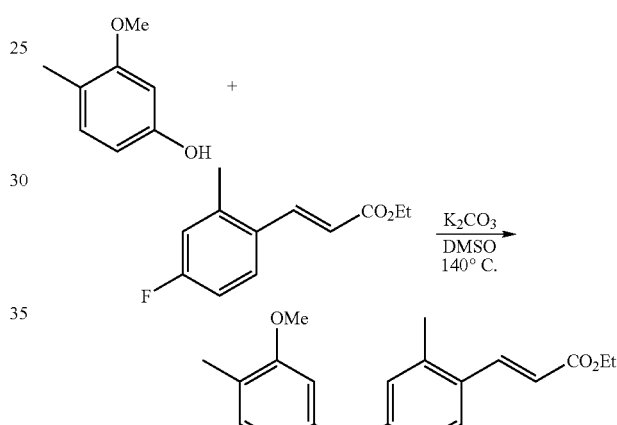

K$_2$CO$_3$ (3 g, 21.7 mmol) is added to a solution of the phenol (2.0 g, 14.5 mmol) and the fluoride (3.6 g, 17.3 mmol) in DMSO (40 mL). The mixture is warmed to 140° C. and stirred at this temperature overnight (c.a. 16 h). The mixture is allowed to reach r.t. and partitioned between EtOAc and HCl (3%). The organic layer is dried, filtered and concentrated to give a crude residue that is flash chromatographed on SiO$_2$ (2-3% EtOAc/hexanes) affording 2.42 g of the coupling product (51%, colorless oil).

Step I

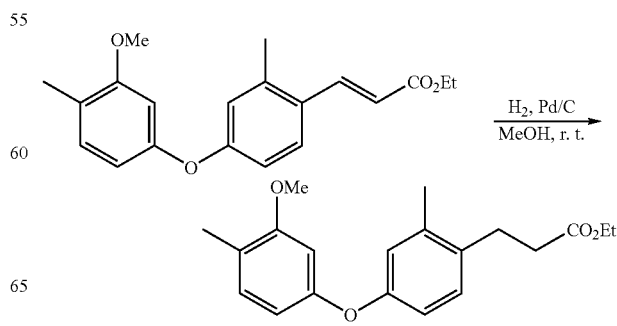

A mixture of Pd/C (500 mg, 10% Pd on activated C, 0.47 mmol) and the unsaturated ester (2.3 g, 7.055 mmol) and MeOH (35 mL) is stirred at r.t. under $H_2$ atmosphere (balloon) for 1 h. The reaction is filtered through Celite, and the solvent is removed in a rotatory evaporator. The crude residue is flash chromatographed on $SiO_2$ (4% EtOAc/hexanes) to afford 2.1 g of the saturated ester (91%, colorless oil).

Step J

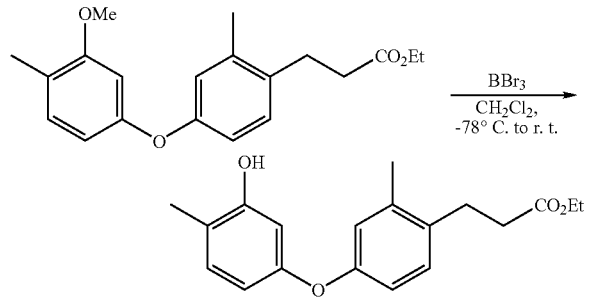

$BBr_3$ (8 mL, 1M solution in $CH_2Cl_2$) is added to a −78° C. cooled solution of the methoxyphenolether (2.0 g, 6.1 mmol) in $CH_2Cl_2$ (30 mL), and the mixture is allowed to reach r.t. After 15 min., it is poured into brine and extracted with $CH_2Cl_2$. The organic layer is washed with $NaHCO_3$ (sat) and $H_2O$, and then dried, filtered and concentrated. The resulting crude residue is flash chromatographed on $SiO_2$ (5-7% EtOAc/hexanes) to afford 1.15 g of the title compound (60%, white solid).

EXAMPLE 83

3-(4-Fluoro-2-methyl-phenyl)-acrylic acid ethyl ester

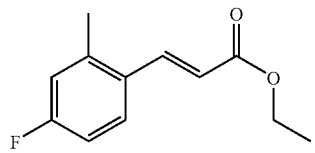

A mixture of 1-bromo-4-fluoro-2-methyl-benzene (5.00 g, 26.45 mmol), palladium acetate (0.59 g, 2.64 mmol), tri-o-tolylphosphine (1.61 g, 5.29 mmol), DIPEA (13.8 mL, 79.35 mmol) and ethyl acrylate (3.34 mL, 105.80 mmol) in propionitrile (106 mL) is stirred at 90° C. under nitrogen overnight. The mixture is ed off through Celite and washed with ethyl acetate. The mixture is concentrated under reduced pressure, purified by flash chromatography by eluting with hexane: ethyl acetate 10:1 to afford the title compound (5.50 g, 99%). Rf=0.49 (hexane:ethyl acetate 5:1). $^1H$ NMR (300 MHz, $CDCl_3$): δ1.33 (t, 3H, J=7.3 Hz), 2.41 (s, 3H), 4.26 (q, 2H, J=7.3 Hz), 6.28 (d, 1H, J=16.0 Hz), 6.88-6.91 (m, 2H), 7.48-7.53 (m, 1H), 7.88 (d, 1H, J=15.8 Hz).

EXAMPLE 84

3-[4-(5-Hydroxy-2-methyl-phenoxy)-2-methyl-phenyl]-propionic acid ethyl ester

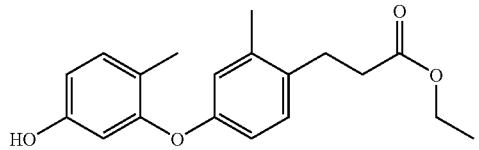

Step A

5-Methoxy-2-methyl-phenol

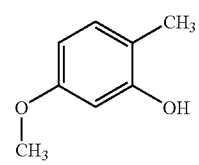

A solution of 2-hydroxy-4-methoxy-benzaldehyde (5.00 g, 32.86 mmol) and palladium under carbon (10%) (3.50 g, 3.28 mmol) in ethanol (32 mL) and acetic acid (3 mL) is stirred under 60 psi of hydrogen. After stirring overnight, the mixture is filtered off through Celite and washed with methanol. The mixture is concentrated under reduced pressure, and purified by flash chromatography by eluting with hexane: ethyl acetate 2:1 to afford the title compound (3.96 g, 87%). Rf=0.58 (hexane:ethyl acetate 2:1). δ$^1$HNMR (300 MHz, $CDCl_3$): 2.18 (s, 3H), 3.75 (s, 3H), 6.42 (m, 2H), 7.00(d, 1H, J=8.9 Hz).

Step B

3-[4-(5-Methoxy-2-methyl-phenoxy)-2-methyl-phenyl]-acrylic acid ethyl ester

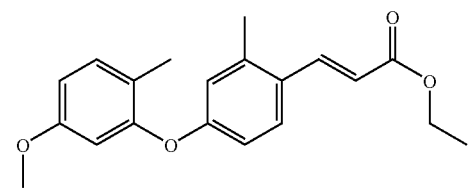

The compounds of 5-methoxy-2-methyl-phenol (1.46 g, 9.60 mmol), 3-(4-fluoro-2-methyl-phenyl)-acrylic acid ethyl ester (1.00 g, 4.80 mmol), potassium carbonate (1.33 g, 9.60 mmol) are dissolved in dimethylsulfoxide (12 mL) under nitrogen, and the mixture is stirred overnight at 140° C. HCl 10% is added, and the mixture is extracted with diethyl ether. The organic layer is washed with water, dried ($Na_2SO_4$) and filtered, and then the solvent is evaporated in vacuo. Purification by flash chromatography by eluting with hexane:ethyl acetate 10:1 to afford the title compound (0.74 g, 47%).

Rf=0.44 (hexane:ethyl acetate 5:1). ¹H NMR (300 MHz, CDCl₃): δ1.34 (t, 3H, J=7.3 Hz), 2.13 (s, 3H), 2.40 (s, 3H), 3.74 (s, 3H), 4.26 (q, 2H, J=7.1 Hz), 6.28 (d, 1H, J=15.9 Hz), 6.53 (d, 1H, J=2.4 Hz), 6.66-6.73 (m, 3H), 7.15 (d, 1H, J=8.3 Hz), 7.51 (d, 1H, J=8.3 Hz), 7.93 (d, 1H, J=16.0 Hz).

Step C

3-[4-(5-Methoxy-2-methyl-phenoxy)-2-methyl-phenyl]-propionic acid ethyl ester

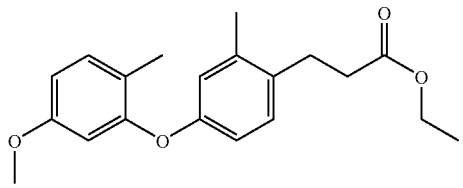

A solution of 3-[4-(5-methoxy-2-methyl-phenoxy)-2-methyl-phenyl]-acrylic acid ethyl ester (1.18 g, 3.63 mmol) and palladium under carbon (10%) (0.39 g, 0.36 mmol) in ethanol (20 mL) and acetic acid (2 mL) is stirred under 1 atm of hydrogen. After stirring overnight, the mixture is filtered off through Celite and washed with methanol. The mixture is concentrated under reduced pressure and purified by flash chromatography by eluting with hexane:ethyl acetate 5:1 to afford the title compound (1.02 g, 85%). Rf=0.42 (hexane: ethyl acetate 5:1). ¹H NMR (300 MHz, CDCl₃): δ1.26 (t, 3H, J=6.9 Hz), 2.16 (s, 3H), 2.28 (s, 3H), 2.56 (t, 2H, J=7.3 Hz), 2.90 (t, 2H, J=7.3 Hz), 3.72 (s, 3H), 4.17 (q, 2H, J=6.9 Hz), 6.45 (d, 1H, J=2.4 Hz), 6.62 (dd, 1H, J=2.8, 8.5 Hz), 6.67 (dd, 1H, J=2.4, 8.1 Hz), 6.74 (d, 1H, J=2.4 Hz), 7.06 (d, 1H, J=8.1 Hz), 7.13 (d, 1H, J=8.1 Hz).

Step D

3-[4-(5-Hydroxy-2-methyl-phenoxy)-2-methyl-phenyl]-propionic acid ethyl ester

The compound of 3-[4-(5-Methoxy-2-methyl-phenoxy)-2-methyl-phenyl]-propionic acid ethyl ester (1.02 g, 3.10 mmol) is dissolved in DCM (15 mL) under nitrogen at −78° C., and BBr₃ (1M, CH₂Cl₂) (4.64 mL, 4.64 mmol) is added. The mixture is stirred at that temperature for 10 minutes and the bath is removed. The mixture is stirred at rt for 2 h, and water is added. The mixture is neutralized to pH=7 with NaOH (10%). The mixture is extracted with DCM. The organic layer is dried with Na₂SO₄ and filtered, and then the solvent is evaporated in vacuo. Purification by flash chromatography by eluting with hexane:ethyl acetate 5:1 to afford the title compound (0.48 g, 50%). R_f=0.13 (hexane:ethyl acetate 5:1). ¹H NMR (300 MHz, CDCl₃): δ1.26 (t, 3H, J=7.3 Hz), 2.16 (s, 3H), 2.26 (s, 3H), 2.57 (t, 2H, J=7.3 Hz), 2.89 (t, 2H, J=7.5 Hz), 4.15 (q, 2H, J=7.3 Hz), 6.44 (d, 1H, J=2.4 Hz), 6.58 (dd, 1H, J=2.4, 8.1 Hz), 6.68 (dd, 1H, J=2.4, 8.3 Hz), 6.75 (d, 1H, J=2.2 Hz), 6.92 (s, 1H), 7.04 (t, 2H, J=8.1 Hz).

EXAMPLE 85

3-(4-{3-[4-Chloro-2-(2-fluoro-phenoxy)-phenoxy]-phenoxy}-2-methyl-phenyl)-propionic acid

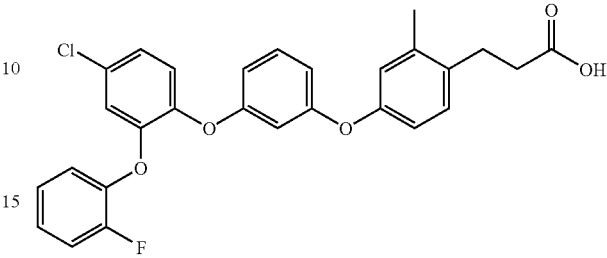

Step A

3-[4-(3-Bromo-phenoxy)-2-methyl-phenyl]-propionic acid methyl ester

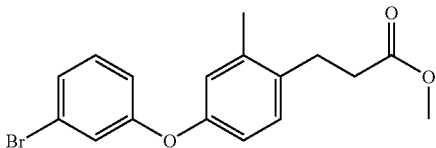

A solution of 3-(4-hydroxy-2-methyl-phenyl)-propionic acid methyl ester (5.0 g, 26 mmol), 1-bromo-3-iodobenzene (21.9 g, 77 mmol), copper(I) chloride (1.3 g, 13 mmol), 2,2,6,6-tetramethyl-3,5-heptanedione (1.3 mL, 6.5 mmol), and cesium carbonate (12.7 g, 39 mmol) in NMP (100 mL) is heated to 120° C. The reaction is stirred overnight, and then is cooled to room temperature. The reaction is then quenched with 1N aqueous hydrochloric acid and extracted with ethyl ether. The organic is washed with brine, dried over sodium sulfate, filtered, and the solvent is removed. The crude is purified by silica gel column chromatography using 9/1 hexanes/ethyl acetate to elute the pure product. The solvent is removed to afford about 7.86 g (87%) of the desired product. ¹H NMR (400 MHz, CDCl₃); MS (ES⁺) m/z mass calcd for C₁₇H₁₇BrO₃ 348, found 349 (M+1, 100%).

Step B

4-Chloro-2-(2-fluoro-phenoxy)-benzaldehyde

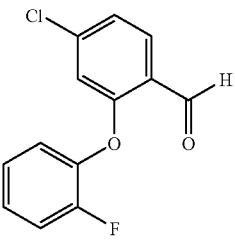

A solution of 4-chloro-2-fluorobenzaldehyde (1.0 g, 6.3 mmol) and 2-fluorophenol (0.78 g, 6.9 mmol) in DMSO (10 mL) is treated with potassium carbonate (1.04 g, 7.6 mmol).

The reaction is heated to 100° C. and stirred overnight. The reaction is cooled to room temperature and quenched with 1N aqueous hydrochloric acid to pH=6. The aqueous is extracted with diethyl ether. The organic is washed with brine, dried over sodium sulfate, filtered, and the solvent is removed. The crude is purified by silica gel column chromatography using 4:1 hexanes:acetone to elute the pure product. The solvent is removed to afford about 0.8 g (51%) of product. $^1$H NMR (400 MHz, CDCl$_3$), TLC (1:1 hexanes:EtOAc) R$_f$=0.8.

Step C

4-Chloro-2-(2-fluoro-phenoxy)-phenol

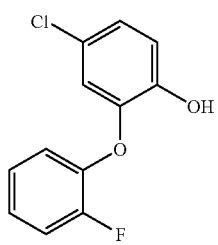

A solution of 4-chloro-2-(2-fluoro-phenoxy)-benzaldehyde (0.8 g, 3.2 mmol) in chloroform (10 mL) is treated with m-CPBA (2.75 g, 16 mmol). The reaction is heated to reflux and stirred for about 2 hr. The reaction is cooled to room temperature and quenched with 10% aqueous NaHSO$_4$. The aqueous is extracted with diethyl ether. The organic is washed with brine, dried over sodium sulfate, and the solvent is removed. The crude is diluted in methanol (20 mL) and treated with potassium carbonate (1.32 g, 9.6 mmol). The reaction stirred for 30 minutes at room temperature. The reaction is filtered and the solvent removed. The crude is purified by silica gel column chromatography using 4:1 hexanes:acetone to elute the pure product. The solvent is removed to afford about 0.64 g (84%) of product. $^1$H NMR (400 MHz, CDCl$_3$). MS (ES−) m/z mass calcd for C$_{12}$H$_8$ClFO$_2$ 238, found 237 (M−1, 100%).

Step D 3-(4-{3-[4-Chloro-2-(2-fluoro-phenoxy)-phenoxy]-phenoxy}-2-methyl-phenyl)-propionic acid methyl ester

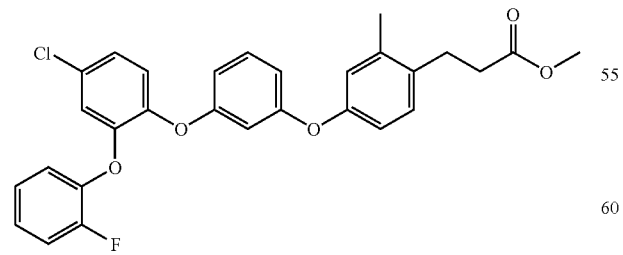

A solution of 3-[4-(3-bromo-phenoxy)-2-methyl-phenyl]-propionic acid methyl ester (0.66 g, 2 mmol), 4-chloro-2-(2-fluoro-phenoxy)-phenol (0.3 g, 1.3 mmol), copper(I) chloride (0.06 g, 0.6 mmol), 2,2,6,6-tetramethyl-3,5-heptanedione (0.06 mL, 0.3 mmol), and cesium carbonate (0.82 g, 2.5 mmol) in NMP (10 mL) is heated to 120° C. The reaction is stirred overnight, and then is cooled to room temperature. The reaction is then quenched with 1N aqueous hydrochloric acid and extracted with ethyl ether. The organic is washed with brine, dried over sodium sulfate, filtered, and the solvent removed. The crude is purified by silica gel column chromatography using 9/1 hexanes/ethyl acetate to elute the pure product. The solvent is removed to afford about 0.072 g (11%) of the desired product. $^1$H NMR (400 MHz, CDCl$_3$); MS (ES$^+$) m/z mass calcd for C$_{29}$H$_{24}$ClFO$_5$ 506, found 524 (M+NH4, 100%).

Step E 3-(4-{3-[4-Chloro-2-(2-fluoro-phenoxy)-phenoxy]-phenoxy}-2-methyl-phenyl)-propionic acid A solution of 3-(4-{3-[4-chloro-2-(2-fluoro-phenoxy]-phenoxy}-2-methyl-phenyl)-propionic acid methyl ester (72 mg, 0.1 mmol) in MeOH (10 mL) is treated with 5N aqueous sodium hydroxide (0.3 mL). The reaction is heated to reflux and stirred for 2 hr. The reaction is cooled to room temperature and quenched with 1N aqueous HCl to pH=4. The aqueous is extracted with diethyl ether. The organic is washed with brine, dried over sodium sulfate and filtered. The solvent is removed to afford about 60 mg (87%) of product. $^1$H NMR (400 MHz, CDCl$_3$); MS (ES$^+$) m/z mass calcd for C$_{28}$H$_{22}$ClFO$_5$ 506, found 524 (M+NH4, 100%).

EXAMPLE 86

3-(4-{3-[4-Chloro-2-(2-o-tolyloxy-phenoxy)-phenoxy]-phenoxy}-2-methyl-phenyl)-propionic acid

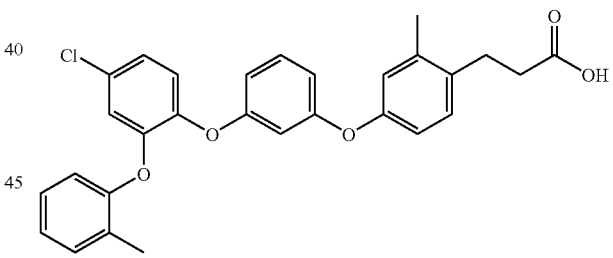

Step A

4-Chloro-2-o-tolyloxy-benzaldehyde

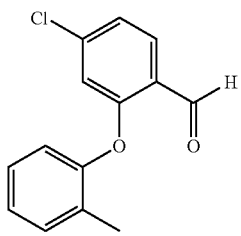

The title compound is prepared according to the procedure described in Example 85, Step B by using o-cresol. $^1$H NMR (400 MHz, CDCl$_3$), TLC (1:1 hexanes:EtOAc) R$_f$=0.8.

Step B

4-Chloro-2-o-tolyloxy-phenol

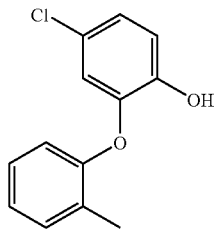

The title compound is prepared according to the procedure described in Example 85, Step C by using 4-chloro-2-o-tolyloxy-benzaldehyde. $^1$H NMR (400 MHz, CDCl$_3$). MS (ES−) m/z mass calcd for C$_{13}$H$_{11}$ClO$_2$ 234, found 233 (M−1, 100%).

Step C

3-{4-[3-(4-Chloro-2-o-tolyloxy-phenoxy)-phenoxy]-2-methyl-phenyl}-propionic acid methyl ester

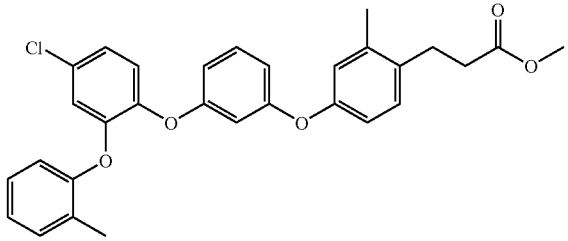

The title compound is prepared according to the procedure described in Example 85, Step D by using 4-chloro-2-o-tolyloxy-phenol. $^1$H NMR (400 MHz, CDCl$_3$); MS (ES$^+$) m/z mass calcd for C$_{30}$H$_{27}$ClO$_5$ 502, found 520 (M+NH4, 100%).

Step E 3-(4-{3-[4-Chloro-2-(2-o-tolyloxy-phenoxy)-phenoxy]-phenoxy}-2-methyl-phenyl)-propionic acid The title compound is prepared according to the procedure described in Example 85, Step E by using 3-{4-[3-(4-chloro-2-o-tolyloxy-phenoxy)-phenoxy]-2-methyl-phenyl}-propionic acid methyl ester. $^1$H NMR (400 MHz, CDCl$_3$); MS (ES$^+$) m/z mass calcd for C$_{29}$H$_{25}$ClO$_5$ 506, found 524 (M+NH4, 100%).

EXAMPLE 87

3-{2-Methyl-4-[3-methyl-5-(3-phenoxy-5-trifluoromethyl-pyridin-2-yloxy)-phenoxy]-phenyl}-propionic acid

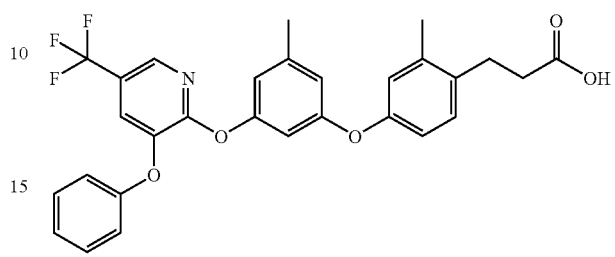

The title compound is prepared according to Example 85 by using 3-phenoxy-5-trifluoromethyl-pyridin-2-ol and 3-[4-(3-bromo-5-methyl-phenoxy)-2-methyl-phenyl]-propionic acid methyl ester to afford about 32 mg (6%). $^1$H NMR (400 MHz, CDCl$_3$); MS (ES$^+$) m/z mass calcd for C$_{29}$H$_{24}$O$_5$NF$_3$ 523, found 524 (M+1, 100%).

EXAMPLE 88

3-{2-Methyl-4-[3-methyl-5-(2-phenoxy-3-trifluoromethyl-phenoxy)-phenoxy]-phenyl}-propionic acid

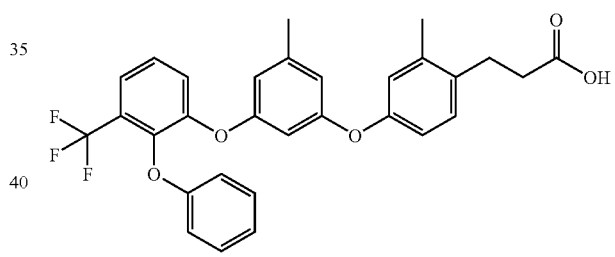

The title compound is prepared according to Example 85 by using 2-phenoxy-3-trifluoromethyl-phenol and 3-[4-(3-bromo-5-methyl-phenoxy)-2-methyl-phenyl]-propionic acid methyl ester to afford about 57 mg (10%). $^1$H NMR (400 MHz, CDCl$_3$); MS (ES$^+$) m/z mass calcd for C$_{30}$H$_{25}$O$_5$F$_3$ 522, found 523 (M+1, 100%).

EXAMPLE 89

3-{2-Methyl-4-[3-(2-o-tolyloxy-4-trifluoromethyl-phenoxy)-phenoxy]-phenyl}-propionic acid

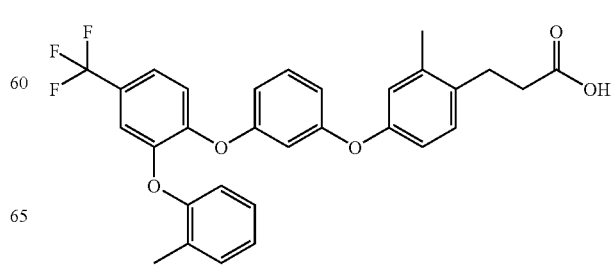

Step A

3-Benzyloxy-1-bromobenzene

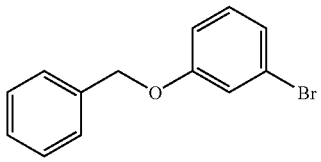

A mixture of 3-bromophenol (10.0 g, 57.8 mmol) and 325 mesh potassium carbonate (8.79 g, 63.6 mmol) in DMF (100 mL) is treated dropwise with benzyl bromide (9.89 g, 57.8 mmol) and then stirred for 20 hours at room temperature under $N_2$. The reaction is filtered, and the filtrate is acidified with 1 N HCl. The mixture is then diluted with water and extracted with $Et_2O$. The organic layer is dried ($Na_2SO_4$), and the solvent is removed in vacuo to afford crude product that is absorbed on silica gel and purified by flash chromatography using 10/1 hexanes/ethyl acetate to afford about 14.55 g (96%) of the titled compound. $R_f$=0.86 (4/1 hexanes/EtOAc). $^1$H NMR (400 MHz, $CDCl_3$).

Step B

3-[4-(3-Benzyloxy-phenoxy)-2-methyl-phenyl]-propionic acid methyl ester

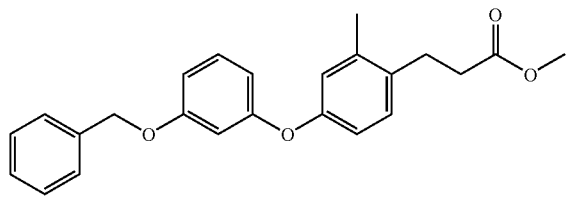

A mixture of 3-benzyloxy-1-bromobenzene (14.53 g, 55.2 mmol), 3-(4-hydroxy-2-methyl-phenyl)-propionic acid methyl ester (10.72 g, 55.2 mmol) cesium carbonate (21.59 g, 66.3 mmol), and 2,2,6,6-tetramethyl-3,5-heptanedione (2.54 g, 13.8 mmol) in 1-methyl-2-pyrrolidinone (100 mL) is purged with $N_2$, and then copper (I) chloride (2.73 g, 27.6 mmol) is added. The reaction mixture is heated to 120° C. for 18 hours under $N_2$. The mixture is diluted with water and extracted with $Et_2O$. The organic layer is dried ($Na_2SO_4$), and the solvent is removed in vacuo to afford crude product that is absorbed on silica gel and purified by flash chromatography using a gradient of 19/1 to 9/1 hexanes/ethyl acetate to afford about 10.54 g (51%) of the titled compound. $R_f$=0.53 (100% hexanes). $^1$H NMR (400 MHz, $CDCl_3$); MS ($ES^+$) m/z mass calcd for $C_{24}H_{24}O_4$ 376, found 377 (M+1, 100%).

Step C

3-[4-(3-Hydroxy-phenoxy)-2-methyl-phenyl]-propionic acid methyl ester

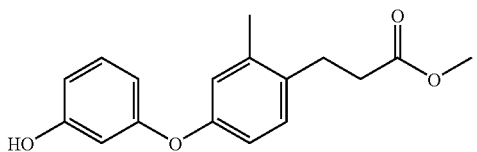

A mixture of 3-[4-(3-benzyloxy-phenoxy)-2-methyl-phenyl]-propionic acid methyl ester (10.54 g, 28.0 mmol) and 10% Pd/C (5 g) in ethyl acetate (150 mL) is purged with $N_2$, and then purged with $H_2$, which is stirred under a hydrogen balloon. Upon reaction completion, the mixture is filtered through Hyflo, and the solvent is removed in vacuo to afford about 8.18 g (100%) of the titled compound. $R_f$=0.59 (4/1 hexanes/EtOAc). $^1$H NMR (400 MHz, $CDCl_3$); MS ($ES^+$) m/z mass calcd for $C_{17}H_{18}O_4$ 286, found 287 (M+1, 100%).

Step D

3-{4-[3-(2-Bromo-4-trifluoromethyl-phenoxy)-phenoxy]-2-methyl-phenyl}-propionic acid methyl ester

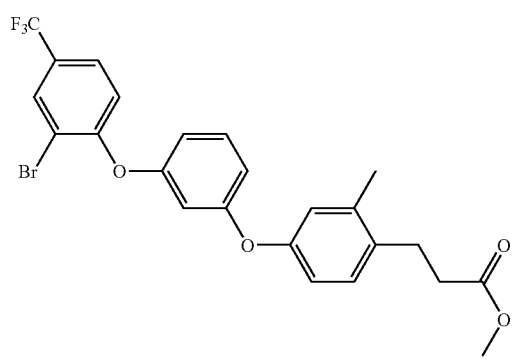

A mixture of 3-[4-(3-hydroxy-phenoxy)-2-methyl-phenyl]-propionic acid methyl ester (8.18 g, 28.6 mmol), 3-bromo-4-fluorobenzotrifluoride (6.80 g, 28.0 mmol) and 325 mesh potassium carbonate (4.64 g, 33.68 mmol) in dry DMSO (80 mL) is heated to 100° C. and stirred for about 6 hours under $N_2$. The reaction is cooled and acidified with 1 N HCl. The mixture is then diluted with water and extracted with $Et_2O$. The organic layer is dried ($Na_2SO_4$), and the solvent is removed in vacuo to afford crude product that is absorbed on silica gel and purified by flash chromatography using 15/1 hexanes/ethyl acetate to afford about 11.74 g (81%) of the titled compound. $R_f$=0.76 (9/1 hexanes/EtOAc). $^1$H NMR (400 MHz, $CDCl_3$); MS ($ES^+$) m/z mass calcd for $C_{24}H_{20}O_4F_3Br$ 509, found 526 and 528 (M+$NH_4$, 100%).

Step E

The title compound is prepared according to Example 38 by using o-cresol and 3-{4-[3-(2-bromo-4-trifluoromethyl-phenoxy)-phenoxy]-2-methyl-phenyl}-propionic acid methyl ester to afford about 229 mg (21%). $^1$H NMR (400 MHz, CDCl$_3$); MS (ES$^+$) m/z mass calcd for C$_{30}$H$_{25}$O$_5$F$_3$ 522, found 523 (M+1, 100%).

EXAMPLE 90

3-{2-Methyl-4-[3-(2-pyridin-2-yl-4-trifluoromethyl-phenoxy)-phenoxy]-phenyl}-propionic acid

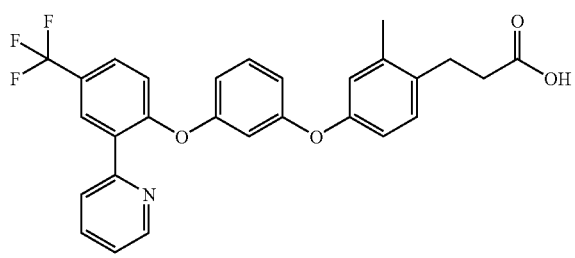

The title compound is prepared according to Example 89 by using 2-tributylstannyl pyridine and 3-{4-[3-(2-bromo-4-trifluoromethyl-phenoxy)-phenoxy]-2-methyl-phenyl}-propionic acid methyl ester to afford about 29 mg (14%). $^1$H NMR (400 MHz, CDCl$_3$); MS (ES$^+$) m/z mass calcd for C$_{28}$H$_{22}$NO$_4$F$_3$ 493, found 494 (M+1, 100%).

EXAMPLE 91

3-{2-Methyl-4-[3-(2-pyridin-3-yl-4-trifluoromethyl-phenoxy)-phenoxy]-phenyl}-propionic acid

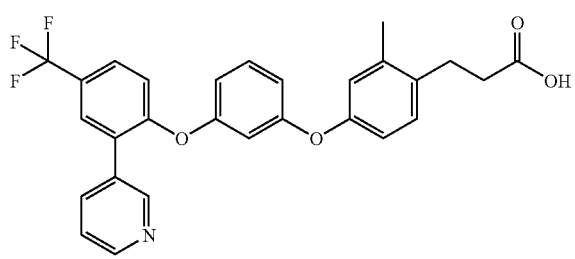

The title compound is prepared according to Example 89 by using 3-pyridyl boronic acid and 3-{4-[3-(2-bromo-4-trifluoromethyl-phenoxy)-phenoxy]-2-methyl-phenyl}-propionic acid methyl ester to afford about 277 mg (88%). $^1$H NMR (400 MHz, CDCl$_3$); MS (ES$^+$) m/z mass calcd for C$_{28}$H$_{22}$NO$_4$F$_3$ 493, found 494 (M+1, 100%).

EXAMPLE 92

3-{2-Methyl-4-[3-(2-phenoxy-5-trifluoromethyl-phenoxy)-phenoxy]-phenyl}-propionic acid

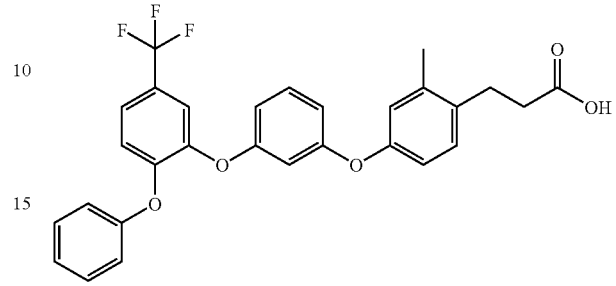

The title compound is prepared according to Example 85 by using 2-phenoxy-5-trifluoromethyl-phenol and 3-[4-(3-bromo-phenoxy)-2-methyl-phenyl]-propionic acid methyl ester to afford about 35 mg (11%). $^1$H NMR (400 MHz, CDCl$_3$); MS (ES$^+$) m/z mass calcd for C$_{29}$H$_{23}$O$_5$F$_3$ 508, found 509 (M+1, 100%).

EXAMPLE 93

3-{2-Methyl-4-[3-(2-phenoxy-3-trifluoromethyl-phenoxy)-phenoxy]-phenyl}-propionic acid

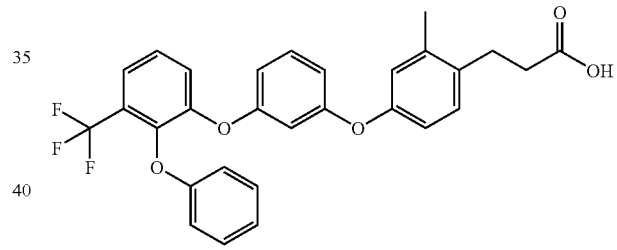

The title compound is prepared according to Example 85 by using 2-phenoxy-3-trifluoromethyl-phenol and 3-[4-(3-bromo-phenoxy)-2-methyl-phenyl]-propionic acid methyl ester to afford about 111 mg (6%). $^1$H NMR (400 MHz, CDCl$_3$); MS (ES$^+$) m/z mass calcd for C$_{29}$H$_{23}$O$_5$F$_3$ 508, found 509 (M+1, 100%).

EXAMPLE 94

3-{2-Methyl-4-[3-(5-trifluoromethyl-biphenyl-2-yloxy)-phenoxy]-phenyl}-propionic acid

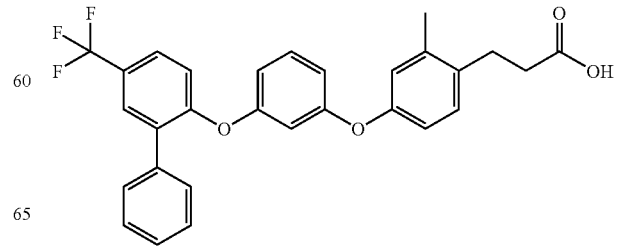

The title compound is prepared according to Example 89 by using phenyl boronic acid and 3-{4-[3-(2-bromo-4-trifluoromethyl-phenoxy)-phenoxy]-2-methyl-phenyl}-propionic acid methyl ester to afford about 74 mg (49%). $^1$H NMR (400 MHz, CDCl$_3$); MS (ES$^+$) m/z mass calcd for C$_{29}$H$_{23}$O$_4$F$_3$ 492, found 493 (M+1, 100%).

EXAMPLE 95

3-{4-[3-(2'-Fluoro-5-trifluoromethyl-biphenyl-2-yloxy)-phenoxy]-2-methyl-phenyl}-propionic acid

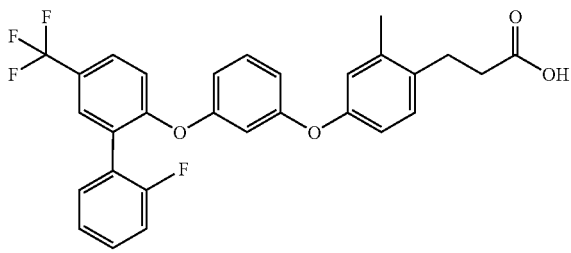

The title compound is prepared according to Example 89 by using 2-fluorophenyl boronic acid and 3-{4-[3-(2-bromo-4-trifluoromethyl-phenoxy)-phenoxy]-2-methyl-phenyl}-propionic acid methyl ester to afford about 132 mg (68%). $^1$H NMR (400 MHz, CDCl$_3$); MS (ES$^+$) m/z mass calcd for C$_{29}$H$_{22}$O$_4$F$_4$ 510, found 511 (M+1, 100%).

EXAMPLE 96

3-{2-Methyl-4-[3-(2'-trifluoromethoxy-5-trifluoromethyl-biphenyl-2-yloxy)-phenoxy]-phenyl}-propionic acid

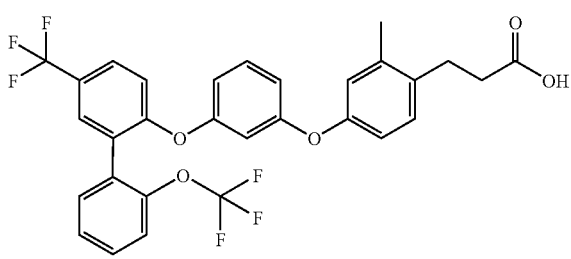

The title compound is prepared according to Example 89 by using 2-trifluoromethoxyphenyl boronic acid and 3-{4-[3-(2-bromo-4-trifluoromethyl-phenoxy)-phenoxy]-2-methyl-phenyl}-propionic acid methyl ester to afford about 94 mg (58%). $^1$H NMR (400 MHz, CDCl$_3$); MS (ES$^+$) m/z mass calcd for C$_{30}$H$_{22}$O$_5$F$_6$ 576, found 577 (M+1, 100%).

EXAMPLE 97

3-{4-[3-(2'-Methoxy-5-trifluoromethyl-biphenyl-2-yloxy)-phenoxy]-2-methyl-phenyl}-propionic acid

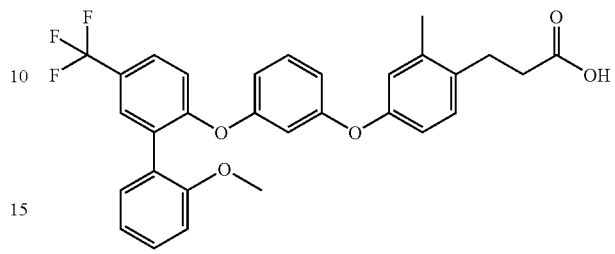

The title compound is prepared according to Example 89 by using 2-methoxyphenyl boronic acid and 3-{4-[3-(2-bromo-4-trifluoromethyl-phenoxy)-phenoxy]-2-methyl-phenyl}-propionic acid methyl ester to afford about 102 mg (64%). $^1$H NMR (400 MHz, CDCl$_3$); MS (ES$^+$) m/z mass calcd for C$_{30}$H$_{25}$O$_5$F$_3$ 522, found 523 (M+1, 100%).

EXAMPLE 98

3-{4-[3-(5,2'-Bis-trifluoromethyl-biphenyl-2-yloxy)-phenoxy]-2-methyl-phenyl}-propionic acid

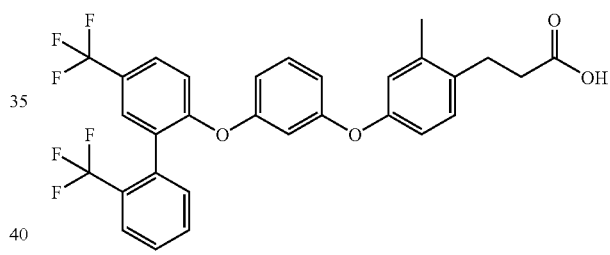

The title compound is prepared according to Example 89 by using 2-trifluoromethylphenyl boronic acid and 3-{4-[3-(2-bromo-4-trifluoromethyl-phenoxy)-phenoxy]-2-methyl-phenyl}-propionic acid methyl ester to afford about 108 mg (68%). $^1$H NMR (400 MHz, CDCl$_3$); MS (ES$^+$) m/z mass calcd for C$_{30}$H$_{22}$O$_4$F$_6$ 560, found 561 (M+1,100%).

EXAMPLE 99

3-{4-[3-(2'-Chloro-5-trifluoromethyl-biphenyl-2-yloxy)-phenoxy]-2-methyl-phenyl}-propionic acid

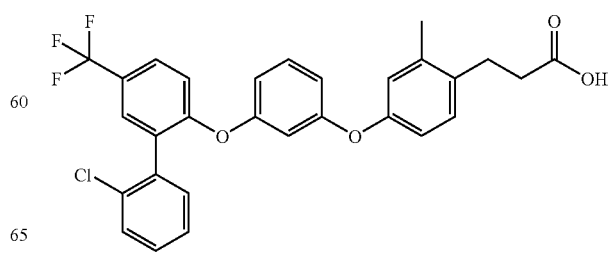

The title compound is prepared according to Example 89 by using 2-chlorophenyl boronic acid and 3-{4-[3-(2-bromo-4-trifluoromethyl-phenoxy)-phenoxy]-2-methyl-phenyl}-propionic acid methyl ester to afford about 122 mg (66%). $^1$H NMR (400 MHz, CDCl$_3$); MS (ES$^+$) m/z mass calcd for C$_{29}$H$_{22}$O$_4$F$_3$Cl 526, found 527 and 529 (M+1 and M+3, 100%).

EXAMPLE 100

3-{4-[3-(4'-Fluoro-5-trifluoromethyl-biphenyl-2-yloxy)-phenoxy]-2-methyl-phenyl}-propionic acid

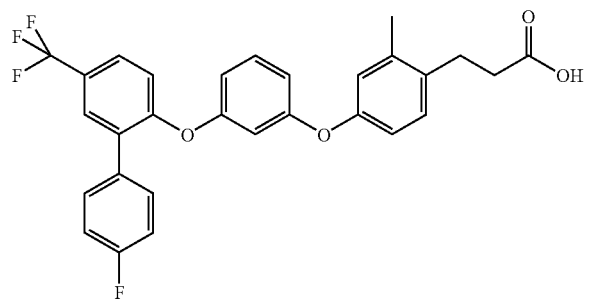

The title compound is prepared according to Example 89 by using 4-fluorophenyl boronic acid and 3-{4-[3-(2-bromo-4-trifluoromethyl-phenoxy)-phenoxy]-2-methyl-phenyl}-propionic acid methyl ester to afford about 129 mg (60%). $^1$H NMR (400 MHz, CDCl$_3$); MS (ES$^+$) m/z mass calcd for C$_{29}$H$_{22}$O$_4$F$_4$ 510, found 511 (M+1, 100%).

EXAMPLE 101

3-{4-[3-(5,4'-Bis-trifluoromethyl-biphenyl-2-yloxy)-phenoxy]-2-methyl-phenyl}-propionic acid

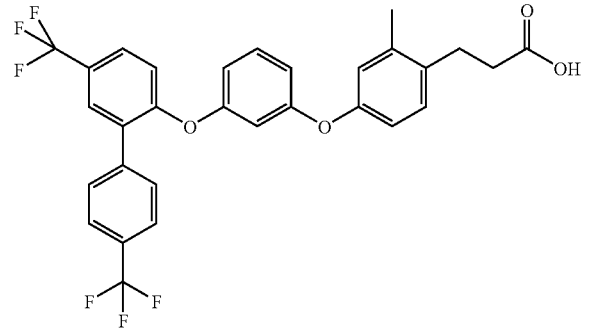

The title compound is prepared according to Example 89 by using 4-trifluoromethylphenyl boronic acid and 3-{4-[3-(2-bromo-4-trifluoromethyl-phenoxy)-phenoxy]-2-methyl-phenyl}-propionic acid methyl ester to afford about 99 mg (62%). $^1$H NMR (400 MHz, CDCl$_3$); MS (ES$^+$) m/z mass calcd for C$_{30}$H$_{22}$O$_4$F$_6$ 560, found 561 (M+1, 100%).

EXAMPLE 102

3-{4-[3-(3'-Fluoro-5-trifluoromethyl-biphenyl-2-yloxy)-phenoxy]-2-methyl-phenyl}-propionic acid

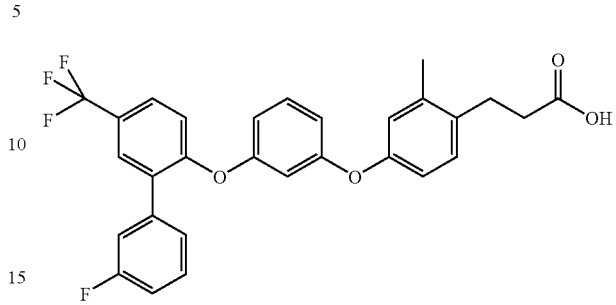

The title compound is prepared according to Example 89 by using 4-trifluoromethylphenyl boronic acid and 3-{4-[3-(2-bromo-4-trifluoromethyl-phenoxy)-phenoxy]-2-methyl-phenyl}-propionic acid methyl ester to afford about 115 mg (64%).
$^1$H NMR (400 MHz, CDCl$_3$); MS (ES$^+$) m/z mass calcd for C$_{29}$H$_{22}$O$_4$F$_4$ 510, found 511 (M+1, 100%).

EXAMPLE 103

3-{4-[3-(5,3'-Bis-trifluoromethyl-biphenyl-2-yloxy)-phenoxy]-2-methyl-phenyl}-propionic acid

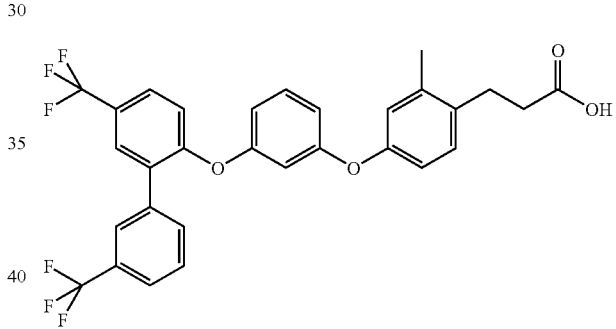

The title compound is prepared according to Example 89 by using 3-trifluoromethylphenyl boronic acid and 3-{4-[3-(2-bromo-4-trifluoromethyl-phenoxy)-phenoxy]-2-methyl-phenyl}-propionic acid methyl ester to afford about 112 mg (63%). $^1$H NMR (400 MHz, CDCl$_3$); MS (ES$^+$) m/z mass calcd for C$_{30}$H$_{22}$O$_4$F$_6$ 560, found 561 (M+1, 100%).

EXAMPLE 104

3-{2-Methyl-4-[4-methyl-3-(2-pyrimidin-5-yl-4-trifluoromethyl-phenoxy)-phenoxy]-phenyl}-propionic acid

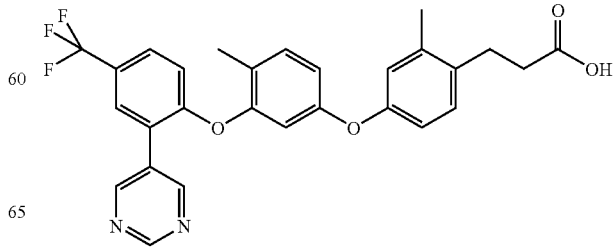

The title compound is prepared according to Example 89 by using pyrimidine-5-boronic acid and 3-{4-[3-(2-bromo-4-trifluoromethyl-phenoxy)-5-chloro-phenoxy]-2-methyl-phenyl}-propionic acid ethyl ester to afford about 66 mg (69%). $^1$H NMR (400 MHz, CDCl$_3$); MS (ES$^+$) m/z mass calcd for C$_{28}$H$_{23}$O$_4$F$_3$N$_2$ 508, found 509 (M+1, 100%).

EXAMPLE 105

3-{4-[3-Chloro-5-(2-pyrimidin-5-yl-4-trifluoromethyl-phenoxy)-phenoxy]-2-methyl-phenyl}-propionic acid

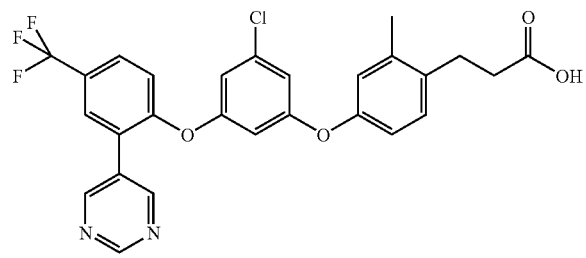

The title compound is prepared according to Example 89 by using pyrimidine-5-boronic acid and 3-{4-[3-(2-bromo-4-trifluoromethyl-phenoxy)-5-chloro-phenoxy]-2-methyl-phenyl}-propionic acid ethyl ester to afford about 31 mg (22%). $^1$H NMR (400 MHz, CDCl$_3$); MS (ES$^+$) m/z mass calcd for C$_{27}$H$_{20}$O$_4$F$_3$N$_2$Cl 528, found 529 (M+1, 100%).

EXAMPLE 106

{2-Methyl-4-[3-methyl-5-(2-phenoxy-4-trifluoromethyl-phenoxy)-phenoxy]-phenoxy}-acetic acid

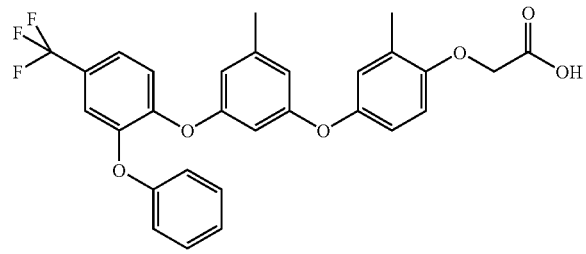

Step A (4-Bromo-2-methyl-phenoxy)-acetic acid ethyl ester

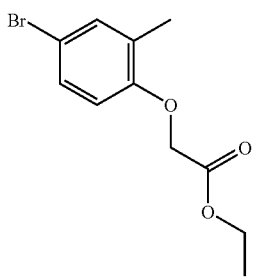

A mixture of 4-bromo-2-methylphenol (10.0 g, 53.5 mmol) and 325 mesh potassium carbonate (11.08 g, 80.2 mmol) in DMF (100 mL) is treated dropwise with bromoethyl acetate (10.71 g, 64.1 mmol) and then stirred for about 20 hours at room temperature under N$_2$. The reaction is filtered, and the filtrate is acidified with 1 N HCl. The mixture is then diluted with water and extracted with Et$_2$O. The organic layer is dried (Na$_2$SO$_4$), and the solvent is removed in vacuo to afford crude product that is absorbed on silica gel and purified by flash chromatography using 5/1 hexanes/ethyl acetate to afford about 15.01 g (100%) of the titled compound. R$_f$=0.33 (4/1 hexanes/EtOAc). $^1$H NMR (400 MHz, CDCl$_3$).

Step B

3-Methyl-5-(2-phenoxy-4-trifluoromethyl-phenoxy)-phenol

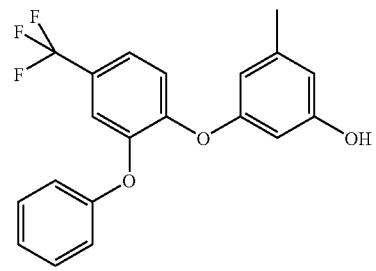

Example 63, step A intermediate (7.0 g, 16.0 mmol), phenol (3.0 g, 32.0 mol), cesium carbonate (10.43 g, 32.0 mol), and 2,2,6,6-tetramethyl-3,5-heptanedione (0.74 g, 4.01 mmol) in 1-methyl-2-pyrrolidinone (70 mL) is purged with N$_2$, and then copper (I) chloride (0.79 g, 7.98 mmol) is added. The reaction mixture is heated to 120° C. for 20 hours under N$_2$. The mixture is diluted with water and extracted with Et$_2$O. The organic layer is dried (Na$_2$SO$_4$), and the solvent is removed in vacuo to afford crude product that is absorbed on silica gel and purified by flash chromatography using 14/1 hexanes/ethyl acetate to afford 5.30 g (74%) product. R$_f$=0.48 (4/1 hexanes/ethyl acetate)

A mixture of 5.30 g of obtained above and 10% Pd/C (2.50 g) in ethyl acetate (150 mL) is purged with N$_2$ and then H$_2$, and the mixture is stirred under a H$_2$ balloon at rt. Upon completion of the reaction, the mixture is filtered through hyflo, and the solvent is removed in vacuo to afford crude product that is purified by flash chromatography using 5/1 hexanes/ethyl acetate to afford 3.83 g (90%) of the title compound. R$_f$=0.28 (4/1 hexanes/ethyl acetate). $^1$H NMR (400 MHz, CDCl$_3$); MS (ES$^+$) m/z mass calculated for C$_{20}$H$_{15}$F$_3$O$_3$ 360, found 359 (M−1, 100%).

Step C

Intermediates 3-methyl-5-(2-phenoxy-4-trifluoromethyl-phenoxy)-phenol (0.49 g, 1.36 mmol) and (4-bromo-2-methyl-phenoxy)-acetic acid ethyl ester (0.37 g, 1.36 mol) were combined with cesium carbonate (0.53 g, 1.63 mol), and 2,2,6,6-tetramethyl-3,5-heptanedione (0.063 g, 0.342 mmol) in 1-methyl-2-pyrrolidinone (10 mL) is purged with N$_2$, and then copper (I) chloride (0.067 g, 0.677 mmol) is added. The reaction mixture is heated to 120° C. for 20 hours under N$_2$.

The mixture is diluted with water and extracted with Et₂O. The organic layer is dried (Na₂SO₄), and the solvent is removed in vacuo to afford crude product that is absorbed on silica gel and purified by flash chromatography using 9/1 hexanes/ethyl acetate to afford 0.094 g (13%) {2-methyl-4-[3-methyl-5-(2-phenoxy-4-trifluoromethyl-phenoxy)-phenoxy]-phenoxy}-acetic acid ethyl ester that was saponified with ethanol and 5 N NaOH to afford 0.072 g (81%) ¹H NMR (400 MHz, CDCl₃); MS (ES⁺) m/z mass calcd for C₂₉H₂₃O₆F₃ 524, found 525 (M+1, 100%).

EXAMPLE 107

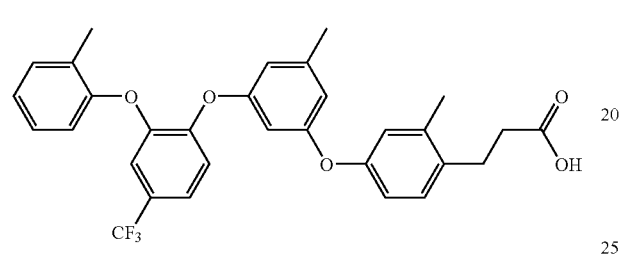

Step A

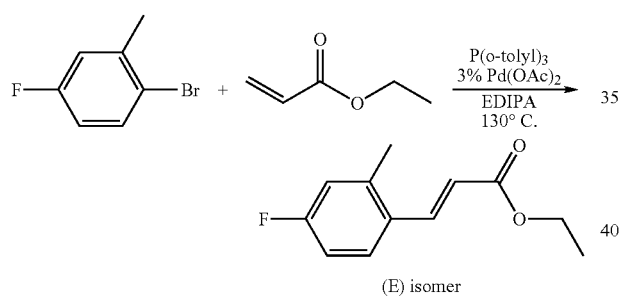

(E) isomer

A 12-L flask is equipped with a heating mantle, air stirrer, condenser, addition funnel and N₂ inlet/outlet using a Firestone valve. The flask is thoroughly purged with nitrogen, and then charged 2-bromo-5-fluorotoluene (500.0 g, 2.65 moles), DMF (1100 mL), ethyl acrylate (278.3 g, 2.78 moles), and N,N-diisopropylethylamine (EDIPA) (359.3 g, 2.78 moles) to form a solution. Tri-o-tolylphosphine (48.7 g, 0.16 moles) and palladium(II) acetate (17.8 g, 0.08 moles) are added to form a brown-orange suspension. After heating the suspension to about 115-120° C., the reaction is monitored by GC. After approximately 4 hours, about <1% starting material is remained, and the reaction is deemed complete. After cooling the reaction to rt, a saturated aq. NH₄Cl solution (1.5 L) and EtOAc (3.0 L) are added to form a biphasic solution. The solution is transferred to a separatory funnel, and the layers are separated. After extracting the aqueous layer with EtOAc (3.0 L), the combined organic layers are washed with 10% aq. NH₄Cl solution (2×1.0 L). The organic layer is dried over Na₂SO₄ and filtered. The filtrate is concentrated to an oil to yield crude product (672 g). Purification by Kugelrohr distillation (bp=110-120° C.@1.0 mm Hg) yielded compound A (507.8 g, 92.2%) as a clear light yellow oil. ¹H-NMR (CDCl₃, 300 MHz) δ 7.89 (d, 1H), 7.56-7.48 (m, 1H), 6.94-6.84 (m, 2H), 6.29 (d, 1H), 4.26 (q, 2H), 2.42 (s, 3H), 1.331 (t, 3H).

Step B

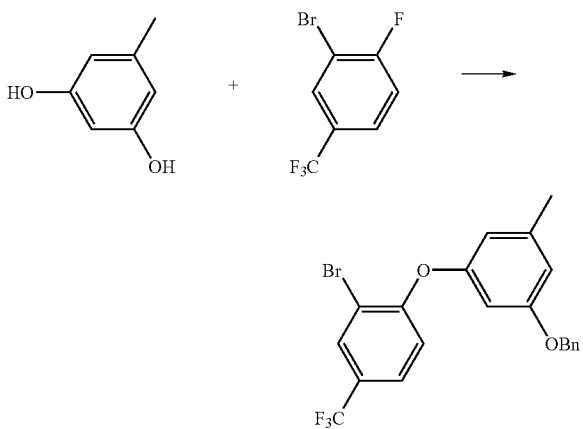

To a solution of orcinol (25.54 g, 0.20 mol) in DMSO (250 mL) is added 5 N NaOH solution (64 mL). The mixture is stirred at 90° C. for 15 min., and then 3-bromo-4-fluoro-benzotrifluoride (25.0 g, 0.10 mol) is added dropwise over 10 minutes. The mixture is stirred at 90° C. for 1.5 h, cooled to rt, diluted with water (300 mL), and extracted with hexanes (3×200 mL). The aqueous layer is split into 2 portions with equal volume. One portion is extracted with EtOAc (3×200 mL). The combined EtOAc layers are washed with 5 N HCl (150 mL) and brine (150 mL), and then dried over Na₂SO₄ and concentrated to provide 15.3 g (67%) of the desired product.

Under nitrogen purge, the compound obtained from the above procedure, CH₃CN (8.6 vol.), 325 mesh K₂CO₃ (3 equiv.) are combined and stirred, and then benzyl bromide (1.02 equiv.) in CH₃CN (1.4 vol.) is added slowly to the solution. Reaction is warmed to reflux (82° C.) and traced via TLC. Upon the reaction is completed, reaction contents are cooled and filtered. Filter cake is washed with 5 volumes of CH₃CN, and filtrate is concentrated to provide an oil.

Step C

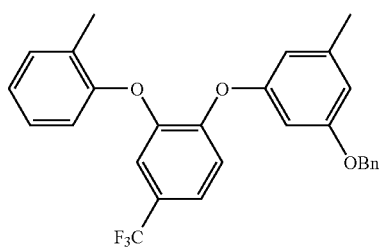

In a 12 L flask with N₂ atmosphere is added the compound obtained from Step C (464 g, 1.06 mol), o-cresol (229.6 g, 2.12 mol), Cs₂CO₃ (690.7 g, 2.12 mol), and 3 L ethyleneglycol diethyl ether. The mixture is stirred at rt for 1 h with N₂ bubbling subsurface. CuCl (26.24 g, 0.265 mol) is added followed by tetramethyl heptanedione (THMD) (19.53 g, 0.106 mol). The mixture is heated at 120° C. for 18 h. Reaction progress is monitored by GC. About 3.5 L MTBE is added, and the solid is filtered and rinsed with 1 L MTBE. The filtrate is diluted with 5 L H₂O, stirred 10 min and the organic layer is separated. The aqueous layer is washed with 2.5 L MTBE. The combined organic layers are washed with 2×2 L conc. NH₄OH, 2 L 2.5 N NaOH, sat. NH₄Cl, and then dried over Na₂SO₄ for 20 min, filtered and evaporated on 55° C. bath. About 517 g (104.8% crude yield) of dark brown oil is collected.

About 3.5 kg of silica is dry packed on glass funnel, and then treated with 15% CH₂Cl₂/heptane. The oil is dissolved in 250 mL CH₂Cl₂. About 1 L heptane is added, loaded on column, and then eluted as follows: 15% CH₂Cl₂/heptane, cuts 1-9, 2 L; 10-12 3.5 L; 20% CH₂Cl₂/heptane cuts 13-15, 3.5 L. Cuts 4-11 are collected and concentrated to provide about 447.1 g product which is used in the next step.

Step D

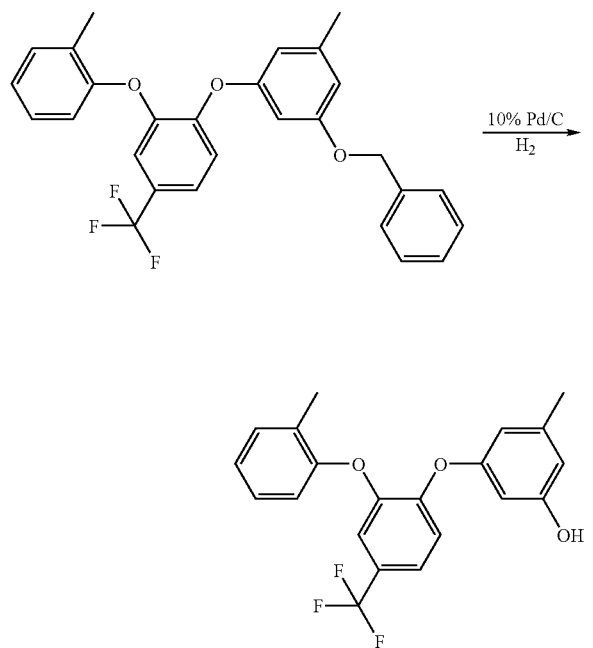

A slurry of 10% Pd/C (54.5 g) and abs. EtOH (0.4 L) are charged to the autoclave reactor (T86A) followed by a solution of the compound obtained from Step C (303.1 g) in abs. EtOH (2.0 L). The solution is stirred under H₂ (40 psi) for 2 hours. The reaction is filtered and washed with abs. EtOH (1.2 L). The filtrate is concentrated to an oil, and then purified by Kugelrohr distillation. Low boiling impurities are removed (bp=175-180° C. @1.0 mm Hg) to afford the product as a thick amber oil. ¹H-NMR(CDCl₃, 300 MHz) δ 7.38-7.00 (m, 6H), 6.82 (d, 1H), 6.38 (d, 2H), 6.25 (m, 1H), 4.63 (s, 1H), 2.25 (s, 3H), 2.13 (s, 3H).

Step E(a)

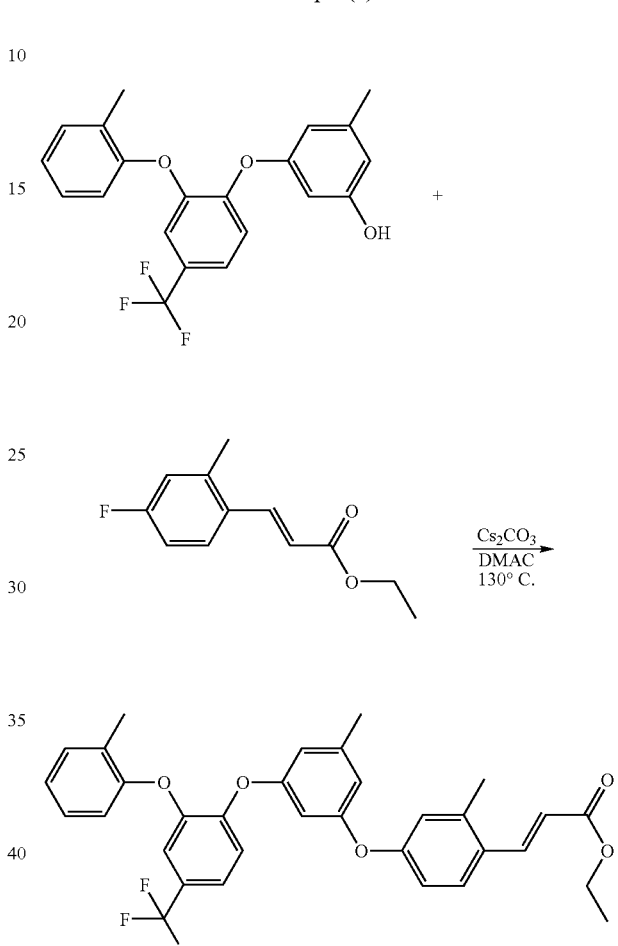

A 5-L flask is equipped with a heating mantle, air stirrer, condenser, addition funnel, and N₂ inlet/outlet using a Firestone valve. The flask is thoroughly purged with nitrogen, and charged with the compound from Step D (206.0 g, 0.550 moles), DMAC (2.00 L), and molecular sieves (82.4 g) followed by CS₂CO₃ (313.8 g). The reaction is stirred for 15 minutes, and the compound obtained from Step A (137.4 g, 0.660 moles) is added to the mixture. The mixture is heated to about 130° C. After about 48 hrs, the reaction is completed, and the mixture is cooled to room temperature. MTBE (3.0 L) is added to the mixture, and then the contents are filtered through Hyflo. After washing the filter cake with MTBE (2×0.50 L), the filtrates are transferred to a separatory funnel, and then 1N aq. HCl (2.8 L) is added. The biphasic solution is separated and the top MTBE layer is washed with D.I. H₂O. The bottom 1N HCl solution is back extracted with MTBE (2.0 L), and the MTBE is washed with D.I. H₂O (1.0 L). The MTBE layers are combined, dried over Na₂SO₄, and filtered to remove the drying agent. The filtrate is concentrated to give the crude ester compound as an oil (330.0 g, 106.6%).

Step E(b)

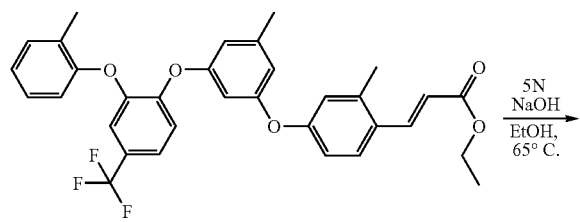

A 12-L reaction flask is equipped with a heating mantle, air stirrer, condenser, addition funnel, and $N_2$ inlet/outlet using a Firestone valve. The flask is thoroughly purged with nitrogen, and then charged the compound obtained from Step E(a) (330.0 g, 0.0.617 moles), EtOH (3.85 L), and 2.5N NaOH (0.88 L). The mixture is heated to about 65° C. for 1 hr. The solution is transferred to a Buchi flask and concentrated to a thick slurry. After adding D.I. $H_2O$ (2.75 L) to form a slurry of fine solids, 1N aq. HCl (2.93 L) is added until about pH=1 is obtained. The solution is extracted with MTBE (6.0 L), and the MTBE layer is washed with aq. saturated NaCl (1.4 L) and 1N aq. HCl (0.37 L). After drying the MTBE layer over $Na_2SO_4$, the drying agent is filtered off, and the filtrate is concentrated to afford crude acid compound (317 g). The crude acid compound is dissolved in acetonitrile (ACN) (15 volumes, 4.75 L) at 65° C., and then slowly cooled to rt overnight. The mixture is filtered, washed with ACN (0.50 L), and dried to yield the final product (214.2 g) as an off-white solid. $^1$H-NMR(CDCl$_3$, 300 MHz) δ 12.42 (s, 1H), 7.52 (d, 1H), 7.35 (d, 1H), 7.27 (d, 1H), 7.20-7.10 (m, 2H), 7.10-7.00 (m, 1H), 6.90-6.84 (m, 1H), 6.79 (d, 2H), 6.60 (d, 2H), 6.45-6.28 (m, 3H), 2.32 (s, 3H), 2.22 (s, 3H), 2.04 (s, 3H).

Step F

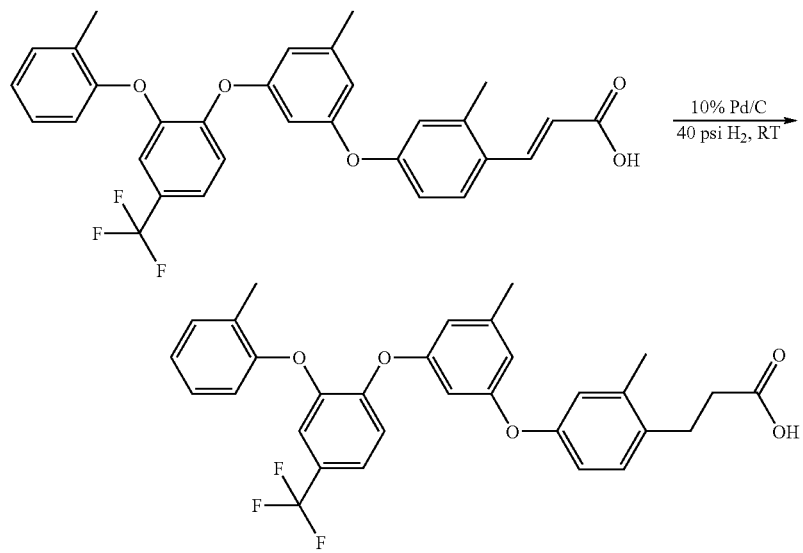

A 3-gallon autoclave (T85) is charged with 10% Pd/C (15.2 g), ethyl alcohol (4.56 L), and the compound obtained from Step E(b) (304.3 g, 0.569 moles) under $H_2$ pressure of 40 psi. The mixture is stirred at rt for about 1 hr. The mixture is filtered to remove palladium. The clear filtrate is concentrated to afford the final acid compound (296.3 g, 97.0%) as a thick oil. $^1$H-NMR(CDCl$_3$, 300 MHz) δ 7.36-7.00 (m, 7H), 6.86-6.70 (m, 3H), 6.56-6.36 (m, 3H), 2.92 (t, 2H), 2.62 (t, 2H), 2.28 (s, 3H), 2.26 (s, 3H), 2.13 (s, 3H).

What is claimed is:

1. The compound having a structural formula III,

III or a pharmaceutically acceptable salt thereof wherein:

A is: a bond, $CH_2$, $(CH_2)_2$, O, S; or A and $R^1$ or A and $R^2$ together being a 3- to 6-membered carbocyclyl when A is a carbon;

n is: 1, 2, 3, 4, 5 or 6 p is: 1 or 2;

r is: 1, 2, 3, or 4;

$R^1$ and $R^2$ are each independently:
hydrogen, $C_1$-$C_6$ alkyl, or $R^1$ and $R^2$ together being a 3- to 8-membered carbocyclic ring;

$R^3$ and $R^4$ are each independently:
hydrogen,
nitro,
cyano,
hydroxyl,
halo,
haloalkyl,
haloalkyloxy,
$C_1$-$C_6$ alkyl,
$C_1$-$C_6$ alkoxy, or
$C_3$-$C_8$ cycloalkyl $R^5$ is: hydrogen,
nitro,
cyano,
hydroxyl,
halo,
haloalkyl,
haloalkyloxy,
aryloxy,
$C_1$-$C_6$ alkyl,
$C_1$-$C_6$ alkoxy,
[T]-aryl,
[T]-heteroaryl,
[T]-heterocyclyl,
[T]-$(CH_2)_n$, $C_3$-$C_8$ cycloalkyl,
$C(O)_p R^7$,
$O(CH_2)_n R^7$,
$SR_7$,
$S(O)_p R^7$ or
$OS(O)_p R^7$,
wherein aryl, aryloxy, alkyl, heteroaryl, heterocyclyl and cycloalkyl are being optionally substituted with one or more substituents independently selected from $R^8$;

[T] is: a bond, O, C(O), S, $NR^7$, or $C_1$-$C_6$ alkyl;

$R^6$ is: hydrogen, $C_1$-$C_6$ alkyl or aminoalkyl;

$R^7$ is: hydrogen,
$C_1$-$C_6$ alkyl,
$C_3$-$C_8$ cycloalkyl,
aryl,
heteroaryl or
heterocyclyl,
wherein alkyl, cycloalkyl, aryl, heteroaryl or heterocyclyl being optionally substituted with one or more substituents independently selected from $R^8$; and $R^8$ is: hydrogen, nitro, cyano, hydroxyl, halo, haloalkyl, haloalkyloxy, aryloxy, oxo, acyl, $C_1$-$C_6$ alkyl, $C_1$-$C_6$ alkoxy or $C_3$-$C_8$ cycloalkyl.

2. The compound of claim 1, wherein the compound is structural formula IV,

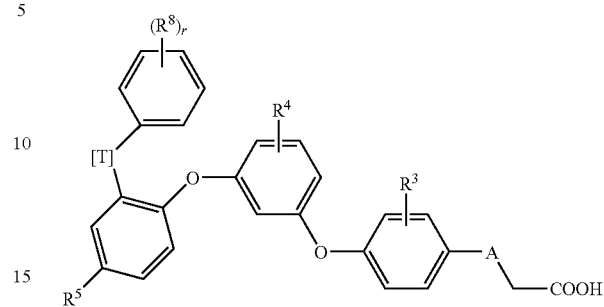

IV or a pharmaceutically acceptable salt or stereoisomer thereof, wherein:
A is: $CH_2$, O, S;
[T] is: a bond, O, C(O) or $C_1$-$C_3$ alkyl;
$R^3$ and $R^4$ are each independently:
hydrogen, $C_1$-$C_3$ alkyl, halo, haloalkyl or haloalkyloxy;
$R^5$ and $R^8$ are each independently:
hydrogen, $C_1$-$C_6$ alkyl, halo, haloalkyl or haloalkyloxy; and
r is 1 or 2.

3. The compound of claim 2, wherein the compound is structural formula V,

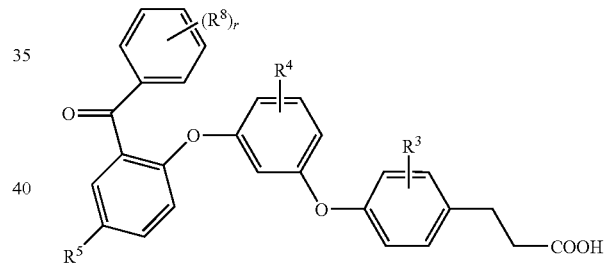

V or a pharmaceutically acceptable salt or stereoisomer thereof, wherein:
$R^3$ and $R^4$ are each independently: hydrogen, methyl, ethyl, Br, Cl or F;
$R^5$ and $R^8$ are each independently: hydrogen, $C_1$-$C_4$ alkyl, Br, Cl, F or $CF_3$; and
r is 1 or 2.

4. The compound of claim 2, wherein the compound is structural formula VI,

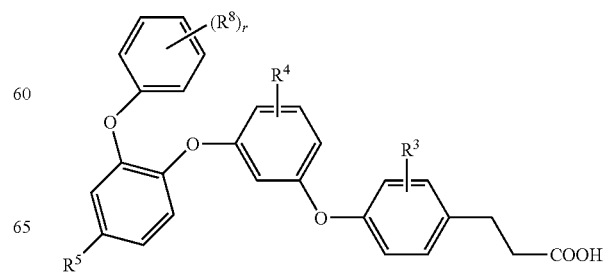

VI or a pharmaceutically acceptable salt or stereoisomer thereof, wherein:
$R^3$ and $R^4$ are each independently: hydrogen, methyl, ethyl, Br, Cl or F;
$R^5$ and $R^8$ are each independently: hydrogen, $C_1$-$C_4$ alkyl, Br, Cl, F or $CF_3$; and
r is 1 or 2.

5. The compound of claim 4, wherein the compound is structural formula VII,

VII

[structure]

or a pharmaceutically acceptable salt thereof.

6. The compound of claim 4, wherein the compound is structural formula VIII,

VIII

[structure]

or a pharmaceutically acceptable salt thereof.

7. The compound of claim 2, wherein the compound is structural formula IX,

IX

[structure]

or a pharmaceutically acceptable salt or stereoisomer thereof, wherein:
$R^3$ and $R^4$ are each independently: hydrogen, methyl, ethyl, Br, Cl or F;
$R^5$ and $R^8$ are each independently: hydrogen, $C_1$-$C_4$ alkyl, Br, Cl, F or $CF_3$; and
r is 1 or 2.

8. The compound having the structural formula X,

X

[structure]

or a pharmaceutically acceptable salt or stereoisomer thereof, wherein:

[Het]

is a 5- or 6-membered heteroaryl or heterocyclyl, wherein heteroaryl and heterocyclyl being optionally substituted with one or more substituents independently selected from $R^8$;
A is: a bond, $CH_2$, $(CH_2)_2$, O, S; or A and $R^1$ or A and $R^2$ together being a 3- to 6-membered carbocyclyl when A is a carbon;
n is: 1,2,3,4,5 or 6;
p is: 1 or 2;
r is: 1,2,3, or 4;
$R^1$ and $R^2$ are each independently:
  hydrogen, $C_1$-$C_6$ alkyl, or $R^1$ and $R^2$ together being a 3- to 8-membered carbocyclic ring;
$R^3$ and $R^4$ are each independently:
  hydrogen,
  nitro,
  cyano,
  hydroxyl,
  halo,
  haloalkyl,
  haloalkyloxy,
  $C_1$-$C_6$ alkyl,
  $C_1$-$C_6$ alkoxy, or
  $C_3$-$C_8$ cycloalkyl
$R^5$ is: hydrogen,
  nitro,
  cyano,
  hydroxyl,
  halo,
  haloalkyl,
  haloalkyloxy,
  aryloxy,
  $C_1$-$C_6$ alkyl,
  $C_1$-$C_6$ alkoxy,
  [T]-aryl,
  [T]-heteroaryl,
  [T]-heterocyclyl,
  [T]-$(CH_2)_n$$C_3$-$C_8$ cycloalkyl,
  $C(O)_p R^7$,
  $O(CH_2)_n R^7$,
  $SR^7$,
  $S(O)_p R^7$ or
  $OS(O)_p R^7$,
  wherein aryl, aryloxy, alkyl, heteroaryl, heterocyclyl and cycloalkyl are being optionally substituted with one or more substituents independently selected from $R^8$;

[T] is: a bond, O, C(O), S, $NR^7$, or $C_1$-$C_6$ alkyl;

$R^6$ is: hydrogen, $C_1$-$C_6$ alkyl or aminoalkyl;

$R^7$ is: hydrogen,
  $C_1$-$C_6$ alkyl,
  $C_{3-8}$ cycloalkyl,
  aryl,
  heteroaryl or
  heterocyclyl,
  wherein alkyl, cycloalkyl, aryl, heteroaryl or heterocyclyl being optionally substituted with one or more substituents independently selected from $R^8$, and $R^8$ is: hydrogen, nitro, cyano, hydroxyl, halo, haloalkyl, haloalkyloxy, aryloxy, oxo, acyl, $C_1$-$C_6$ alkyl, $C_1$-$C_6$ alkoxy or $C_3$-$C_8$ cycloalkyl.

9. The compound of claim 8, wherein the heteroaryl is pyrazolyl, pyrrolyl, pyrazinyl, pyridyl, pyrimidyl, or pyrimidinyl.

10. The compound of claim 8, wherein the compound is structural formula XI,

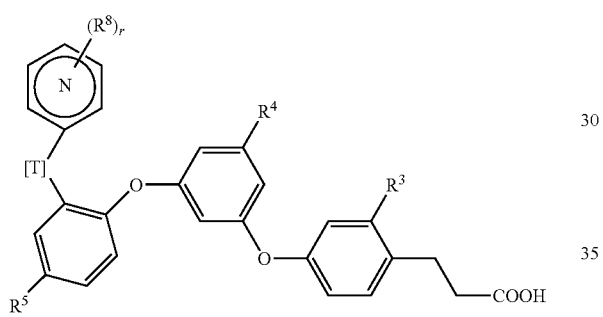

XI or a pharmaceutically acceptable salt, solvate, hydrate or stereoisomer thereof, wherein:

[T] is: a bond, O, C(O) or $C_1$-$C_3$ alkyl;

$R^3$ and $R^4$ are each independently: hydrogen, methyl, ethyl, Br, Cl or F;

$R^5$ and $R^8$ are each independently: hydrogen, $C_1$-$C_4$ alkyl, Br, Cl, F or $CF_3$; and r is 1 or 2.

11. The compound having the structural formula XII,

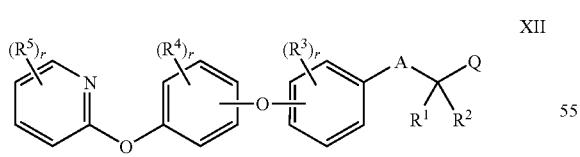

XII or a pharmaceutically acceptable salt or stereoisomer thereof;

A is: a bond, $CH_2$, $(CH_2)_2$, O, S; or A and $R^1$ or A and $R^2$ together being a 3- to 6-membered carbocyclyl when A is a carbon;

Q is $COOR^6$;

n is: 1,2,3,4,5 or 6;

p is: 1 or 2;

r is: 1,2,3, or 4;

$R^1$ and $R^2$ are each independently:
  hydrogen, $C_1$-$C_6$ alkyl, or $R^1$ and $R^2$ together being a 3- to 8-membered carbocyclic ring;

$R^3$ and $R^4$ are each independently:
  hydrogen,
  nitro,
  cyano,
  hydroxyl,
  halo,
  haloalkyl,
  haloalkyloxy,
  $C_1$-$C_6$ alkyl,
  $C_1$-$C_6$ alkoxy, or
  $C_3$-$C_8$ cycloalkyl $R^5$ is: hydrogen,
  nitro,
  cyano,
  hydroxyl,
  halo,
  haloalkyl, haloalkyloxy,
  aryloxy,
  $C_1$-$C_6$ alkyl,
  $C_1$-$C_6$ alkoxy,
  [T]-aryl,
  [T]-heteroaryl,
  [T]-heterocyclyl,
  [T]-$(CH_2)_n$$C_3$-$C_8$ cycloalkyl,
  $C(O)_pR^7$,
  $O(CH_2)_nR_7$,
  $SR^7$,
  $S(O)_pR^7$, or
  $OS(O)_pR^7$, wherein aryl, aryloxy, alkyl, heteroaryl, heterocyclyl and cycloalkyl are being optionally substituted with one or more substituents independently selected from $R^8$
  ;

[T] is: a bond, O, C(O), S, $NR^7$, or $C_1$-$C_6$ alkyl;

$R^6$ is: hydrogen, $C_1$-$C_6$ alkyl or aminoalkyl;

$R^7$ is: hydrogen,
  $C_1$-$C_6$ alkyl,
  $C_3$-$C_8$ cycloalkyl,
  aryl,
  heteroaryl or
  heterocyclyl,
  wherein alkyl, cycloalkyl, aryl, heteroaryl or heterocyclyl being optionally substituted with one or more substituents independently selected from $R^8$; and $R^8$ is: hydrogen, nitro, cyano, hydroxyl, halo, haloalkyl, haloalkyloxy, aryloxy, oxo, acyl, $C_1$-$C_6$ alkyl, $C_1$-$C_6$ alkoxy or $C_3$-$C_8$ cycloalkyl.

12. The compound of claim 11, wherein the compound is formula XIII,

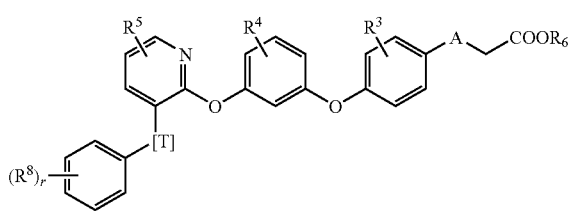

or a pharmaceutically acceptable salt or stereoisomer thereof, wherein:
  A is: $CH_2$, O, S;
  [T] is: a bond, O, C(O) or $C_1$-$C_3$ alkyl;
  $R^3$ and $R^4$ are each independently:
    hydrogen, $C_1$-$C_3$ alkyl, halo, haloalkyl or haloalkyloxy;
  $R^5$ and $R^8$ are each independently:
    hydrogen, $C_1$-$C_6$ alkyl, halo, haloalkyl or haloalkyloxy; and
  $R^6$ is: hydrogen or $C_1$-$C_6$ alkyl; and
  r is 1 or 2.

13. The compound of claim 12, wherein the compound is formula XIV,

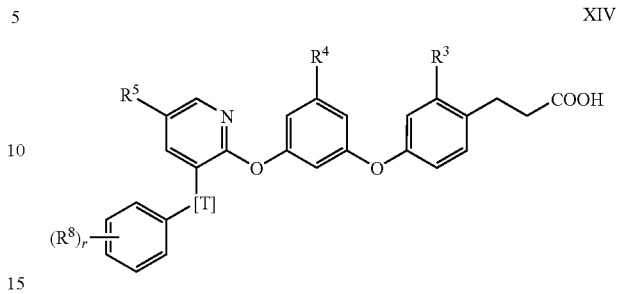

or a pharmaceutically-acceptable salt or stereoisomer thereof, wherein:
  [T] is: a bond, O or $C_1$-$C_3$ alkyl;
  $R^3$ and $R^4$ are each independently: hydrogen, methyl, ethyl, Br, Cl or F;
  $R^5$ and $R^8$ are each independently: hydrogen, $C_1$-$C_4$ alkyl, Br, Cl, F or $CF_3$; and
  r is 1 or 2.

14. A compound selected from the group consisting of the following compounds:

| No. | Structure | Name |
|---|---|---|
| 1 | 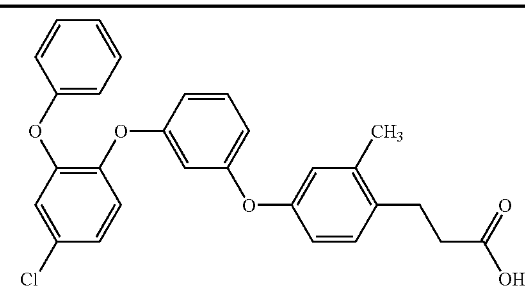 | 3-{4-[3-(4-Chloro-2-phenoxy-phenoxy)-phenoxy]-2-methyl-phenyl}-propionic acid |
| 2 | 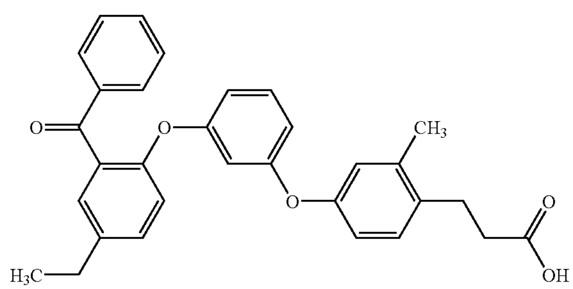 | 3-{4-[3-(2-Benzoyl-4-ethyl-phenoxy)-phenoxy]-2-methyl-phenyl}-propionic acid |
| 3 | 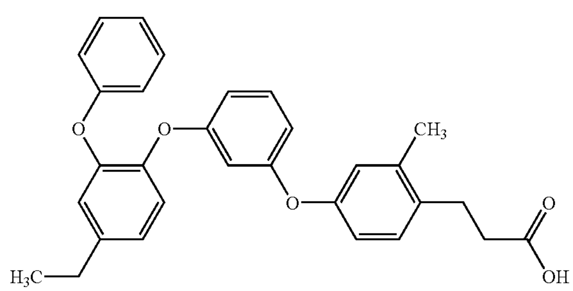 | 3-{4-[3-(4-Ethyl-2-phenoxy-phenoxy)-phenoxy]-2-methyl-phenyl}-propionic acid |

-continued

| No. | Structure | Name |
| --- | --- | --- |
| 4 | 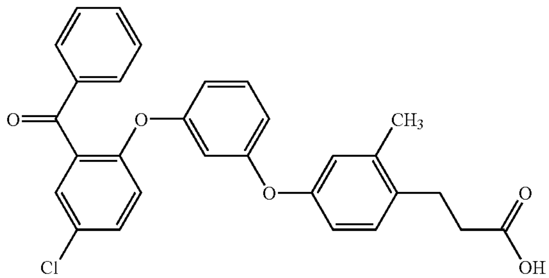 | 3-{4-[3-(2-Benzoyl-4-chloro-phenoxy)-phenoxy]-2-methyl-phenyl}-propionic acid |
| 5 | 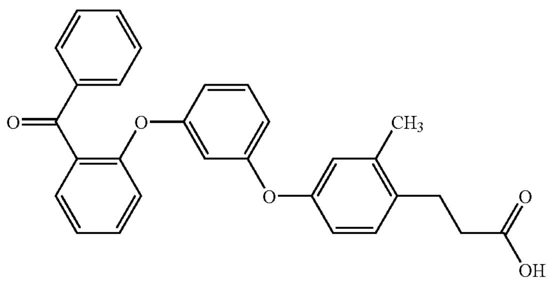 | 3-{4-[3-(2-Benzoyl-phenoxy)-phenoxy]-2-methyl-phenyl}-propionic acid |
| 6 | 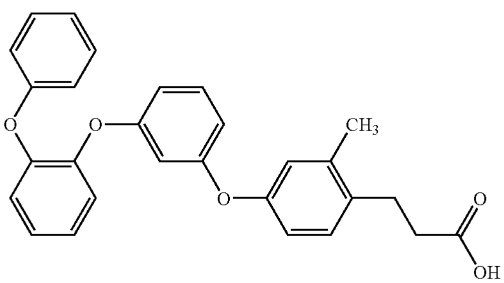 | 3-{2-Methyl-4-[3-(2-phenoxy-phenoxy)-phenoxy]-phenyl}-propionic acid |
| 7 | 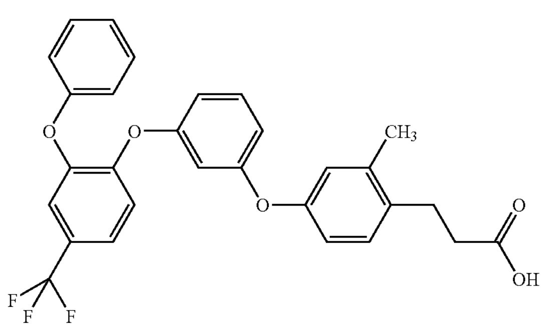 | 3-{2-Methyl-4-[3-(2-phenoxy-4-trifluoromethyl-phenoxy)-phenoxy]-phenyl}-propionic acid |
| 8 | 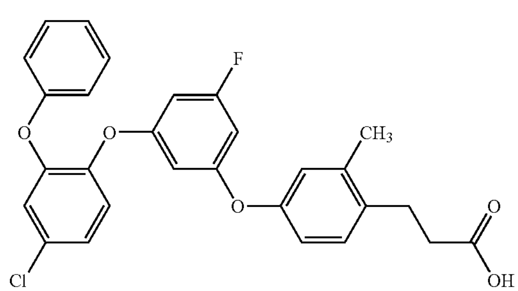 | 3-{4-[3-(4-Chloro-2-phenoxy-phenoxy)-5-fluoro-phenoxy]-2-methyl-phenyl}-propionic acid |

| No. | Structure | Name |
|---|---|---|
| 9 | 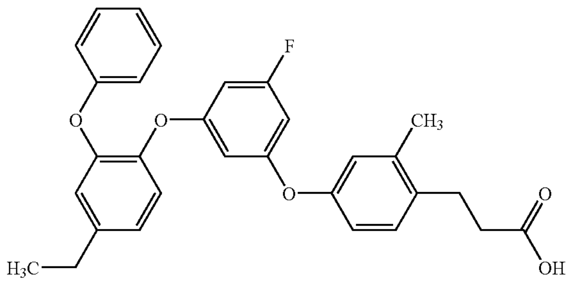 | 3-{4-[3-(4-Ethyl-2-phenoxy-phenoxy)-5-fluoro-phenoxy]-2-methyl-phenyl}-propionic acid |
| 10 | 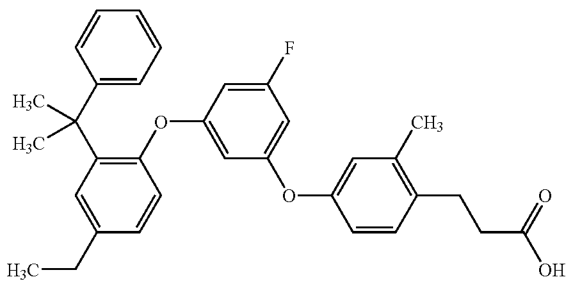 | 3-(4-{3-[4-Ethyl-2-(1-methyl-1-phenyl-ethyl)-phenoxy]-5-fluoro-phenoxy}-2-methyl-phenyl)-propionic acid |
| 11 | 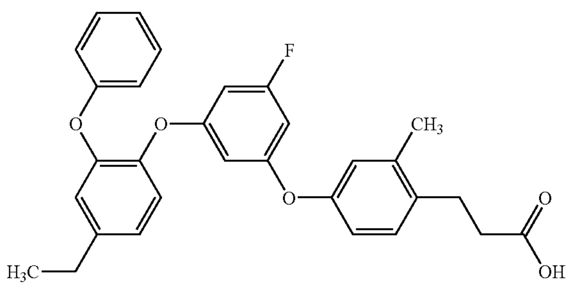 | 3-{4-[3-(4-Ethyl-2-phenoxy-phenoxy)-5-fluoro-phenoxy]-2-methyl-phenyl}-propionic acid |
| 12 | 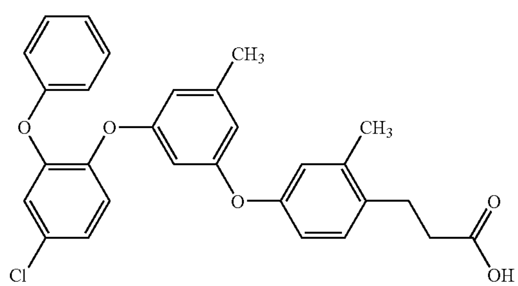 | 3-{4-[3-(4-Chloro-2-phenoxy-phenoxy)-5-methyl-phenoxy]-2-methyl-phenyl}-propionic acid |
| 13 | 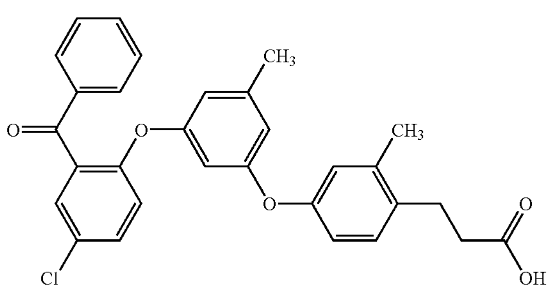 | 3-{4-[3-(2-Benzoyl-4-chloro-phenoxy)-5-methyl-phenoxy]-2-methyl-phenyl}-propionic acid |

| No. | Structure | Name |
|---|---|---|
| 14 | 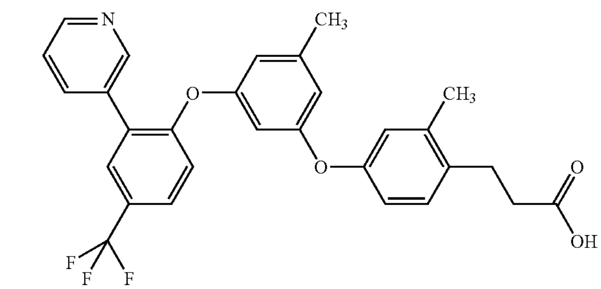 | 3-{2-Methyl-4-[3-methyl-5-(2-pyridin-3-yl-4-trifluoromethyl-phenoxy)-phenoxy]-phenyl}-propionic acid |
| 15 | 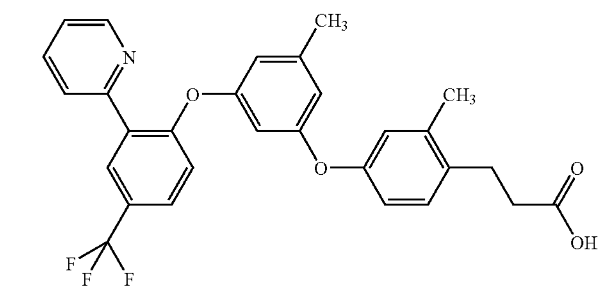 | 3-{2-Methyl-4-[3-methyl-5-(2-pyridin-2-yl-4-trifluoromethyl-phenoxy)-phenoxy]-phenyl}-propionic acid |
| 16 | 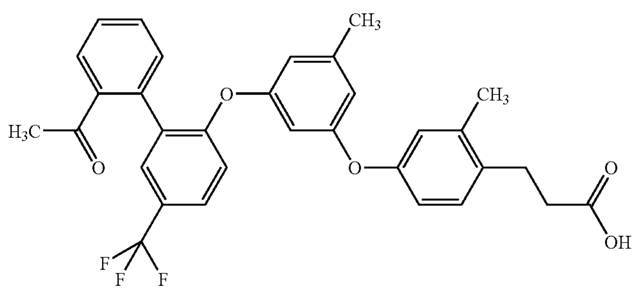 | 3-{4-[3-(2'-Acetyl-5-trifluoromethyl-biphenyl-2-yloxy)-5-methyl-phenoxy]-2-methyl-phenyl}-propionic acid |
| 17 | 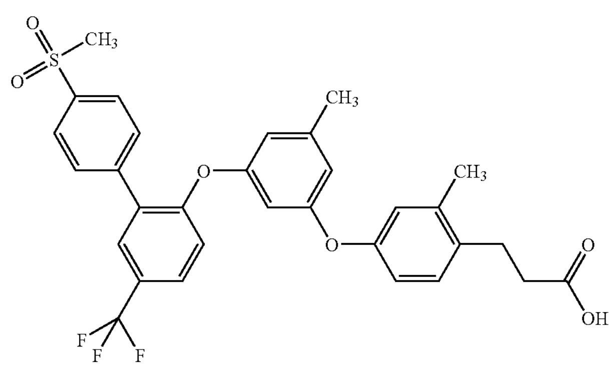 | 3-{4-[3-(4'-Methanesulfonyl-5-trifluoromethyl-biphenyl-2-yloxy)-5-methyl-phenoxy]-2-methyl-phenyl}-propionic acid |
| 18 | 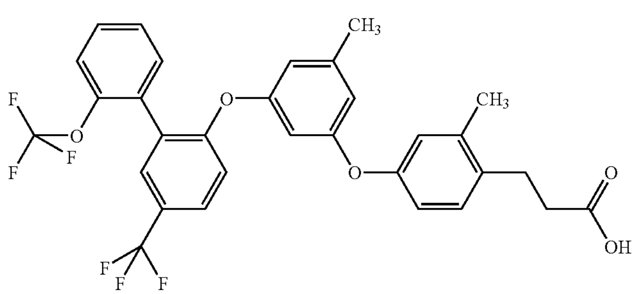 | 3-{2-Methyl-4-[3-methyl-5-(2'-trifluoromethoxy-5-trifluoromethyl-biphenyl-2-yloxy)-phenoxy]-phenyl}-propionic acid |

-continued

| No. | Structure | Name |
|---|---|---|
| 19 | 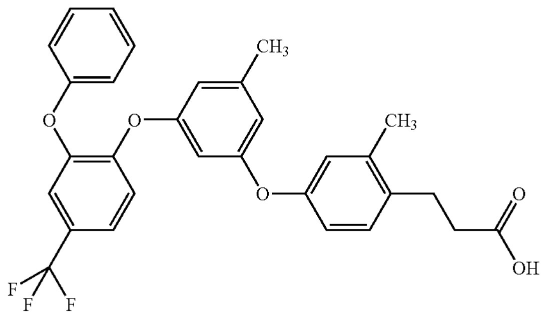 | 3-{2-Methyl-4-[3-methyl-5-(2-phenoxy-4-trifluoromethyl-phenoxy)-phenoxy]-phenyl}-propionic acid |
| 20 | 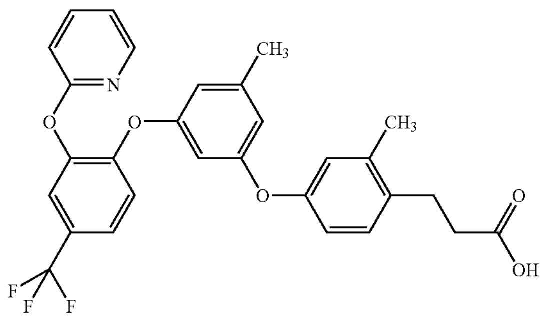 | 3-(2-Methyl-4-{3-methyl-5-[2-(pyridin-2-yloxy)-4-trifluoromethyl-phenoxy]-phenoxy}-phenyl)-propionic acid |
| 21 | 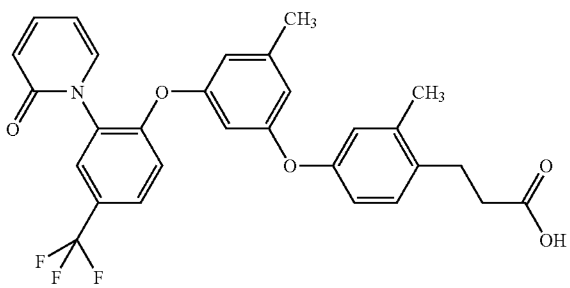 | 3-(2-Methyl-4-{3-methyl-5-[2-(2-oxo-2H-pyridin-1-yl)-4-trifluoromethyl-phenoxy]-phenoxy}-phenyl)-propionic acid |
| 22 | 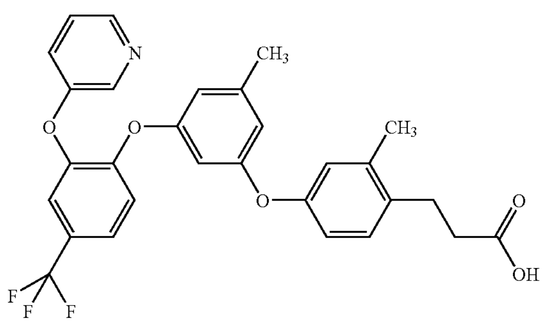 | 3-(2-Methyl-4-{3-methyl-5-[2-(pyridin-3-yloxy)-4-trifluoromethyl-phenoxy]-phenoxy}-phenyl)-propionic acid |
| 23 | 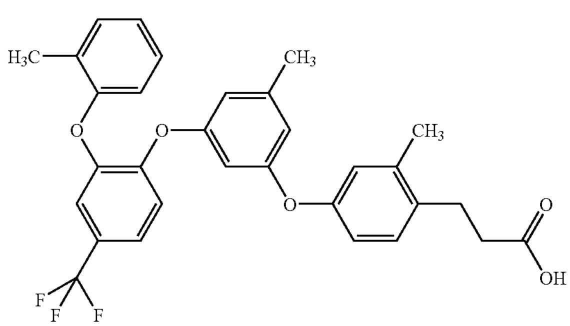 | 3-{2-Methyl-4-[3-methyl-5-(2-o-tolyloxy-4-trifluoromethyl-phenoxy)-phenoxy]-phenyl}-propionic acid |

-continued

| No. | Structure | Name |
|---|---|---|
| 24 | 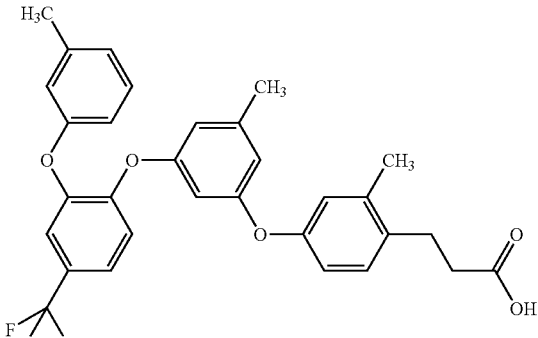 | 3-{2-Methyl-4-[3-methyl-5-(2-m-tolyloxy-4-trifluoromethyl-phenoxy)-phenoxy]-phenyl}-propionic acid |
| 25 | 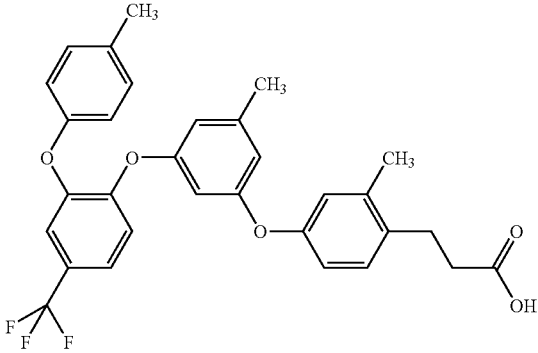 | 3-{2-Methyl-4-[3-methyl-5-(2-p-tolyloxy-4-trifluoromethyl-phenoxy)-phenoxy]-phenyl}-propionic acid |
| 26 | 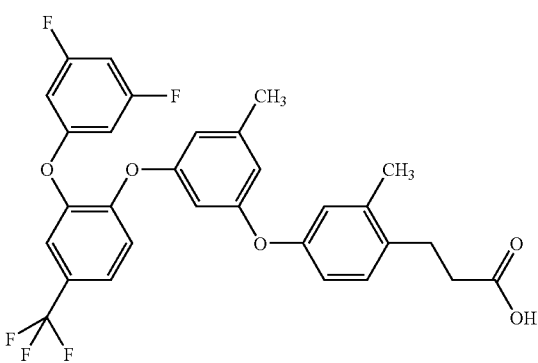 | 3-(4-{3-[2-(3,5-Difluoro-phenoxy)-4-trifluoromethyl-phenoxy]-5-methyl-phenoxy}-2-methyl-phenyl)-propionic acid |
| 27 | 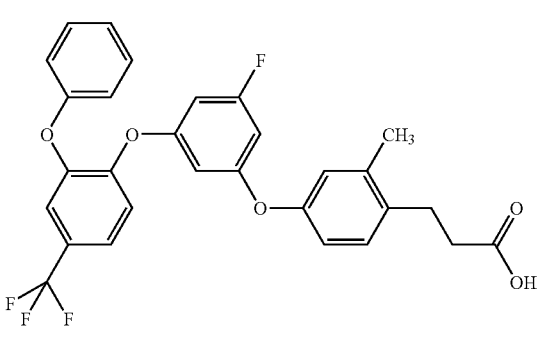 | 3-{4-[3-Fluoro-5-(2-phenoxy-4-trifluoromethyl-phenoxy)-phenoxy]-2-methyl-phenyl}-propionic acid |

-continued

| No. | Structure | Name |
|---|---|---|
| 28 | 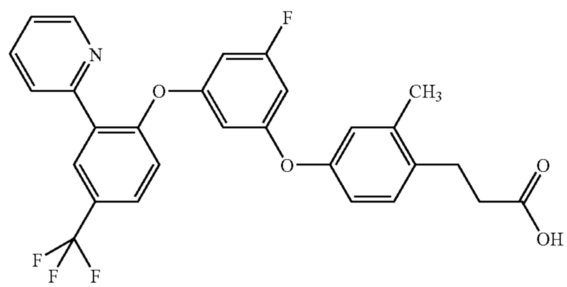 | 3-{4-[3-Fluoro-5-(2-pyridin-2-yl-4-trifluoromethyl-phenoxy)-phenoxy]-2-methyl-phenyl}-propionic acid |
| 29 | 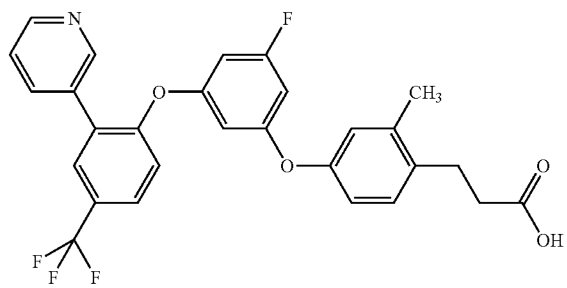 | 3-{4-[3-Fluoro-5-(2-pyridin-3-yl-4-trifluoromethyl-phenoxy)-phenoxy]-2-methyl-phenyl}-propionic acid |
| 30 | 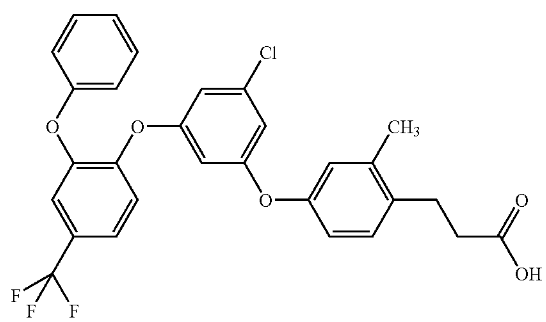 | 3-{4-[3-Chloro-5-(2-phenoxy-4-trifluoromethyl-phenoxy)-phenoxy]-2-methyl-phenyl}-propionic acid |
| 31 | 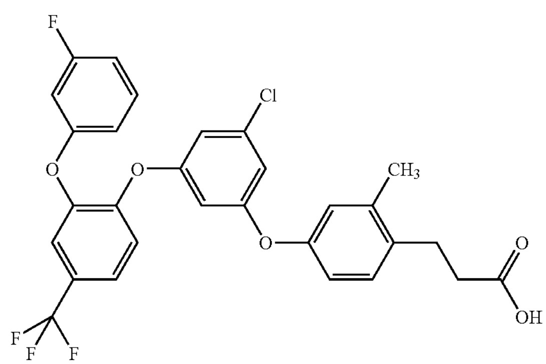 | 3-(4-{3-Chloro-5-[2-(3-fluoro-phenoxy)-4-trifluoromethyl-phenoxy]-phenoxy}-2-methyl-phenyl)-propionic acid |
| 32 | 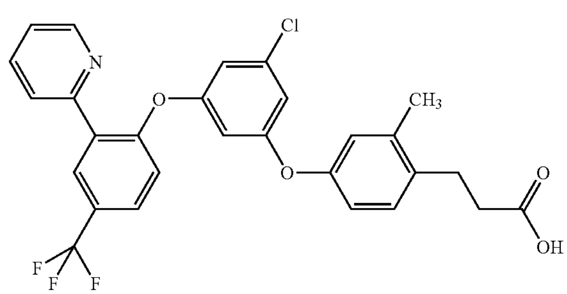 | 3-{4-[3-Chloro-5-(2-pyridin-2-yl-4-trifluoromethyl-phenoxy)-phenoxy]-2-methyl-phenyl}-propionic acid |

-continued

| No. | Structure | Name |
|---|---|---|
| 33 | 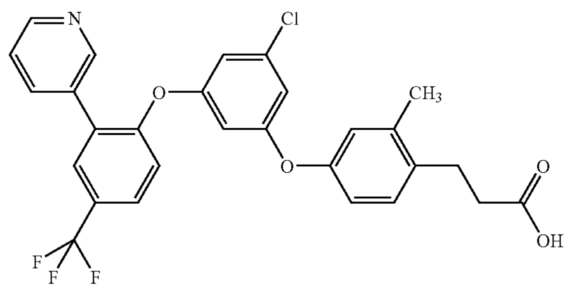 | 3-{4-[3-Chloro-5-(2-pyridin-3-yl-4-trifluoromethyl-phenoxy)-phenoxy]-2-methyl-phenyl}-propionic acid |
| 34 | 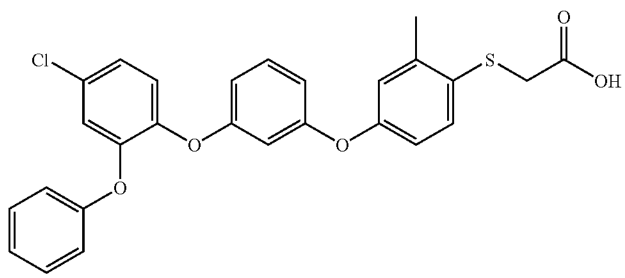 | {4-[3-(4-Chloro-2-phenoxy-phenoxy)-phenoxy]-2-methyl-phenylsulfanyl}-acetic acid |
| 35 | 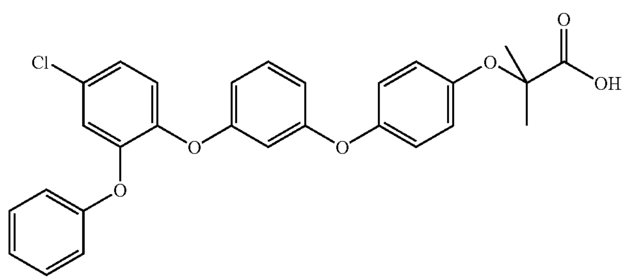 | 2-{4-[3-(4-Chloro-2-phenoxy-phenoxy)-phenoxy]-phenoxy}-2-methyl-propionic acid |
| 36 | 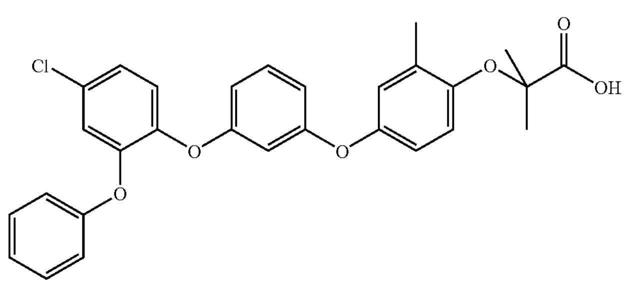 | 2-{4-[3-(4-Chloro-2-phenoxy-phenoxy)-phenoxy]-2-methyl-phenoxy}-2-methyl-propionic acid |
| 37 | 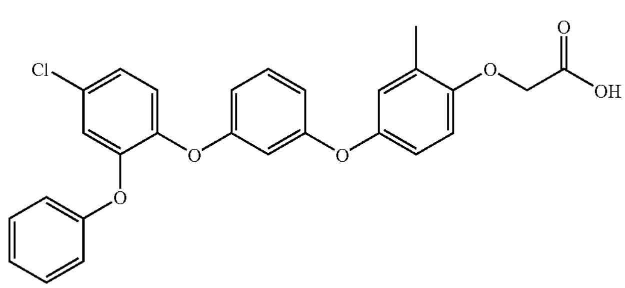 | {4-[3-(4-Chloro-2-phenoxy-phenoxy)-phenoxy]-2-methyl-phenoxy}-acetic acid |

| No. | Structure | Name |
|---|---|---|
| 38 | 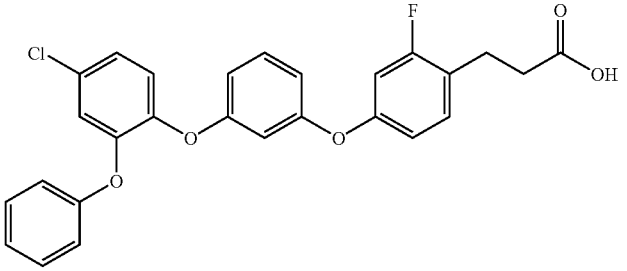 | 3-{4-[3-(4-Chloro-2-phenoxy-phenoxy)-phenoxy]-2-fluoro-phenyl}-propionic acid |
| 39 | 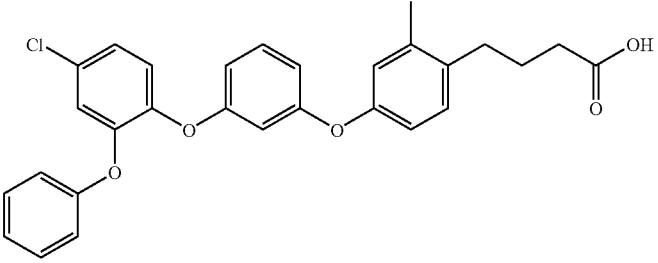 | 4-{4-[3-(4-Chloro-2-phenoxy-phenoxy)-phenoxy]-2-methyl-phenyl}-butyric acid |
| 40 | 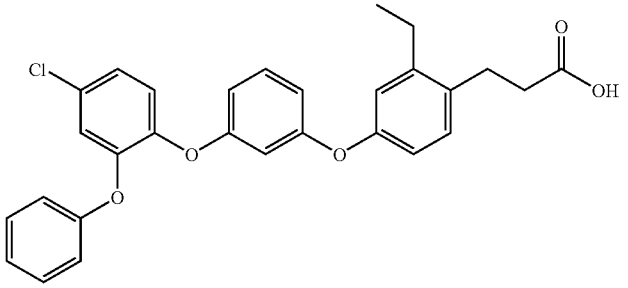 | 3-{4-[3-(4-Chloro-2-phenoxy-phenoxy)-phenoxy]-2-ethyl-phenyl}-propionic acid |
| 41 | 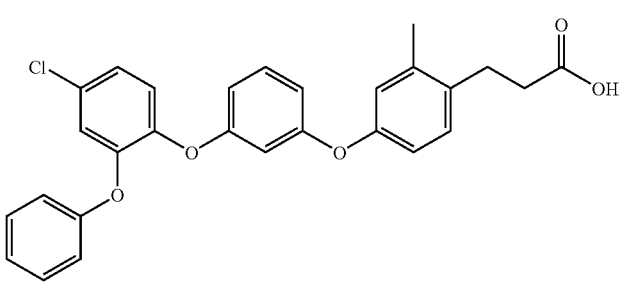 | 3-{4-[3-(2-Benzyl-4-chloro-phenoxy)-phenoxy]-2-methyl-phenyl}-propionic acid |
| 42 | 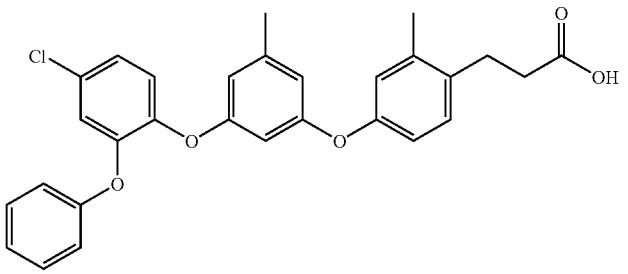 | 3-{4-[3-(2-Benzyl-4-chloro-phenoxy)-5-methyl-phenoxy]-2-methyl-phenyl}-propionic acid |

| No. | Structure | Name |
|---|---|---|
| 43 | 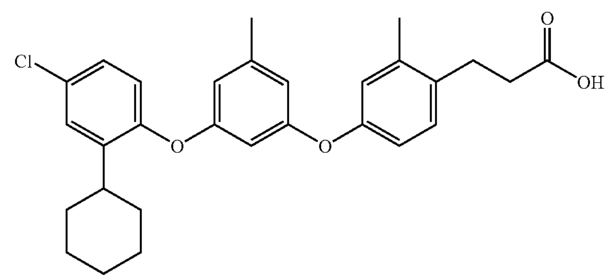 | 3-{4-[3-(4-Chloro-2-cyclohexyl-phenoxy)-5-methyl-phenoxy]-2-methyl-phenyl}-propionic acid |
| 44 | 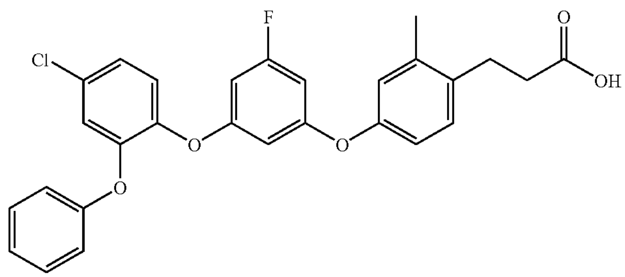 | 3-{4-[3-(2-Benzyl-4-chloro-phenoxy)-5-fluoro-phenoxy]-2-methyl-phenyl}-propionic acid |
| 45 | 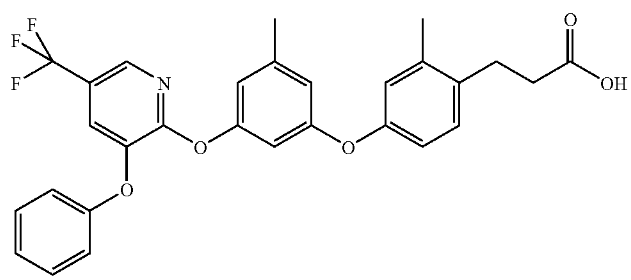 | 3-{2-Methyl-4-[3-methyl-5-(3-phenoxy-5-trifluoromethyl-pyridin-2-yloxy)-phenoxy]-phenyl}-propionic acid. |

15. The compound of claim 14, wherein the compound is 3-{4-[3-(4-chloro-2-phenoxy-phenoxy)-5-methyl-phenoxy]-2-methyl-phenyl}-propionic acid

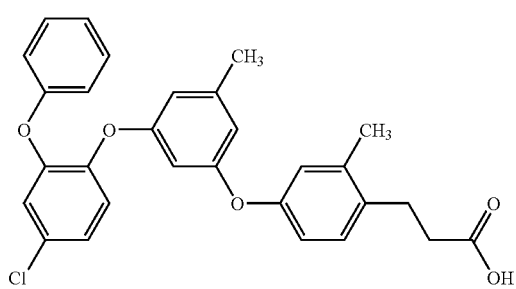

or a pharmaceutically acceptable salt thereof.

16. The compound of claim 14, wherein the compound is: {4-[3-(4-chloro-2-phenoxy-phenoxy)-phenoxy]-2-methyl-phenoxy}-acetic acid

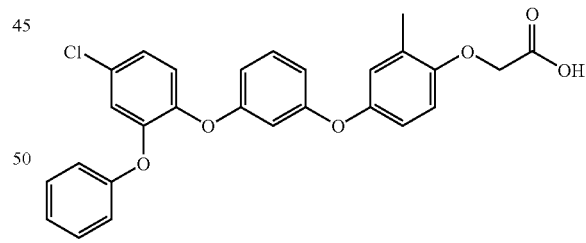

or a pharmaceutically acceptable salt thereof.

17. A pharmaceutical composition comprising a pharmaceutically acceptable carrier and a compound of claim 1 or a pharmaceutically acceptable salt thereof.

18. A method for lowering blood-glucose in a mammal in need thereof, comprising the step of administering an effective amount of a compound of claim 1.